(12) United States Patent
Hirao et al.

(10) Patent No.: US 8,030,478 B2
(45) Date of Patent: Oct. 4, 2011

(54) METHOD FOR NUCLEIC ACID REPLICATION AND NOVEL ARTIFICIAL BASE PAIRS

(75) Inventors: Ichiro Hirao, Komae (JP); Shigeyuki Yokoyama, Yokohama (JP)

(73) Assignee: Riken, Saitama (JP)

( * ) Notice: Subject to any disclaimer, the term of this patent is extended or adjusted under 35 U.S.C. 154(b) by 486 days.

(21) Appl. No.: 12/096,517

(22) PCT Filed: Dec. 7, 2006

(86) PCT No.: PCT/JP2006/324484
§ 371 (c)(1),
(2), (4) Date: Sep. 8, 2008

(87) PCT Pub. No.: WO2007/066737
PCT Pub. Date: Jun. 14, 2007

(65) Prior Publication Data
US 2010/0036111 A1 Feb. 11, 2010

(30) Foreign Application Priority Data
Dec. 9, 2005 (JP) .................................. 2005-356883
Jul. 10, 2006 (JP) .................................. 2006-189806

(51) Int. Cl.
*C07H 21/00* (2006.01)
(52) U.S. Cl. .................... 536/25.3; 536/23.1; 536/27.1; 536/27.13
(58) Field of Classification Search .......................... None
See application file for complete search history.

(56) References Cited

FOREIGN PATENT DOCUMENTS

| EP | 1921141 A1 | 5/2008 |
|---|---|---|
| WO | WO-01/05801 A1 | 1/2001 |
| WO | WO-2004/007713 A1 | 1/2004 |
| WO | WO-2005/026187 A1 | 3/2005 |
| WO | WO-2007/015557 A1 | 2/2007 |

OTHER PUBLICATIONS

Doronin et al. FEBS Letters (1987), vol. 216, pp. 221-224.*
Benner, S. A., et al., "Did the RNA World Exploit an Expanded Genetic Alphabet?", Cold Spring Harbor Laboratory Press, pp. 163-181 (1999).
Henry, A. A., et al., "Beyond A, C, G and T: augmenting nature's alphabet," Curr. Opin. Chem. Biol., vol. 7, pp. 727-733 (2003).
Moser, M. J., et al., "Enzymatic repair of an expanded genetic information system," Nucleic Acids Res., vol. 31, No. 17, pp. 5048-5053 (2003).
Bergstrom, D. E., "Orthogonal Base Pairs Continue to Evolve," Chem. Biol., vol. 11, pp. 18-20 (2004).
Benner, S. A., et al., "Synthetic Biology," Nature Reviews, Genetics, vol. 6, pp. 533-543 (2005).
Piccirilli, J. A., et al., "Enzymatic incorporation of a new base pair into DNA and RNA extends the genetic alphabet," Nature, vol. 343, pp. 33-37 (1990).
Sismour, A. M., et al., "PCR amplification of DNA containing non-standard base pairs by variants of reverse transcriptase from Human Immunodeficiency Virus-1," Nucleic Acids Research, vol. 32, No. 2, pp. 728-735 (2004).
Switzer, C. Y., "Enzymatic Recognition of the Base Pair between Isocytidine and Isoguanosine," Biochemistry, vol. 32, pp. 10489-10496 (1993).
Johnson, S. C., "A third base pair for the polymerase chain reaction: inserting isoC and isoG," Nucleic Acids Research, vol. 32, No. 6, pp. 1937-1941 (2004).
Ahle, J. D., "Sequence determination of nucleic acids containing 5-methylisocytosine and isoguanine: identification and insight into polymerase replication of the non-natural nucleobases," Nucleic Acids Research, vol. 33, No. 10, pp. 3176-3184 (2005).
Morales, J. C., et al., "Efficient replication between non-hydrogen-bonded nucleoside shape analogs," Nat. Struct. Biol., vol. 5, No. 11, pp. 950-954 (1998).
Kool, E. T., "Mimicking the Structure and Function of DNA: Insights into DNA Stability and Replication," Angew. Chem. Int. Ed., vol. 39, pp. 990-1009 (2000).
McMinn, D. L., et al., "Efforts toward Expansion of the Genetic Alphabet: DNA Polymerase Recognition of a Highly Stable, Self-Pairing Hydrophobic Base," J. Am. Chem. Soc., vol. 121, pp. 11585-11586 (1999).
Wu, Y., et al., "Efforts toward Expansion of the Genetic Alphabet: Optimization of Interbase Hydrophobic Interactions," J. Am. Chem. Soc., vol. 122, No. 32, pp. 7621-7632 (2000).
Ogawa, A. K., et al., "Efforts toward the Expansion of the Genetic Alphabet: Information Storage and Replication with Unnatural Hydrophobic Base Pairs," J. Am. Chem. Soc., vol. 122, pp. 3274-3287 (2000).
Fujiwara, T., et al., "Synthesis of 6-(2-Thienyl)purine Nucleoside Derivatives That Form Unnatural Base Pairs with Pyridin-2-one Nucleosides," Bioorg. Med. Chem. Letters, vol. 11, pp. 2221-2223 (2001).
Hirao, I., et al., "An unnatural base pair for incorporating amino acid analogs into proteins," Nat. Biotechnol., vol. 20, pp. 177-182 (2002).
Mitsui, T., et al., "An Efficient Unnatural Base Pair for a Base-Pair-Expanded Transcription System," J. Am. Chem. Soc., vol. 127, pp. 8652-8658 (2005).
Kimoto, M., et al., "Site-Specific Incorporation of a Photo-Crosslinking Component into RNA by T7 Transcription Mediated by Unnatural Base Pairs," Chem. Biol., vol. 11, pp. 47-55 (2004).
Moriyama, K., et al., "Site-specific biotinylation of RNA molecules by transcription using unnatural base pairs," Nucleic Acids Research, vol. 33, No. 15, e129 (8 pgs).

(Continued)

Primary Examiner — Patrick Lewis
(74) Attorney, Agent, or Firm — Birch Stewart Kolasch & Birch, LLP

(57) ABSTRACT

The present invention relates to a method for nucleic acid replication and novel artificial base pairs.
The method of the present invention for nucleic acid replication is characterized in that a deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group, is used as a substrate during replication reaction. The novel artificial base pairs of the present invention are characterized in that 7-(2-thienyl)-imidazo[4,5-b]pyridine (Ds) or an analog thereof forms a base pair with pyrrole-2-carbaldehyde (Pa) or an analog thereof.

27 Claims, 65 Drawing Sheets

OTHER PUBLICATIONS

Kawai, R., et al., "Site-Specific Fluorescent Labeling of RNA Molecules by Specific Transcription Using Unnatural Base Pairs," J. Am. Chem. Soc., vol. 127, pp. 17286-17295 (2005).

Matray, T. J., et al., "A specific partner for abasic damage in DNA," Nature, vol. 399, pp. 704-708 (1999).

Doublie, S., et al., "Crystal structure of a bacteriophage T7 DNA replication complex at 2.2 A resolution," Nature, vol. 391, pp. 251-258 (1998).

Kiefer, J. R., et al., "Visualizing DNA replication in a catalytically active *Bacillus* DNA polymerase crystal," Nature, vol. 391, pp. 304-307 (1998).

Morales, J. C., et al., "Functional Hydrogen-Bonding Map of the Minor Groove Binding Tracks of Six DNA Polymerases," Biochem., vol. 39, No. 42, pp. 12979-12988 (2000).

Mitsui, T., et al., "An Unnatural Hydrophobic Base Pair with Shape Complementarity between Pyrrole-2-carbaldehyde and 9-Methylimidazo[(4,5)-b]pyridine," J. Am. Chem. Soc., vol. 125, No. 18, pp. 5298-5307 (2003).

Morales, J. C., et al., "Minor Groove Interactions between Polymerase and DNA: More Essential to Replication than Watson-Crick Hydrogen Bonds?," J. Am. Chem. Soc., vol. 121, pp. 2323-2324 (1999).

Hirao, I., et al., "A Two-Unnatural-Base-Pair System toward the Expansion of the Genetic Code," J. Am. Chem. Soc., vol. 126, No. 41, pp. 13298-13305 (2004).

Tae, E. L., et al., "Efforts toward Expansion of the Genetic Alphabet: Replication of DNA with Three Base Pairs," J. Am. Chem. Soc., vol. 123, No. 30, pp. 7439-7440 (2001).

Petruska, J., et al., "Comparison between DNA melting thermodynamics and DNA polymerase fidelity," Proc. Natl. Acad. Sci., vol. 85, pp. 6252-6256 (1988).

Goodman, M.F., et al., "Biochemical Basis of DNA Replication Fidelity," Critical Reviews in Biochem. and Mol. Biol., vol. 28, No. 2 pp. 83-126 (1993).

Kimoto, M., et al., "A quantitative, non-radioactive single-nucleotide insertion assay for analysis of DNA replication fidelity by using an automated DNA sequencer," Biotechnol. Letters, vol. 26, pp. 999-1005 (2004).

Ohtsuki, T., et al., "Unnatural bse pairs for specific transcription," Proc. Natl. Acad. Sci, vol. 98, No. 9, pp. 4922-4925 (2001).

Mitsui, T., et al., "An Unnatural Hydrophobic Base, 4-Propynylpyrrole-2-carbaldehyde, as an Efficient Pairing Partner of 9-Methylimidazo[(4,5)-*b*]pyridine," Bioorg. Med. Chem. Letters, vol. 13, pp. 4515-4518 (2003).

Cha, R. S., et al., "Specificity, Efficiency, and Fidelity of PCR," Intro to PCR, pp. 37-51.

Himeno, H., et al., "Conversion of aminoacylation specificity from tRNA$^{Tyr}$ to tRNA$^{Ser}$ in vitro," Nucleic Acids Res., vol. 18, No. 23, pp. 6815-6819 (1990).

Bedouelle, H., "Recognition of tRNATyr by tyrosyl-tRNA synthetase," Biochimie, vol. 72, pp. 589-598 (1990).

Mulder, B. A., et al., "Nucleotide modification at the γ-phosphate leads to the improved fidelity of HIV-1 reverse transcriptase," Nucleic Acids Res., vol. 33, No. 15, pp. 4865-4873 (2005).

De Roos, K. B., et al., "Deazapurine Derivatives. V, A new synthesis of 1- and 3-deaza-adenine and related compounds," Recueil, vol. 88, pp. 1263-1274 (1963).

Rolland, V., et al., "Convenient Preparation of 2-Deoxy-3,5-di-O-p-Toluoyl-α-D-*etythro*-Pentofuranosyl Chloride," Synthetic Comm., vol. 27, No. 20, pp. 3505-3511 (1997).

Ludwig, J., et al., "Rapid and Efficient Synthesis of Nucleoside 5'-O-(1-Thiotriphosphates), 5'-Triphosphates and 2',3'-Cyclophosphorothioates Using 2-Chloro-4*H*-1,3,2-benzodioxaphosphorin-4-one," J. Org. Chem., vol. 54, pp. 631-635 (1989).

Stevens, J. D., et al., "Syntheses with Partially Benzylated Sugars. XI. Studies on the Synthesis of the Anomeric 5,6-Dimethyl-1-d-ribofuranosylbenzimidazoles (Ribazoles). Comparison of the Condensation of 2,3,5-Tri-benzoyl-d-ribofuranosyl Bromide and 2,3,5-Tri-O-benzyl-d-ribofuranosyl Chloride with 5,6-Dimethylbenzimidazole," J. Org. Chem., vol. 33, No. 5, pp. 1806-1810 (1968).

Kovacs, T., et al., "Simple Synthesis of 5-Vinyl- and 5-Ethynyl-2'-Deoxyuridine-5'-Triphosphates," Tetrahedron Letters, vol. 29, No. 36, pp. 4525-4528 (1988).

Ti, G. S., et al., "Transient Protection: Efficient One-Flask Syntheses of Protected Deoxynucleosides," J. Am. Chem. Soc., vol. 104, No. 5, pp. 1316-1319 (1982).

Knorre, D.G., et al., "General Method for the Synthesis of ATP Gamma-Derivatives," FEBS Letters, vol. 70, No. 1, pp. 105-108 (1976).

Stumber et al., "Synthesis, characterization and application of two nucleoside triphosphate analogues, GTPγNH$_2$ and GTPγF", Eur. J. Biochem, 2002, vol. 269, No. 13: pp. 3270-3278.

Hirao et al., "Non-hydrogen-bonded base pairs for specific transcription", Nucleic Acids Symposium Series No. 49, 2005; pp. 33-34.

Hirao et al., "Ill Shinki Idenshi to Tanpakushitsu o Sosei suru Shinki Indenshi no Jinko Sosei", Protein, Nucleic acid and Enzyme, 2003, vol. 48, No. 11, pp. 1496-1502.

Mitsui et al., "An Unnatural Hydrophobic Base Pair with Shape Complementarity between Pyrrole-2-carbaldehyde and 9-Methylimidazo[(4,5)-b]pyridine", J. Am. Chem. Soc. 2003, col. 125, No. 18: pp. 5298-5307.

Leconte et al., "Amplify this! DNA and RNA get a third base pair", Nature Methods, vol. 3 No. 9, Sep. 2006; pp. 667-668.

Hirao et al., "An unnatural hydrophobic base pair system: site-specific incorporation of nucleotide analogs into DNA and RNA", Nature Methods, vol. 3 No. 9, Sep. 2006: pp. 729-735.

Hirao et al., "Indeshi ni Aratana Moji o Kumikomu-Jinkoteki na Sosuisei Enkitai no Kaihatsu-", Bionics, Dec. 2006, 1st, vol. 3, No. 12, pp. 68-71.

Hirao., "Seimei o Tsukuru Ichi Seimei System no Rikai no Nozomu Kagaku Indenshi no Sekkei Kaihatsu", Chemistry & chemical industry, Aug. 2006, 1st, vol. 59, No. 8, pp. 848-851.

Mitsui, T., et al., "An Unnatural Hydrophobic Base Pair with Shape Complementarity between Pyrrole-2-carbaldehyde and 9-Methylimidazo[(4,5)-b]pyridine," J. Am. Chem. Soc., vol. 125, pp. 5298-5307 (2003).

Mitsui, T., et al., "An Unnatural Hydrophobic Base, 4-Propynylpyrrol-2-carbaldehyde, as an Efficient Pairing Partner of 9-Methylimidazo[(4,5)-*b*]pyridine," Bioorg. Med. Chem. Lett., vol. 13, pp. 4515-4518 (2003).

Morgan, K.J., et al., "Nitropyrrol-I, The Preparation and Properties of 2- and 3-Nitropyrrole," Tetrahedron, vol. 22, pp. 57-62 (1966).

* cited by examiner

Pa : R = H
Pa' : R = -C≡C-CH₃

Unmodified dNTP: R=OH
Modified dNTP (dNTP$_N$): R=NH$_2$

Figure 6
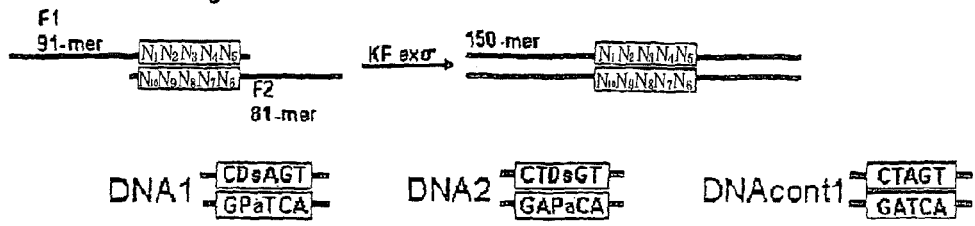
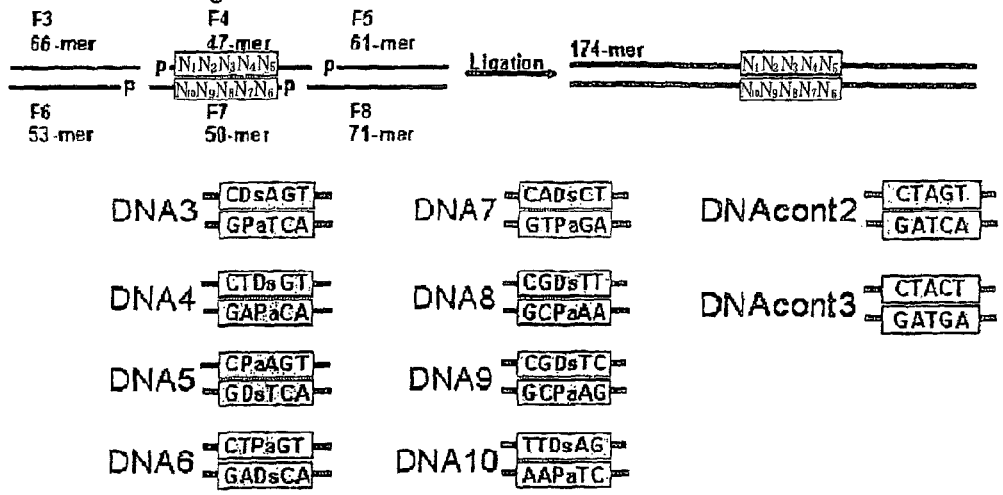
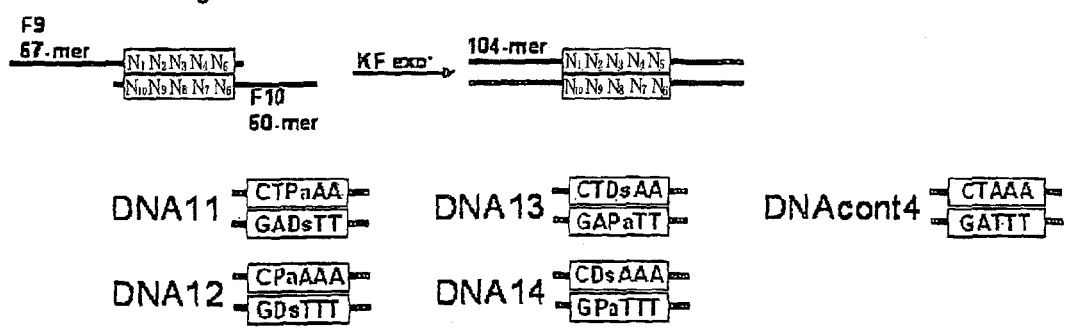
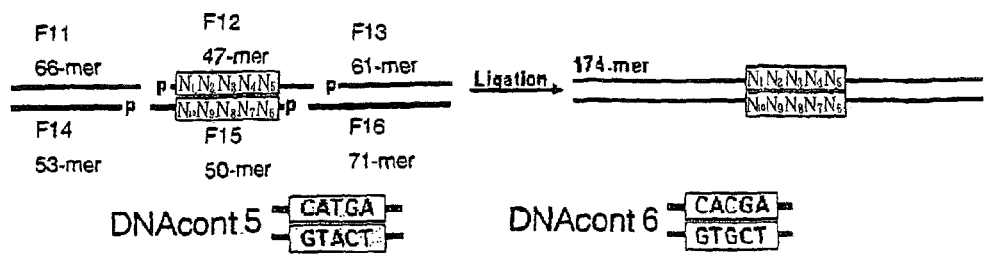

*Figure 7a*

Sequences of chemically synthesized DNA fragments.

F1 (91-mer)
5'-GAAATTAATACGACTCACTATAGGGTTAACTTTAAGAAGGAGATATACCATG
GGCTCCAAGAAGCCGGTCCCCATCAT$N_1N_2N_3N_4N_5$GCAACCGC F2 (81-mer)
5'-TTTCACACAGGAAACAGCTATGACCCGGGTTATTACATGCGCTGGCACTTGC
CCGTACGGCGGTTGC$N_6N_7N_8N_9N_{10}$ATGATGGGG F3 (66-mer)
5'-GAAATTAATACGACTCACTATAGGGTTAACTTTAAGAAGGAGATATACCATG
GGCTCCAAGAAGCC F4 (47-mer)
5'-pGGTCCCCATCAT$N_1N_2N_3N_4N_5$GCAACCGCCGTACGGGCAAGACGCAGCGCG F5 (61-mer)
5'-pGGGGTTCTCATCATCATCATCATCATTAATAACCCGGGTCATAGCTGTTTCC
TGTGTGAAA F6 (71-mer)
5'-TTTCACACAGGAAACAGCTATGACCCGGGTTATTAATGATGATGATGATGAT
GAGAACCCCCGCGCTGCGT F7 (50-mer)
5'-pCTTGCCCGTACGGCGGTTGC$N_6N_7N_8N_9N_{10}$ATGATGGGGACCGGCTTCTTGGA
GC F8 (53-mer)
5'-pCCATGGTATATCTCCTTCTTAAAGTTAACCCTATAGTGAGTCGTATTAATTT
C F9 (67-mer)
5'-GATAATACGACTCACTATAGGTGGGGTTCCCGAGCGGCCAAAGGGAGCAGA
CT$N_1N_2N_3N_4N_5$TCTGCCGTC F10 (60-mer)
5'-TmGmGTGGTGGGGGAAGGATTCGAACCTTCGAAGTCTGTGACGGCAGA$N_6N_7$
$N_8N_9N_{10}$AGTCTGCTC (Tm=2'-*O*-methylthymidine, Gm=2'-*O*-methylguanosine)

Primer 1 (5'-primer for sequencing and PCR, 25-mer)
5'-GAAATTAATACGACTCACTATAGGG Primer 2 (3'-primer for sequencing and PCR, 24-mer)
5'-TTTCACACAGGAAACAGCTATGAC

*Figure 7b*

Sequences of chemically synthesized DNA fragments.

F11 (66-mer)
5'-GAAATTAATACGACTCACTATAGGGCCAACCAGAAGAAGGAGACAGACCAAGGGCACCAAGAAGCC F12 (47-mer)
5'-pGGACCCCAACAA CANGAGCAACCGCCGAACGGGCAAGACGCAGCGCG F13 (61-mer)
5'-pGGGGAACACAACAGCACCAACAGCACCAACAACCCGGGACAAAGCAGCAACCAGGGAGAAA F14 (53-mer)
5'-CCTTGGTCTGTCTCCTTCTTCTGGTTGGCCCTATAGTGAGTCGTATTAATTTC F15 (50-mer)
5'-pCTTGCCCGTTCGGCGGTTGCTCNTGTTGTTGGGGTCCGGCTTCTTGGTGC F16 (71-mer)
5'-TTTCTCCCTGGTTGCTGCTTTGTCCCGGGTTGTTGGTGCTGTTGGTGCTGTTGTTCCCCGCGCTGCGT Figure 9
DNA1: PCR 300 μM dDsTP_N, dPaTP, dATP, dGTP, dCTP, dTTP
a PCR 0 cycle, Sequencing with dPa'TP
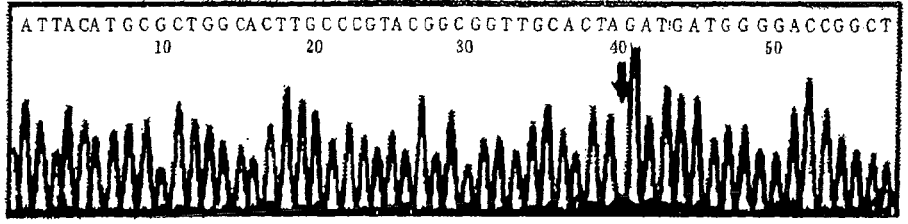
b PCR 10 cycles, Sequencing with dPa'TP
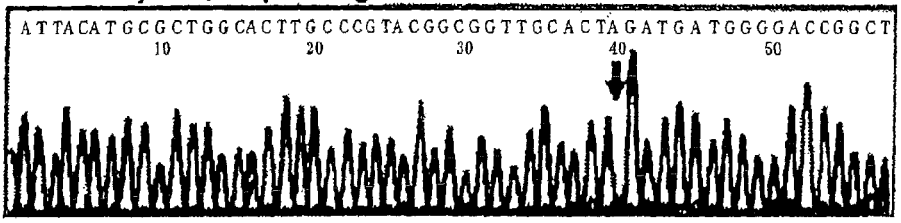
c PCR 10+10 cycles, Sequencing with dPa'TP
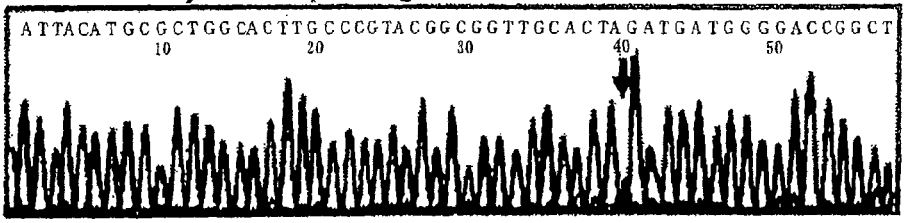
d PCR 0 cycle, Sequencing without dPa'TP
e PCR 10 cycles, Sequencing without dPa'TP
f PCR 10+10 cycles, Sequencing without dPa'TP

Figure 10
a
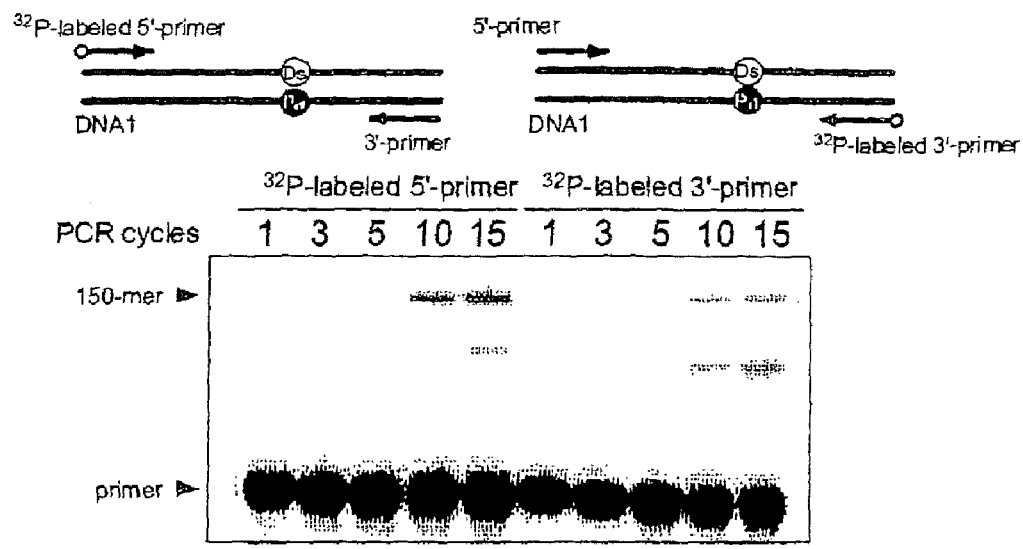
b
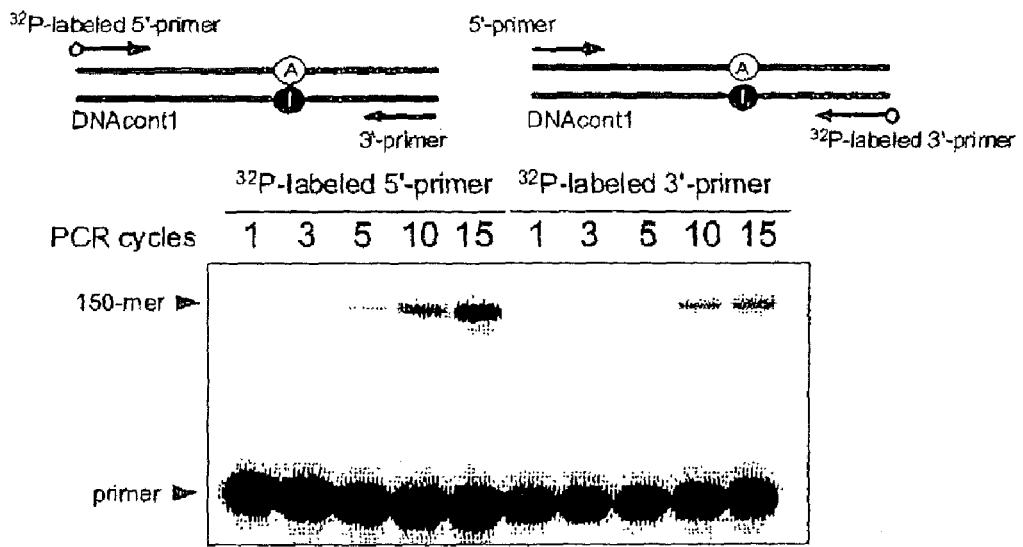

Figure 12
Agarose Gel for DNA1 and DNAcont1 (150 bp)
[ 94°C 30 sec - 45°C 30 sec - 65°C 4 min ] x 10 cycles (Vent DNA polymerase 4 units/100 μl)
300 μM dATP$_N$, dDsTP$_N$, dPaTP, dGTP, dCTP, dTTP
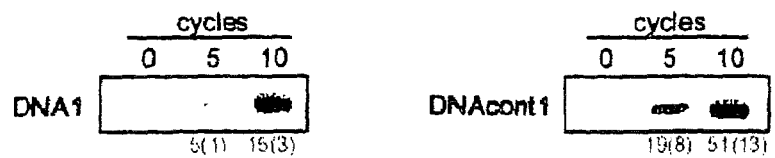
[ 94°C 30 sec - 45°C 30 sec - 72°C 1 min ] x 10 cycles (Vent DNA polymerase 1 unit/100 μl)
200 μM dATP, dGTP, dCTP, dTTP
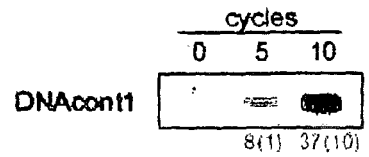
Agarose Gel for DNA3-10 (174 bp)
[ 94°C 30 sec - 45°C 30 sec - 65°C 4 min ] x 10 cycles (Vent DNA polymerase 4 units/100 μl)
300 μM dATP$_N$, dDsTP$_N$, dPaTP, dGTP, dCTP, dTTP
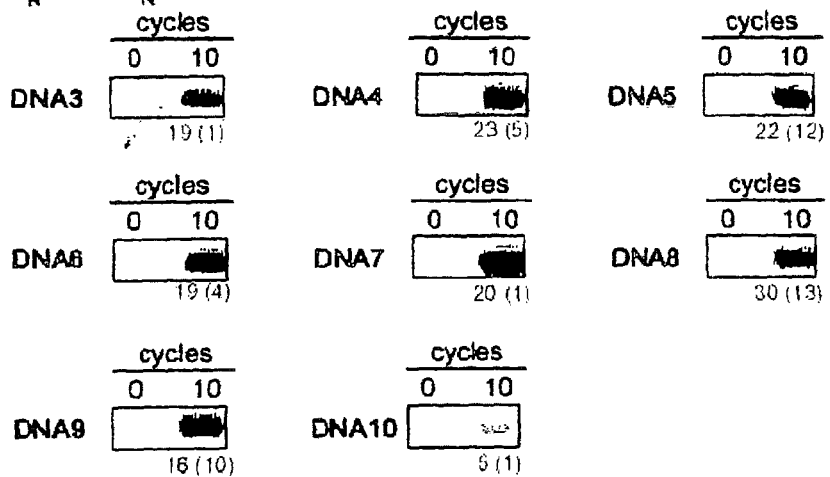

Figure 21
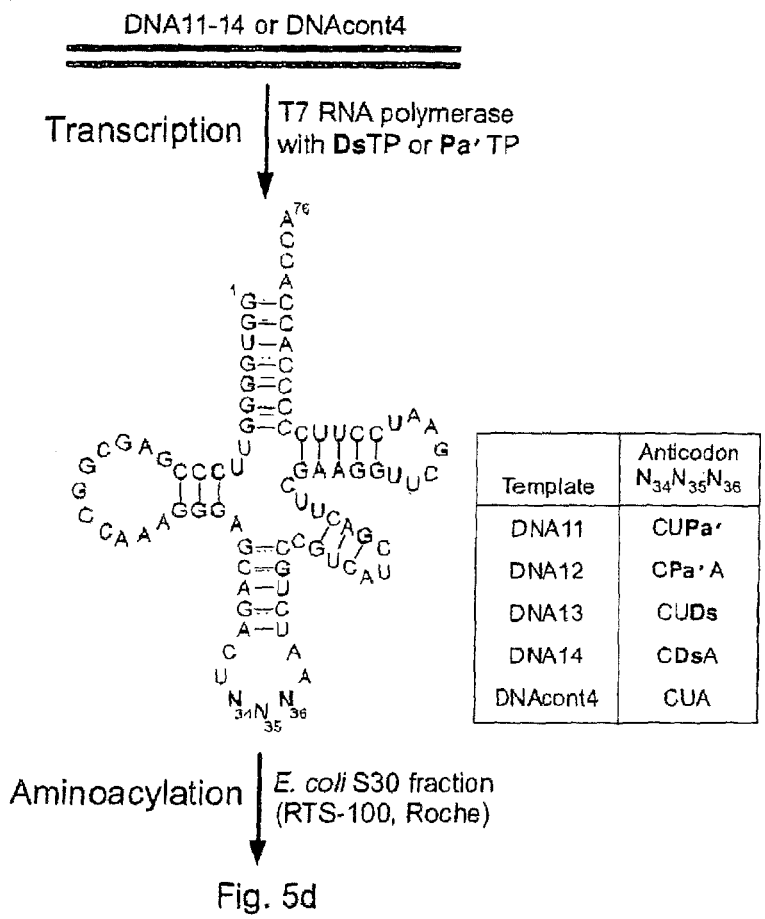
Fig. 5d
Figure 22
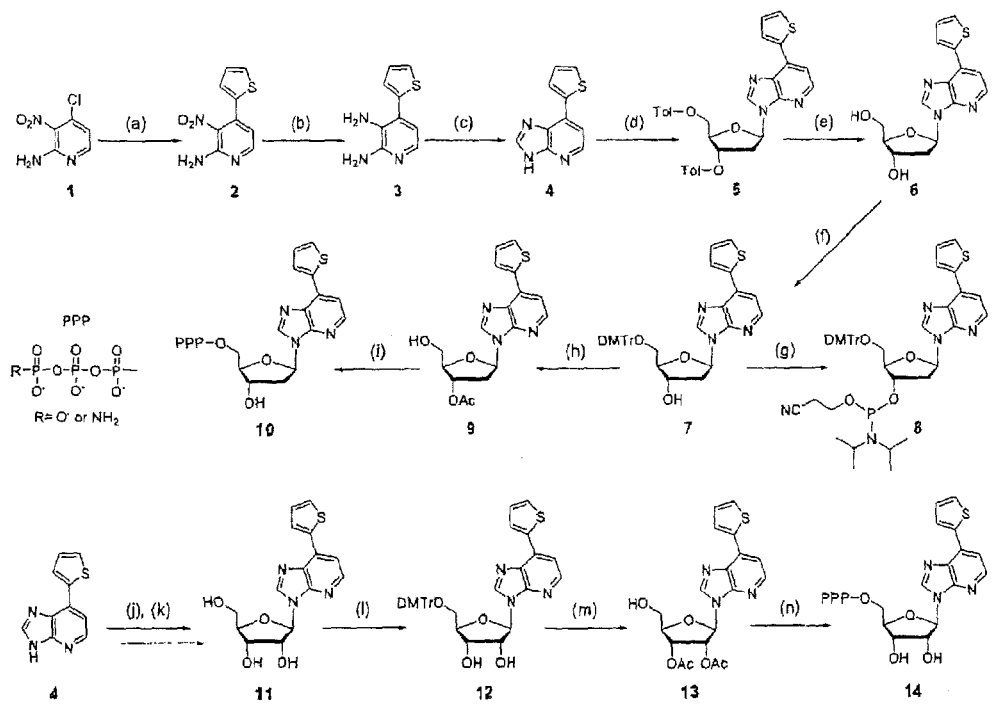

$^1$H NMR (270MHz, DMSO-$d_6$) spectra of compound 6 and 11.

$^1$H NMR (270MHz, DMSO-$d_6$) spectra of compound 6 and 11.

1D NOE spectra of compound 6 in DMSO-$d_6$.

1D NOE spectra of compound 11 in DMSO-$d_6$.

$^{13}$C NMR (75MHz, DMSO-$d_6$) spectrum of compound 6.

Figure 24f
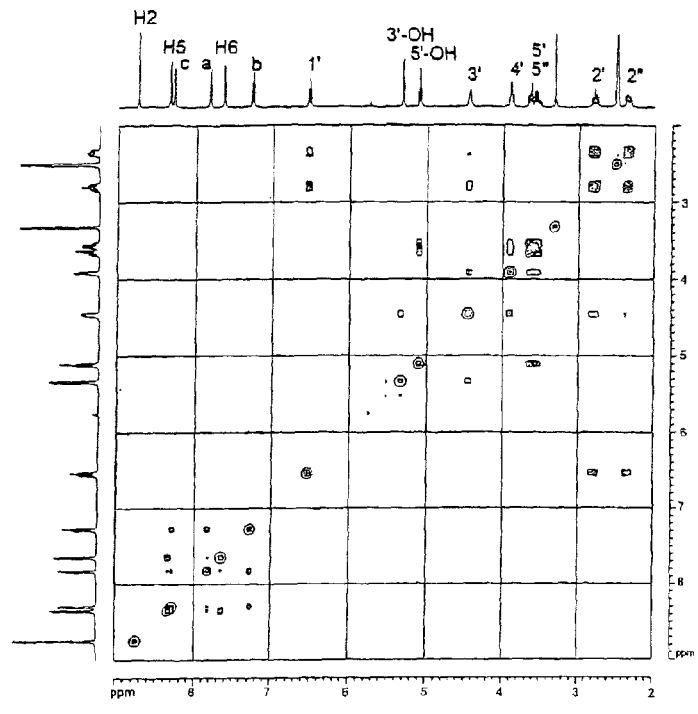
2D COSY spectrum of compound 6.
Figure 24g
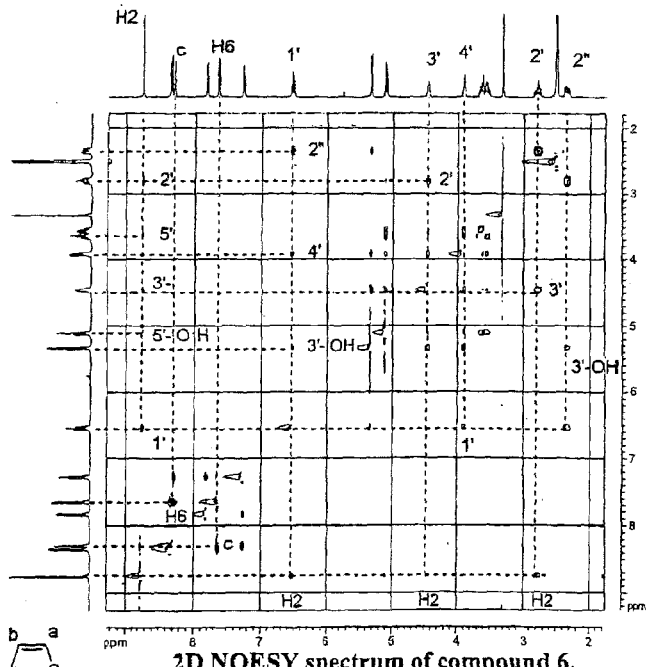
2D NOESY spectrum of compound 6.
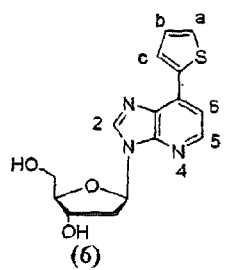
(6)

2D HSQC spectrum of compound 6.

2D HMBC spectrum of compound 6.

2D HMBC spectrum of compound 6.

$^{13}$C NMR (75MHz, DMSO-$d_6$) spectrum of compound 11.

2D COSY spectrum of compound 11.

2D NOESY spectrum of compound 11.

2D HSQC spectrum of compound 11.

2D HMBC spectrum of compound 11.

$^1$H NMR (300MHz, DMSO-$d_6$) spectrum of compound 17.

$^{13}$C NMR (75MHz, DMSO-$d_6$) spectrum of compound 17.

2D COSY spectrum of compound 17.

2D HSQC spectrum of compound 17.

2D HMBC spectrum of compound 17.

2D NOESY spectrum of compound 17.

$^1$H NMR (300MHz, DMSO-$d_6$) spectrum of compound 18.

$^{13}$C NMR (75MHz, DMSO-$d_6$) spectrum of compound 18.

2D COSY spectrum of compound 18.

2D NOESY spectrum of compound 18.

2D HSQC spectrum of compound 18.

2D HMBC spectrum of compound 18.

1D NOE spectra of compound 17 in DMSO-$d_6$.

1D NOE spectra of compound 18 in DMSO-$d_6$.

Figure. DEAE Sephadex ion-exchange column elution pattern of γ-amidotriphosphate of deoxyadenosine.

Figure. ESI-mass spectra of γ-amidotriphosphate of deoxyadenosine.

¹H NMR (270MHz, D₂O) spectrum of γ-amidotriphosphate of deoxyadenosine.

$^{31}$P NMR (109MHz, D$_2$O) spectrum of γ-amidotriphosphate of deoxyadenosine.

$^1$H NMR (270MHz, D$_2$O) spectra of γ-amidotriphosphate (upper) and triphospate (lower) of 7-(2-Thienyl)-3-(2-deoxy-β-D-ribofuranosyl)-3H-imidazo[4,5-b]pyridine.

$^{31}$P NMR (109MHz, D$_2$O) spectra of γ-amidotriphosphate (upper) and triphospate (lower) of 7-(2-Thienyl)-3-(2-deoxy-β-D-ribofuranosyl)-3H-imidazo[4,5-b]pyridine.

¹H NMR (500 MHz, DMSO-*d6*) spectrum of ribonucleoside of 4-iodopyrrole-2-carbaldehyde.

¹H NMR (300 MHz, DMSO-*d6*) spectrum of compound 24.

$^{13}$C NMR (75 MHz, DMSO-*d6*) spectrum of compound 24.

2D COSY spectrum of compound 24.

2D NOESY spectrum of compound 24.

2D HMQC spectrum of compound 24.

2D HMBC spectrum of compound 24.

2D HMBC spectrum of compound 24.

$^1$H NMR (500 MHz, DMSO-$d6$) spectrum of compound 25.

$^1$H NMR (500 MHz, DMSO-$d6$) spectrum of compound 26.

S2-6. DEAE Sephadex ion-exchange column elution patterns, ESI-MS spectra, and NMR spectra of 5'-triphosphates.

DEAE Sephadex ion-exchange column elution patterns of compound 27 and 28.

ESI-mass spectra of compound 27 (upper) and 28 (lower).

$^1$H NMR (300 MHz, D$_2$O) spectrum of compound 28.

2D COSY spectrum of compound 28.

$^{31}$P NMR (109 MHz, D$_2$O) spectrum of compound 28.

a

Bio-PaTP

Figure 48
A
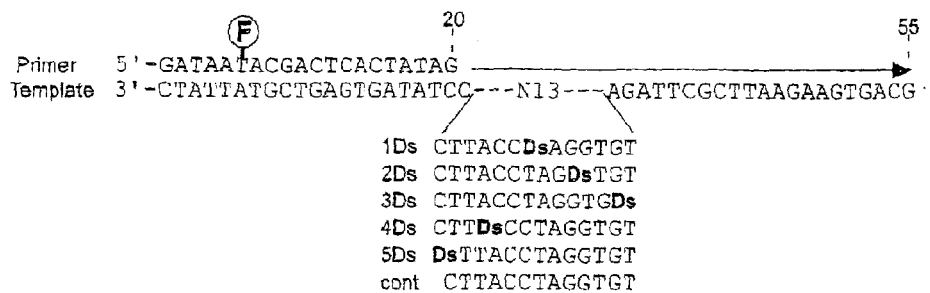
B 100 μM dNTPs (N = A, G, C, T)
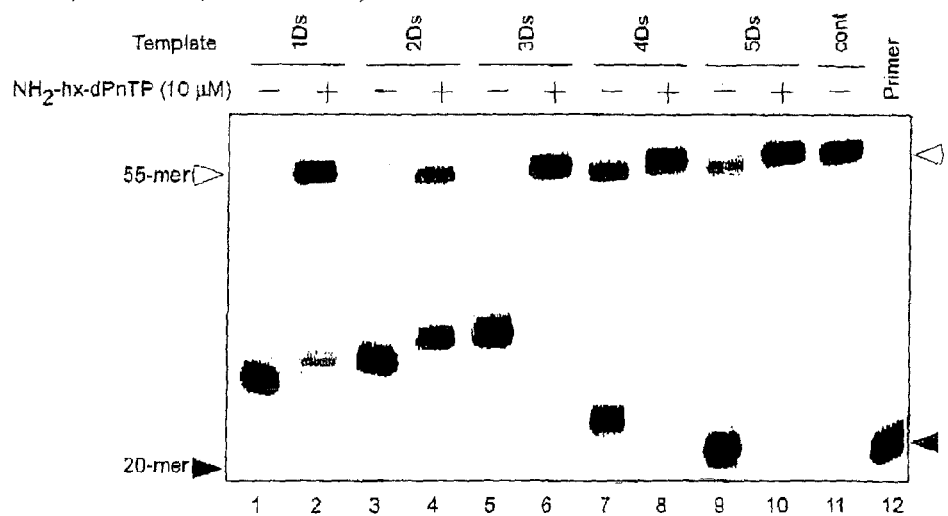
C 200 μM dNTPs (N = A, G, C, T)
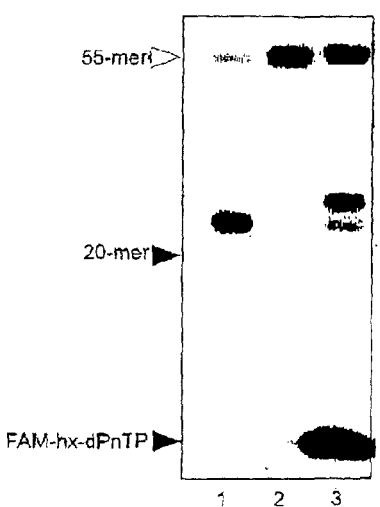

SEQUENCE LISTING

```
<160> NUMBER OF SEQ ID NOS: 41

<210> SEQ ID NO 1
<211> LENGTH: 20
<212> TYPE: DNA
<213> ORGANISM: Artificial sequence
<220> FEATURE:
<223> OTHER INFORMATION: Synthesized primer for replication

<400> SEQUENCE: 1
actcactata gggagcttct                                              20

<210> SEQ ID NO 2
<211> LENGTH: 35
<212> TYPE: DNA
<213> ORGANISM: Artificial sequence
<220> FEATURE:
<221> NAME/KEY: misc_feature
<222> LOCATION: 7
<223> OTHER INFORMATION: n means any one of the following:
      2-formyl-1H-pyrrol-1-yl,
      2-formyl-4-(1-propynyl)-1H-pyrrol-1-yl,
      adenine, guanine, thymine, cytosine
<220> FEATURE:
<223> OTHER INFORMATION: Synthesized template strand for replication

<400> SEQUENCE: 2
tcgaganaga agctccctat agtgagtcgt attat                             35

<210> SEQ ID NO 3
<211> LENGTH: 20
<212> TYPE: DNA
<213> ORGANISM: Artificial sequence
<220> FEATURE:
<223> OTHER INFORMATION: Synthesized primer for replication

<400> SEQUENCE: 1
actcactata gggaggaaga                                              20

<210> SEQ ID NO 4
<211> LENGTH: 35
<212> TYPE: DNA
<213> ORGANISM: Artificial sequence
<220> FEATURE:
<221> NAME/KEY: misc_feature
<222> LOCATION: 7
<223> OTHER INFORMATION: n means any one of the following:
      7-(2-thienyl)-3H-imidazo[4,5-b]pyridin-3-yl,
      adenine, guanine, thymine, cytosine
<220> FEATURE:
<223> OTHER INFORMATION: Synthesized template strand for replication

<400> SEQUENCE: 4
agctctntct tcctccctat agtgagtcgt attat                             35

<210> SEQ ID NO 5
<211> LENGTH: 16
<212> TYPE: DNA
```

```
<213> ORGANISM: Artificial sequence
<220> FEATURE:
<223> OTHER INFORMATION: Synthesized primer for replication

<400> SEQUENCE: 5
actataggga gcttct                                                          16

<210> SEQ ID NO 6
<211> LENGTH: 16
<212> TYPE: DNA
<213> ORGANISM: Artificial sequence
<220> FEATURE:
<223> OTHER INFORMATION: Synthesized primer for replication

<400> SEQUENCE: 6
actataggga ggaaga                                                          16

<210> SEQ ID NO 7
<211> LENGTH: 23
<212> TYPE: DNA
<213> ORGANISM: Artificial sequence
<220> FEATURE:
<223> OTHER INFORMATION: Synthesized primer for replication

<400> SEQUENCE: 7
ataatacgac tcactatagg gag                                                  23

<210> SEQ ID NO 8
<211> LENGTH: 21
<212> TYPE: DNA
<213> ORGANISM: Artificial sequence
<220> FEATURE:
<223> OTHER INFORMATION: Synthesized non-template strand for
      transcription

<400> SEQUENCE: 8
ataatacgac tcactatagg g                                                    21

<210> SEQ ID NO 9
<211> LENGTH: 35
<212> TYPE: DNA
<213> ORGANISM: Artificial sequence
<220> FEATURE:
<221> NAME/KEY: misc_feature
<222> LOCATION: 5
<223> OTHER INFORMATION: n means any one of the following:
      7-(2-thienyl)-3H-imidazo[4,5-b]pyridin-3-yl,
      adenine, guanine
<220> FEATURE:
<223> OTHER INFORMATION: Synthesized template strand for transcription

<400> SEQUENCE: 9
cactnctcgg gattccctat agtgagtcgt attat                                     35

<210> SEQ ID NO 10
<211> LENGTH: 35
<212> TYPE: DNA
<213> ORGANISM: Artificial sequence
<220> FEATURE:
<221> NAME/KEY: misc_feature
<222> LOCATION: 5
<223> OTHER INFORMATION: n means any one of the followings:
      2-formyl-1H-pyrrol-1-yl,
      2-formyl-4-(1-propynyl)-1H-pyrrol-1-yl,
      thymine, cytosine
<220> FEATURE:
<223> OTHER INFORMATION: Synthesized template strand for transcription

<400> SEQUENCE: 10
```

```
ctcanaggga agctccctat agtgagtcgt attat                             35
```

<210> SEQ ID NO 11
<211> LENGTH: 17
<212> TYPE: RNA
<213> ORGANISM: Artificial sequence
<220> FEATURE:
<221> NAME/KEY: misc_feature
<222> LOCATION: 13
<223> OTHER INFORMATION: n means any one of the following:
      2-formyl-1H-pyrrol-1-yl,
      2-formyl-4-(1-propynyl)-1H-pyrrol-1-yl,
      uracil, cytosine
<220> FEATURE:
<223> OTHER INFORMATION: RNA transcript from synthesized template

<400> SEQUENCE: 11

```
gggaaucccg agnagug                                                 17
```

<210> SEQ ID NO 12
<211> LENGTH: 17
<212> TYPE: RNA
<213> ORGANISM: Artificial sequence
<220> FEATURE:
<221> NAME/KEY: misc_feature
<222> LOCATION: 13
<223> OTHER INFORMATION: n means any one of the following:
      7-(2-thienyl)-3H-imidazo[4,5-b]pyridin-3-yl,
      adenine, guanine
<220> FEATURE:
<223> OTHER INFORMATION: RNA transcript from synthesized template

<400> SEQUENCE: 12

```
gggagcuucc cunugag                                                 17
```

<210> SEQ ID NO 13
<211> LENGTH: 91
<212> TYPE: DNA
<213> ORGANISM: Artificial sequence
<220> FEATURE:
<221> NAME/KEY: misc_feature
<222> LOCATION: 79...83
<223> OTHER INFORMATION: nnnnn means:  cytosine
      - 7-(2-thienyl)-3H-imidazo[4,5-b]pyridin-3-yl - adenine
      - guanine - thymine, or
<220> FEATURE:
<221> NAME/KEY: misc_feature
<222> LOCATION: 79...83
<223> OTHER INFORMATION: nnnnn means:
      cytosine - thymine -
      7-(2-thienyl)-3H-imidazo[4,5-b]pyridin-3-yl -
      guanine - thymine, or
<220> FEATURE:
<221> NAME/KEY: misc_feature
<222> LOCATION: 79...83
<223> OTHER INFORMATION: nnnnn means:
      cytosine - thymine - adenine - guanine - thymine
<220> FEATURE:
<223> OTHER INFORMATION: Synthesized DNA fragment for PCR, sequencing
      and transcription

<400> SEQUENCE: 13

```
gaaattaata cgactcacta tagggttaac tttaagaagg agatatacca tgggctccaa  60
gaagccggtc cccatcatnn nnngcaaccg c                                 91
```

<210> SEQ ID NO 14
<211> LENGTH: 81
<212> TYPE: DNA
<213> ORGANISM: Artificial sequence
<220> FEATURE:
<221> NAME/KEY: misc_feature
<222> LOCATION: 68...72

```
<223> OTHER INFORMATION: nnnnn means any one of the following:
      adenine - cytosine - thymine - 2-formyl-1H-pyrrol-1-yl - guanine
      adenine - cytosine - 2-formyl-1H-pyrrol-1-yl - adenine - guanine
      adenine - cytosine - thymine - adenine - guanine
<220> FEATURE:
<223> OTHER INFORMATION: Synthesized DNA fragment for PCR, sequencing
      and transcription

<400> SEQUENCE: 14
tttcacacag gaaacagcta tgacccgggt tattacatgc gctggcactt gcccgtacgg    60
cggttgcnnn nnatgatggg g                                              81

<210> SEQ ID NO 15
<211> LENGTH: 66
<212> TYPE: DNA
<213> ORGANISM: Artificial sequence
<220> FEATURE:
<223> OTHER INFORMATION: Synthesized DNA fragment for PCR, sequencing
      and transcription

<400> SEQUENCE: 15
gaaattaata cgactcacta tagggttaac tttaagaagg agatatacca tgggctccaa    60
gaagcc                                                               66

<210> SEQ ID NO 16
<211> LENGTH: 47
<212> TYPE: DNA
<213> ORGANISM: Artificial sequence
<220> FEATURE:
<221> NAME/KEY: misc_feature
<222> LOCATION: 13...17
<223> OTHER INFORMATION: nnnnn means:
      cytosine - 7-(2-thienyl)-3H-imidazo[4,5-b]pyridin-3-yl -
      adenine - guanine - thymine, or
<220> FEATURE:
<221> NAME/KEY: misc_feature
<222> LOCATION: 13...17
<223> OTHER INFORMATION: nnnnn means:
      cytosine - thymine -
      7-(2-thienyl)-3H-imidazo[4,5-b]pyridin-3-yl -
      guanine - thymine, or
<220> FEATURE:
<221> NAME/KEY: misc_feature
<222> LOCATION: 13...17
<223> OTHER INFORMATION: nnnnn means:
      cytosine - 2-formyl-1H-pyrrol-1-yl -
      adenine - guanine - thymine, or
<220> FEATURE:
<221> NAME/KEY: misc_feature
<222> LOCATION: 13...17
<223> OTHER INFORMATION: nnnnn means:
      cytosine - thymine - 2-formyl-1H-pyrrol-1-yl -
      guanine - thymine, or
<220> FEATURE:
<221> NAME/KEY: misc_feature
<222> LOCATION: 13...17
<223> OTHER INFORMATION: nnnnn means:
      cytosine - adenine -
      7-(2-thienyl)-3H-imidazo[4,5-b]pyridin-3-yl -
      cytosine - thymine, or
<220> FEATURE:
<221> NAME/KEY: misc_feature
<222> LOCATION: 13...17
<223> OTHER INFORMATION: nnnnn means:
      cytosine - guanine -
      7-(2-thienyl)-3H-imidazo[4,5-b]pyridin-3-yl -
      thymine - thymine, or
<220> FEATURE:
<221> NAME/KEY: misc_feature
<222> LOCATION: 13...17
<223> OTHER INFORMATION: nnnnn means:
      cytosine - guanine -
      7-(2-thienyl)-3H-imidazo[4,5-b]pyridin-3-yl -
      thymine - cytosine, or
```

```
<220> FEATURE:
<221> NAME/KEY: misc_feature
<222> LOCATION: 13...17
<223> OTHER INFORMATION: nnnnn means:
      thymine - 7-(2-thienyl)-3H-imidazo[4,5-b]pyridin-3-yl -
      adenine - guanine - thymine, or
<220> FEATURE:
<221> NAME/KEY: misc_feature
<222> LOCATION: 13...17
<223> OTHER INFORMATION: nnnnn means:
      cytosine - thymine - adenine - guanine - thymine, or
<220> FEATURE:
<221> NAME/KEY: misc_feature
<222> LOCATION: 13...17
<223> OTHER INFORMATION: nnnnn means:
      cytosine - thymine - adenine - cytosine - thymine
<220> FEATURE:
<223> OTHER INFORMATION: Synthesized DNA fragment for PCR, sequencing
      and transcription

<400> SEQUENCE: 16
ggtccccatc atnnnnngca accgccgtac gggcaagacg cagcgcg              47

<210> SEQ ID NO 17
<211> LENGTH: 61
<212> TYPE: DNA
<213> ORGANISM: Artificial sequence
<220> FEATURE:
<223> OTHER INFORMATION: Synthesized DNA fragment for PCR, sequencing
      and transcription

<400> SEQUENCE: 17
ggggttctca tcatcatcat catcattaat aacccgggtc atagctgttt cctgtgtgaa   60
a                                                                  61

<210> SEQ ID NO 18
<211> LENGTH: 71
<212> TYPE: DNA
<213> ORGANISM: Artificial sequence
<220> FEATURE:
<223> OTHER INFORMATION: Synthesized DNA fragment for PCR, sequencing
      and transcription

<400> SEQUENCE: 18
tttcacacag gaaacagcta tgacccgggt tattaatgat gatgatgatg atgagaaccc   60
ccgcgctgcg t                                                       71

<210> SEQ ID NO 19
<211> LENGTH: 50
<212> TYPE: DNA
<213> ORGANISM: Artificial sequence
<220> FEATURE:
<221> NAME/KEY: misc_feature
<222> LOCATION: 21...25
<223> OTHER INFORMATION: nnnnn means:
      adenine - cytosine - thymine -
      2-formyl-1H-pyrrol-1-yl - guanine, or
<220> FEATURE:
<221> NAME/KEY: misc_feature
<222> LOCATION: 21...25
<223> OTHER INFORMATION: nnnnn means:
      adenine - cytosine -
      2-formyl-1H-pyrrol-1-yl - adenine -
      guanine, or
<220> FEATURE:
<221> NAME/KEY: misc_feature
<222> LOCATION: 21...25
<223> OTHER INFORMATION: nnnnn means:
      adenine - cytosine - thymine -
      7-(2-thienyl)-3H-imidazo[4,5-b]pyridin-3-yl -
      guanine, or
<220> FEATURE:
```

```
<221> NAME/KEY: misc_feature
<222> LOCATION: 21...25
<223> OTHER INFORMATION: nnnnn means:
      adenine - cytosine -
      7-(2-thienyl)-3H-imidazo[4,5-b]pyridin-3-yl -
      adenine - guanine, or
<220> FEATURE:
<221> NAME/KEY: misc_feature
<222> LOCATION: 21...25
<223> OTHER INFORMATION: nnnnn means:
      adenine - guanine - 2-formyl-1H-pyrrol-1-yl -
      thymine - guanine, or
<220> FEATURE:
<221> NAME/KEY: misc_feature
<222> LOCATION: 21...25
<223> OTHER INFORMATION: nnnnn means:
      adenine - adenine - 2-formyl-1H-pyrrol-1-yl -
      cytosine - guanine, or
<220> FEATURE:
<221> NAME/KEY: misc_feature
<222> LOCATION: 21...25
<223> OTHER INFORMATION: nnnnn means:
      guanine - adenine - 2-formyl-1H-pyrrol-1-yl -
      cytosine - guanine, or
<220> FEATURE:
<221> NAME/KEY: misc_feature
<222> LOCATION: 21...25
<223> OTHER INFORMATION: nnnnn means:
      adenine - cytosine - thymine -
      2-formyl-1H-pyrrol-1-yl - adenine, or
<220> FEATURE:
<221> NAME/KEY: misc_feature
<222> LOCATION: 21...25
<223> OTHER INFORMATION: nnnnn means:
      adenine - cytosine - thymine - adenine -
      guanine, or
<220> FEATURE:
<221> NAME/KEY: misc_feature
<222> LOCATION: 21...25
<223> OTHER INFORMATION: nnnnn means:
      adenine - guanine - thymine - adenine - guanine
<220> FEATURE:
<223> OTHER INFORMATION: Synthesized DNA fragment for PCR, sequencing
      and transcription

<400> SEQUENCE: 19
cttgcccgta cggcggttgc nnnnnatgat ggggaccggc ttcttggagc          50

<210> SEQ ID NO 20
<211> LENGTH: 53
<212> TYPE: DNA
<213> ORGANISM: Artificial sequence
<220> FEATURE:
<223> OTHER INFORMATION: Synthesized DNA fragment for PCR, sequencing
      and transcription

<400> SEQUENCE: 20
ccatggtata tctccttctt aaagttaacc ctatagtgag tcgtattaat ttc        53

<210> SEQ ID NO 21
<211> LENGTH: 67
<212> TYPE: DNA
<213> ORGANISM: Artificial sequence
<220> FEATURE:
<221> NAME/KEY: misc_feature
<222> LOCATION: 54...58
<223> OTHER INFORMATION: nnnnn means:
      cytosine - thymine - 2-formyl-1H-pyrrol-1-yl -
      adenine - adenine, or
<220> FEATURE:
<221> NAME/KEY: misc_feature
<222> LOCATION: 54...58
<223> OTHER INFORMATION: nnnnn means:
      cytosine - 2-formyl-1H-pyrrol-1-yl -adenine -
      adenine - adenine, or
<220> FEATURE:
```

```
<221> NAME/KEY: misc_feature
<222> LOCATION: 54...58
<223> OTHER INFORMATION: nnnnn means:
      cytosine - thymine -
      7-(2-thienyl)-3H-imidazo[4,5-b]pyridin-3-yl -
      adenine - adenine, or
<220> FEATURE:
<221> NAME/KEY: misc_feature
<222> LOCATION: 54...58
<223> OTHER INFORMATION: nnnnn means:
      cytosine -
      7-(2-thienyl)-3H-imidazo[4,5-b]pyridin-3-yl -
      adenine - adenine - adenine, or
<220> FEATURE:
<221> NAME/KEY: misc_feature
<222> LOCATION: 54...58
<223> OTHER INFORMATION: nnnnn means:
      cytosine - thymine - adenine - adenine - adenine
<220> FEATURE:
<223> OTHER INFORMATION: Synthesized DNA fragment for PCR, sequencing
      and transcription

<400> SEQUENCE: 21
gataatacga ctcactatag gtggggttcc cgagcggcca aagggagcag actnnnnntc    60
tgccgtc                                                              67

<210> SEQ ID NO 22
<211> LENGTH: 60
<212> TYPE: DNA
<213> ORGANISM: Artificial sequence
<220> FEATURE:
<221> NAME/KEY: misc_feature
<222> LOCATION: 1
<223> OTHER INFORMATION: n means tm
<220> FEATURE:
<221> NAME/KEY: misc_feature
<222> LOCATION: 2
<223> OTHER INFORMATION: n means gm
<220> FEATURE:
<221> NAME/KEY: misc_feature
<222> LOCATION: 47...51
<223> OTHER INFORMATION: nnnnn means:
      thymine - thymine -
      7-(2-thienyl)-3H-imidazo[4,5-b]pyridin-3-yl -
      adenine - guanine, or
<220> FEATURE:
<221> NAME/KEY: misc_feature
<222> LOCATION: 47...51
<223> OTHER INFORMATION: nnnnn means:
      thymine - thymine - thymine -
      7-(2-thienyl)-3H-imidazo[4,5-b]pyridin-3-yl -
      guanine, or
<220> FEATURE:
<221> NAME/KEY: misc_feature
<222> LOCATION: 47...51
<223> OTHER INFORMATION: nnnnn means:
      thymine - thymine - 2-formyl-1H-pyrrol-1-yl -
      adenine - guanine, or
<220> FEATURE:
<221> NAME/KEY: misc_feature
<222> LOCATION: 47...51
<223> OTHER INFORMATION: nnnnn means:
      thymine - thymine - thymine -
      2-formyl-1H-pyrrol-1-yl - guanine, or
<220> FEATURE:
<221> NAME/KEY: misc_feature
<222> LOCATION: 47...51
<223> OTHER INFORMATION: nnnnn means:
      thymine - thymine - thymine - adenine - guanine
<220> FEATURE:
<223> OTHER INFORMATION: Synthesized DNA fragment for PCR, sequencing
      and transcription

<400> SEQUENCE: 22
nngtggtggg ggaaggattc gaaccttcga agtctgtgac ggcagannnn nagtctgctc    60
```

```
<210> SEQ ID NO 23
<211> LENGTH: 25
<212> TYPE: DNA
<213> ORGANISM: Artificial sequence
<220> FEATURE:
<223> OTHER INFORMATION: Synthesized primer for PCR and sequencing

<400> SEQUENCE: 23
gaaattaata cgactcacta taggg                                              25

<210> SEQ ID NO 24
<211> LENGTH: 24
<212> TYPE: DNA
<213> ORGANISM: Artificial sequence
<220> FEATURE:
<223> OTHER INFORMATION: Synthesized primer for PCR and sequencing

<400> SEQUENCE: 24
tttcacacag gaaacagcta tgac                                               24

<210> SEQ ID NO 25
<211> LENGTH: 85
<212> TYPE: RNA
<213> ORGANISM: Artificial sequence
<220> FEATURE:
<221> NAME/KEY: misc_feature
<222> LOCATION: 35...37
<223> OTHER INFORMATION: nnn means:
      cytosine - uracil -
      2-formyl-4-(1-propynyl)-1H-pyrrol-1-yl, or
<220> FEATURE:
<221> NAME/KEY: misc_feature
<222> LOCATION: 35...37
<223> OTHER INFORMATION: nnn means:
      cytosine - 2-formyl-4-(1-propynyl)-1H-pyrrol-1-yl -
      adenine, or
<220> FEATURE:
<221> NAME/KEY: misc_feature
<222> LOCATION: 35...37
<223> OTHER INFORMATION: nnn means:
      cytosine - uracil -
      7-(2-thienyl)-3H-imidazo[4,5-b]pyridin-3-yl, or
<220> FEATURE:
<221> NAME/KEY: misc_feature
<222> LOCATION: 35...37
<223> OTHER INFORMATION: nnn means:
      cytosine - 7-(2-thienyl)-3H-imidazo[4,5-b]pyridin-3-yl -
      adenine, or
<220> FEATURE:
<221> NAME/KEY: misc_feature
<222> LOCATION: 35...37
<223> OTHER INFORMATION: nnn means:
      cytosine - uracil - adenine
<220> FEATURE:
<223> OTHER INFORMATION: RNA transcript from synthesized template

<400> SEQUENCE: 25 gguggguuc ccgagcggcc aaagggagca gacunnnaau cugccgucau cgacuucgaa         60
gguucgaauc cuuccccac cacca                                               85

<210> SEQ ID NO 26
<211> LENGTH: 66
<212> TYPE: DNA
<213> ORGANISM: Artificial sequence
<220> FEATURE:
<223> OTHER INFORMATION: Synthesized DNA fragment for PCR, sequencing
      and transcription

<400> SEQUENCE: 26
gaaattaata cgactcacta tagggccaac cagaagaagg agacagacca agggcaccaa        60
``` gaagcc 66

<210> SEQ ID NO 27
<211> LENGTH: 47
<212> TYPE: DNA
<213> ORGANISM: Artificial sequence
<220> FEATURE:
<223> OTHER INFORMATION: Synthesized DNA fragment for PCR, sequencing and transcription

<400> SEQUENCE: 27
ggaccccaac aacaygagca accgccgaac gggcaagacg cagcgcg 47

<210> SEQ ID NO 28
<211> LENGTH: 61
<212> TYPE: DNA
<213> ORGANISM: Artificial sequence
<220> FEATURE:
<223> OTHER INFORMATION: Synthesized DNA fragment for PCR, sequencing and transcription

<400> SEQUENCE: 28
ggggaacaca acagcaccaa cagcaccaac aacccgggac aaagcagcaa ccagggagaa 60
a 61

<210> SEQ ID NO 29
<211> LENGTH: 53
<212> TYPE: DNA
<213> ORGANISM: Artificial sequence
<220> FEATURE:
<223> OTHER INFORMATION: Synthesized DNA fragment for PCR, sequencing and transcription

<400> SEQUENCE: 29
ccttggtctg tctccttctt ctggttggcc ctatagtgag tcgtattaat ttc 53

<210> SEQ ID NO 30
<211> LENGTH: 50
<212> TYPE: DNA
<213> ORGANISM: Artificial sequence
<220> FEATURE:
<223> OTHER INFORMATION: Synthesized DNA fragment for PCR, sequencing and transcription

<400> SEQUENCE: 30
cttgcccgtt cggcggttgc tcrtgttgtt ggggtccggc ttcttggtgc 50

<210> SEQ ID NO 31
<211> LENGTH: 71
<212> TYPE: DNA
<213> ORGANISM: Artificial sequence
<220> FEATURE:
<223> OTHER INFORMATION: Synthesized DNA fragment for PCR, sequencing and transcription

<400> SEQUENCE: 31
tttctccctg gttgctgctt tgtcccgggt tgttggtgct gttggtgctg ttgtgttccc 60
ccgcgctgcg t 71

<210> SEQ ID NO 32
<211> LENGTH: 20
<212> TYPE: DNA
<213> ORGANISM: Artificial sequence
<220> FEATURE:
<223> OTHER INFORMATION: Synthesized DNA fragment for replication

<400> SEQUENCE: 32
gataatacga ctcactatag 20

<210> SEQ ID NO 33
<211> LENGTH: 55
<212> TYPE: DNA
<213> ORGANISM: Artificial sequence
<220> FEATURE:
<221> NAME/KEY: misc_feature
<222> LOCATION: 28
<223> OTHER INFORMATION: n means 7-(2-thienyl)-3H-imidazo[4,5-b]
      pyridin-3-yl
<220> FEATURE:
<223> OTHER INFORMATION: Synthesized DNA fragment for replication

<400> SEQUENCE: 33
gcagtgaaga attcgcttag atgtggancc attccctata gtgagtcgta ttatc 55

<210> SEQ ID NO 34
<211> LENGTH: 55
<212> TYPE: DNA
<213> ORGANISM: Artificial sequence
<220> FEATURE:
<221> NAME/KEY: misc_feature
<222> LOCATION: 25
<223> OTHER INFORMATION: n means 7-(2-thienyl)-3H-imidazo[4,5-b]
      pyridin-3-yl
<220> FEATURE:
<223> OTHER INFORMATION: Synthesized DNA fragment for replication

<400> SEQUENCE: 34
gcagtgaaga attcgcttag atgtngatcc attccctata gtgagtcgta ttatc 55

<210> SEQ ID NO 35
<211> LENGTH: 55
<212> TYPE: DNA
<213> ORGANISM: Artificial sequence
<220> FEATURE:
<221> NAME/KEY: misc_feature
<222> LOCATION: 22
<223> OTHER INFORMATION: n means 7-(2-thienyl)-3H-imidazo[4,5-b]
      pyridin-3-yl
<220> FEATURE:
<223> OTHER INFORMATION: Synthesized DNA fragment for replication

<400> SEQUENCE: 35
gcagtgaaga attcgcttag angtggatcc attccctata gtgagtcgta ttatc 55

<210> SEQ ID NO 36
<211> LENGTH: 55
<212> TYPE: DNA
<213> ORGANISM: Artificial sequence
<220> FEATURE:
<221> NAME/KEY: misc_feature
<222> LOCATION: 31
<223> OTHER INFORMATION: n means 7-(2-thienyl)-3H-imidazo[4,5-b]
      pyridin-3-yl
<220> FEATURE:
<223> OTHER INFORMATION: Synthesized DNA fragment for replication

<400> SEQUENCE: 36
gcagtgaaga attcgcttag atgtggatcc nttccctata gtgagtcgta ttatc 55

<210> SEQ ID NO 37
<211> LENGTH: 55
<212> TYPE: DNA
<213> ORGANISM: Artificial sequence
<220> FEATURE:
<221> NAME/KEY: misc_feature
<222> LOCATION: 34
<223> OTHER INFORMATION: n means 7-(2-thienyl)-3H-imidazo[4,5-b]

```
                    pyridin-3-yl
<220> FEATURE:
<223> OTHER INFORMATION: Synthesized DNA fragment for replication

<400> SEQUENCE: 37
gcagtgaaga attcgcttag atgtggatcc attncctata gtgagtcgta ttatc       55

<210> SEQ ID NO 38
<211> LENGTH: 55
<212> TYPE: DNA
<213> ORGANISM: Artificial sequence
<220> FEATURE:
<223> OTHER INFORMATION: Synthesized DNA fragment for replication

<400> SEQUENCE: 38
gcagtgaaga attcgcttag atgtggatcc attccctata gtgagtcgta ttatc       55

<210> SEQ ID NO 39
<211> LENGTH: 21
<212> TYPE: DNA
<213> ORGANISM: Artificial sequence
<220> FEATURE:
<223> OTHER INFORMATION: Synthesized DNA fragment for transcription

<400> SEQUENCE: 39
ataatacgac tcactatagg g                                            21

<210> SEQ ID NO 40
<211> LENGTH: 35
<212> TYPE: DNA
<213> ORGANISM: Artificial sequence
<220> FEATURE:
<221> NAME/KEY: misc_feature
<222> LOCATION: 5
<223> OTHER INFORMATION: n means 7-(2-thienyl)-3H-imidazo[4,5-b]
      pyridin-3-yl or adenine
<220> FEATURE:
<223> OTHER INFORMATION: Synthesized DNA fragment for transcription

<400> SEQUENCE: 40
cactnctcgg gattccctat agtgagtcgt attat                             35

<210> SEQ ID NO 41
<211> LENGTH: 17
<212> TYPE: RNA
<213> ORGANISM: Artificial sequence
<220> FEATURE:
<221> NAME/KEY: misc_feature
<222> LOCATION: 13
<223> OTHER INFORMATION: n means any one of the followings:
      2-formyl-4-[3-[6-(fluorescein-5-carboxamido)hexanamido]-1-
      propynyl]-1H-pyrrol-1-yl,
      2-formyl-4-[3-[6-(tetramethylrhodamine-5-carboxamido)
      hexanamido]-1-propynyl]-1H-pyrrol-1-yl,
<220> FEATURE:
<223> OTHER INFORMATION: RNA transcript from synthesized template

<400> SEQUENCE: 41 gggaauccncg agnagug                                                17
```

METHOD FOR NUCLEIC ACID REPLICATION AND NOVEL ARTIFICIAL BASE PAIRS

The following application is the National Phase application under 27 C.F.R §371 of International Patent Application No.: PCT/JP2006/0324484 with an International Filing date of Dec. 7, 2006; which claims priority to Japanese Patent Application No.: 2005-356883, filed on Dec. 9, 2005; and Japanese Patent Application No.: 2006-189806, filed on Jul. 10, 2006.

TECHNICAL FIELD

The present application claims priority to Japanese Patent Application Nos. 2005-356883 (filed on Dec. 9, 2005) and 2006-189806 (filed on Jul. 10, 2006), the entire contents of which are incorporated herein by reference.

The present invention relates to a method for nucleic acid replication and novel artificial base pairs.

BACKGROUND ART

Nucleic acids are amplified and act as catalysts and ligands through complementarity of A-T(U) and G-C base pairs. However, unlike 20 different amino acids in natural proteins, natural nucleic acids are composed of nucleotides consisting of only 4 different bases. This number limit restricts the functions of DNA and RNA molecules. Unnatural base pair systems provide a resolution to this problem because they increase the types of nucleic acid bases to allow expansion of genetic information (Non-patent Documents 1-5). Unnatural base pairs are required to have highly specific complementarity which allows site-specific incorporation of special nucleotide analogs into DNA and RNA through polymerase-catalyzed reactions. If this requirement is achieved, current genetic engineering technology, which is limited by the number of naturally-occurring bases, can be replaced with a novel technology using unnatural base pair systems.

The first attempt to create unnatural base pairs was made by Benner et al (Non-patent Documents 6-7). They developed some unnatural base pairs, including isoguanine-isocytosine (isoG-isoC) and xanthosine-diaminopyrimidine, based on different hydrogen bonding patterns than those of natural base pairs. Recently, these unnatural base pairs have been applied to PCR amplification (Non-patent Documents 8-9) and sequence analysis (Non-patent Document 10) of DNA fragments containing these base pairs. However, the fidelity is relatively not high and/or complicated procedures are required. In addition to these problems, 2-aminopyrimidine analogs such as isoC and diaminopyrimidine are not recognized as substrates by T7 RNA polymerase. Thus, these base pairs are of limited use.

Subsequently, Kool et al. synthesized hydrophobic bases having shapes similar to those of natural bases, but lacking the ability to form a hydrogen bond during base pairing (Non-patent Documents 11-12). These hydrophobic bases were selectively recognized by DNA polymerases, suggesting that geometric shape complementarity between paring bases is more important during replication, rather than hydrogen bonding interaction. Recently, a series of hydrophobic base pairs have been developed by Romesberg et al. and introduced into DNA in a complementary manner by the action of the Klenow fragment of *E. coli*-derived DNA polymerase I (Non-patent Documents 13-15). However, these hydrophobic bases did not conform to shape complementarity during replication, and their non-selective introduction through enzymatic reactions occurred between hydrophobic bases (Non-patent Document 14). Moreover, there is no report of these hydrophobic base pairs functioning during transcription.

By combining the ideas of hydrogen bonding pattern and shape complementarity, the inventors of the present invention developed unnatural base pairs between 2-amino-6-(2-thienyl)purine (s) and 2-oxopyridine (y) (Non-patent Documents 16-17) as well as between 2-amino-6-(2-thiazolyl)purine (v) and y (Non-patent Document 18). The bulky substituents at the 6-position of s and v efficiently prevented undesirable base pairing (non-cognate pairing) with a natural base, and a substrate (nucleoside 5'-triphosphate) of y or modified y was introduced in a site-specific manner into RNA opposite s or v in the template by the action of T7 RNA polymerase. This specific transcription is available for practical use as a means for developing functional RNA molecules (Non-patent Documents 19-21), but the selectivity of s-y and v-y base pairings during replication is not notably higher than that during transcription (Non-patent Documents 16 and 18).

To solve the problems stated above, there is a demand for a novel artificial base pair showing excellent efficiency and selectivity during replication and transcription (for design of functional nucleic acids) or during all of replication, transcription and translation (for design of functional proteins).

The following documents are listed as reference documents, the entire contents of which are incorporated herein by reference.

Patent Document 1: WO2001/005801
Patent Document 2: WO2004/007713
Patent Document 3: WO2005/026187
Patent Document 4: Japanese Patent Application No. 2005-226492
Non-patent Document 1: Benner, S. A., Burgstaller, P., Battersby, T. R. & Jurczyk, S. in The RNA World (eds Gesteland, R. F., Cech, T. R. & Atkins, J. F.) 163-181 (Cold Spring Harbor Laboratory Press, Cold Spring Harbor, N.Y., 1999).
Non-patent Document 2: Henry, A. A. & Romesberg, F. E. Beyond A, C, G and T: augmenting nature's alphabet. Curr. Opin. Chem. Biol. 7, 727-733 (2003).
Non-patent Document 3: Moser, M. J. & Prudent, J. R. Enzymatic repair of an expanded genetic information system. Nucleic Acids Res. 31, 5048-5053 (2003).
Non-patent Document 4: Bergstrom, D. E. Orthogonal base pairs continue to evolve. Chem. Biol. 11, 18-20 (2004).
Non-patent Document 5: Benner, S. A. & Sismour, A. M. Synthetic biology. Nat. Rev. 6, 533-543 (2005).
Non-patent Document 6: Piccirilli, J. A., Krauch, T., Moroney, S. E. & Benner, S. A. Enzymatic incorporation of a new base pair into DNA and RNA extends the genetic alphabet. Nature 343, 33-37 (1990).
Non-patent Document 7: Switzer, C. Y., Moroney, S. E. & Benner, S. A. Enzymatic recognition of the base pair between isocytidine and isoguanosine. Biochemistry 32, 10489-10496 (1993).
Non-patent Document 8: Sismour, A. M. et al. PCR amplification of DNA containing non-standard base pairs by variants of reverse transcriptase from Human Immunodeficiency Virus-1. Nucleic Acids Res. 32, 728-735 (2004).
Non-patent Document 9: Johnson, S. C., Sherrill, C. B., Marshall, D. J., Moser, M. J. & Prudent, J. R. A third base pair for the polymerase chain reaction: inserting isoC and isoG. Nucleic Acids Res. 32, 1937-1941 (2004).
Non-patent Document 10: Ahle, J. D., Barr, S., Chin, A. M. & Battersby, T. R. Sequence determination of nucleic acids containing 5-methylisocytosine and isoguanine: identification and insight into polymerase replication of the non-natural nucleobases. Nucleic Acids Res. 33, 3176-3184 (2005).

Non-patent Document 11: Morales, J. C. & Kool, E. T. Efficient replication between non-hydrogen-bonded nucleoside shape analogs. Nat. Struct. Biol. 5, 950-954 (1998).

Non-patent Document 12: Kool, E. T., Morales, J. C. & Guckian, K. M. Mimicking the structure and function of DNA: Insights into DNA stability and replication. Angew. Chem. Int. Ed. 39, 990-1009 (2000).

Non-patent Document 13: McMinn, D. L. et al. Efforts toward expansion of the genetic alphabet: DNA polymerase recognition of a highly stable, self-pairing hydrophobic base. J. Am. Chem. Soc. 121, 11585-11586 (1999).

Non-patent Document 14: Wu, Y. et al. Efforts toward expansion of the genetic alphabet: optimization of interbase hydrophobic interactions. J. Am. Chem. Soc. 122, 7621-7632 (2000).

Non-patent Document 15: Ogawa, A. K. et al. Efforts toward the expansion of the genetic alphabet: Information storage and replication with unnatural hydrophobic base pairs. J. Am. Chem. Soc. 122, 3274-3287 (2000).

Non-patent Document 16: Fujiwara, T., Kimoto, M., Sugiyama, H., Hirao, I. & Yokoyama, S. Synthesis of 6-(2-thienyl)purine nucleoside derivatives that form unnatural base pairs with pyridin-2-one nucleosides. Bioorg. Med. Chem. Lett. 11, 2221-2223 (2001).

Non-patent Document 17: Hirao, I. et al. An unnatural base pair for incorporating amino acid analogs into proteins. Nat. Biotechnol. 20, 177-182 (2002).

Non-patent Document 18: Mitsui, T., Kimoto, M., Harada, Y., Yokoyama, S. & Hirao, I. An efficient unnatural base pair for a base-pair-expanded transcription system. J. Am. Chem. Soc. 24, 8652-8658 (2005).

Non-patent Document 19: Kimoto M. et al. Site-specific incorporation of a photo-crosslinking component into RNA by T7 transcription mediated by unnatural base pairs. Chem. Biol. 11, 47-55 (2004).

Non-patent Document 20: Moriyama, K., Kimoto, M., Mitsui, T., Yokoyama, S. & Hirao, I. Site-specific biotinylation of RNA molecules by transcription using unnatural base pairs. Nucleic Acids Res. 33, e129 (2005).

Non-patent Document 21: Kawai, R. et al. Site-specific fluorescent labeling of RNA molecules by specific transcription using unnatural base pairs. J. Am. Chem. Soc. in press.

Non-patent Document 22: Matray, T. J. & Kool, E. T. A specific partner for abasic damage in DNA. Nature 399, 704-708 (1999).

Non-patent Document 23: Doublié, S., Tabor, S., Long, A. M., Richardson, C. C. & Elenberger, T. Crystal structure of a bacteriophage T7 DNA replication complex at 2.2 Å resolution. Nature 391, 251-258 (1998).

Non-patent Document 24: Kiefer, J. R., Mao, C., Braman, J. C. & Beese, L. S. Visualizing DNA replication in a catalytically active Bacillus DNA polymerase crystal. Nature 391, 304-307 (1998).

Non-patent Document 25: Morales, J. C. & Kool, E. T. Functional hydrogen-bonding map of the minor groove binding tracks of six DNA polymerases. Biochemistry 39, 12979-12988 (2000).

Non-patent Document 26: Mitsui, T. et al. An unnatural hydrophobic base pair with shape complementarity between pyrrole-2-carbaldehyde and 9-methylimidazo[(4,5)-b]pyridine. J. Am. Chem. Soc. 125, 5298-5307 (2003).

Non-patent Document 27: Morales, J. C. & Kool, E. T. Minor groove interactions between polymerase and DNA: More essential to replication than Watson-Crick hydrogen bonds? J. Am. Chem. Soc. 121, 2323-2324 (1999).

Non-patent Document 28: Hirao, I. et al. A two-unnatural-base-pair system toward the expansion of the genetic code. J. Am. Chem. Soc. 126, 13298-13305 (2004).

Non-patent Document 29: Tae, E. L., Wu, Y., Xia, G., Schultz, P. G. & Romesberg, F. E. Efforts toward expansion of the genetic alphabet: Replication of DNA with three base pairs. J. Am. Chem. Soc. 123, 7439-7440 (2001).

Non-patent Document 30: Petruska, J. et al. Comparison between DNA melting thermodynamics and DNA polymerase fidelity. Proc. Natl. Acad. Sci. USA 85, 6252-6256 (1988).

Non-patent Document 31: Goodman, M. F., Creighton, S., Bloom, L. B. & Petruska, J. Biochemical basis of DNA replication fidelity. Crit. Rev. Biochem. Mol. Biol. 28, 83-126 (1993).

Non-patent Document 32: Kimoto, M., Yokoyama, S. & Hirao, I. A quantitative, non-radioactive single-nucleotide insertion assay for analysis of DNA replication fidelity by using an automated DNA sequencer. Biotechnol. Lett. 26, 999-1005 (2004).

Non-patent Document 33: Ohtsuki, T. et al. Unnatural base pair for specific transcription. Proc. Natl. Acad. Sci. USA 98, 4922-4925 (2001).

Non-patent Document 34: Mitsui, T., Kimoto, M., Sato, A., Yokoyama, S. & Hirao, I. An unnatural hydrophobic base, 4-propynylpyrrole-2-carbaldehyde, as an efficient pairing partner of 9-methylimidazo[(4,5)-b]pyridine. Bioorg. Med. Chem. Lett. 13, 4515-4518 (2003).

Non-patent Document 35: Cha, R. S. & Thilly W, G. in PCR Primer (eds Dieffenbach, C. W. & Dveksler, G. S.) 37-51 (Cold Spring Harbor Laboratory Press, Cold Spring Harbor, N.Y., 1995).

Non-patent Document 36: Himeno, H., Hasegawa, T., Ueda, T., Watanabe, K. & Shimizu, M. Conversion of aminoacylation specificity from tRNATyr to tRNASer in vitro. Nucleic Acids Res. 18, 6815-6819 (1990).

Non-patent Document 37: Bedouelle, H. Recognition of tRNATyr by tyrosyl-tRNA synthetase. Biochimie 72, 589-598 (1990).

Non-patent Document 38: Mulder, B. A. et al. Nucleotide modification at the γ-phosphate leads to the improved fidelity of HIV-1 reverse transcriptase. Nucleic Acids Res. 33, 4865-4873 (2005).

Non-patent Document 39: Mitsui, T., Kitamura, A., Kimoto, M., To, T., Sato, A., Hirao, I. & Yokoyama, S. An unnatural hydrophobic base pair with shape complementarity between pyrrole-2-carbaldehyde and 9-methylimidazo[(4,5)-b]pyridine. J. Am. Chem. Soc. 125, 5298-5307 (2003).

Non-patent Document 40: Mitsui, T., Kimoto, M., Sato, A., Yokoyama, S. & Hirao, I. An unnatural hydrophobic base, 4-propynylpyrrole-2-carbaldehyde, as an efficient pairing partner of 9-methylimidazo[(4,5)-b]pyridine. Bioorg. Med. Chem. Lett. 13, 4515-4518 (2003).

Non-patent Document 41: De Roos, K. B. & Salemink, C. A., Deazapurine derivatives. V, A new synthesis of 1- and 3-deaza-adenine and related compound. Recueil. 88, 1263-1274 (1963).

Non-patent Document 42: Rolland, V., Kotera, M. & Lhomme, J. Convenient preparation of 2-deoxy 3,5-di-O-p-toluoyl-a-D-erythro-pentofuranosyl chloride. Synthetic Commun. 27, 3505-3511 (1997).

Non-patent Document 43: Ludwig, J. & Eckstein, F. Rapid and efficient synthesis of 5'-O-(1-thiotriphosphates), 5'-O-triphosphates and 2',3'-cyclophosphorothioates using 2-chloro-4H-1,3,2-benzodioxaphosphorin-4-one. J. Org. Chem. 54, 631-635 (1989).

Non-patent Document 44: Stevens, J. D., Ness, R. K. & Fletcher. Jr, H. G. Syntheses with partially benzylated sugars. XI. Studies on the synthesis of the anomeric 5,6-dimethyl-1-D-ribofuranosylbenzimidazole (Ribazoles). Comparison of the condensation of 2,3,5-tri-O-benzoyl-D-ribofuranosyl bromide and 2,3,5-tri-O-benzoyl-D-ribofuranosyl chloride with 5,6-dimethylbenzimidazole. J. Org. Chem. 33, 1806-1810 (1968).

Non-patent Document 45: Kovacs, T. & Otvos, L. Simple synthesis of 5-vinyl- and 5-ethynyl-2'-deoxyuridine-5'-triphosphates. Tetrahedron Lett. 29, 4525-4528 (1988).

Non-patent Document 46: Ti, G. S., Gaffney, B. L. & Jones, R. A., Transient protection: Efficient One-Flask Syntheses of Protected Deoxynucleosides. J. Am. Chem. Soc. 104, 1316-1319 (1982)

Non-patent Document 47: Stumber, M., Herrmann, C., Wohlgemuth, S., Kalbitzer, H. R., Jahn, W. & Geyer, M. Synthesis, characterization and application of two nucleoside triphosphate analogues, $GTP\gamma NH_2$ and $GTP\gamma F$. Eur. J. Biochem. 269, 3270-3278 (2002).

Non-patent Document 48: Knorre, D. G., Kurbatov, V. A. & Samukov, V. V. General method for the synthesis of ATP gamma-derivatives. FEBS Lett. 70, 105-108 (1976).

Non-patent Document 49: K. J. Morgan and D. P. Morrey. Nitropyrrole-I, The preparation and properties of 2- and 3-nitropyrrole, Tetrahedron, 22, 57-62, 1966.

DISCLOSURE OF THE INVENTION

Problems to be Solved by the Invention

The present invention aims to provide the following embodiments 1-27.

Embodiment 1

A method for replicating a nucleic acid, wherein a deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group, is used as a substrate during replication reaction (preferably in combination with usual substrates).

Embodiment 2

The method according to embodiment 1, wherein the substituent is an amino group.

Embodiment 3

The method according to embodiment 1 or 2, wherein a DNA polymerase having exonuclease activity is used during the replication reaction.

Embodiment 4

The method according to any one of embodiments 1 to 3, wherein the polymerase having exonuclease activity is selected from the group consisting of Klenow fragment, T4 DNA polymerase and thermophilic DNA polymerase (e.g., *Thermococcus litoralis*-derived Vent DNA polymerase), each having 3'→5' exonuclease activity.

Embodiment 5

The method according to any one of embodiments 1 to 4, wherein the deoxyribonucleoside 5'-triphosphate used as a substrate has an unnatural base.

Embodiment 6

The method according to any one of embodiments 1 to 4, wherein the deoxyribonucleoside 5'-triphosphate used as a substrate has a natural base.

Embodiment 7

The method according to any one of embodiments 1 to 5, wherein the deoxyribonucleoside 5'-triphosphate used as a substrate has a base represented by the following formula 1:

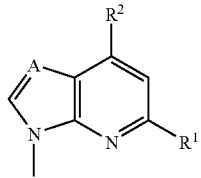

[Formula 1]

[wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH].

Embodiment 8

The method according to any one of embodiments 1 to 5, wherein the deoxyribonucleoside 5'-triphosphate used as a substrate has a base represented by the following formula 2:

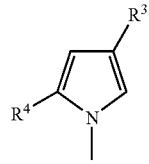

[Formula 2]

[wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group].

Embodiment 9

A deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group.

Embodiment 10

A deoxyribonucleoside 5'-triphosphate having an unnatural base, in which the hydroxyl group of phosphoric acid at the γ-position is substituted with a group selected from the group consisting of an amino group, a methylamino group, a dimethylamino group, a mercapto group and a fluoro group.

Embodiment 11

A deoxyribonucleoside 5'-triphosphate having a natural base, in which the hydroxyl group of phosphoric acid at the γ-position is substituted with a group selected from the group consisting of an amino group, a methylamino group, a dimethylamino group, a mercapto group and a fluoro group.

Embodiment 12

The use of a deoxyribonucleoside 5'-triphosphate as a substrate in the method for replicating a nucleic acid according to any one of embodiments 1 to 8, in which the hydroxyl group of phosphoric acid at the γ-position is substituted with a group selected from the group consisting of an amino group, a methylamino group, a dimethylamino group, a mercapto group and a fluoro group.

Embodiment 13

A nucleic acid, in which a nucleotide having a base represented by the following formula 1:

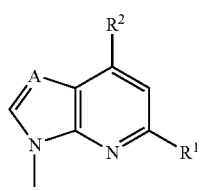

[Formula 3]

[wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH]
forms a base pair with a nucleotide having a base represented by the following formula 2:

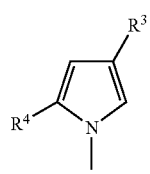

[Formula 4]

[wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group].

Embodiment 14

The nucleic acid according to embodiment 13, wherein the base of formula 1 is selected from the group consisting of:
A1) a 7-(2-thienyl)-3H-imidazo[4,5-b]pyridin-3-yl group;
A2) a 7-(2-thiazolyl)-3H-imidazo[4,5-b]pyridin-3-yl group;
A3) a 7-(1H-2-imidazolyl)-3H-imidazo[4,5-b]pyridin-3-yl group;
A4) a 5-amino-7-(2-thienyl)-3H-imidazo[4,5-b]pyridin-3-yl group;
A5) a 5-amino-7-(2-thiazolyl)-3H-imidazo[4,5-b]pyridin-3-yl group;
A6) a 5-amino-7-(1H-2-imidazolyl)-3H-imidazo[4,5-b]pyridin-3-yl group;
A7) a 4-(2-thienyl)-1H-pyrrolo[2,3-b]pyridin-1-yl group;
A8) a 4-(2-thiazolyl)-1H-pyrrolo[2,3-b]pyridin-1-yl group;
A-9) a 4-(1H-2-imidazolyl)-1H-pyrrolo[2,3-b]pyridin-1-yl group;
A-10) a 6-amino-4-(2-thienyl)-1H-pyrrolo[2,3-b]pyridin-1-yl group;
A-11) a 6-amino-4-(2-thiazolyl)-1H-pyrrolo[2,3-b]pyridin-1-yl group; and
A-12) a 6-amino-4-(1H-2-imidazolyl)-1H-pyrrolo[2,3-b]pyridin-1-yl group.

Embodiment 15

The nucleic acid according to embodiment 13, wherein the base of formula 2 is selected from the group consisting of:
B1) a 2-formyl-1H-pyrrol-1-yl group;
B2) a 2-formyl-4-iodo-1H-pyrrol-1-yl group;
B3) a 2-formyl-4-methyl-1H-pyrrol-1-yl group;
B4) a 2-formyl-4-(1-propyn-1-yl)-1H-pyrrol-1-yl group;
B5) a 2-formyl-4-(2-substituted aminovinyl)-1H-pyrrol-1-yl group;
B6) a 2-formyl-4-(3-substituted amino-1-propyn-1-yl)-1H-pyrrol-1-yl group;
B7) a 2-nitro-1H-pyrrol-1-yl group;
B8) a 2-nitro-4-iodo-1H-pyrrol-1-yl group;
B9) a 2-nitro-4-methyl-1H-pyrrol-1-yl group;
B10) a 2-nitro-4-(1-propyn-1-yl)-1H-pyrrol-1-yl group;
B11) a 2-nitro-4-(2-substituted aminovinyl)-1H-pyrrol-1-yl group; and
B12) a 2-nitro-4-(3-substituted amino-1-propyn-1-yl)-1H-pyrrol-1-yl group.

Embodiment 16

The nucleic acid according to any one of embodiments 13 to 15, which forms a base pair(s) in the step of transcription, reverse transcription, replication or translation.

Embodiment 17

A method for preparing a nucleic acid containing a nucleotide having a base represented by the following formula 1:

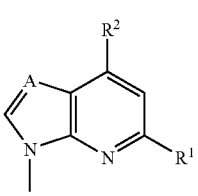

[Formula 5]

[wherein
R¹ is hydrogen or an amino group,
R² is a substituted or unsubstituted 2-thienyl group, a substituted or unsubstituted 2-thiazolyl group, or a substituted or unsubstituted 1H-2-imidazolyl group, and
A is N or CH],
wherein the method comprises effecting transcription, reverse transcription or replication by using, as a template, a nucleic acid containing a nucleotide having a base represented by the following formula 2:

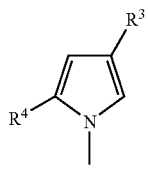

[Formula 6]

[wherein
R³ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
R⁴ is a formyl group or a nitro group],
whereby the nucleotide having a base of formula 1 is incorporated at a site complementary to the nucleotide having a base of formula 2.

Embodiment 18

A method for preparing a nucleic acid containing a nucleotide having a base represented by the following formula 2:

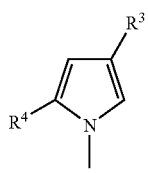

[Formula 7]

[wherein
R³ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
R⁴ is a formyl group or a nitro group],
wherein the method comprises effecting transcription, reverse transcription or replication by using, as a template, a nucleic acid containing a nucleotide having a base represented by the following formula 1:

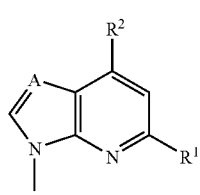

[Formula 8]

[wherein
R¹ is hydrogen or an amino group,
R² is a substituted or unsubstituted 2-thienyl group, a substituted or unsubstituted 2-thiazol yl group, or a substituted or unsubstituted 1H-2-imidazolyl group, and
A is N or CH],
whereby the nucleotide having a base of formula 2 is incorporated at a site complementary to the nucleotide having a base of formula 1.

Embodiment 19

A nucleic acid containing a nucleotide having a base of formula 1 and/or formula 2, which is prepared by the method according to embodiment 17 or 18.

Embodiment 20

The nucleic acid according to embodiment 19, which is tRNA, mRNA, antisense DNA or RNA, a ribozyme, an aptamer or siRNA.

Embodiment 21

A ribonucleoside 5'-triphosphate having a base represented by the following formula 1:

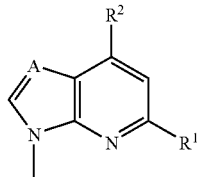

[Formula 9]

[wherein
R¹ is hydrogen or an amino group,
R² is a substituted or unsubstituted 2-thienyl group, a substituted or unsubstituted 2-thiazol yl group, or a substituted or unsubstituted 1H-2-imidazolyl group, and
A is N or CH].

Embodiment 22

A ribonucleoside 5'-triphosphate having a base represented by the following formula 2:

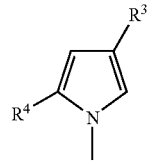

[Formula 10]

[wherein
R³ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
R⁴ is a formyl group or a nitro group].

Embodiment 23

A 5'-O-(4,4'-dimethoxytrityl)-3'-O-(2-cyanoethyl N,N-diisopropylphosphoramidite)deoxyribonucleoside having a base represented by the following formula 3:

[Formula 11]

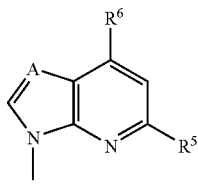

[wherein
R⁵ is hydrogen or a substituted amino group,
R⁶ is a substituted or unsubstituted 2-thienyl group, a substituted or unsubstituted 2-thiazol yl group, or a substituted or unsubstituted 1H-2-imidazolyl group, and
A is N or CH].

Embodiment 24

A 5'-O-(4,4'-dimethoxytrityl)-3'-O-(2-cyanoethyl N,N-diisopropylphosphoroamidite)deoxyribonucleoside having a base represented by the following formula 4:

[Formula 12]

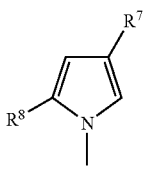

[wherein
R⁷ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
R⁸ is a formyl group or a nitro group,
excluding the case where R⁷ is hydrogen or a 1-propynyl group and R⁸ is a formyl group].

Embodiment 25

A nucleic acid containing a nucleotide having a base represented by formula 2, which is prepared by the method according to embodiment 18, wherein the substituent R³ in formula 2 is a $C_1$-$C_3$ alkyl group, a $C_2$-$C_3$ alkenyl group or a $C_2$-$C_3$ alkynyl group, each being substituted with biotin or a fluorescent molecule.

Embodiment 26

The ribonucleoside 5'-triphosphate according to embodiment 22, wherein R³ is a $C_1$-$C_3$ alkyl group, a $C_2$-$C_3$ alkenyl group or a $C_2$-$C_3$ alkynyl group, each being substituted with biotin or a fluorescent molecule.

Embodiment 27

The 5'-O-(4,4'-dimethoxytrityl)-3'-O-(2-cyanoethyl N,N-diisopropylphosphoroamidite)deoxyribonucleoside according to embodiment 24, wherein R⁷ is a $C_1$-$C_3$ alkyl group, a $C_2$-$C_3$ alkenyl group or a $C_2$-$C_3$ alkynyl group, each being substituted with biotin or a fluorescent molecule.

Means for Solving the Problems

As a result of extensive and intensive efforts made to solve the problems stated above, the inventors of the present invention have arrived at the present invention.

Development of Unnatural Base Pair Systems of the Present Invention

To obtain an artificial base pair showing excellent efficiency and selectivity during reactions of replication and transcription, the inventors of the present invention have studied base pairs constructed by combining several unnatural base pairs which had been developed on their own.

The inventors of the present invention have found that a combination between 2-amino-6-(2-thienyl)purin-9-yl (s) (Non-patent Documents 17 and 33) and 2-formyl-1H-pyrrol-1-yl (Pa) (Non-patent Document 26) is highly selective and efficient during transcription (Patent Document 4: not yet published). In the present invention, the inventors have further prepared a 7-(2-thienyl)-3H-imidazo[4,5-b]pyridin-3-yl group (Ds) from s through CH substitution for one of the two N atoms in the 6-membered ring of the purine ring and replacement of the amino group at the 2-position with hydrogen, i.e., through deaza modification and deamination, and have studied the fidelity of artificial base pairing between Ds and Pa. As a result, the inventors have found that artificial base pairing between Ds and Pa is highly selective and efficient during replication and transcription, regardless of which of them serves as a template or substrate, thereby arriving at the present invention.

More specifically, it has been found that hydrophobic base pairings between 7-(2-thienyl)-imidazo[4,5-b]pyridine (Ds) and pyrrole-2-carbaldehyde (Pa) as well as between Ds and 4-propynylpyrrole-2-carbaldehyde (Pa') (FIG. 1a) are highly selective during in vitro replication and transcription (FIG. 1c). During replication, the inventors of the present invention have used usual 5'-triphosphate substrates in combination with modified 5'-triphosphate substrates, i.e., 5'-γ-amidotriphosphates (FIG. 1b), and have further used DNA polymerases having 3'→5' exonuclease activity to thereby achieve high selectivity which allows PCR amplification of DNA fragments containing a Ds-Pa base pair. Moreover, these unnatural bases have been introduced into RNA in a complementary manner during normal transcription with T7 RNA polymerase.

More specifically, the inventors of the present invention have designed this Ds-Pa base pair in consideration of the following two ideas: 1) hydrophobic bases whose shape differs from that of natural bases are used with the aim of improving the selectivity of base pairing (Non-patent Documents 12 and 22); and 2) proton acceptor groups required for interaction with polymerases (Non-patent Documents 23-25) are further provided, including the nitrogen at the 4-position of Ds (corresponding to the 3-position of A and G) and the aldehyde group of Pa (corresponding to the keto group at the 2-position of C and T) (FIG. 1a).

Hydrophobic base pairs have a fatal problem in that non-cognate base paring efficiently occurs between hydrophobic bases, whose are not complementary in shape (e.g., Ds-Ds pairing) (Non-patent Documents 14 and 29). To test the selectivity of Ds-Pa base pairing during replication, the inventors of the present invention have studied the base pairing capacity between substrate and template in a single nucleotide insertion experiment using the Klenow fragment lacking exonuclease activity (KF exo⁻) (FIG. 2a) (Non-patent Documents 30-32).

The substrates (dDsTP and dPaTP) and template DNA containing Ds or Pa used in the experiment were chemically synthesized (Examples I and II). The results from the experiment indicated that Ds-Pa base pairing and A-T base pairing each showed higher selectivity than the pairing selectivity of the other, non-cognate, base paring combinations (FIG. 2b, Tables 1 and 2).

TABLE 1

Experiment of single-nucleotide insertion into template DNA with the Klenow fragment
primer    5'-ACTCACTATAGGGAGCTTCT
temp35N-2 3'-TATTATGCTGAGTGATATCCCTCGAAGA$\underline{N}$AGAGCT

| Entry | Template ($\underline{N}$) | Nucleoside triphosphate | $K_M$ (µM) | $V_{max}$ (% min$^{-1}$) | Efficiency ($V_{max}/K_M$)$^d$ |
|---|---|---|---|---|---|
| 1 | Pa | dDsTP | 26 (12)$^b$ | 28 (5) | $1.1 \times 10^4$ |
| 2 | Pa | dDsTP$_N$ | 180 (20) | 12 (1) | $6.7 \times 10^4$ |
| 3 | Pa | dATP | 490 (260) | 21 (6) | $4.3 \times 10^4$ |
| 4 | Pa | dATP$_N$ | 1200 (400) | 2.2 (1.3) | $1.8 \times 10^3$ |
| 5 | Pa | dGTP | 480 (140) | 0.42 (0.09) | $8.8 \times 10^2$ |
| 6 | Pa | dCTP | n.d.$^c$ | n.d. | — |
| 7 | Pa | dTTP | 880 (530) | 0.097 (0.025) | $1.1 \times 10^2$ |
| 8 | Pa | dPaTP | 380 (90) | 0.56 (0.09) | $1.5 \times 10^3$ |
| 9 | Pa' | dDsTP | 24 (2) | 21 (6) | $8.8 \times 10^5$ |
| 10 | Pa' | dDSTP$_N$ | 230 (50) | 13 (5) | $5.7 \times 10^4$ |
| 11 | Pa' | dATP | 570 (240) | 21 (11) | $3.7 \times 10^4$ |
| 12 | Pa' | dATP$_N$ | 800 (400) | 2.4 (1.3) | $3.0 \times 10^3$ |
| 13 | Pa' | dGTP | 800 (170) | 0.44 (0.09) | $5.5 \times 10^2$ |
| 14 | Pa' | dCTP | n.d. | n.d. | — |
| 15 | Pa' | dTTP | 1400 (100) | 0.14 (0.04) | $1.0 \times 10^2$ |
| 16 | Pa' | dPa'TP | 190 (90) | 7.8 (2.4) | $4.1 \times 10^4$ |
| 17 | A | dDsTP | 33 (9) | 1.2 (0.1) | $3.6 \times 10^4$ |
| 18 | G | dDsTP | 37 (6) | 1.5 (0.3) | $4.1 \times 10^4$ |
| 19 | C | dDsTP | 47 (26) | 1.3 (0.1) | $2.8 \times 10^4$ |
| 20 | T | dDsTP | 45 (14) | 3.9 (0.3) | $8.7 \times 10^4$ |
| 21 | A | dDsTP$_N$ | 270 (150) | 0.52 (0.16) | $1.9 \times 10^3$ |
| 22 | G | dDSTP$_N$ | 300 (80) | 0.58 (0.06) | $1.9 \times 10^3$ |
| 23 | C | dDsTP$_N$ | 440 (130) | 0.64 (0.15) | $1.5 \times 10^3$ |
| 24 | T | dDSTP$_N$ | 480 (110) | 1.7 (0.2) | $3.5 \times 10^3$ |
| 25 | T | dATP | 0.81 (0.44) | 3.3 (1.8) | $4.1 \times 10^6$ |
| 26 | T | dATP$_N$ | 13 (11) | 3.2 (1.7) | $2.5 \times 10^5$ |
| 27 | C | dATP | 500 (90) | 2.3 (0.8) | $4.6 \times 10^3$ |
| 28 | C | dATP$_N$ | 590 (110) | 0.20 (0.04) | $3.4 \times 10^2$ |
| 29 | C | dGTP | 2.3 (0.1) | 16 (4) | $7.0 \times 10^6$ |
| 30 | T | dGTP | 420 (20) | 12 (0.1) | $2.9 \times 10^3$ |

$^a$Assays were carried out at 37° C. for 1 to 35 minutes using 5 µM template-primer duplex, 5-50 nM enzyme and 0.3-1500 µM nucleoside 5'-triphosphate in a solution (10 µl) containing 50 mM Tris-HCl (pH 7.5), 10 mM MgCl$_2$, 1 mM DTT and 0.05 mg/ml bovine serum albumin. Each parameter was averaged from 3 to 8 data sets.
$^b$Standard deviations are given in parenthesis.
$^c$Minimal inserted products (<2%) were detected after incubation for 20 minutes with 1500 µM nucleoside 5'-triphosphate and 50 nM enzyme.
$^d$The units of this term are % min$^{-1}$M$^{-1}$.

TABLE 2

Experiment of single-nucleotide insertion
into template DNA with the Klenow fragment
[Table 2-1]

primer     5'-ACTCACTATAGGGAGGAAGA
temp35N-1  3'-TATTATGCTGAGTGATATCCCTCCTTCTNTCTCGA

| Entry | Template (N) | Nucleoside triphosphate | $K_M$ (μM) | $V_{max}$ (% min$^{-1}$) | Efficiency $(V_{max}/K_M)^d$ |
|---|---|---|---|---|---|
| 1  | Ds | dPaTP   | 340 (150)$^b$ | 21 (3)         | $6.2 \times 10^4$ |
| 2  | Ds | dPa'TP  | 82 (17)       | 21 (6)         | $2.6 \times 10^5$ |
| 3  | Ds | dATP    | 150 (40)      | 0.36 (0.09)    | $2.4 \times 10^3$ |
| 4  | Ds | dATP$_N$ | 150 (30)     | 0.048 (0.022)  | $3.2 \times 10^2$ |
| 5  | Ds | dGTP    | n.d.$^c$      | n.d.           | —                 |
| 6  | Ds | dCTP    | 410 (190)     | 0.34 (0.05)    | $8.3 \times 10^2$ |
| 7  | Ds | dTTP    | 220 (20)      | 0.41 (0.17)    | $1.9 \times 10^3$ |
| 8  | Ds | dDsTP   | 8.0 (3.9)     | 1.6 (0.1)      | $2.0 \times 10^5$ |
| 9  | Ds | dDsTP$_N$ | 79 (13)     | 0.78 (0.12)    | $9.9 \times 10^3$ |
| 10 | A  | dPaTP   | 330 (160)     | 17 (7)         | $5.2 \times 10^4$ |
| 11 | G  | dPaTP   | 140 (20)      | 0.061 (0.006)  | $4.4 \times 10^2$ |
| 12 | C  | dPaTP   | n.d.          | n.d.           | —                 |
| 13 | T  | dPaTP   | 170 (60)      | 0.053 (0.016)  | $3.1 \times 10^2$ |
| 14 | A  | dPa'TP  | 110 (40)      | 20 (6)         | $1.8 \times 10^5$ |
| 15 | G  | dPa'TP  | 80 (14)       | 0.13 (0.03)    | $1.6 \times 10^3$ |
| 16 | C  | dPa'TP  | 80 (34)       | 0.059 (0.023)  | $7.4 \times 10^2$ |
| 17 | T  | dPa'TP  | 120 (80)      | 0.19 (0.07)    | $1.6 \times 10^3$ |
| 18 | A  | dTTP    | 0.70 (0.40)   | 2.8 (1.5)      | $4.0 \times 10^6$ |
| 19 | A  | dCTP    | 1200 (600)    | 2.2 (0.9)      | $1.8 \times 10^3$ |
| 20 | G  | dCTP    | 0.24 (0.18)   | 5.5 (1.7)      | $2.3 \times 10^7$ |
| 21 | G  | dTTP    | 140 (70)      | 0.29 (0.12)    | $2.1 \times 10^3$ |

$^a$Assays were carried out at 37° C. for 1 to 35 minutes using 5 μM template-primer duplex, 5-50 nM enzyme and 0.3-1500 μM nucleoside 5'-triphosphate in a solution (10 μl) containig 50 mM Tris-HCl (pH 7.5), 10 mM MgCl$_2$, 1 mM DTT and 0.05 mg/ml bovine serum albumin. Each parameter was averaged from 3 to 8 data sets.
$^b$Standard deviations are given in parenthesis.
$^c$Minimal inserted products (<2%) were detected after incubation for 20 minutes with 1500 μM nucleoside 5'-triphosphate and 50 nM enzyme.
$^d$The units of this term are % min$^{-1}$M$^{-1}$.

However, dDsTP was incorporated opposite Ds in the template with high efficiency ($V_{max}/K_M$=2.0×10$^5$), which was higher than the incorporation efficiency of dPaTP opposite Ds ($V_{max}/K_M$=6.2×10$^4$). This Ds-Ds pairing falls within a problematic base paring with no shape fitting between hydrophobic bases, and hence will cause deformation in the B-type DNA structure. As a result, dDsTP incorporation opposite Ds in the template will stop the subsequent extension during replication. For example, when Ds-containing template DNA was used to perform primer extension in a solution containing both dPaTP and dDsTP substrates, primer extension with the Klenow fragment having 3'→5' exonuclease activity (KF exo$^+$) was inhibited (FIG. 2d, Lanes 3 and 4) because dDsTP incorporation opposite Ds in the template would be facilitated with increase in dDsTP (0.5 or 1 molar equivalent of dPaTP).

To solve this fundamental problem of hydrophobic base pairing during replication, the inventors of the present invention have further used a modified 5'-triphosphate, i.e., 5'-γ-amidotriphosphate of Ds (FIG. 1b; denoted as dDsTP$_N$) as a substrate. The inventors have found that the incorporation efficiency of dDsTP$_N$ opposite Ds in the template was significantly reduced ($V_{max}/K_M$=9.9×10$^3$). However, a further problem arose in that the incorporation efficiency of dDsTP$_N$ opposite Pa in the template ($V_{max}/K_M$=6.7×10$^4$) was reduced to a level close to the incorporation efficiency of A opposite Pa in the template ($V_{max}/K_M$=4.3×10$^4$). This problem could be solved by using 5'-γ-amidotriphosphate of A (dATP$_N$). When using dATP$_N$ instead of dATP, the incorporation efficiency of dDsTP$_N$ opposite template Pa was 37-fold higher than that of dATP$_N$ opposite template Pa ($V_{max}/K_M$=1.8×10$^3$), so that the high selectivity of Pa-Ds base pairing could be maintained.

Thus, the inventors of the present invention have achieved the highly complementary selectivity of unnatural base pairing during replication by using usual 5'-triphosphates, dPaTP, dGTP, dCTP and dTTP in combination with 5'-γ-amidotriphosphates dDsTP$_N$ and dATP$_N$ (FIG. 2c).

In the presence of the modified substrate dDsTP$_N$, primer extension after Pa incorporation opposite template Ds proceeded without being inhibited (FIG. 2d, Lanes 5 and 6). Moreover, primer extension after dDsTP$_N$ incorporation opposite template Pa or after dATP$_N$ incorporation opposite template T also proceeded efficiently (FIG. 2e, Lanes 2 and 14). Interestingly, when dATP$_N$ was misincorporated opposite template Pa, the subsequent extension reaction showed significantly reduced efficiency as compared to the extension reaction after misincorporation of dATP opposite template Pa (FIG. 2e, Lanes 4 and 5).

To further improve the selectivity of unnatural base pairing, the inventors of the present invention have used a DNA polymerase having 3'→5' exonuclease activity in this system. The use of KF exo+ significantly reduced the efficiency of primer extension after formation of undesired A-Pa and Ds-T base pairs, whereby primer extension paused around the unnatural base position (FIG. 2d, Lane 1 and FIG. 2e, Lanes 9, 10, 17 and 18).

Thus, the inventors of the present invention have preferably used a DNA polymerase having 3'→5' exonuclease activity in combination with usual 5'-triphosphate substrates and modified 5'-triphosphate substrates to create a specific unnatural base pair system which functions together with A-T and G-C base pairs during replication.

Unnatural base pairing is formed by specific shape complementarity between bases, and hence lacks hydrogen bonding interaction between bases. During replication, this unnatural base pairing shows particularly high selectivity when combining usual 5'-triphosphates and modified 5'-triphosphates (i.e., 5'-γ-amidotriphosphates) for use as substrates of a DNA polymerase having 3'→5' exonuclease activity (3'→5' exonuclease-proficient DNA polymerase) which allows PCR amplification, preferably on a practical level and with high fidelity. DNA fragments containing unnatural bases can be confirmed for their sequences by dideoxynucleotide chain termination sequencing supplemented with substrates of the unnatural bases. Moreover, the complementarity of unnatural base pairs can mediate incorporation of these bases into RNA during normal T7 transcription.

The present invention provides a novel nucleic acid amplification system using any one of or a combination of 1) to 3) shown below:

1) a deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group, is used as a substrate during replication reaction;

2) a DNA polymerase having exonuclease activity is used during replication reaction; and 3) artificial base pairing between a nucleotide having a base of formula 1 described later and a nucleotide having a base of formula 2 is used.

To enable a better understanding of the present invention, development of the background and of the present invention has been explained above. The scope of the present invention is not limited by the above explanation, but is defined by the claims.

Method for Nucleic Acid Replication

In one embodiment, the present invention provides a novel method for nucleic acid replication. The method of the present invention is characterized in that a deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group, is used as a substrate during replication reaction.

When the hydroxyl group of phosphoric acid at the γ-position of a deoxyribonucleoside 5'-triphosphate to be used as a substrate during replication reaction is substituted with such a substituent as listed above, the selectivity of replication reaction is further improved. Because of their improved selectivity, the use of such modified 5'-triphosphates allows the replication reaction involving artificial base pairing to proceed in a substantially available manner, even if the efficiency of substrate incorporation is reduced as compared to unsubstituted substrates.

The above substituent is preferably an amino group.

The hydroxyl group of phosphoric acid at the γ-position of deoxyribonucleoside 5'-triphosphates can be modified in any known manner. For example, Example I-3-(15) and (16) described herein later disclose synthesis examples from corresponding nucleosides where the substituent is an amino group. Alternatively, Non-patent Document 47 also discloses synthesis procedures for γ-amidated nucleotides.

Likewise, in other cases where the substituent is a group other than an amino group, i.e., a methylamino group, a dimethylamino group, a mercapto group or a fluoro group, such modified triphosphates can also be synthesized in a manner known to those skilled in the art.

Replication reaction is not limited in any way except for using the above substrates, and can be effected in a known manner. Without being limited thereto, for example, it is preferable to use a DNA polymerase having exonuclease activity for the purpose of avoiding undesired non-specific base pairing during replication reaction. The polymerase having exonuclease activity is selected from the group consisting of the Klenow fragment, T4 DNA polymerases and thermophilic DNA polymerase (e.g., *Thermococcus litoralis*-derived Vent DNA polymerase), each having 3'→5' exonuclease activity.

As an embodiment of the method of the present invention, a deoxyribonucleoside 5'-triphosphate having an unnatural base may be used as a substrate. In recent years, studies have been conducted to develop base pairs having hydrogen modes different from those of natural base pairs and capable of eliminating base pairing with natural bases by steric hindrance; and hence some artificial base pairs have been reported. Combinations known as artificial base pairs include those based on hydrogen bonding between bases, and those based on the hydrophobicity of bases. In nucleic acids having these unnatural bases, the present invention has achieved increased selectivity and efficiency during transcription, replication and/or translation reaction by modifying the hydroxyl group of phosphoric acid at the γ-position.

There is no particular limitation on the type of unnatural bases in the present invention. For example, the present invention encompasses the use of deoxyribonucleotides having any known unnatural bases shown below:

2-amino-6-dimethylaminopurine (x) and 2-amino-6-thienylpurine (s) (Non-patent Document 33);

a 2-amino-6-(2-thienyl)-9H-purin-9-yl group (s) and a 2-oxo-(1H)pyridin-3-yl group (y) (Patent Document 1, Non-patent Document 17);

a 2-amino-6-(2-thiazolyl)purin-9-yl group (v) and a 2-oxo-(1H)pyridin-3-yl group (y) (Patent Document 3, Non-patent Document 18); and pyrrole-2-carbaldehyde (Pa) and 7-methyl-imidazo[4,5-b]pyridine (Q) (Non-patent Documents 26 and 34).

The inventors of the present invention have further invented a novel artificial base pair, and filed a patent application on Aug. 4, 2005 (Japanese Patent Application No. 2005-226492). The above application relates to an artificial base pair between pyrrole-2-carbaldehyde (Pa) and a 2-amino-6-(2-thienyl)-9H-purin-9-yl group (s). The above base pair shows excellent selectivity, particularly during transcription reaction where Pa is used as a template and s is used as a substrate.

Moreover, the inventors of the present invention provides a further novel artificial base pair in the present invention. This novel artificial base pair may also be used effectively during replication reaction in the present invention. Thus, without being limited thereto, the deoxyribonucleoside 5'-triphosphate used as a substrate has a base represented by the following formula 1:

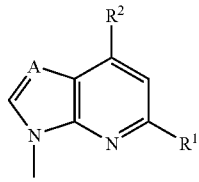

[Formula 13]

[wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH].

Alternatively, the deoxyribonucleoside 5'-triphosphate used as a substrate has a base represented by the following formula 2:

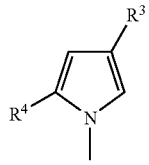

[Formula 14]

[wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group].

Bases of formulae 1 and 2 each show excellent selectivity and efficiency during replication reaction, regardless of which of them is used as a substrate or template. Moreover, these bases also show excellent selectivity and efficiency during transcription reaction.

The novel artificial base pair between bases of formulae 1 and 2 provided in the present invention will be described in detail below in the section "Nucleic acids of the present invention based on artificial base pairing."

Alternatively, the deoxyribonucleoside 5'-triphosphate used as a substrate may have a natural base. There are 4 types of natural bases known for deoxyribonucleosides, including adenine (A), guanine (G), cytosine (C) and thymine (T). For these natural bases, deoxyribonucleoside 5'-triphosphates whose hydroxyl group of phosphoric acid at the γ-position is substituted may also be used effectively as substrates during replication reaction of nucleic acids, as in the case of unnatural bases.

Deoxyribonucleoside 5'-triphosphates

The present invention also provides a deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group.

The deoxyribonucleoside 5'-triphosphate of the present invention may have either an unnatural base or a natural base. The terms "unnatural base" and "natural base" are as defined above in the method for nucleic acid replication.

The deoxyribonucleoside 5'-triphosphate of the present invention can be used as a substrate in the above method of the present invention for nucleic acid replication.

Nucleic Acids of the Present Invention Based on Artificial Base Pairing

To obtain an artificial base pair showing excellent efficiency and selectivity during all reactions of replication, transcription and translation, the inventors of the present invention have studied base pairs constructed by combining several unnatural base pairs which had been developed on their own. As a result, the inventors have found that a combination between 2-amino-6-(2-thienyl)purin-9-yl (s) (Non-patent Documents 17 and 33) and 2-formyl-1H-pyrrol-1-yl (Pa) (Non-patent Document 26) is highly selective and efficient during transcription (Patent Document 4: not yet published).

In the present invention, the inventors have further prepared a 7-(2-thienyl)-3H-imidazo[4,5-b]pyridin-3-yl group (Ds) from s through CH substitution for one of the two N atoms in the 6-membered ring of the purine ring and replacement of the amino group at the 2-position with hydrogen, i.e., through deaza modification and deamination, and have studied the fidelity of artificial base pairing between Ds and Pa. As a result, the inventors have found that artificial base pairing between Ds and Pa is highly selective and efficient during replication and transcription, regardless of which of them serves as a template or substrate, thereby arriving at the present invention.

Thus, in one embodiment, the present invention provides a nucleic acid, in which a nucleotide having a base represented by the following formula 1:

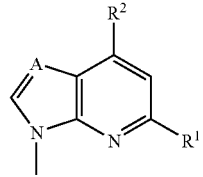

[Formula 15]

[wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH]

forms a base pair with a nucleotide having a base represented by the following formula 2:

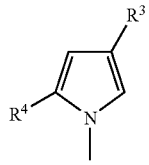

[Formula 16]

[wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group].

As used herein, the term "nucleoside" is intended to mean a glycoside compound formed through glycosidic linking between a nucleic acid base and a reducing group of a sugar. It should be noted that the term "nucleic acid base" is intended to encompass adenine, guanine, cytosine, thymine, uracil, and also derivatives thereof. The type of "derivative" is not limited in any way. Specific examples include bases represented by the above formulae 1 and 2. The term "nucleotide" refers to a compound in which the sugar moiety of the above nucleoside forms an ester with phosphoric acid, more preferably a mono-, di- or tri-phosphate ester. The sugar moiety of such a nucleoside or nucleotide may be ribofuranosyl, 2'-deoxyribofuranosyl, or 2'-substituted ribofuranosyl having a substituent (e.g., halogen) at the 2'-position. Without being limited thereto, in the phosphoric acid moiety, the hydroxyl group of phosphoric acid at the γ-position is desirably substituted with a group selected from the group consisting of an amino group, a methylamino group, a dimethylamino group, a mercapto group and a fluoro group. The sugar and phosphoric acid moieties may be in the same form as found in known nucleosides, nucleotides, or derivatives thereof. A ribonucleotide whose sugar moiety is ribofuranosyl can be used as a component of RNA, while a deoxyribonucleotide whose sugar moiety is deoxyribofuranosyl can be used as a component of DNA.

In bases of formula 1, the thienyl, thiazolyl or imidazolyl group listed as $R^2$ may be unsubstituted or may be substituted at the 4- and/or 5-position(s) with one or more groups independently selected from the group consisting of a methyl group, an amino group, a nitro group and a hydroxy group.

Among bases of formula 1 in the present invention, those in which $R^2$ is a substituted or unsubstituted 2-thienyl group are herein referred to as "Ds" or "Ds analog," depending on the context. Among bases of formula 1 in the present invention, those in which $R^2$ is a substituted or unsubstituted 2-thiazolyl group are herein referred to as "Dv" or "Dv analog," depending on the context. Among bases of formula 1 in the present invention, those in which $R^2$ is a substituted or unsubstituted 1H-2-imidazolyl group are herein referred to as "Dm" or "Dm analog," depending on the context.

With respect to $R^1$ in formula 1, for example, "Ds" as used herein encompasses both cases where $R^1$ in hydrogen and an amino group. On the other hand, in some prior art documents, such a base is described in different terminology depending on the embodiment of $R^1$, for example, "s" for the case where $R^1$ is an amino group or "s'" for the case where $R^1$ is hydrogen.

A may either be N or CH. In a case where A is N (deaza form), such a base is expressed as, e.g., "Ds", "Dv" or "Dm."

In a case where A is CH, such a base is expressed as, e.g., "DDs", "DDv" or "DDm." For example, the term "Ds analog" as used herein includes "DDs." Moreover, "DDs" and "Ds analog" may also be collectively referred to as "Ds," depending on the context.

Without being limited thereto, the base of formula 1 is preferably selected from the group consisting of:
A1) a 7-(2-thienyl)-3H-imidazo[4,5-b]pyridin-3-yl group (Ds);
A2) a 7-(2-thiazolyl)-3H-imidazo[4,5-b]pyridin-3-yl group (Dv);
A3) a 7-(1H-2-imidazolyl)-3H-imidazo[4,5-b]pyridin-3-yl group;
A4) a 5-amino-7-(2-thienyl)-3H-imidazo[4,5-b]pyridin-3-yl group (Ds);
A5) a 5-amino-7-(2-thiazolyl)-3H-imidazo[4,5-b]pyridin-3-yl group (Dv);
A6) a 5-amino-7-(1H-2-imidazolyl)-3H-imidazo[4,5-b]pyridin-3-yl group;
A7) a 4-(2-thienyl)-1H-pyrrolo[2,3-b]pyridin-1-yl group (DDs);
A8) a 4-(2-thiazolyl)-1H-pyrrolo[2,3-b]pyridin-1-yl group (DDv);
A-9) a 4-(1H-2-imidazolyl)-1H-pyrrolo[2,3-b]pyridin-1-yl group;
A-10) a 6-amino-4-(2-thienyl)-1H-pyrrolo[2,3-b]pyridin-1-yl group (DDs);
A-11) a 6-amino-4-(2-thiazolyl)-1H-pyrrolo[2,3-b]pyridin-1-yl group (DDv); and
A-12) a 6-amino-4-(1H-2-imidazolyl)-1H-pyrrolo[2,3-b]pyridin-1-yl group.

Among the above bases, A1 and A4 are members of Ds, while A7 and A10 are members of DDs. A2 and A5 are members of Dv, while A8 and A11 are members of DDv. A3 and A6 are members of "Dm," while A9 and A12 are members of "DDm."

More preferred is A1) a 7-(2-thienyl)-3H-imidazo[4,5-b]pyridin-3-yl group (Ds), A2) a 7-(2-thiazolyl)-3H-imidazo[4,5-b]pyridin-3-yl group (Dv), A4) a 5-amino-7-(2-thienyl)-3H-imidazo[4,5-b]pyridin-3-yl group (Ds), or A5) a 5-amino-7-(2-thiazolyl)-3H-imidazo[4,5-b]pyridin-3-yl group (Dv). Most preferred is a 7-(2-thienyl)-3H-imidazo[4,5-b]pyridin-3-yl group (Ds) (Compound 10 or 14 in Example I).

The base of formula 1 in the present invention and a nucleoside or nucleotide containing the same may be synthesized in a known manner. More specifically, Example I-3 described later discloses procedures for synthesis of nucleoside 5'-triphosphates or 5'-γ-amidotriphosphates of a 7-(2-thienyl)-3H-imidazo[4,5-b]pyridin-3-yl group (Ds) (Compound 10 or 14 in Example I) from 2-amino-3-nitro-4-chloropyridine (Compound 1 in Example I) (Non-patent Document 41), by way of example. Likewise, Example II-1 discloses procedures for synthesis of nucleoside 5'-triphosphates of 7-(2-thiazolyl)-3H-imidazo[4,5]pyridine (Compound 4 in Example II) (Dv).

Further, Example II-3 discloses procedures for synthesis of nucleoside 5'-triphosphates of 4-(2-thienyl)-1H-pyrrolo[2,3-b]pyridine (DDs) and 4-(2-thiazolyl)-1H-pyrrolo[2,3-b]pyridine (DDv).

Nucleosides, nucleotides or 5'-γ-amidotriphosphates having other bases of formula 1 in the present invention may also be synthesized in the same manner as actually disclosed herein and/or in a manner known to those skilled in the art.

In bases of formula 2 in the present invention, $R^3$ is a group selected from hydrogen, iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group.

Such an alkyl, alkenyl or alkynyl group may further be substituted with one or more groups independently selected from the group consisting of a lower alkyl group, a halogen group, a hydroxyl group, an amino group, an alkylamino group and an aromatic heterocyclic ring.

Alternatively, such an alkyl, alkenyl or alkynyl group may further be substituted with biotin or a fluorescent molecule.

Biotin is also called Coenzyme R and is a member of vitamins B. Biotin is known to specifically bind to and form a complex with avidin (a glycoprotein contained in albumen). Thus, a nucleoside and others having biotin as a substituent will specifically bind to avidin protein. This means that a nucleic acid containing a biotin-labeled nucleoside and others can be attached to and hence immobilized and separated on avidin-bound carriers. If nucleic acids (e.g., aptamers) binding to specific molecules are immobilized, such immobilized nucleic acids can be used for detection and isolation of specific substances or used as diagnostic reagents, by way of example. To introduce biotin into the alkyl, alkenyl or alkynyl group listed as $R^3$ in the base of formula 2, biotin may be attached via an amino group, either directly or through a linker.

As a fluorescent molecule, any known molecule may be used and is preferably selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX), 6-carboxy-X-rhodamine (6-ROX), and derivatives thereof. In general, fluorescein and rhodamine are expressed in both open-ring and spiro forms.

For example, FAM has an absorption peak wavelength of 493 nm and a fluorescence peak wavelength of 522 nm. Likewise, TAMRA has an absorption peak wavelength of 553 nm and a fluorescence peak wavelength of 578 nm. DANSYL has an absorption peak wavelength of 335 nm and a fluorescence peak wavelength of 518 nm. HEX has an absorption peak wavelength of 535 nm and a fluorescence peak wavelength of 556 nm. TET has an absorption peak wavelength of 521 nm and a fluorescence peak wavelength of 536 nm. 5-ROX has an absorption peak wavelength of 567 nm and a fluorescence peak wavelength of 591 nm. 6-ROX has an absorption peak wavelength of 570 nm and a fluorescence peak wavelength of 590 nm. A nucleoside or nucleotide having a base of formula 2 in which $R^3$ is substituted with a fluorescent molecule allows nucleic acid detection in a manner dependent on the type of fluorescent molecule. Thus, a nucleic acid containing a nucleotide having a base of formula 2 in which the alkyl, alkenyl or alkynyl group listed as $R^3$ is substituted with a fluorescent molecule can be used as a labeled nucleic acid probe to detect substances interacting with the nucleic acid. Moreover, since these individual fluorescent molecules have fluorescent colors different from each other, they can also be used in multiple staining. To introduce a fluorescent molecule into the alkyl, alkenyl or alkynyl group listed as $R^3$ in the base of formula 2, the fluorescent molecule may be attached via an amino group, either directly or through a linker.

It should be noted that in a case where biotin or a fluorescent molecule is attached through a linker to the alkyl, alkenyl or alkynyl group listed as $R^3$ in the base of formula 2, the type of linker is not limited in any way and may be determined as appropriate by those skilled in the art. Without being limited thereto, the linker is preferably selected from the group consisting of chemical formulae I and II shown below:

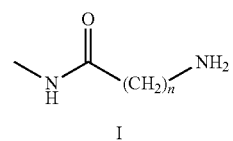

[Formula 17]

I

[wherein n is selected from integers of 1 to 5]; and

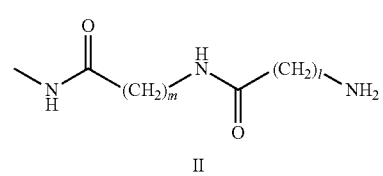

[Formula 18]

II

[wherein m and l are each independently selected from integers of 1 to 5].

$R^4$ is a formyl group or a nitro group. Among bases of formula 2, those in which $R^4$ is a formyl group are herein referred to as "Pa" or "Pa analog," depending on the context. Those in which $R^4$ is a nitro group are herein referred to as "Pn" or "Pn analog," depending on the context. "Pa", "Pa analog", "Pn" and "Pn analog" may also be collectively referred to as "Pa."

Without being limited thereto, the base of formula 2 is preferably selected from the group consisting of:
  B1) a 2-formyl-1H-pyrrol-1-yl group (Pa);
  B2) a 2-formyl-4-iodo-1H-pyrrol-1-yl group;
  B3) a 2-formyl-4-methyl-1H-pyrrol-1-yl group;
  B4) a 2-formyl-4-(1-propyn-1-yl)-1H-pyrrol-1-yl group;
  B5) a 2-formyl-4-(2-substituted aminovinyl)-1H-pyrrol-1-yl group;
  B6) a 2-formyl-4-(3-substituted amino-1-propyn-1-yl)-1H-pyrrol-1-yl group;
  B7) a 2-nitro-1H-pyrrol-1-yl group (Pn);
  B8) a 2-nitro-4-iodo-1H-pyrrol-1-yl group;
  B9) a 2-nitro-4-methyl-1H-pyrrol-1-yl group;
  B10) a 2-nitro-4-(1-propyn-1-yl)-1H-pyrrol-1-yl group;
  B11) a 2-nitro-4-(2-substituted aminovinyl)-1H-pyrrol-1-yl group; and
  B12) a 2-nitro-4-(3-substituted amino-1-propyn-1-yl)-1H-pyrrol-1-yl group.

Among the above bases, B1 to B6 are members of "Pa" or "Pa derivative," while B7 to B12 are members of "Pn" or "Pn derivative."

More preferred is B1) a 2-formyl-1H-pyrrol-1-yl group (Pa) (Compound 19 in Example I) or B4) a 2-formyl-4-(1-propyn-1-yl)-1H-pyrrol-1-yl group (Compound 20 in Example I).

A nucleoside or nucleotide having a base of formula 2 in the present invention may be synthesized in a known manner. Taking Pa as an example, starting materials (e.g., pyrrole-2-carbaldehyde) can be purchased from, for example, Aldrich [1003-29-8] or Merck [807574]. Likewise, Pa derivatives may be synthesized by being derived from Pa, in principle. For example, a derivative having propyne introduced at the 4-position of Pa can be found in Bioorg. Med. Chem. Lett., 13, p. 4515-4518 (2003) (Non-patent Document 28).

In Example I-3-(12) described later, 1-(β-D-ribofuranosyl) pyrrole-2-carbaldehyde (Compound 17) was synthesized from pyrrole-2-carbaldehyde. Likewise, in Example I-3-(13), 4-propynyl-1-(β-D-ribofuranosyl)pyrrole-2-carbaldehyde (Compound 18) was synthesized from 4-propynyl-2-pyrrole-carbaldehyde (Compound 16) (Non-patent Document 40). Moreover, their nucleoside 5'-triphosphates and 5'-γ-amidot-riphosphates were synthesized (Compounds 19 and 20).

Further, in Example II-2 described later, nucleoside 5'-triphosphates of 2-nitropyrrole (Compound 1) (Pn) were synthesized from 2-nitropyrrole (Compound 1) (Non-patent Document 49).

The present invention provides a nucleic acid in which a nucleotide having a base of formula 1 forms a base pair with a nucleotide having a base of formula 2. As used herein, the term "nucleic acid" is intended to mean a molecule of a nucleic acid strand in which more than one nucleotide is linked in the direction of 5'→3'. The nucleic acid of the present invention encompasses single-stranded or double-stranded RNA or DNA. The double-stranded nucleic acid may be DNA/DNA, RNA/RNA, or DNA/RNA. DNA also includes cDNA obtained by reverse transcription using RNA as a template. Alternatively, the nucleic acid may form a triplex, a quadruplex, etc.

With the aim of further expansion of nucleic acid functions, the inventors of the present invention have attempted to design nucleosides or nucleotides having unnatural bases. Embodiments of newly developed artificial base pairs include a base pair between a nucleotide having a base of formula 1 and a nucleotide having a base of formula 2. Such a nucleotide having a base of formula 1 and such a nucleotide having a base of formula 2 each function as a substrate and as a template with high efficiency and/or high selectivity in the mechanisms of both replication and transcription.

Although there is no significant hydrogen bonding interaction between bases of formulae 1 and 2, e.g., between Ds and Pa (non-hydrogen-bonded Ds-Pa base pair), the efficiency and selectivity of Ds-Pa base pairing is as high as that of natural base pairing. This Ds-Pa base pair shows a higher efficiency than the previously developed hydrophilic s-z base pair. The complementary shapes of Ds and Pa are fitted to each other, but their shapes differ from those of natural purines and pyrimidines. This specific stereochemical fitting would eliminate undesired base pairing with natural bases, thereby resulting in high selectivity between Ds and Pa during replication and transcription. In this way, shape complementarity plays an important role in specific base pairing during replication and transcription.

In the present invention, a nucleotide having a base of formula 1 and a nucleotide having a base of formula 2 are present in two separate nucleic acid strands and can form a duplex through base pairing. Alternatively, these nucleotides may be present in the same single-stranded nucleic acid. In this case, such a single strand may form a loop structure through base pairing.

In the present invention, such a nucleotide having a base of formula 1 or 2 can be incorporated into nucleic acids such as DNA or RNA through replication, transcription or reverse transcription reaction. Alternatively, such a nucleotide may be incorporated into DNA or RNA through chemical synthesis, as in the case of nucleosides or nucleotides having natural bases.

These replication, transcription and reverse transcription reactions may be accomplished according to known techniques. Without being limited thereto, for example, it is possible to use T7 RNA polymerase (Takara or other suppliers) for transcription, Klenow fragment (KF) for replication, and AMV Reverse Transcriptase XL (AMV-RT, Life Science) for reverse transcription.

Without being limited thereto, in one embodiment, the nucleic acid of the present invention forms a base pair(s) in the step of replication, transcription or reverse transcription of the nucleic acid. In a case where the nucleic acid of the present invention forms a base pair(s) in the transcription step, a nucleotide having a base of formula 1 may be a part of DNA, while a nucleotide having a base of formula 2 may be a part of RNA, or alternatively, vice versa.

The unnatural base pair system of the present invention is summarized in FIG. 1c. Effects provided by the system of the present invention during replication are shown in, for example, FIGS. 2b to 2e, FIGS. 3b to 3i, and FIGS. 8 to 20. Effects provided by the system of the present invention during transcription are shown in, for example, FIGS. 4c to 4e and FIGS. 5a to 5c.

Method for Nucleic Acid Preparation

The present invention also provides a method for preparing a nucleic acid containing a nucleotide having a base represented by the following formula 1:

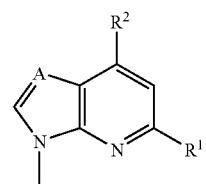

[Formula 19]

[wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH],
wherein the method comprises effecting transcription, reverse transcription or replication by using, as a template, a nucleic acid containing a nucleotide having a base represented by the following formula 2:

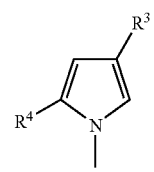

[Formula 20]

[wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group],
whereby the nucleotide having a base of formula 1 is incorporated at a site complementary to the nucleotide having a base of formula 2.

The present invention also provides a method for preparing a nucleic acid containing a nucleotide having a base represented by the following formula 2:

[Formula 21]

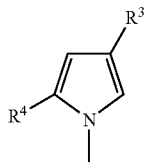

[wherein
R³ is a group selected from hydrogen, an iodo group, a substituted or unsubstituted C₁-C₃ alkyl group, a substituted or unsubstituted C₂-C₃ alkenyl group, or a substituted or unsubstituted C₂-C₃ alkynyl group, and
R⁴ is a formyl group or a nitro group],
wherein the method comprises effecting transcription, reverse transcription or replication by using, as a template, a nucleic acid containing a nucleotide having a base represented by the following formula 1:

[Formula 22]

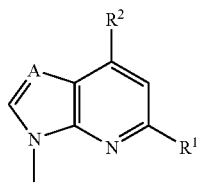

[wherein
R¹ is hydrogen or an amino group,
R² a substituted or unsubstituted 2-thienyl group, a substituted or unsubstituted 2-thiazolyl group, or a substituted or unsubstituted 1H-2-imidazolyl group, and
A is N or CH],
whereby the nucleotide having a base of formula 2 is incorporated at a site complementary to the nucleotide having a base of formula 1.

The nucleotide having a base of formula 1 and the nucleotide having a base of formula 2 are as defined herein above in the section "Nucleic acids of the present invention based on artificial base pairing."

The present invention further aims to provide such a nucleic acid containing a nucleotide having a base of formula 1 and/or 2, which is prepared by the above method of the present invention.

The nucleic acid incorporating the nucleotide(s) of the present invention may be used as tRNA, mRNA, antisense DNA or RNA, a ribozyme or an aptamer. The term "antisense DNA or RNA" refers to DNA or RNA capable of inhibiting the expression of a specific gene. It was named to mean that such DNA or RNA is complementary to the full-length or partial sequence of a target gene sequence (sense strand). Antisense DNA or RNA may be used as a tool for artificial regulation of gene expression. Because of containing unnatural bases, such antisense DNA or RNA incorporating the nucleotide(s) of the present invention can be designed to have a different complementarity to a target when compared to the case of using natural bases only. The term "ribozyme" is a generic name for catalysts composed of RNA. The term "aptamer" refers to an in vitro-selected nucleic acid having the ability to bind to a specific molecule such as a protein.

The nucleic acid (DNA or RNA) (e.g., mRNA, synthetic RNA) incorporating the nucleotide(s) of the present invention may also encode all or part of a protein or peptide. The nucleic acid of the present invention may be used, e.g., as a gene fragment or a probe. The present invention also encompasses the following embodiments: partial or complete replacement of native genes by the nucleic acids of the present invention; addition of one or more nucleotides of the present invention to native genes; or combinations thereof.

Furthermore, the nucleic acids of the present invention incorporating nucleotides having unnatural bases may also be used in RNA interference (RNAi). RNA interference is a phenomenon in which double-stranded RNA (dsRNA) induces mRNA degradation in a sequence-specific manner and hence inhibits gene expression. In a typical example of RNA interference, dsRNA is processed by Dicer belonging to the RNaseIII family into siRNA (short interfering RNA) of approximately 21 to 23 bases in length, which has a 3'-terminal overhang of approximately 2 bases. siRNA is associated into an siRNA-protein complex called RISC and induces mRNA degradation in a sequence-specific manner. RNA interference is shown to be a phenomenon conserved among a wide range of organism species including mammals (e.g., human, mouse), nematodes, plants, *drosophila* and fungi. The nucleic acids of the present invention incorporating nucleotides having unnatural bases can be used as siRNA in RNA interference or as a part of mRNA to be degraded.

Ribonucleoside 5'-triphosphates

The present invention further provides a ribonucleoside 5'-triphosphate having a base represented by the following formula 1:

[Formula 23]

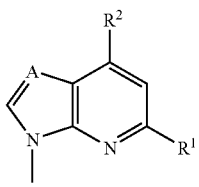

[wherein
R¹ is hydrogen or an amino group,
R² is a substituted or unsubstituted 2-thienyl group, a substituted or unsubstituted 2-thiazolyl group, or a substituted or unsubstituted 1H-2-imidazolyl group, and
A is N or CH].
The structure of formula 1 including substituents is as defined above for deoxyribonucleotides.

The present invention furthermore provides a ribonucleoside 5'-triphosphate having a base represented by the following formula 2:

[Formula 24]

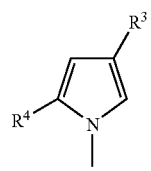

[wherein
R³ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
R⁴ is a formyl group or a nitro group].

The structure of formula 2 including substituents is as defined above for deoxyribonucleotides.

Further, the present invention provides a 5'-O-(4,4'-dimethoxytrityl)-3'-O-(2-cyanoethyl N,N-diisopropylphosphoroamidite)deoxyribonucleoside having a base represented by the following formula 3:

[Formula 25]

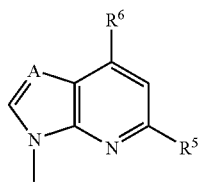

[wherein
R⁵ is hydrogen or a substituted amino group,
R⁶ is a substituted or unsubstituted 2-thienyl group, a substituted or unsubstituted 2-thiazolyl group, or a substituted or unsubstituted 1H-2-imidazolyl group, and
A is N or CH].

The substituted amino group listed as R⁵ includes an amino group substituted with a methyl group, an isobutyryl group, a benzoyl group or the like.

R⁶ is the same as R² in formula 1.

As an example of compounds falling within formula 3, Compound 8 was synthesized in Example I.

Compounds of formula 3 are useful, for example, as starting materials in chemical synthesis of DNA templates for replication and transcription.

Furthermore, the present invention provides a 5'-O-(4,4'-dimethoxytrityl)-3'-O-(2-cyanoethyl N,N-diisopropylphosphoroamidite)deoxyribonucleoside having a base represented by the following formula 4:

[Formula 26]

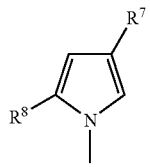

[wherein
R⁷ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
R⁸ is a formyl group or a nitro group,
excluding the case where R⁷ is hydrogen or a 1-propynyl group and R⁸ is a formyl group].

R⁷ is the same as R³ in formula 2.
R⁸ is the same as R⁴ in formula 2.

Compounds of formula 4 are useful, for example, as starting materials in chemical synthesis of DNA templates for replication and transcription.

BRIEF DESCRIPTION OF THE DRAWINGS

FIGS. 1a to 1c show an unnatural base pair system which allows specific replication and transcription. FIG. 1a shows an unnatural Ds-Pa base pair, along with natural base pairs.

[FIG. 1b] FIGS. 1a to 1c show an unnatural base pair system which allows specific replication and transcription. FIG. 1b shows the structures of unmodified 5'-triphosphate (dNTP) and modified 5'-γ-amidotriphosphate for use as substrates for PCR and primer extension.

[FIG. 1c] FIGS. 1a to 1c show an unnatural base pair system which allows specific replication and transcription. FIG. 1c shows an unnatural base pair system which functions in PCR amplification, primer extension, DNA sequencing and T7 transcription.

FIGS. 2a to 2e show single nucleotide insertion and primer extension experiments with an unnatural base pair system based on Ds-Pa base pairing. FIG. 2a shows the sequences of template-primer duplexes for use in the single nucleotide insertion experiment.

[FIG. 2b] FIGS. 2a to 2e show single nucleotide insertion and primer extension experiments with an unnatural base pair system based on Ds-Pa base pairing. FIG. 2b shows the incorporation efficiency of each unmodified substrate (dNTP) opposite each template base by KF exo⁻.

[FIG. 2c] FIGS. 2a to 2e show single nucleotide insertion and primer extension experiments with an unnatural base pair system based on Ds-Pa base pairing. FIG. 2c shows the incorporation efficiency of each substrate (unmodified substrate dNTP, N=Pa, G, C and T, and modified substrate dN'TP$_N$, N=Ds and A) opposite each template base by KF exo⁻.

[FIG. 2d] FIGS. 2a to 2e show single nucleotide insertion and primer extension experiments with an unnatural base pair system based on Ds-Pa base pairing. FIG. 2d shows the results of primer extension by KF exo⁺ for 5 minutes using a Ds-containing template with dPaTP and natural substrates in the presence or absence of dDsTP or dDsTP$_N$.

[FIG. 2e] FIGS. 2a to 2e show single nucleotide insertion and primer extension experiments with an unnatural base pair system based on Ds-Pa base pairing. FIG. 2e shows 3 minute primer extension by KF exo⁻ or exo⁺ using a Pa-containing template or a natural template with a series of substrates ($D_{SN}$=dDsTP$_N$ and $A_N$=dATP$_N$). Since dGTP is absent from each reaction, the full-length products are mainly 33-mers.

FIGS. 3a to 3i show DNA sequencing and PCR amplification of DNA fragments containing a Ds-Pa base pair. FIG. 3a shows the experimental scheme. A double-stranded DNA fragment (150-mer, DNA1) was prepared by primer extension using chemically synthesized DNA fragments (91-mer and 81-mer) containing Ds and Pa.

[FIG. 3b] FIGS. 3a to 3i show DNA sequencing and PCR amplification of DNA fragments containing a Ds-Pa base pair. FIG. 3b shows agarose gel analysis of original DNA fragments (0 cycle) and their PCR products after 5 and 10 cycles. DNA1 was amplified by PCR with 0.04 units/µl VENT DNA polymerase under the following cycle conditions: 94° C. for 0.5 minutes, 45° C. for 0.5 minutes, and 65° C. for 4 minutes. DNAcont1 composed only of natural bases was amplified by PCR with 0.01 units/µl VENT DNA polymerase under the following cycle conditions: 94° C. for 0.5 minutes, 45° C. for 0.5 minutes, and 72° C. for 1 minute.

[FIG. 3c] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. Sequencing in the presence (c-f) or absence (g-i) of dPa'TP performed on the original DNA1 (c, g) and its PCR products after 10 cycles (d, g) an 10+10 cycles (e, h) using the unnatural base pair system or after 10 cycles using natural substrates alone (f).

FIG. 3c shows the results of sequencing with dPa'TP obtained before PCR (0 cycle). The base at position 40 is a base corresponding to a site complementary to Ds in the template, and Pa' is incorporated at this site during sequencing reaction. Thus, peaks of A, G, C and T all disappear only at this site.

[FIG. 3d] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. FIG. 3d shows the results of sequencing with dPa'TP obtained after 10 cycle PCR. The base at position 40 is a base corresponding to a site complementary to Ds in the template, and Pa' is incorporated at this site during sequencing reaction. Thus, peaks of A, G, C and T all disappear only at this site.

[FIG. 3e] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. FIG. 3e shows the results of sequencing with dPa'TP obtained after 10+10 cycle PCR. The base at position 40 is a base corresponding to a site complementary to Ds in the template, and Pa' is incorporated at this site during sequencing reaction. Thus, peaks of A, G, C and T all disappear only at this site.

[FIG. 3f] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. FIG. 3f shows the results of sequencing with dPa'TP obtained after PCR (10 cycles) with natural substrates alone, without using Ds and Pa substrates. The Ds-Pa base pair in the template DNA1, which corresponds to the base at position 40, is completely replaced with an A-T base pair (base T at position 40).

[FIG. 3g] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. FIG. 3g shows the results of sequencing without dPa'TP obtained before PCR (0 cycle). The base at position 40 is a base corresponding to a site complementary to Ds in the template, but there is no base which forms a specific base pair with Ds, so that the subsequent peaks almost disappear.

[FIG. 3h] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. FIG. 3h shows the results of sequencing without dPa'TP obtained after 10 cycle PCR. The base at position 40 is a base corresponding to a site complementary to Ds in the template, but there is no base which forms a specific base pair with Ds, so that the subsequent peaks almost disappear. However, non-specific incorporation (read-through) of bases is also observed. These read-through peaks were slightly increased with an increase in the number of cycles required for PCR amplification.

[FIG. 3i] FIGS. 3a to 3i show DNA sequencing and PCR amplification of DNA fragments containing a Ds-Pa base pair. FIGS. 3c to 3i show the results of PCR and sequencing performed according to the procedures explained for FIGS. 3a and 3b. FIG. 3i shows the results of sequencing without dPa'TP obtained after 10+10 cycle PCR. The base at position 40 is a base corresponding to a site complementary to Ds in the template, but there is no base which forms a specific base pair with Ds, so that the subsequent peaks almost disappear. However, non-specific incorporation (read-through) of bases is also observed. These read-through peaks were slightly increased with an increase in the number of cycles required for PCR amplification.

FIG. 4 shows T7 transcription mediated by Ds-Pa base pairing. FIGS. 4a and 4b show the experimental schemes.

[FIG. 4b] FIG. 4 shows T7 transcription mediated by Ds-Pa base pairing. FIGS. 4a and 4b show the experimental schemes.

FIG. 4 shows T7 transcription mediated by Ds-Pa base pairing. FIG. 4c shows gel electrophoresis of transcripts obtained using a template (N=Ds, Pa, Pa', A or C) with natural NTPs (1 mM) in the presence (1 mM) or absence of PaTP, Pa'TP or DsTP. The transcripts were labeled with $[\gamma-^{32}P]$ GTP. The yield of each transcript was determined in comparison with the yield of a natural transcript from a template composed only of natural bases (N=A or C), and the transcription efficiency (yield) was averaged from 3 data sets for each case.

FIG. 4 shows T7 transcription mediated by Ds-Pa base pairing. FIGS. 4d and 4e show the results of 2D-TLC analysis on labeled ribonucleoside 3'-monophosphates obtained from nuclease digestion of transcripts (17-mer).

[FIG. 4e] FIG. 4 shows T7 transcription mediated by Ds-Pa base pairing. FIGS. 4d and 4e show the results of 2D-TLC analysis on labeled ribonucleoside 3'-monophosphates obtained from nuclease digestion of transcripts (17-mer).

FIG. 5 shows specific T7 transcription of tRNA molecules containing unnatural anticodons. FIG. 5a shows the results of gel electrophoresis on tRNA transcripts obtained using templates (DNA11 to DNA14 and DNAcont4) with natural NTPs (2 or 3 mM) in the presence of Pa'TP (3 mM) or DsTP (2 mM). The transcripts were internally labeled with $[\alpha-^{32}P]$GTP. The yield of each transcript was determined in comparison with the yield of a suppressor $tRNA_{CUA}$ transcript from DNAcont4, and the transcription efficiency (yield) was averaged from 3 data sets for each case.

FIG. 5 shows specific T7 transcription of tRNA molecules containing unnatural anticodons. FIGS. 5b and 5c show the results of 2D-TLC analysis on labeled ribonucleoside 3'-monophosphates obtained from nuclease digestion of $tRNA_{CPA'A}$ and $tRNACUDs$ transcripts.

[FIG. 5c] FIG. 5 shows specific T7 transcription of tRNA molecules containing unnatural anticodons. FIGS. 5b and 5c show the results of 2D-TLC analysis on labeled ribonucleoside 3'-monophosphates obtained from nuclease digestion of $tRNA_{CPA'A\ and\ tRNACUDs}$ transcripts.

FIG. 5 shows specific T7 transcription of tRNA molecules containing unnatural anticodons. FIG. 5d shows aminoacylation of tRNA transcripts in an E. coli cell-free system (RTS-100, Roche). The tRNA transcripts internally labeled with $[\alpha-^{32}P]$GTP were incubated in the cell-free system at 30° C. for 30 minutes, and the aminoacylated tRNAs were then analyzed by electrophoresis on a 10% polyacrylamide gel containing 0.2 M Tris-acetate (pH 4.75) and 3 mM EDTA.

[FIG. 6] FIG. 6 shows the sequences of DNA fragments for use in PCR, sequencing and transcription experiments.

[FIG. 7a] FIG. 7 shows the sequences of chemically synthesized DNA fragments.

[FIG. 7b] FIG. 7 shows the sequences of chemically synthesized DNA fragments.

FIG. 8 shows dye terminator sequencing of DNA1 containing 0-10% DNAcontl in the absence of dPa'TP. The fidelity of Ds-Pa base pairing during PCR can be studied by comparing this peak pattern with that of DNA fragment PCR containing a Ds-Pa base pair.

[FIG. 9] FIG. 9 shows dye terminator sequencing of PCR products from DNA1 with 300 μM dDSTP$_N$, dPaTP, dATP, dGTP, dCTP and dTTP. Sequencing in the presence (a-c) or absence (d-f) of dPa'TP performed on the original DNA1 (a, d) and its PCR products after 10 cycles (b, e) or 10+10 cycles (c, f). When using dATP instead of dATP$_N$ to perform PCR, the fidelity was significantly reduced (e, f).

[FIG. 10] FIG. 10 shows autoradiographs of PCR products obtained with a $^{32}$P-labeled 5'- or 3'-primer. PCR was performed using $^{32}$P-labeled 5'- and non-labeled 3'-primers or $^{32}$P-labeled 3'- and non-labeled 5'-primers in 100 μl buffer solution for Vent DNA polymerase containing DNA1 (a) or DNAcontl (b). An aliquot (10 μl) from each reaction solution after 1, 3, 5, 10 or 15 PCR cycles was analyzed on a 10% polyacrylamide-7 M urea gel. The products on the gel were analyzed and quantified with a bio-imaging analyzer. The efficiency per cycle (Y) was calculated with KaleidaGraph using a general curve fit: $N_f=N_0\times(1+Y)^n$ [where n is the number of PCR cycles (n=1, 3, 5 and 10), $N_0$ is the initial copy number, and $N_f$ is the copy number of a product after n cycles]. $N_f$ was determined from the following equation: $N_f=N_0+P_0\times(I_{full}/I_{total})$ [where $P_0$ is the number of $^{32}$P-labeled primer molecules, $I_{full}$ is the intensity of a band corresponding to the full-length product, and $I_{total}$ is the total intensity of bands in the lane]. The Y values thus determined are shown in the table below.

TABLE 2-2

| PCR condition | substrate | elongation step | Vent DNA polymerase (unit/μl) | Y values 5'-/3'-labeled primer |
|---|---|---|---|---|
| Unnatural using DNA1(a) | 0.3 mM dNTPs and dNTP$_N$s | 65° C., 4 min | 0.04 | 0.38/0.29 |
| Conventional using DNAcontl(b) | 0.2 mM natural dNTPs | 72° C., 1 min | 0.01 | 0.43/0.35 |

Figure 11:
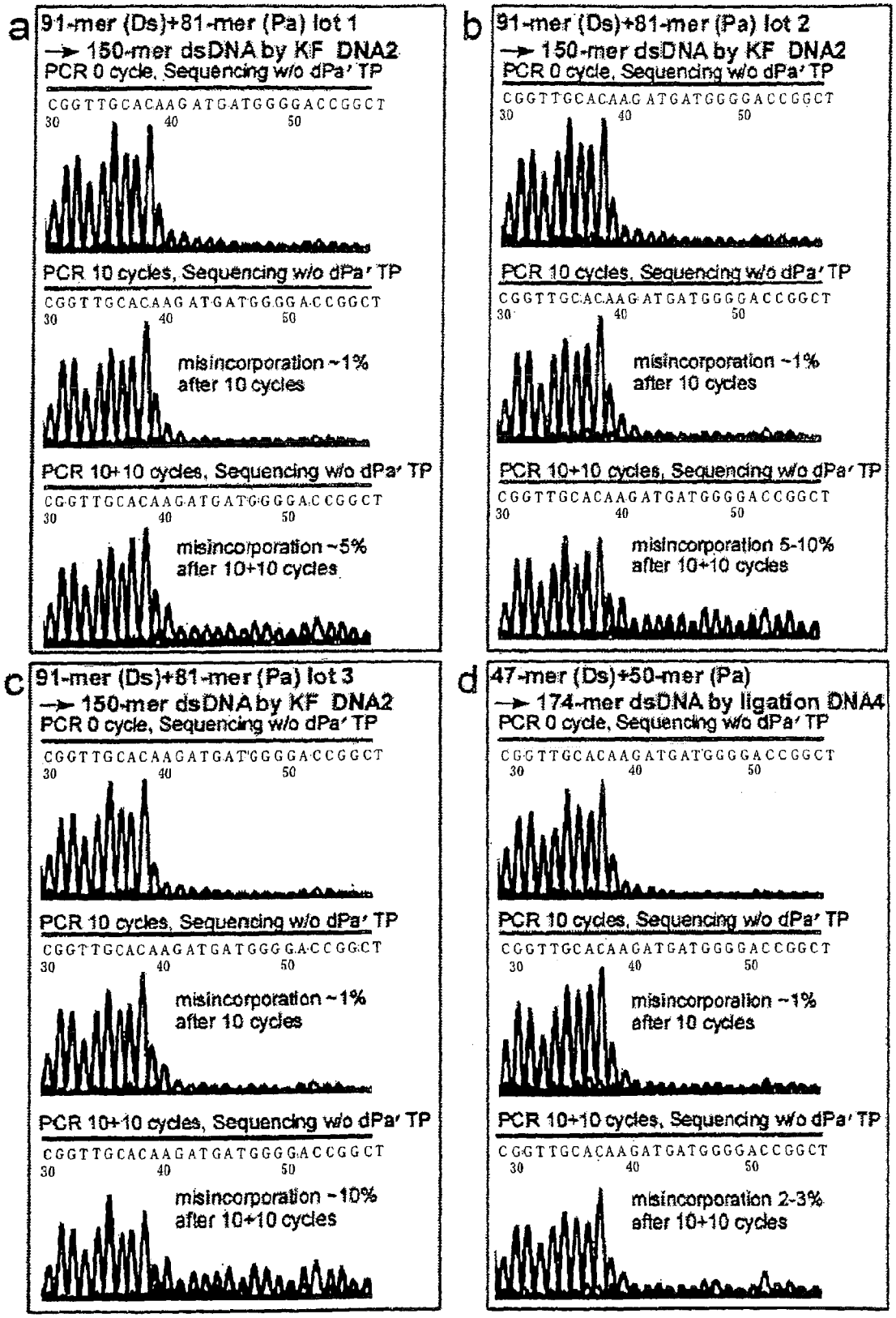

[FIG. 11] FIG. 11 shows the results of dye terminator sequencing without dPa'TP obtained for PCR products of DNA2 and DNA4 fragments prepared from different samples (a-d) of chemically synthesized fragments containing Ds and Pa. These results indicate that the purity of the chemically synthesized DNA fragments containing a Ds-Pa base pair affects their peak patterns after PCR. This means that the previously determined fidelity of Ds-Pa base pairing during PCR (99.8%) depends on the purity of chemically synthesized DNA fragments. Thus, the fidelity appears to be much higher than 99.8%

[FIG. 12] FIG. 12 shows the amplification efficiency of PCR products from DNA1, DNA3 to DNA10 and DNAcontl, as determined by agarose gel electrophoresis. The PCR products were detected on a 4% agarose gel and stained with ethidium bromide. The stained bands were then quantified for their intensity using a Molecular Imager FX Pro system and Quantity One software (Bio-Rad). The amplification efficiency was determined using the following equation: (Intensity of PCR product)/(Intensity of input DNA for PCR). The efficiency was averaged from 3 to 4 data sets. Standard deviations are given in parentheses.

Figure 13:
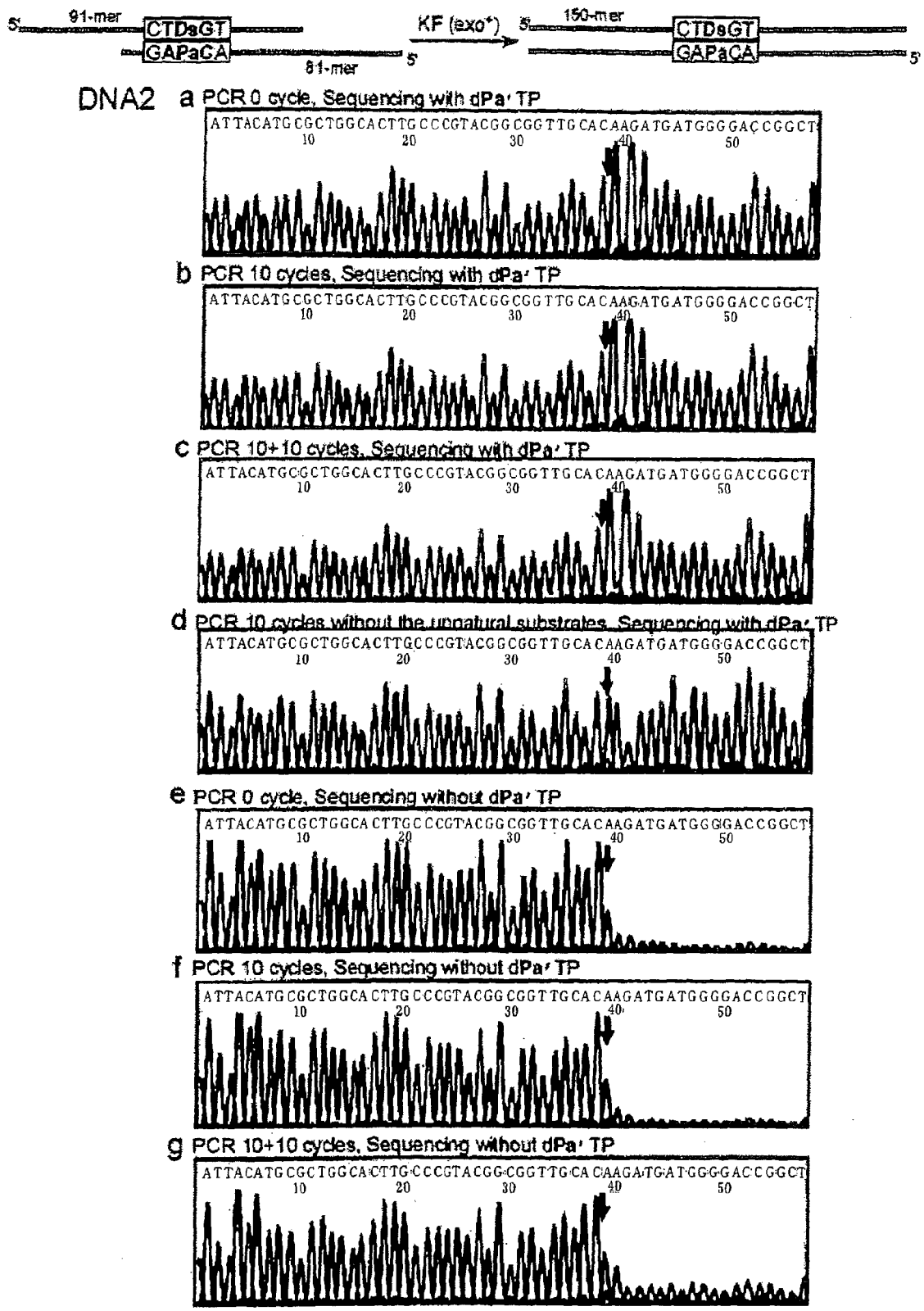

[FIG. 13] FIG. 13 shows the results of dye terminator sequencing obtained for PCR products from DNA2 with primer 2.

Figure 14:
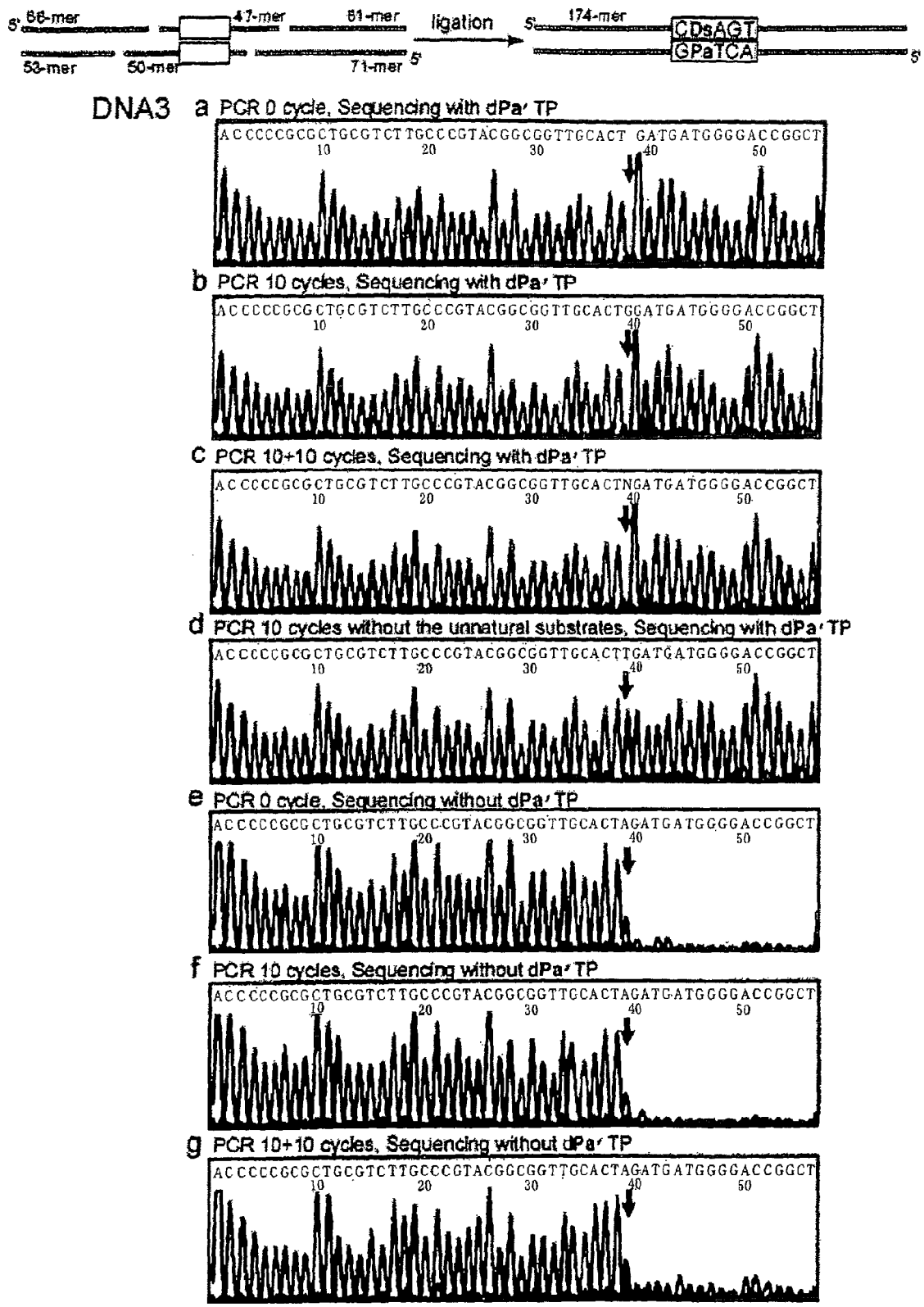

[FIG. 14] FIG. 14 shows the results of dye terminator sequencing obtained for PCR products from DNA3 with primer 2.

Figure 15:
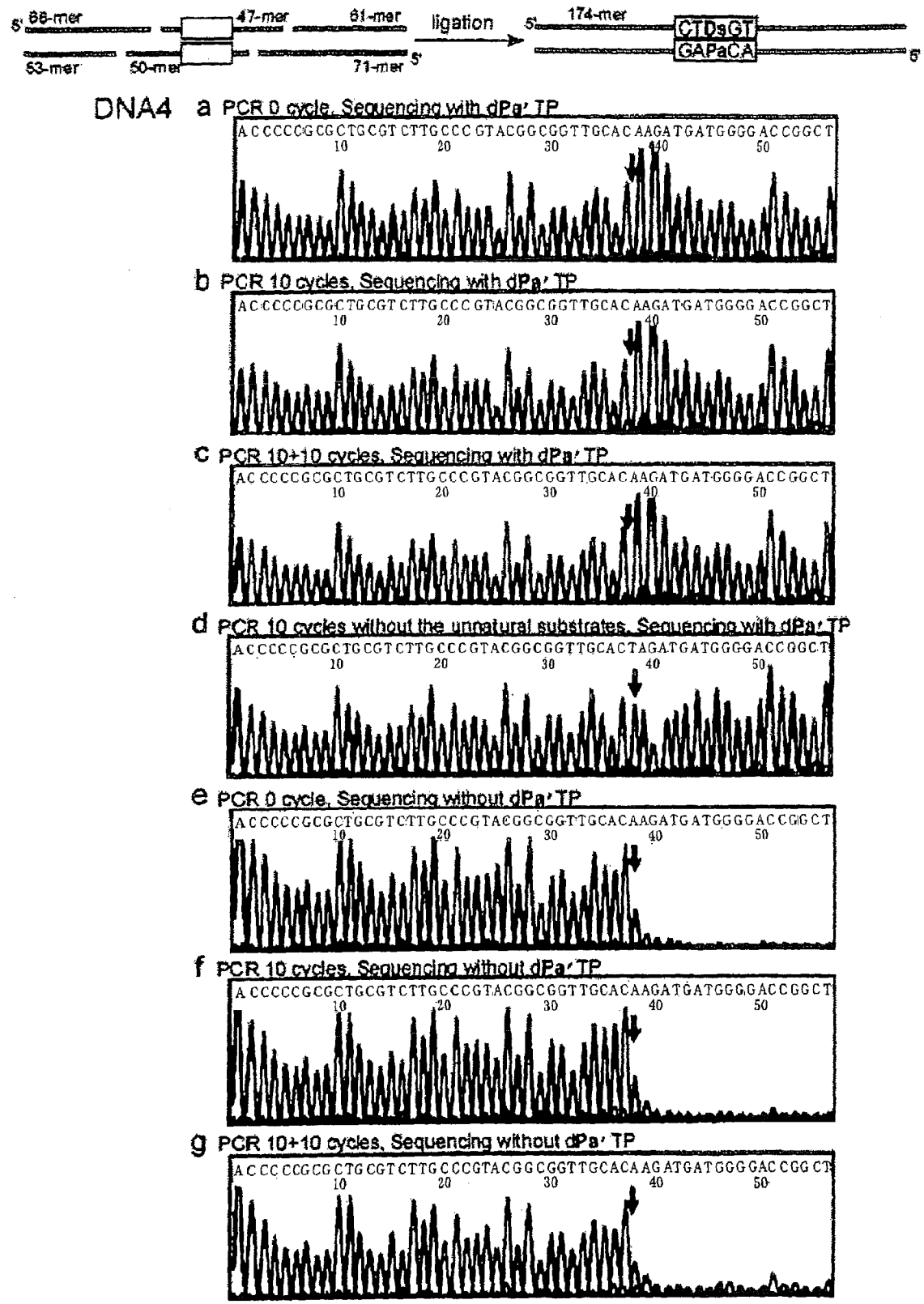

[FIG. 15] FIG. 15 shows the results of dye terminator sequencing obtained for PCR products from DNA4 with primer 2.

Figure 16:
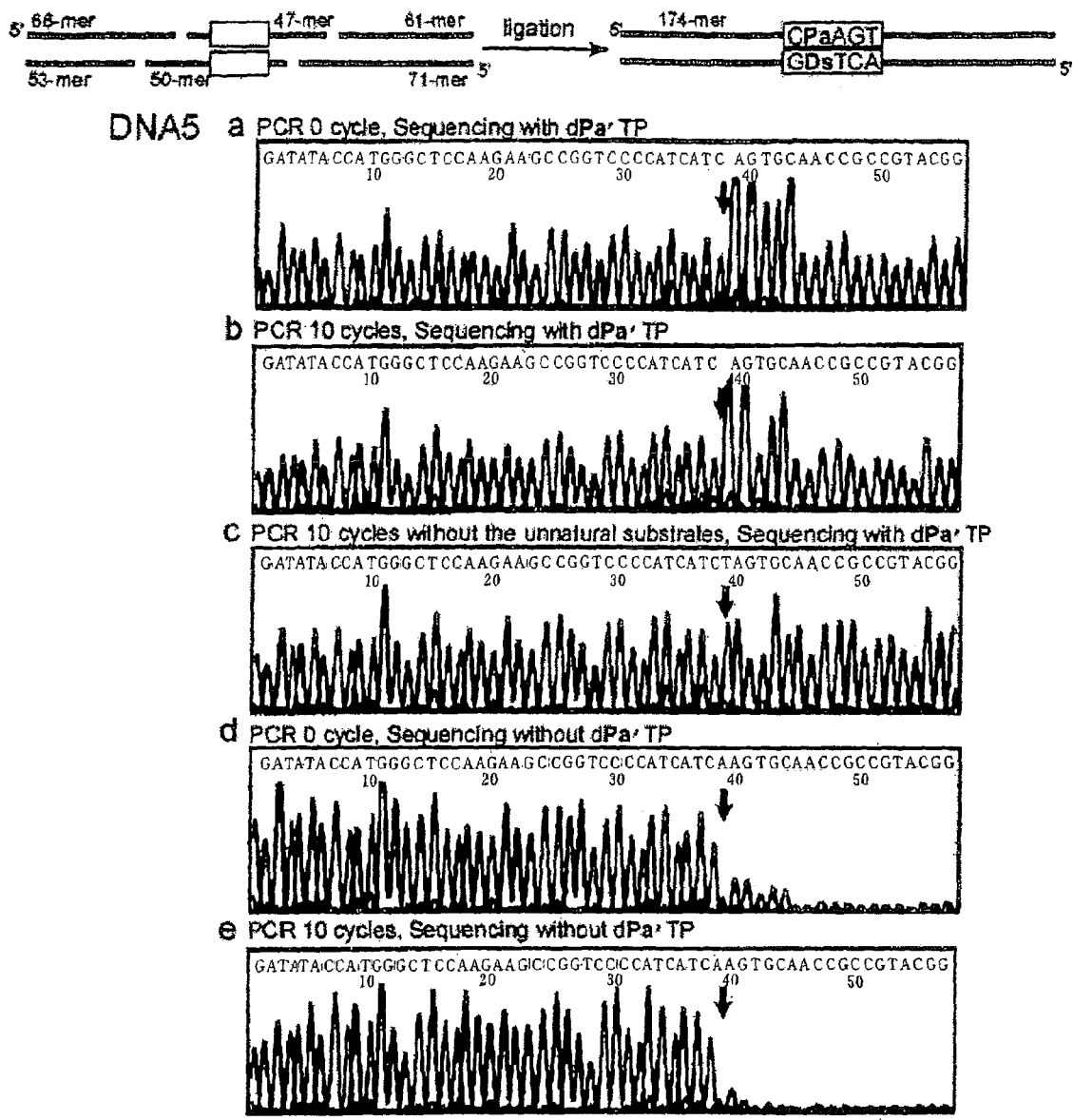

[FIG. 16] FIG. 16 shows the results of dye terminator sequencing obtained for PCR products from DNA5 with primer 1.

Figure 17:
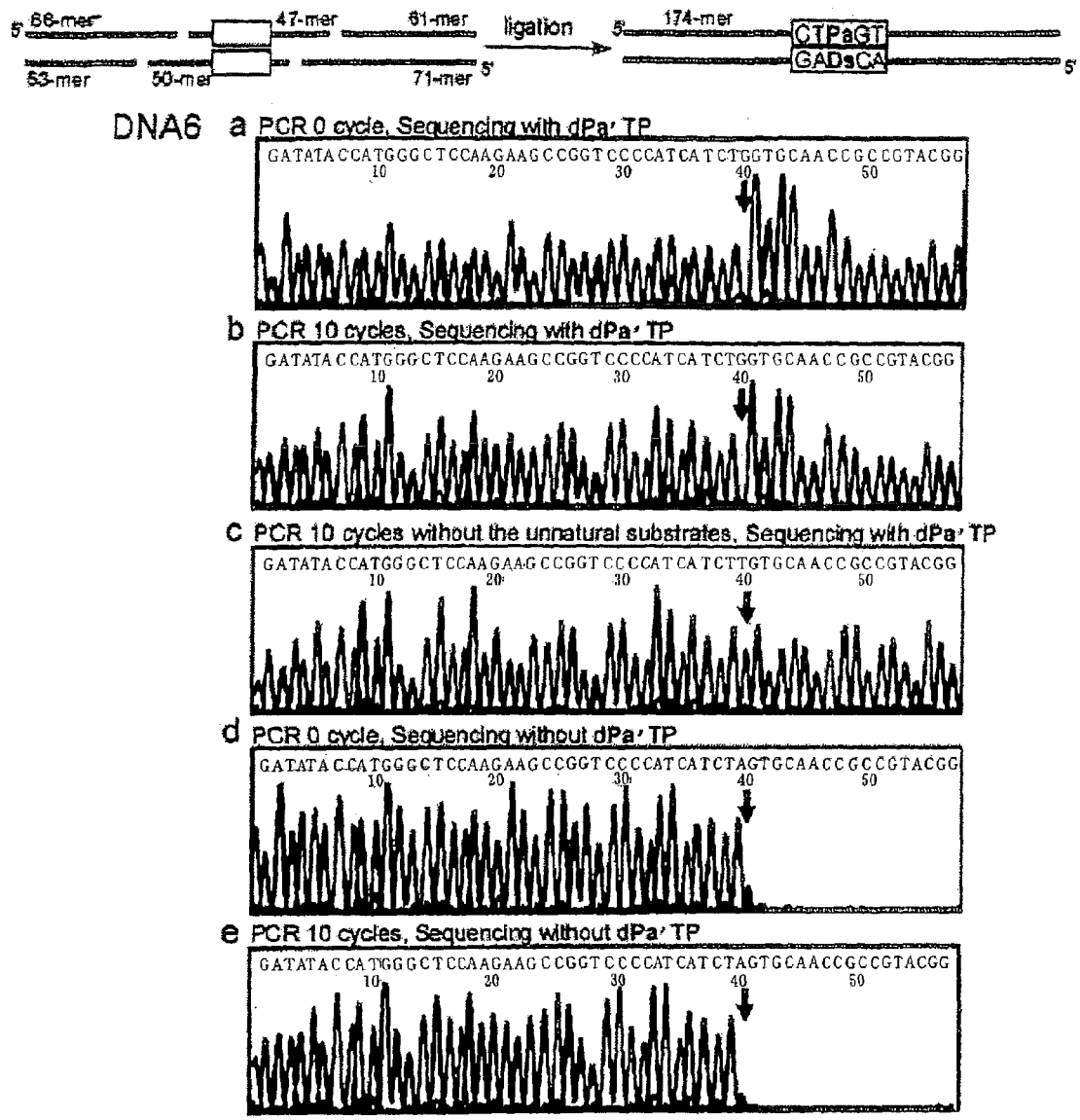

[FIG. 17] FIG. 17 shows the results of dye terminator sequencing obtained for PCR products from DNA6 with primer 1.

Figure 18:
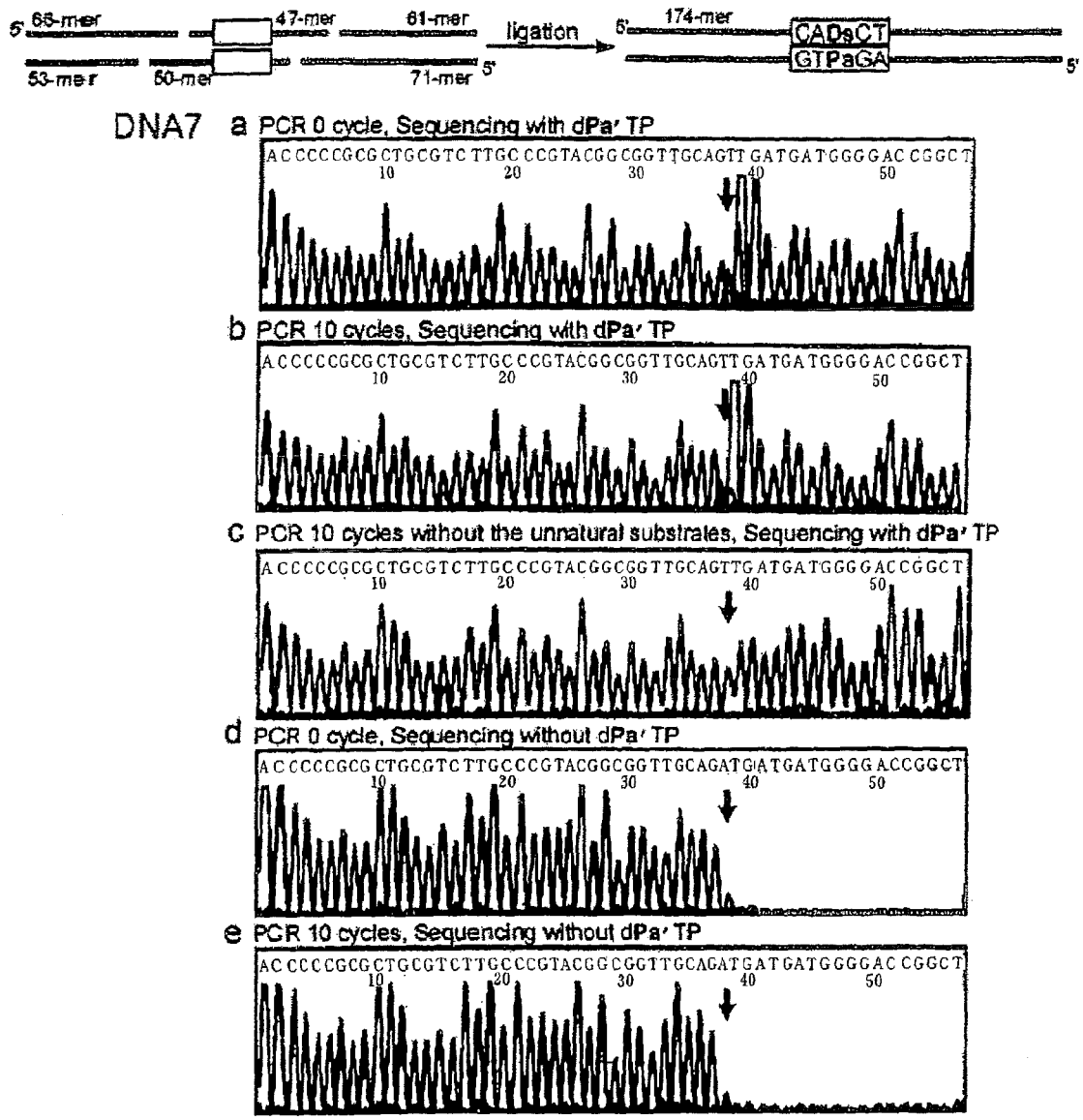

[FIG. 18] FIG. 18 shows the results of dye terminator sequencing obtained for PCR products from DNA7 with primer 2.

Figure 19:
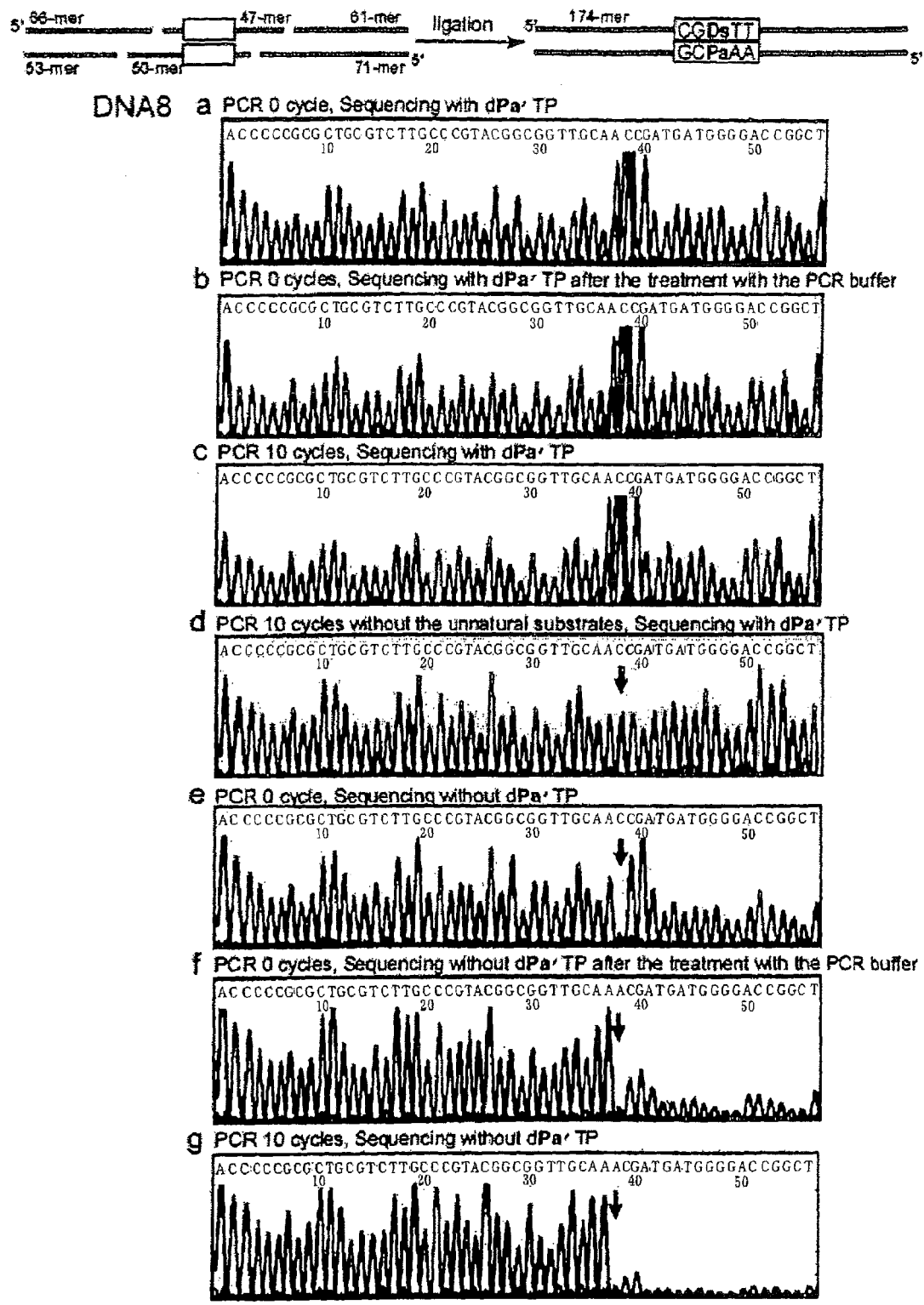

[FIG. 19] FIG. 19 shows the results of dye terminator sequencing obtained for PCR products from DNA8 with primer 2.

Figure 20:
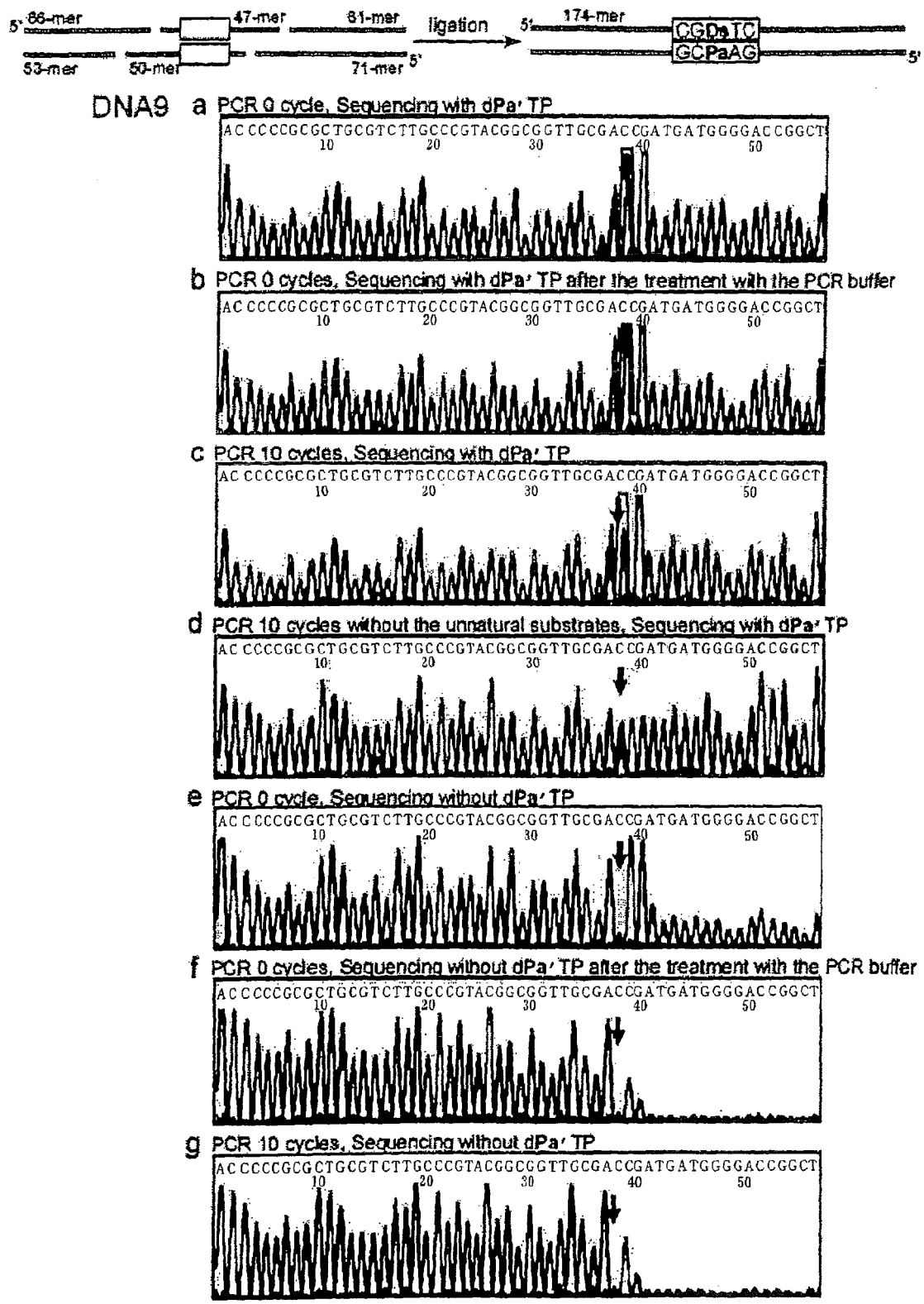

[FIG. 20] FIG. 20 shows the results of dye terminator sequencing obtained for PCR products from DNA9 with primer 2.

[FIG. 21] FIG. 21 shows a scheme for aminoacylation of unnatural anticodon-containing tRNAs in an *E. coli*-derived cell-free translation system.

[FIG. 22] FIG. 22 shows a synthesis scheme for nucleoside derivatives of 7-(2-thienyl)-3H-imidazo[4,5-b]pyridine. Reagents and abbreviations: (a) dichlorobis(triphenylphosphine)palladium, 2-(tributylstanyl)thiophene, DMF; (b) palladium carbon, sodium borohydride, ethanol, ethyl acetate; (c) formic acid; (d) NaH, 2-deoxy-3,5-di-O-p-toluoyl-α-D-erythro-pentofuranosyl chloride, CH$_3$CN; (e) NH$_3$, methanol; (f) and (l) 4,4'-dimethoxytrityl chloride, pyridine; (g) 2-cyanoethyl tetraisopropylphosphordiamidite, tetrazole, CH$_3$CN; (h) and (m) acetic anhydride, pyridine, then dichloroacetic acid, dichloromethane; (i) and (n) 2-chloro-4H-1,3, 2,-benzodioxaphosphorin-4-one, dioxane, pyridine, tributylamine, bis(tributylammonium)pyrophosphate, DMF, then I$_2$/pyridine, water, NH$_4$OH (for 5'-triphosphate), I$_2$/pyridine, NH$_4$OH (for 5'-γ-amidotriphosphate); (j) tetra-O-acetyl-β-D-ribofuranose, chloroacetic acid; (k) ammonia-saturated methanol. Tol: toluoyl; DMT: 4,4'-dimethoxytrityl; Ac: acetyl.

Figure 23:
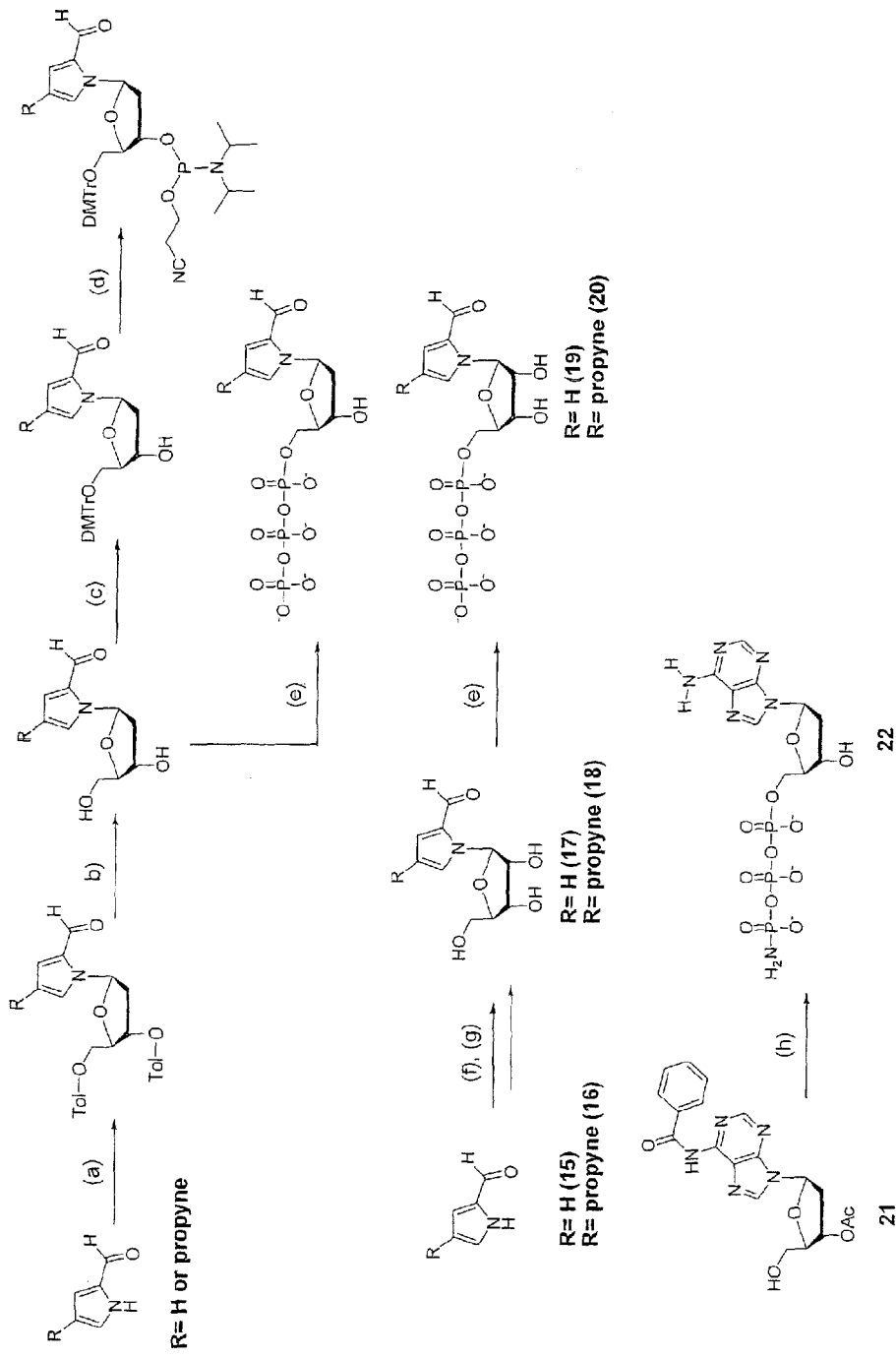

[FIG. 23] FIG. 23 shows a synthesis scheme for nucleoside derivatives of pyrrole-2-carbaldehyde and 4-propynylpyrrole-2-carbaldehyde, as well as a synthesis scheme for 6-amino-9-(2-deoxy-β-D-ribofuranosyl)purine 5'-γ-amidotriphosphate. Reagents and abbreviations: (a) NaH, 2-deoxy-3,5-di-O-p-toluoyl-α-D-erythro-pentofuranosyl chloride, CH$_3$CN; (b) ammonia-saturated methanol; (c) 4,4'-dimethoxytrityl chloride, pyridine; (d) 2-cyanoethyl-N,N'-diisopropylamino chloro phosphoramidite, diisopropylethylamine, THF; (e) proton sponge, POCl$_3$, trimethyl phosphate, then tributylamine, bis(tributylammonium)pyrophosphate, DMF; (f) NaH, CH$_3$CN, then 2,3,5-tri-O-benzyl-D-ribofuranosyl chloride; (g) BBr$_3$, dichloromethane; (h) 2-chloro-4H-1,3,2-benzodioxaphosphorin-4-one, dioxane, pyridine, tributylamine, bis(tributylammonium)pyrophosphate, DMF, then I$_2$/pyridine, water, NH$_4$OH (for 5'-γ-amidotriphosphate); Tol: toluoyl; DMT: 4,4'-dimethoxytrityl; Ac: acetyl.

Figure 24A:
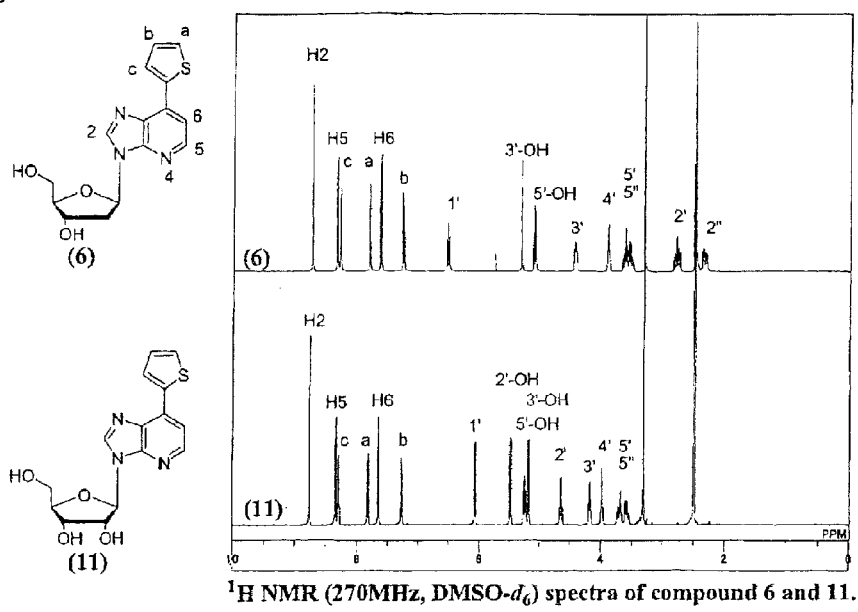

[FIG. 24a] FIG. 24 shows NMR spectra for nucleosides of 7-(2-thienyl)-3H-imidazo[4,5-b]pyridine (Ds). FIG. 24a shows $^1$H NMR (270 MHz, DMOSO-d$_6$) spectra of Compounds 6 and 11.

Figure 24B:
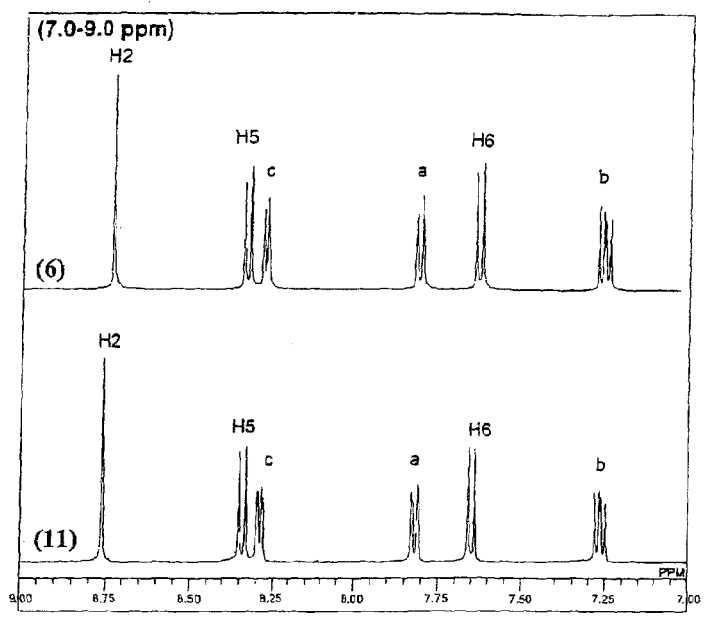

[FIG. 24b] FIG. 24 shows NMR spectra for nucleosides of 7-(2-thienyl)-3H-imidazo[4,5-b]pyridine (Ds). FIG. 24b shows $^1$H NMR (270 MHz, DMOSO-$d_6$) spectra of Compounds 6 and 11 (7.0-9.0 ppm).

Figure 24C:
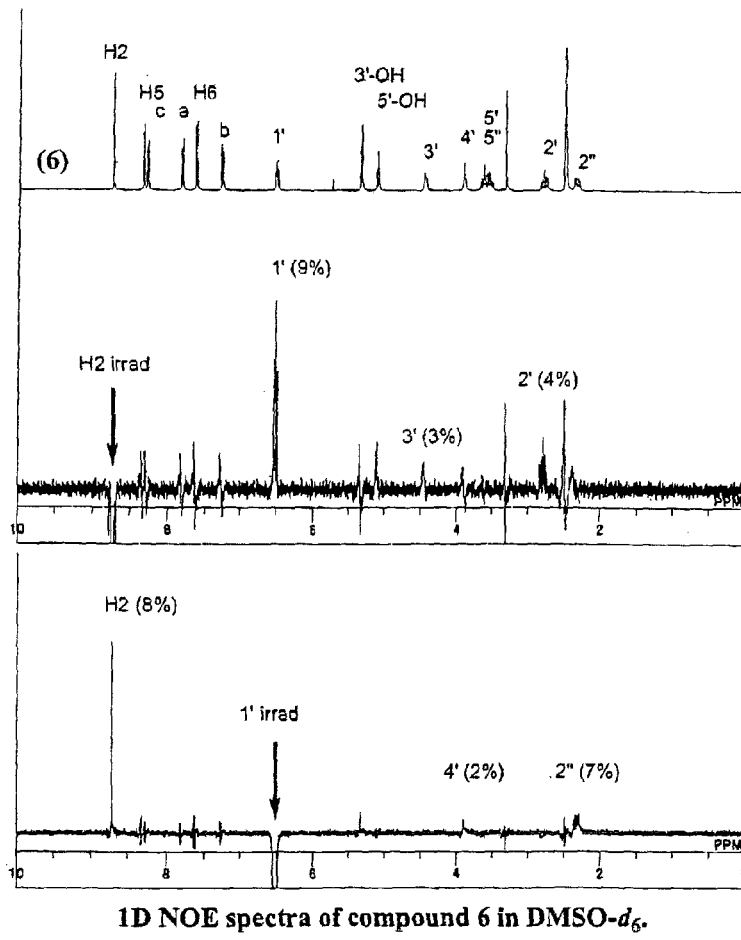

[FIG. 24c] FIG. 24 shows NMR spectra for nucleosides of 7-(2-thienyl)-3H-imidazo[4,5-b]pyridine (Ds). FIG. 24c shows 1D NOE spectra of Compound 6 (in DMOSO-$d_6$).

Figure 24D:
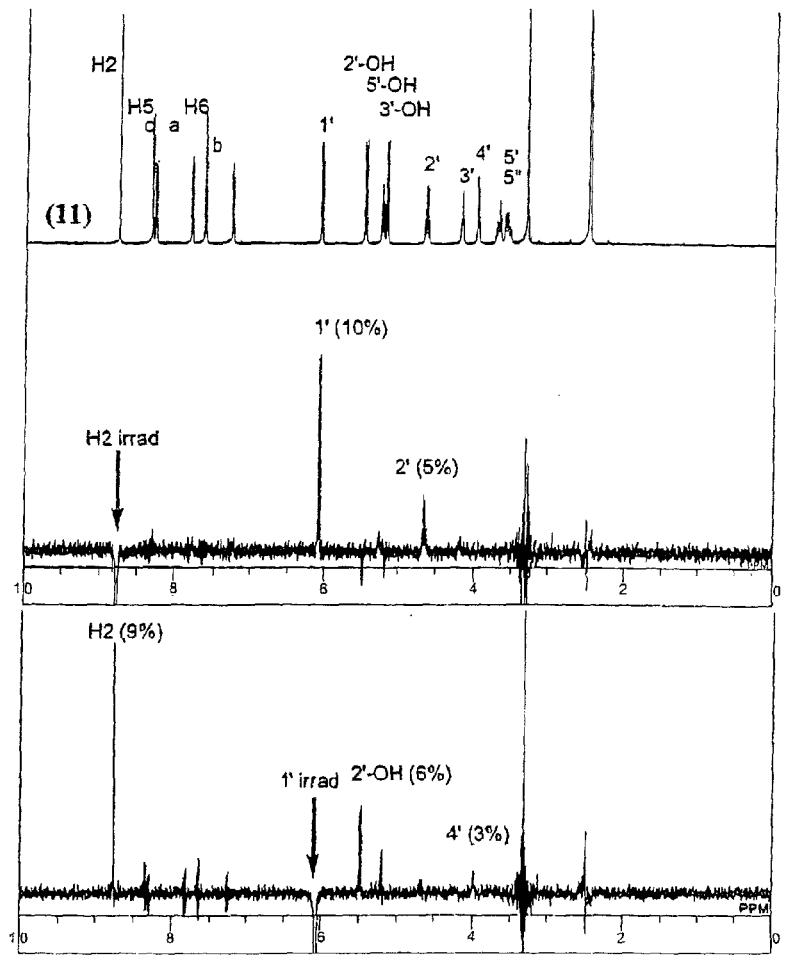

[FIG. 24d] FIG. 24 shows NMR spectra for nucleosides of 7-(2-thienyl)-3H-imidazo[4,5-b]pyridine (Ds). FIG. 24d shows 1D NOE spectra of Compound 11 (in DMOSO-$d_6$).

Figure 24E:
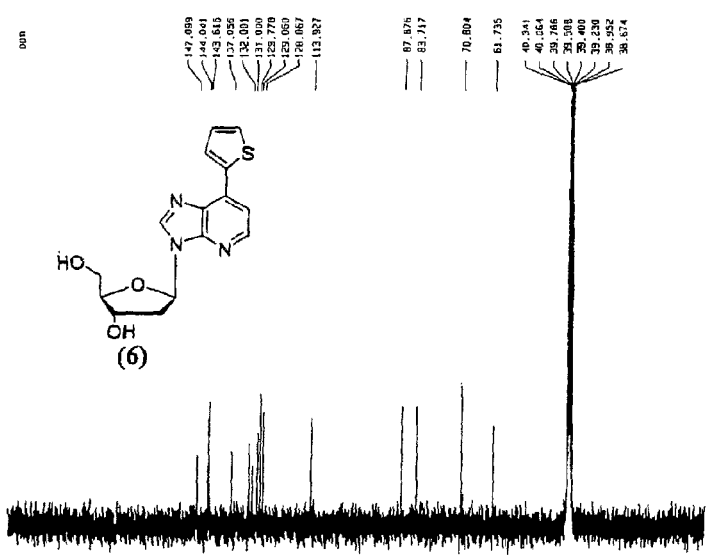

[FIG. 24e] FIG. 24 shows NMR spectra for nucleosides of 7-(2-thienyl)-3H-imidazo[4,5-b]pyridine (Ds). FIG. 24e shows a $^{13}$C NMR (75 MHz, DMOSO-$d_6$) spectrum of Compound 6.

[FIG. 24f] FIG. 24 shows NMR spectra for nucleosides of 7-(2-thienyl)-3H-imidazo[4,5-b]pyridine (Ds). FIG. 24f shows a 2D COSY spectrum of Compound 6.

[FIG. 24g] FIG. 24 shows NMR spectra for nucleosides of 7-(2-thienyl)-3H-imidazo[4,5-b]pyridine (Ds). FIG. 24g shows a 2D NOESY spectrum of Compound 6.

Figure 24H:
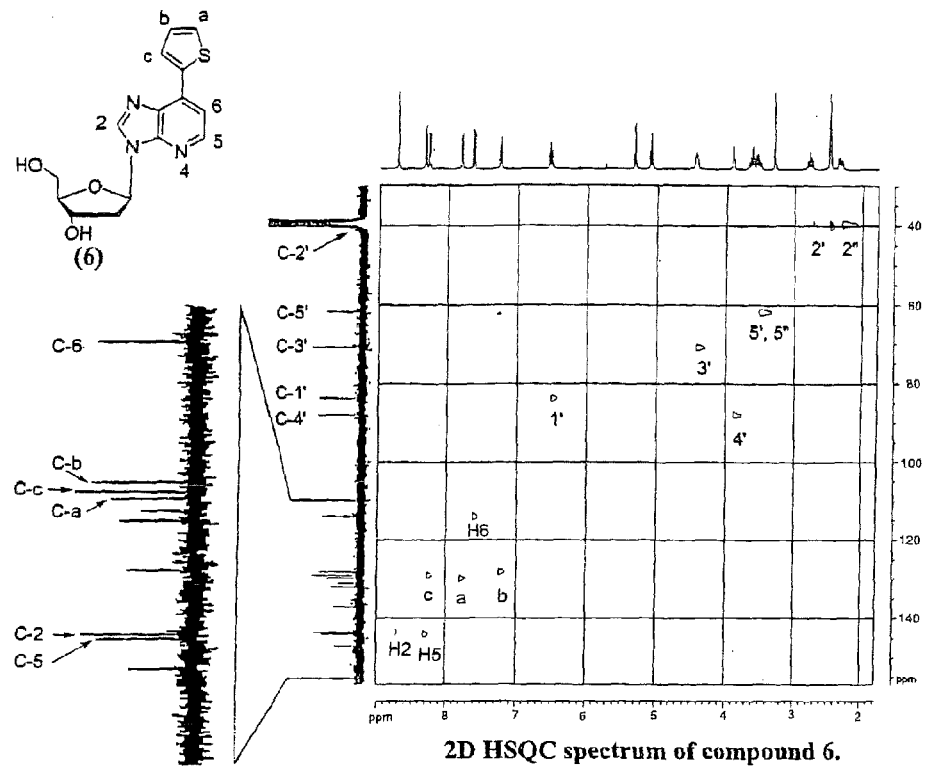

[FIG. 24h] FIG. 24 shows NMR spectra for nucleosides of 7-(2-thienyl)-3H-imidazo[4,5-b]pyridine (Ds). FIG. 24h shows a 2D HSQC spectrum of Compound 6.

Figure 24I:
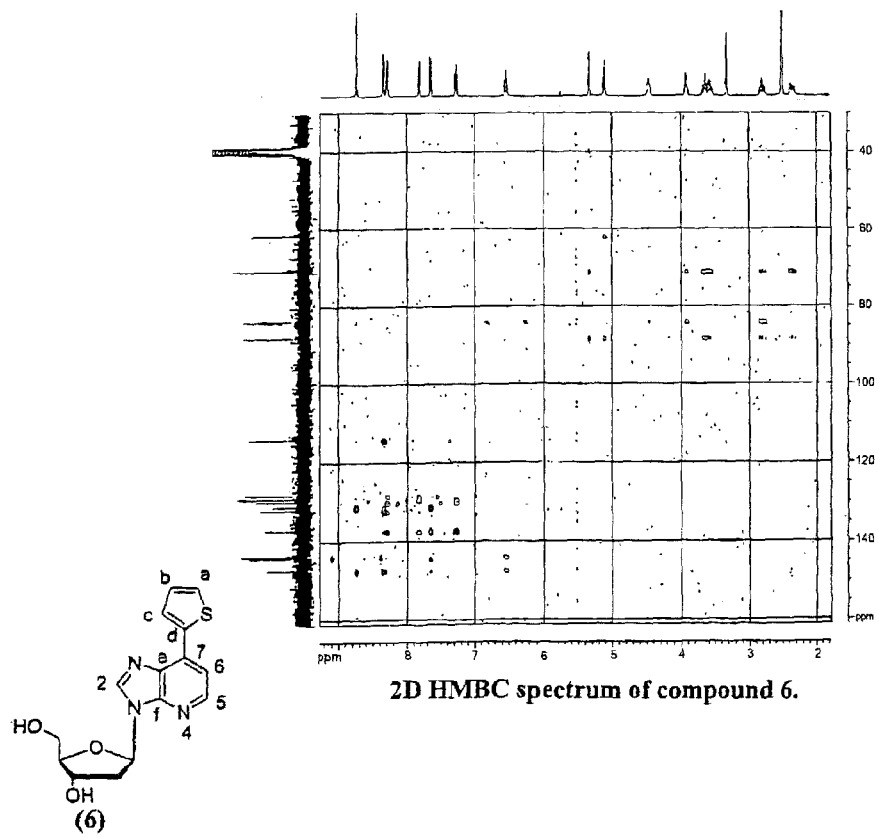

[FIG. 24i] FIG. 24 shows NMR spectra for nucleosides of 7-(2-thienyl)-3H-imidazo[4,5-b]pyridine (Ds). FIG. 24i shows a 2D HMBC spectrum of Compound 6.

Figure 24J:
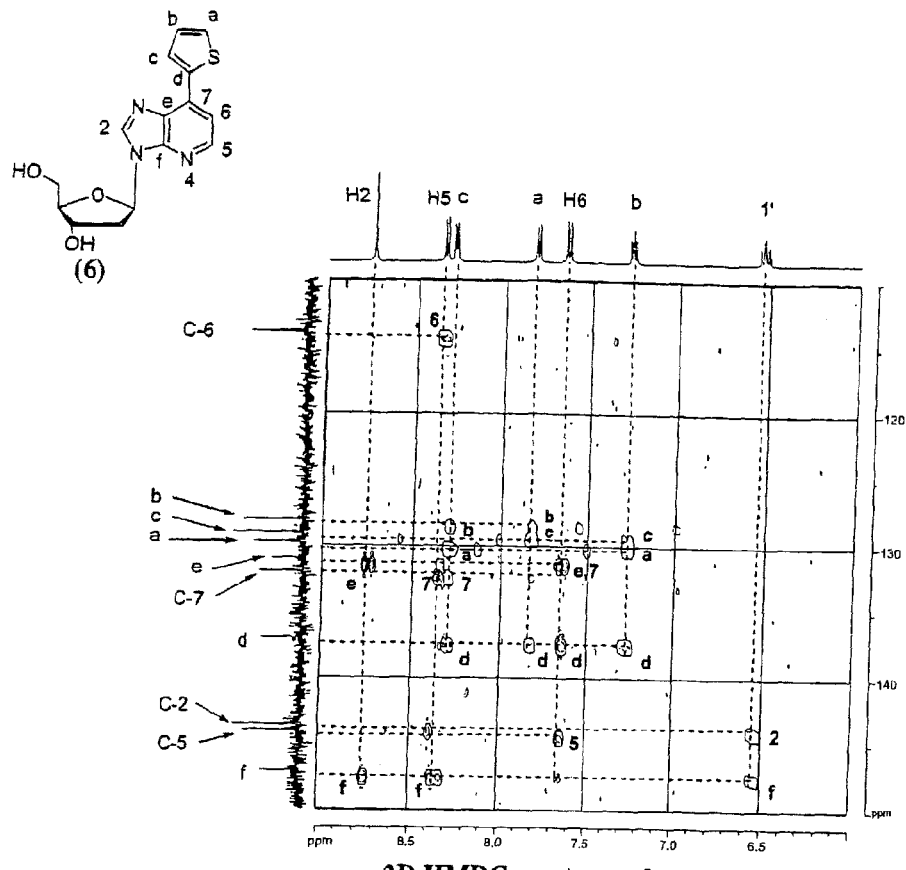

[FIG. 24j] FIG. 24 shows NMR spectra for nucleosides of 7-(2-thienyl)-3H-imidazo[4,5-b]pyridine (Ds). FIG. 24j shows a 2D HMBC spectrum of Compound 6 (enlarged).

Figure 24K:
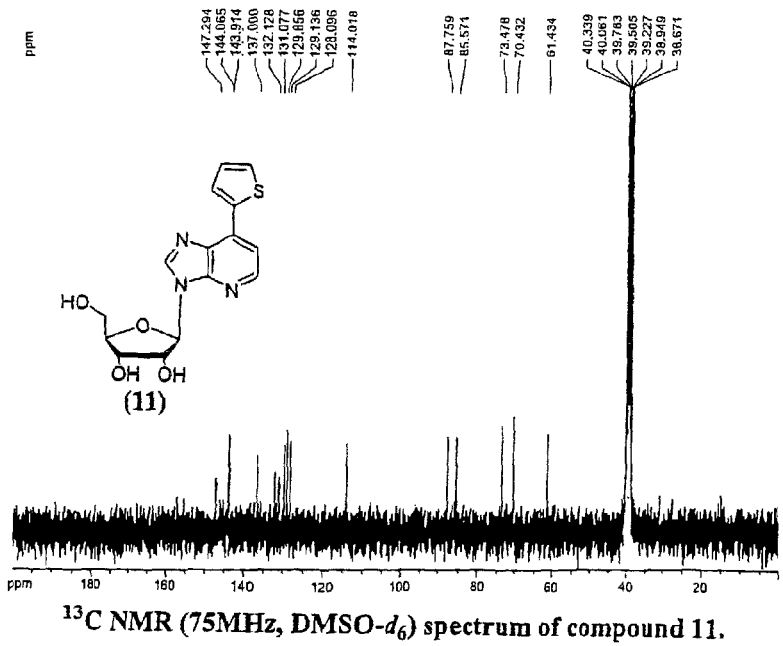

[FIG. 24k] FIG. 24 shows NMR spectra for nucleosides of 7-(2-thienyl)-3H-imidazo[4,5-b]pyridine (Ds). FIG. 24k shows a $^{13}$C NMR (75 MHz, DMOSO-$d_6$) spectrum of Compound 11.

Figure 24L:
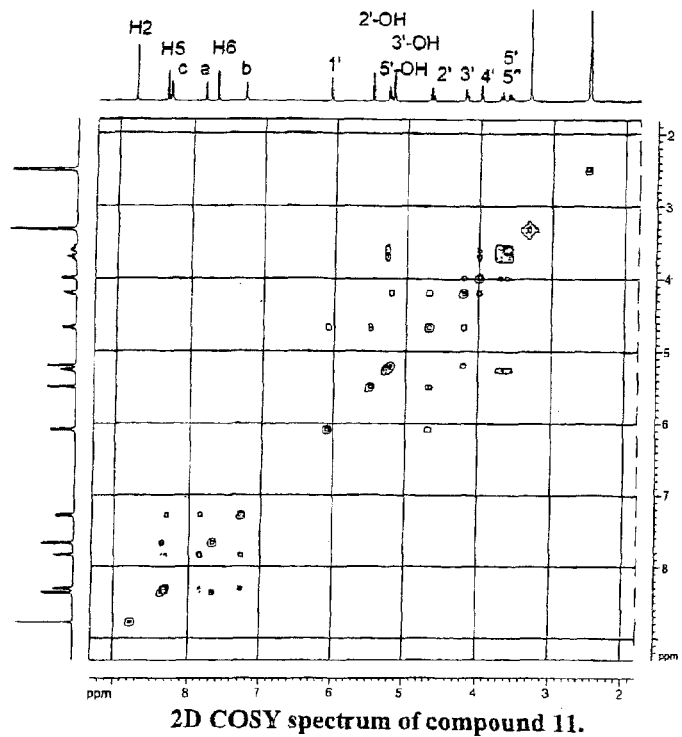

[FIG. 24l] FIG. 24 shows NMR spectra for nucleosides of 7-(2-thienyl)-3H-imidazo[4,5-b]pyridine (Ds). FIG. 24l shows a 2D COSY spectrum of Compound 11.

Figure 24M:
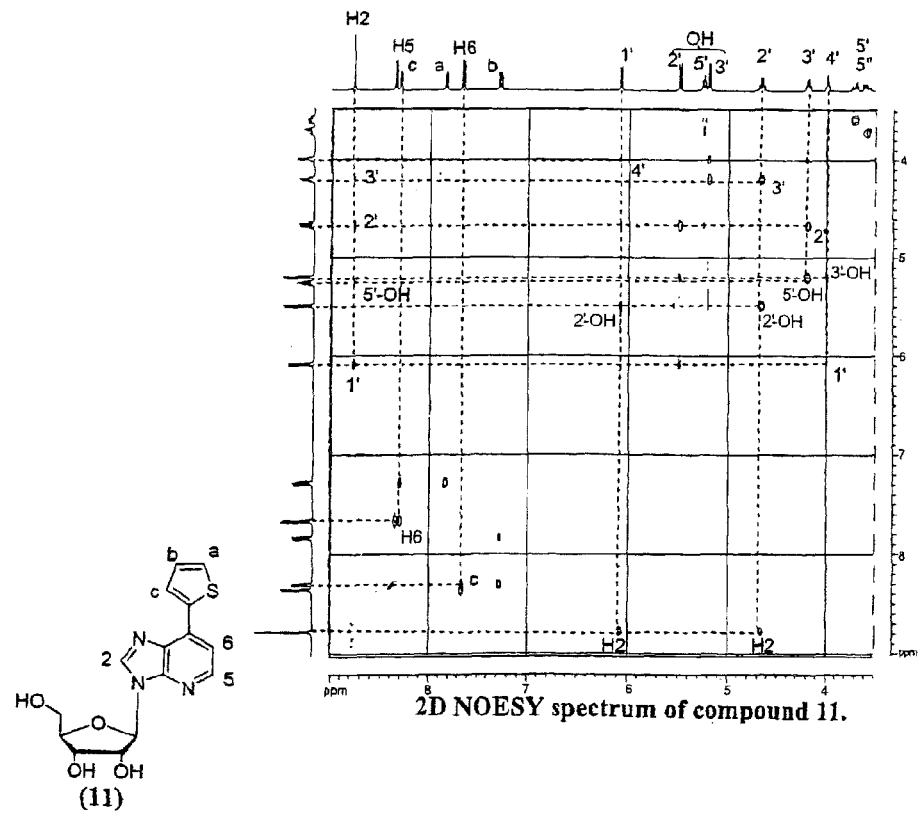

[FIG. 24m] FIG. 24 shows NMR spectra for nucleosides of 7-(2-thienyl)-3H-imidazo[4,5-b]pyridine (Ds). FIG. 24m shows a 2D NOESY spectrum of Compound 11.

Figure 24N:
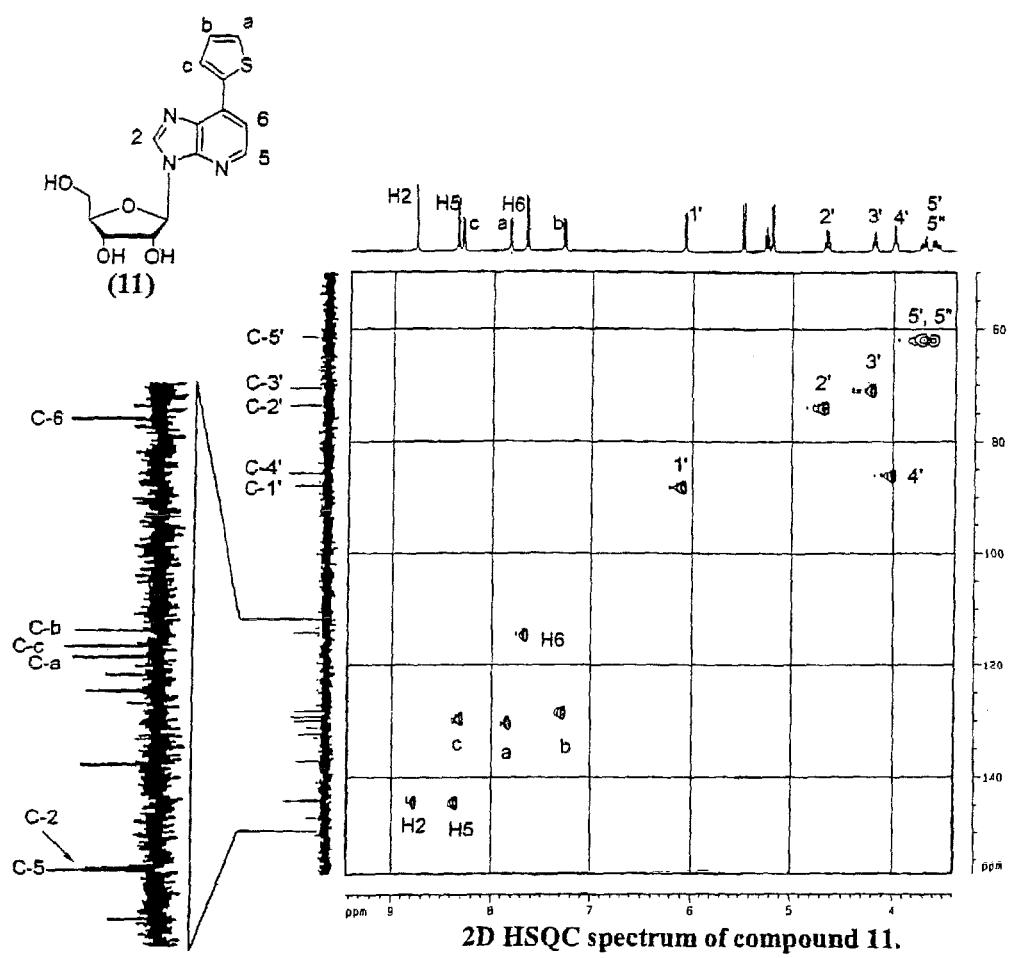

[FIG. 24n] FIG. 24 shows NMR spectra for nucleosides of 7-(2-thienyl)-3H-imidazo[4,5-b]pyridine (Ds). FIG. 24n shows a 2D HSQC spectrum of Compound 11.

Figure 24O:
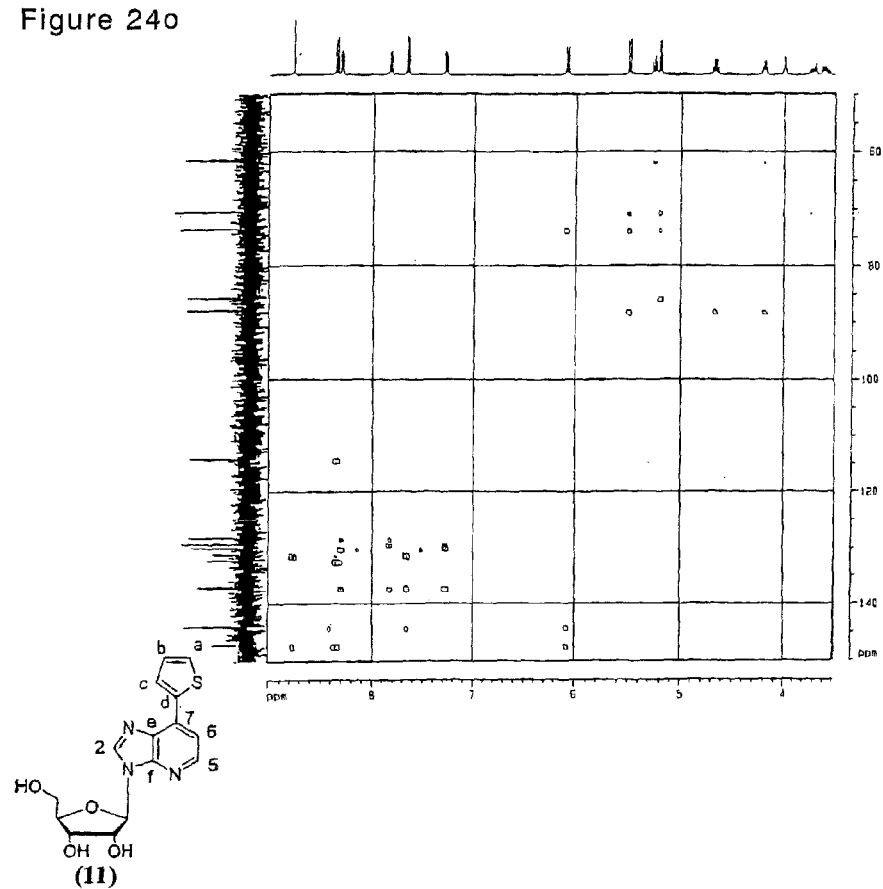

[FIG. 24o] FIG. 24 shows NMR spectra for nucleosides of 7-(2-thienyl)-3H-imidazo[4,5-b]pyridine (Ds). FIG. 24o shows a 2D HMBC spectrum of Compound 11.

Figure 24P:
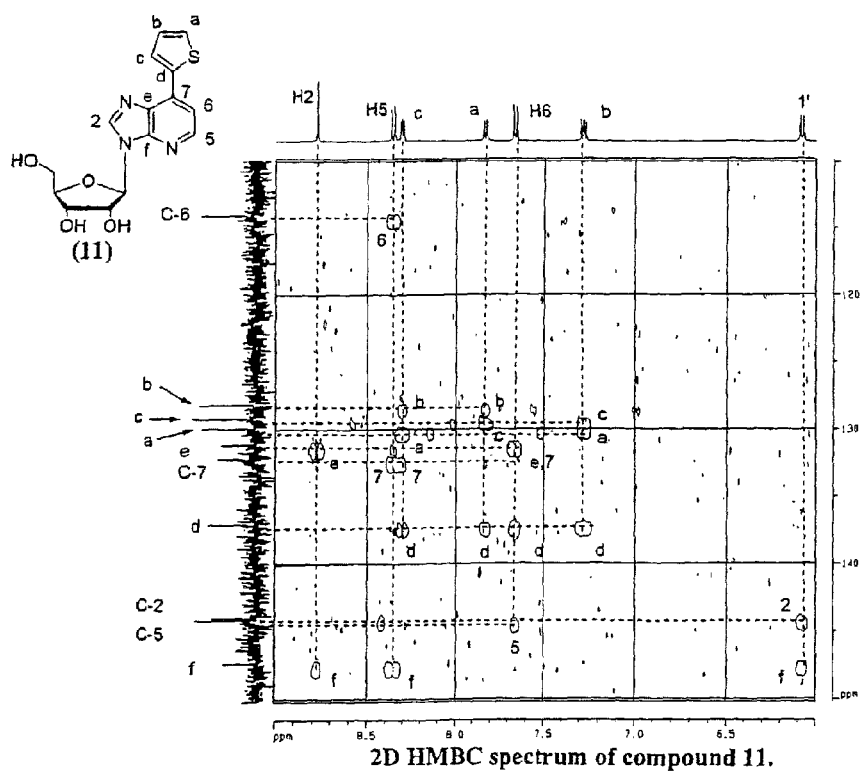

[FIG. 24p] FIG. 24 shows NMR spectra for nucleosides of 7-(2-thienyl)-3H-imidazo[4,5-b]pyridine (Ds). FIG. 24p shows a 2D HMBC spectrum of Compound 11 (enlarged).

Figure 25A:
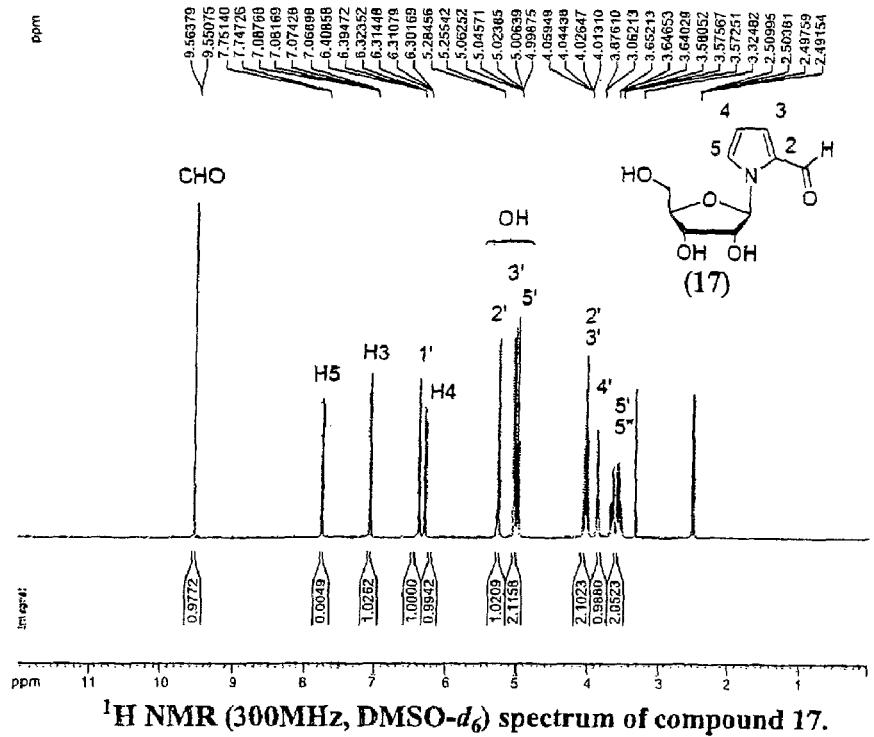

[FIG. 25a] FIG. 25 shows NMR spectra for nucleosides of pyrrole-2-carbaldehyde and 4-propynylpyrrole-2-carbaldehyde. FIG. 25a shows a $^1$H NMR (300 MHz, DMOSO-$d_6$) spectrum of Compound 17.

Figure 25B:
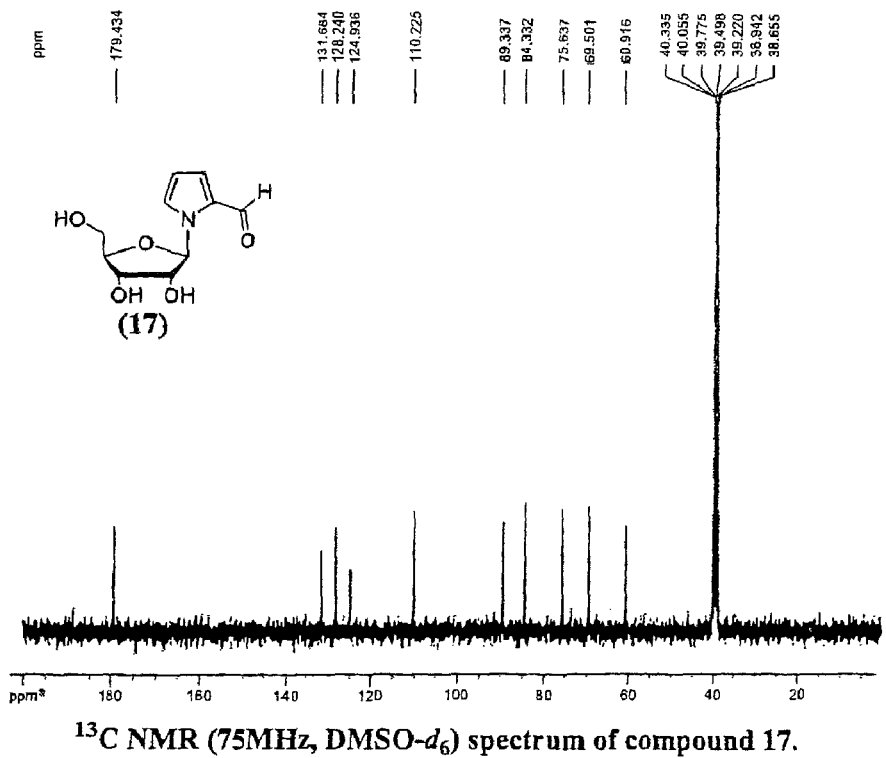

[FIG. 25b] FIG. 25 shows NMR spectra for nucleosides of pyrrole-2-carbaldehyde and 4-propynylpyrrole-2-carbaldehyde. FIG. 25b shows a $^{13}$C NMR (75 MHz, DMOSO-$d_6$) spectrum of Compound 17.

Figure 25C:
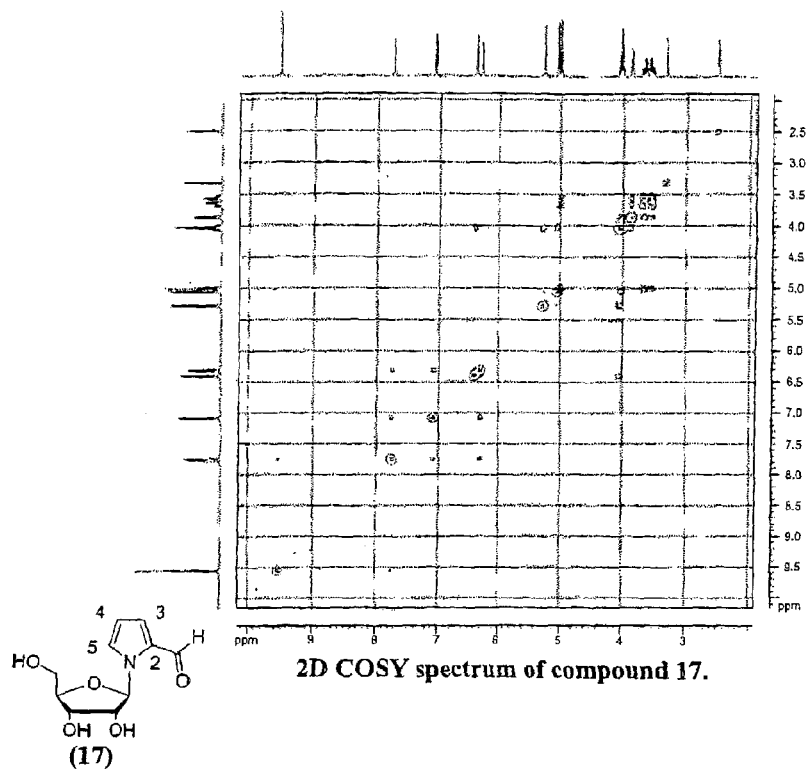

[FIG. 25c] FIG. 25 shows NMR spectra for nucleosides of pyrrole-2-carbaldehyde and 4-propynylpyrrole-2-carbaldehyde. FIG. 25c shows a 2D COSY spectrum of Compound 17.

Figure 25D:
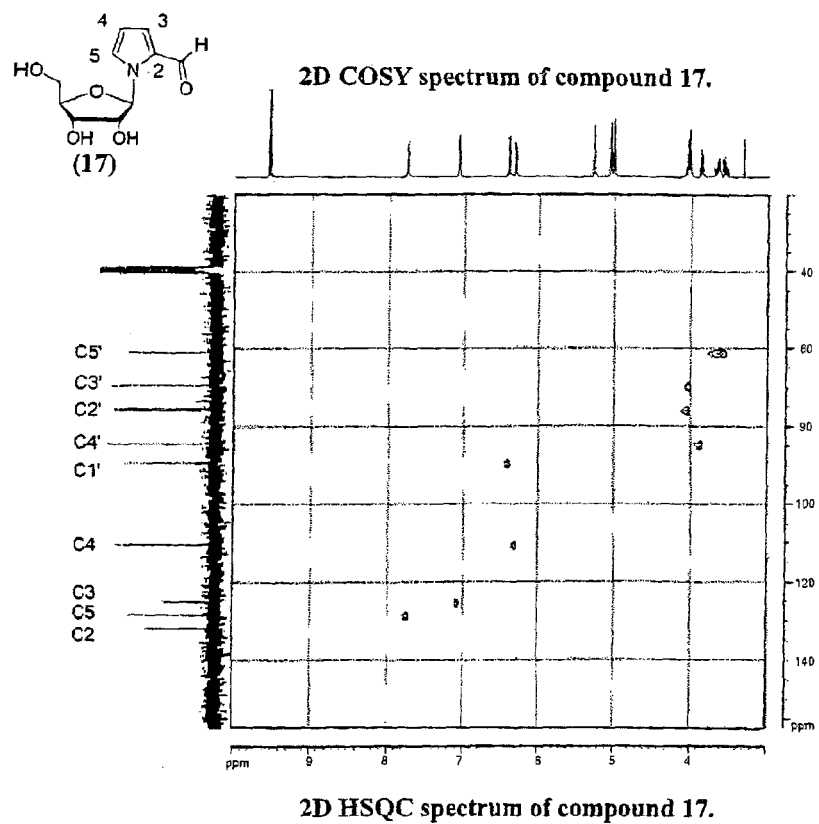

[FIG. 25d] FIG. 25 shows NMR spectra for nucleosides of pyrrole-2-carbaldehyde and 4-propynylpyrrole-2-carbaldehyde. FIG. 25d shows a 2D HSQC spectrum of Compound 17.

Figure 25E:
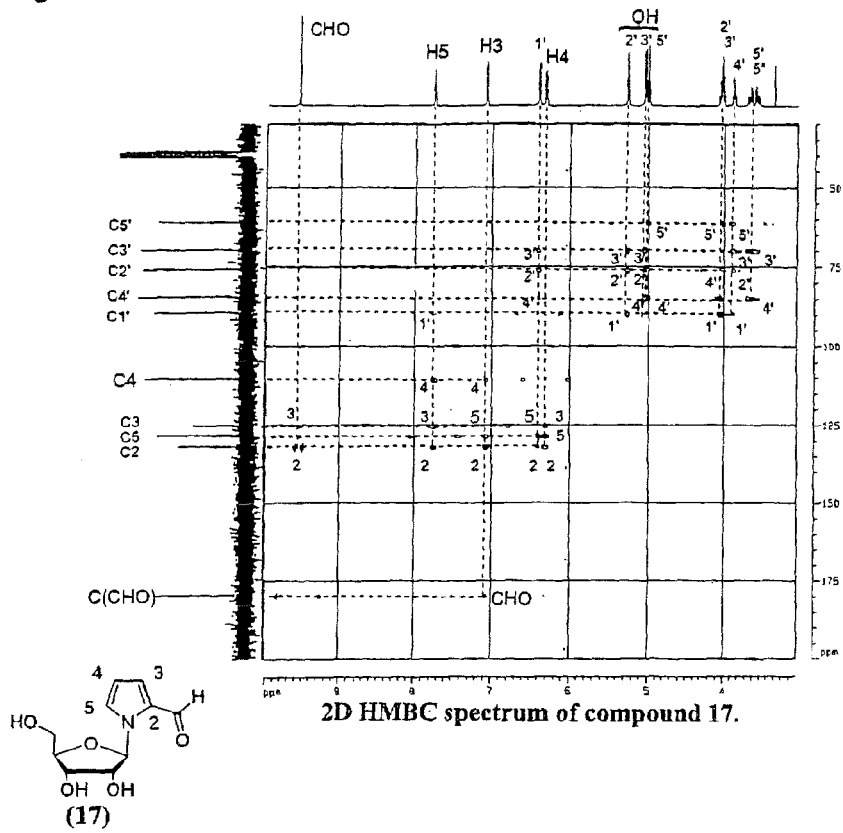

[FIG. 25e] FIG. 25 shows NMR spectra for nucleosides of pyrrole-2-carbaldehyde and 4-propynylpyrrole-2-carbaldehyde. FIG. 25e shows a 2D HMBC spectrum of Compound 17.

Figure 25F:
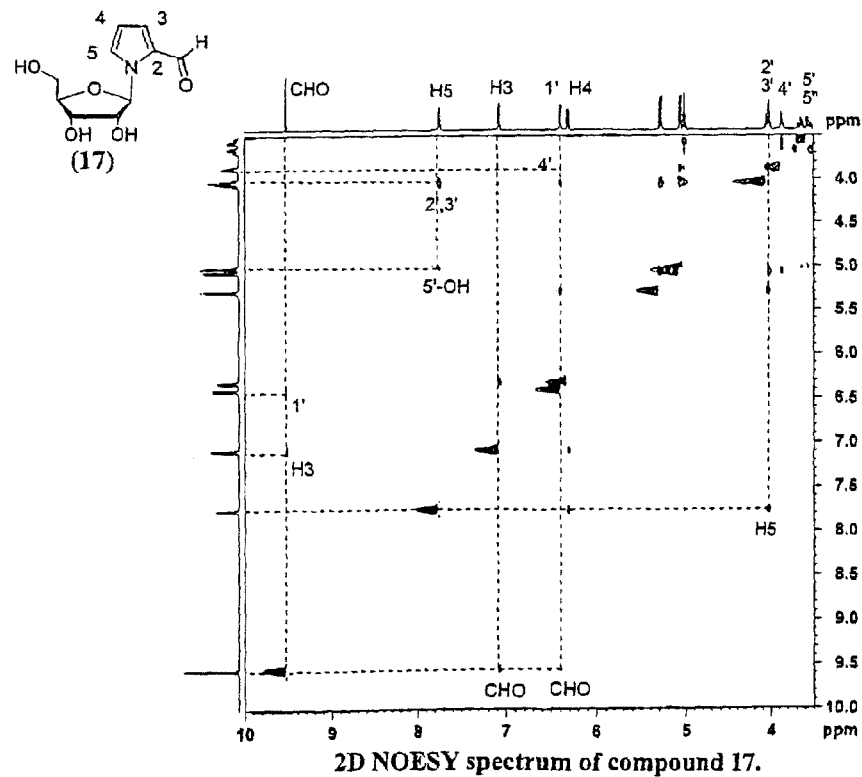

[FIG. 25f] FIG. 25 shows NMR spectra for nucleosides of pyrrole-2-carbaldehyde and 4-propynylpyrrole-2-carbaldehyde. FIG. 25f shows a 2D NOESY spectrum of Compound 17.

Figure 25G:
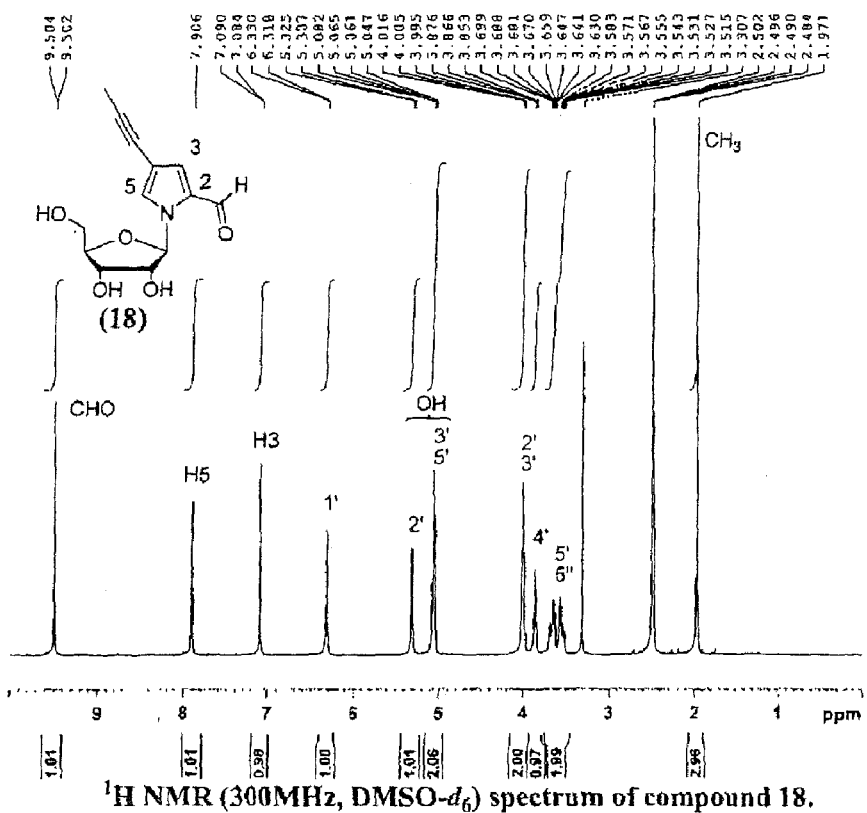

[FIG. 25g] FIG. 25 shows NMR spectra for nucleosides of pyrrole-2-carbaldehyde and 4-propynylpyrrole-2-carbaldehyde. FIG. 25g shows a $^1$H NMR (300 MHz, DMOSO-$d_6$) spectrum of Compound 18.

Figure 25H:
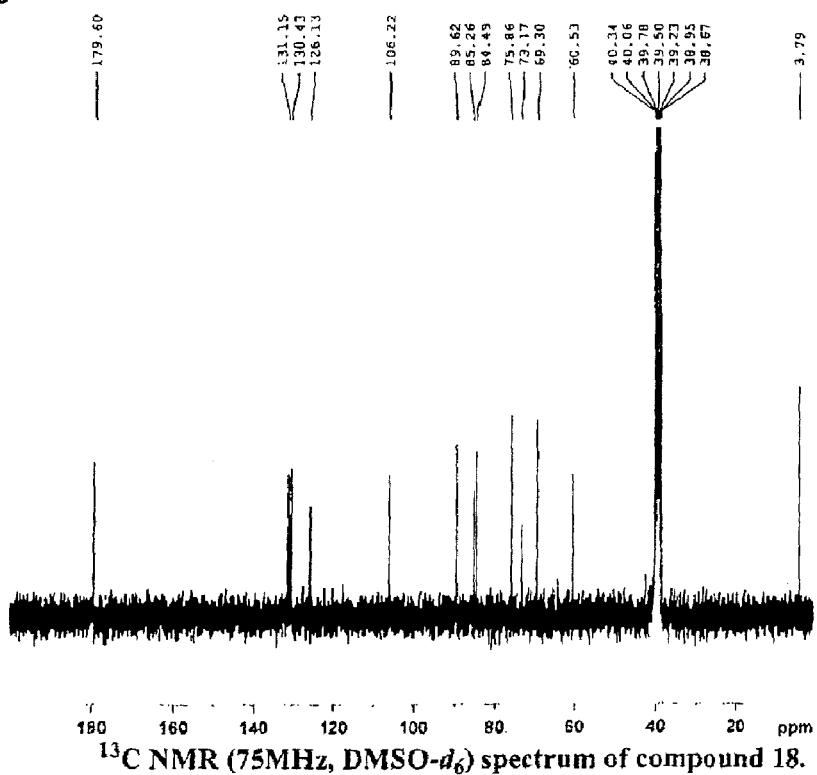

[FIG. 25h] FIG. 25 shows NMR spectra for nucleosides of pyrrole-2-carbaldehyde and 4-propynylpyrrole-2-carbaldehyde. FIG. 25h shows a $^{13}$C NMR (75 MHz, DMOSO-$d_6$) spectrum of Compound 18.

Figure 25I:
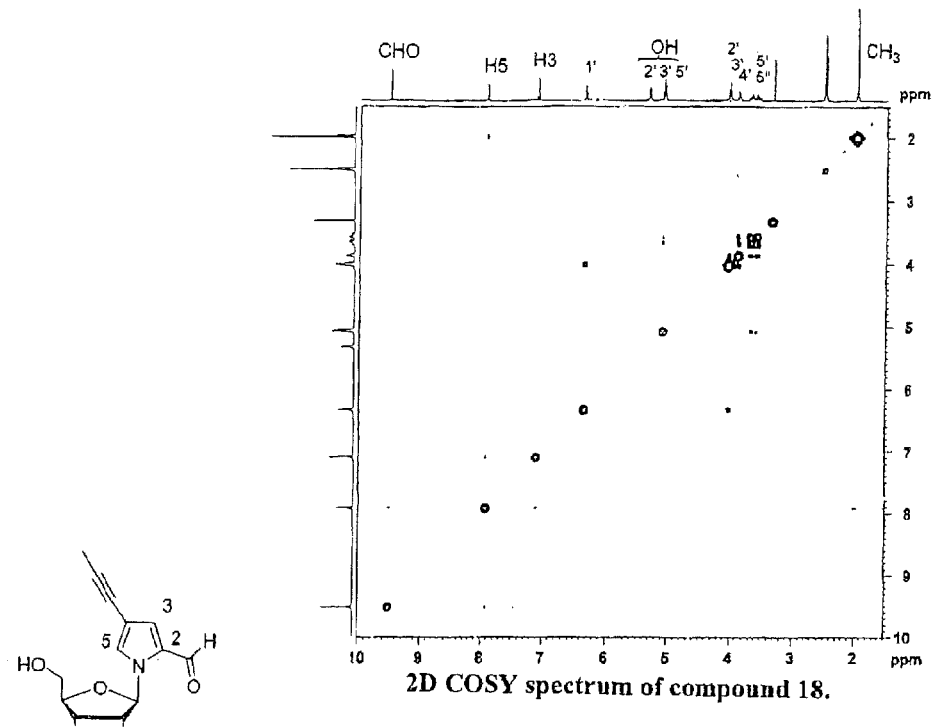

[FIG. 25i] FIG. 25 shows NMR spectra for nucleosides of pyrrole-2-carbaldehyde and 4-propynylpyrrole-2-carbaldehyde. FIG. 25i shows a 2D COSY spectrum of Compound 18.

Figure 25J:
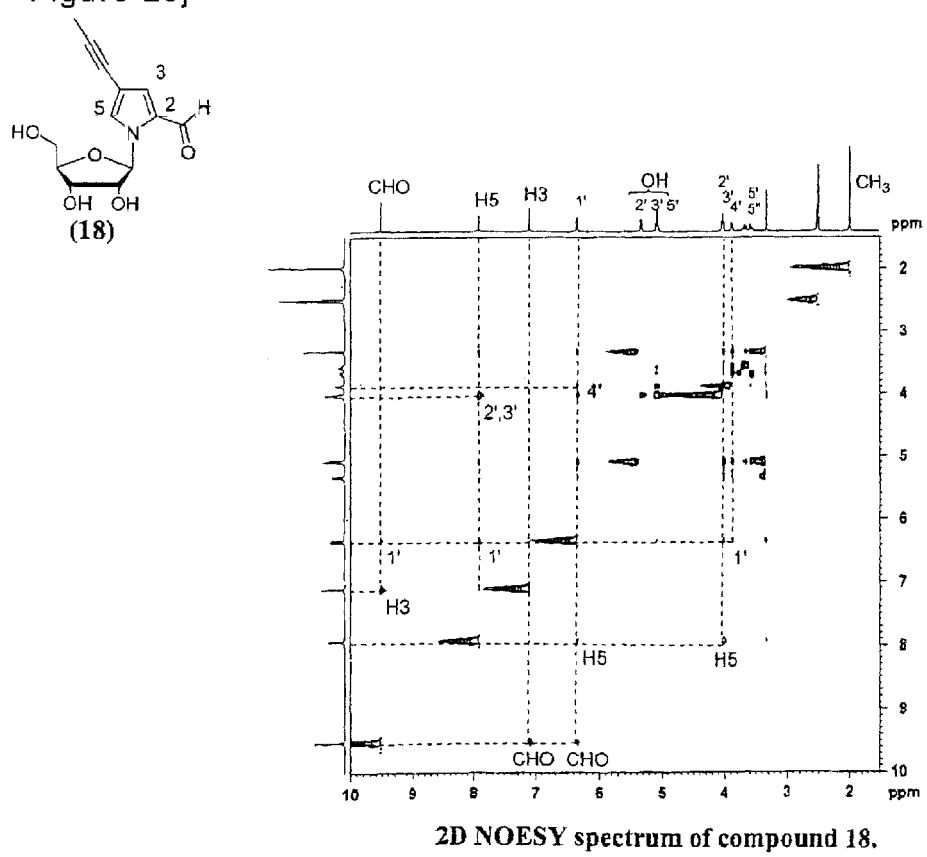

[FIG. 25j] FIG. 25 shows NMR spectra for nucleosides of pyrrole-2-carbaldehyde and 4-propynylpyrrole-2-carbaldehyde. FIG. 25j shows a 2D NOESY spectrum of Compound 18.

Figure 25K:
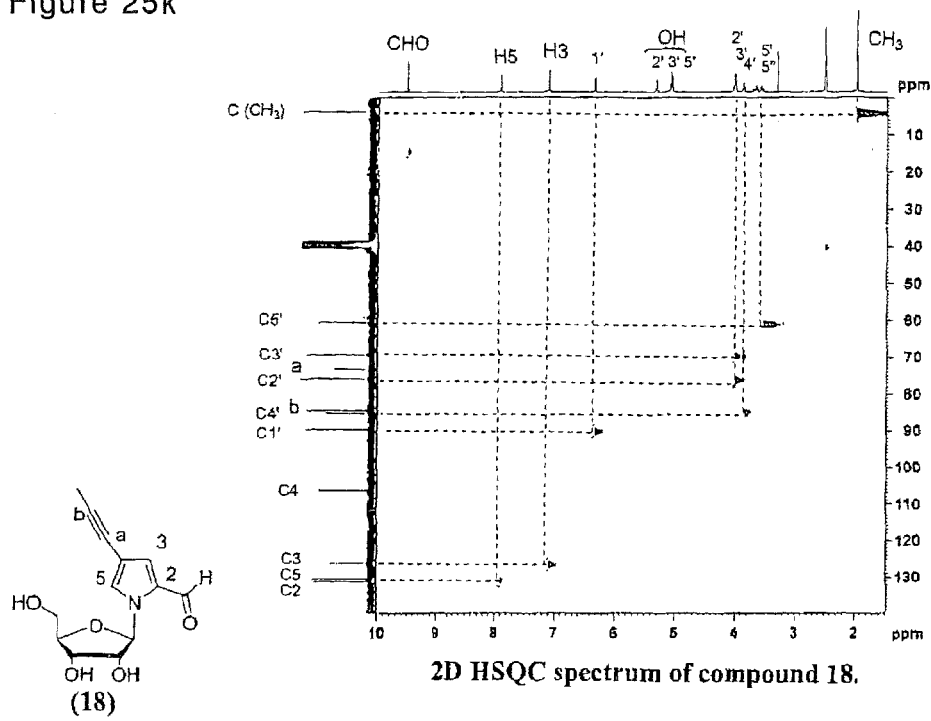

[FIG. 25k] FIG. 25 shows NMR spectra for nucleosides of pyrrole-2-carbaldehyde and 4-propynylpyrrole-2-carbaldehyde. FIG. 25k shows a 2D HSQC spectrum of Compound 18.

Figure 25L:
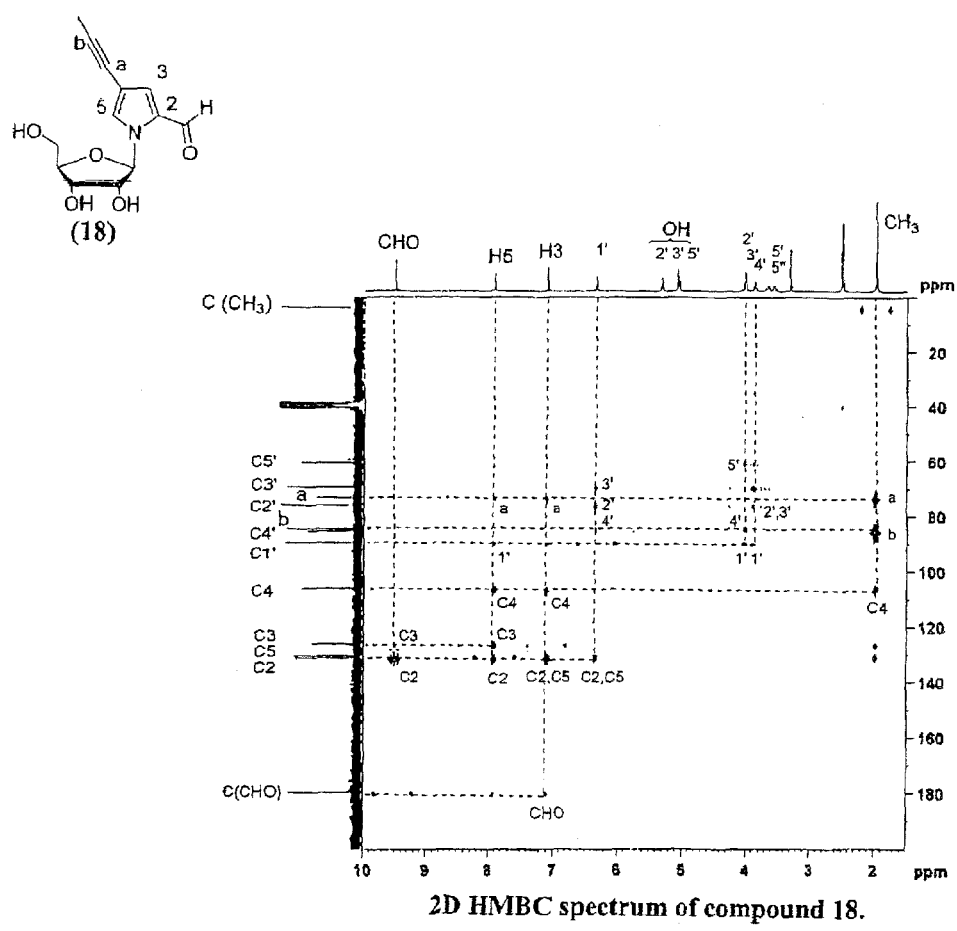

[FIG. 25l] FIG. 25 shows NMR spectra for nucleosides of pyrrole-2-carbaldehyde and 4-propynylpyrrole-2-carbaldehyde. FIG. 25l shows a 2D HMBC spectrum of Compound 18.

Figure 25M:
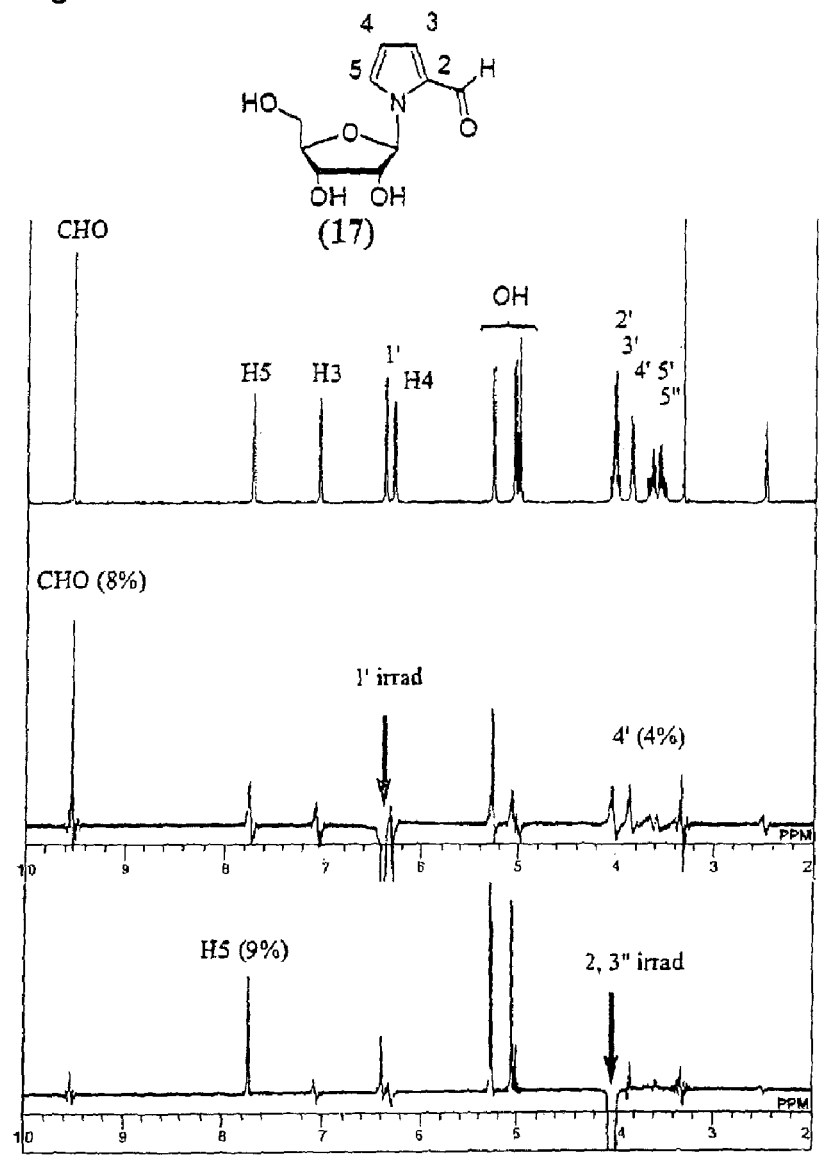

[FIG. 25m] FIG. 25 shows NMR spectra for nucleosides of pyrrole-2-carbaldehyde and 4-propynylpyrrole-2-carbaldehyde. FIG. 25m shows 1D NOE spectra of Compound 17 (in DMOSO-$d_6$).

Figure 25N:
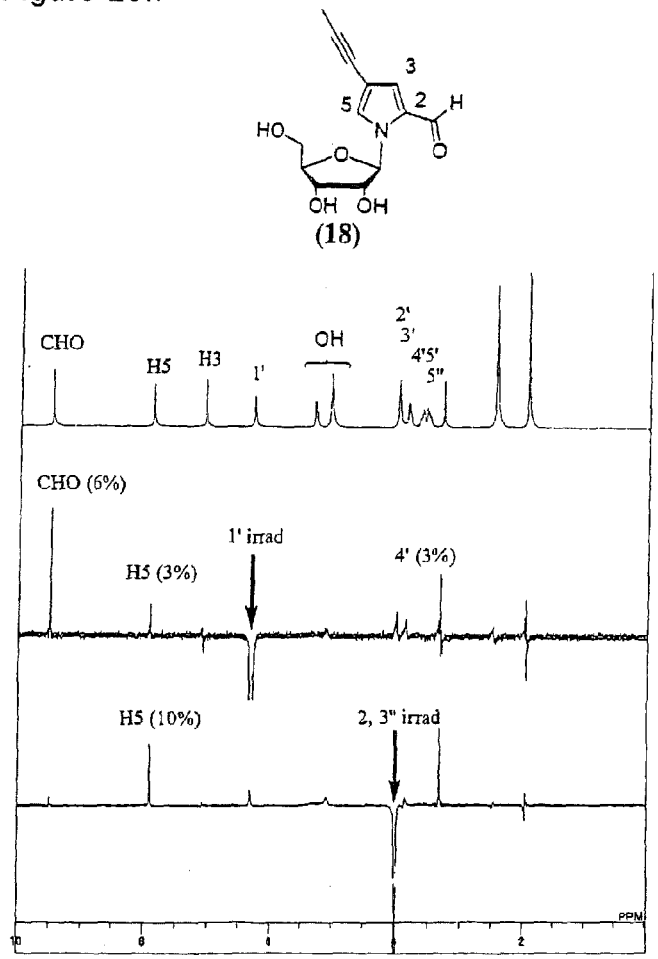

[FIG. 25n] FIG. 25 shows NMR spectra for nucleosides of pyrrole-2-carbaldehyde and 4-propynylpyrrole-2-carbaldehyde. FIG. 25n shows 1D NOE spectra of Compound 18 (in DMOSO-$d_6$).

Figure 26:
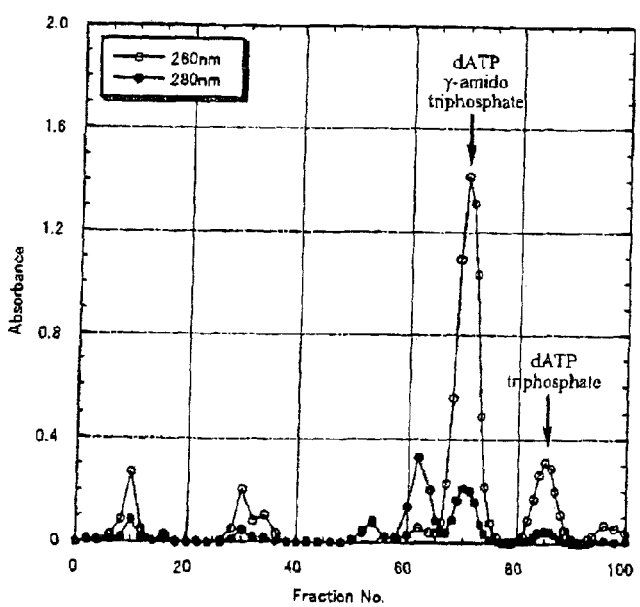

[FIG. 26] FIG. 26 shows DEAE Sephadex ion exchange column elution patterns of deoxyadenosine 5'-γ-amidotriphosphate. Open circles indicate the results at 260 nm, while solid circles indicate the results at 280 nm.

Figure 27:
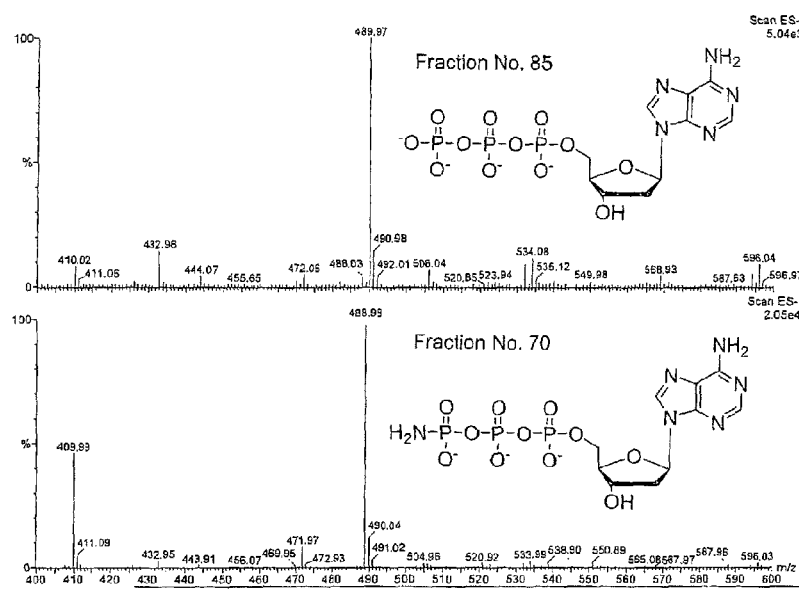

[FIG. 27] FIG. 27 shows ESI-mass spectra of deoxyadenosine 5'-γ-amidotriphosphate.

Figure 28A:
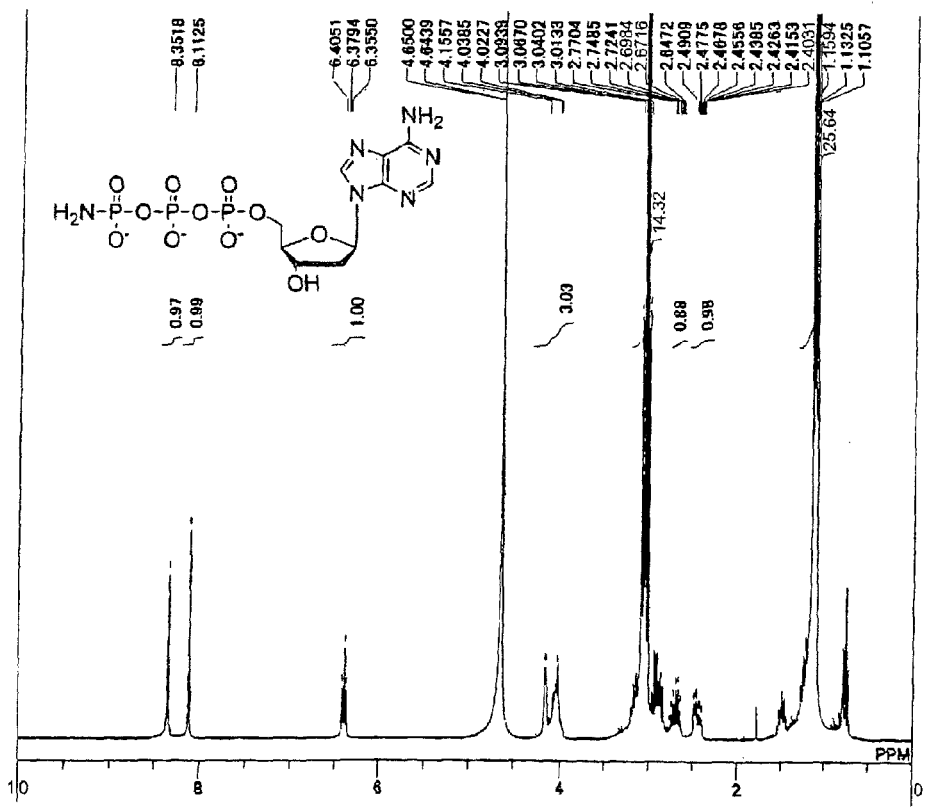

[FIG. 28a] FIG. 28a shows a $^1$H NMR (270 MHz, D$_2$O) spectrum of deoxyadenosine 5'-γ-amidotriphosphate.

Figure 28B:
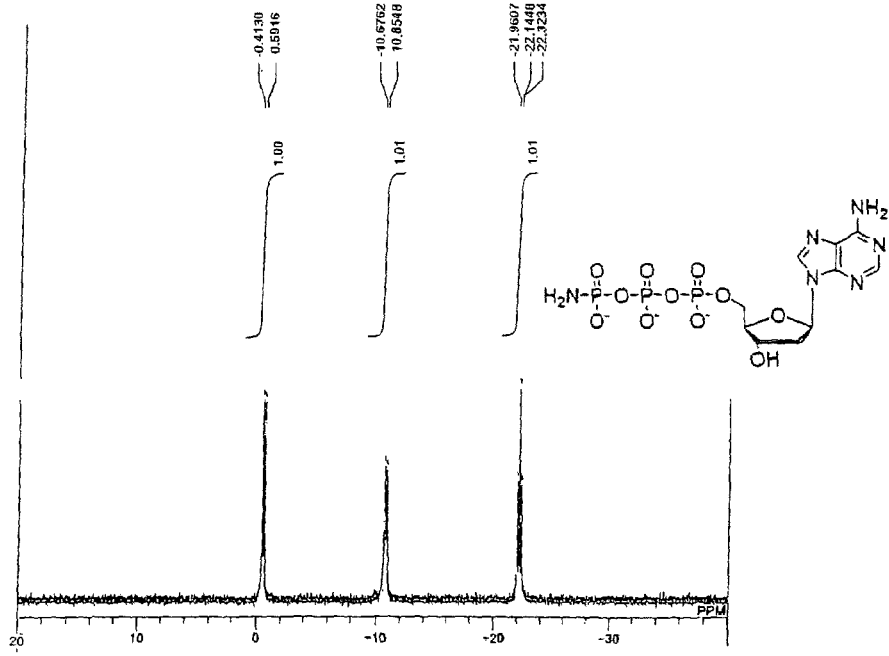

[FIG. 28b] FIG. 28b shows a $^1$P NMR (109 MHz, D$_2$O) spectrum of deoxyadenosine 5'-γ-amidotriphosphate.

Figure 29A:
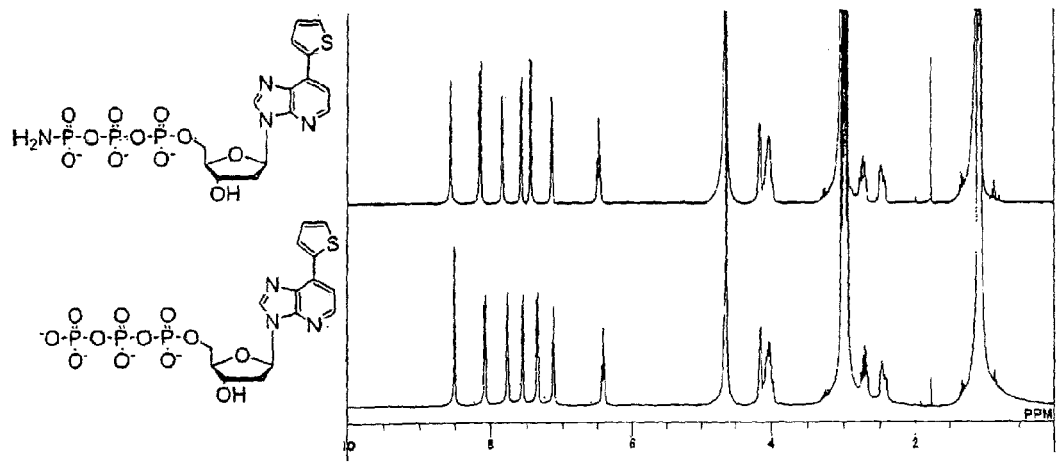

[FIG. 29a] FIG. 29a shows $^1$H NMR (270 MHz, D$_2$O) spectra of 7-(2-thienyl)-3-(2-deoxy-β-D-ribofuranosyl)3H-imidazo[4,5-b]pyridine 5'-γ-amidotriphosphate (upper) and 5'-triphosphate (lower).

Figure 29B:
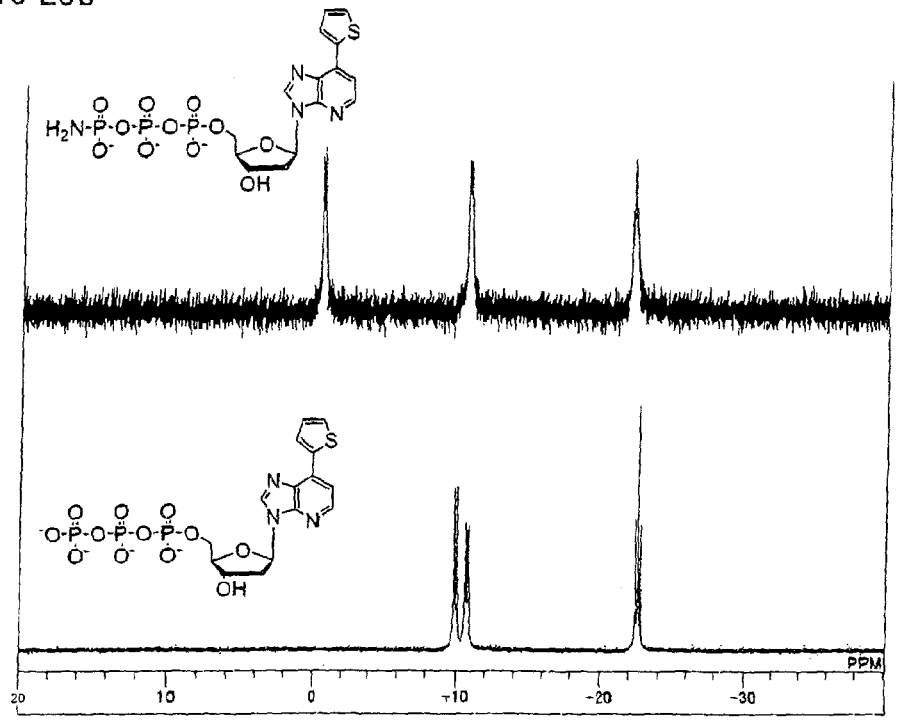

[FIG. 29b] FIG. 29b shows $^1$P NMR (109 MHz, D$_2$O) spectra of 7-(2-thienyl)-3-(2-deoxy-β-D-ribofuranosyl)3H-imidazo[4,5-b]pyridine 5'-γ-amidotriphosphate (upper) and 5'-triphosphate (lower).

Figure 30A:
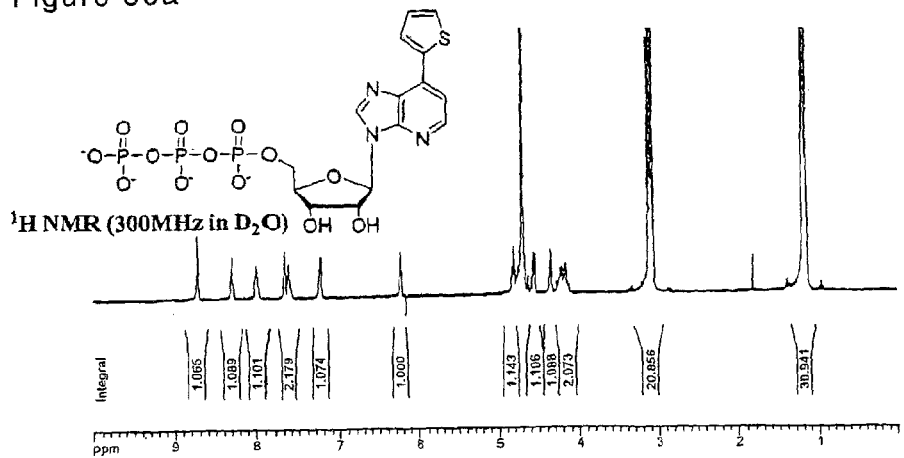

[FIG. 30a] FIG. 30a shows a $^1$H NMR (300 MHz, D$_2$O) spectrum of 7-(2-thienyl)-3-(β-D-ribofuranosyl)-3H-imidazo[4,5-b]pyridine 5'-triphosphate (Compound 14).

Figure 30B:
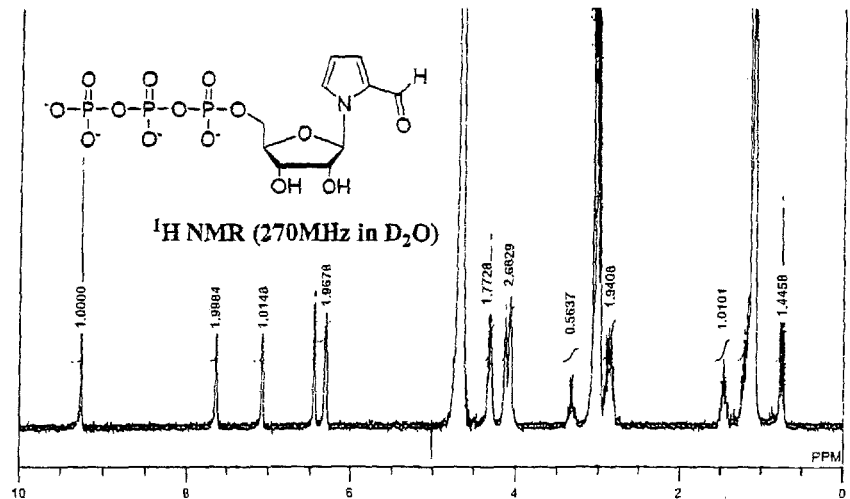

[FIG. 30b] FIG. 30b shows a $^1$H NMR (270 MHz, D$_2$O) spectrum of 1-(β-D-ribofuranosyl)pyrrole-2-carbaldehyde 5'-triphosphate (Compound 19).

Figure 30C:
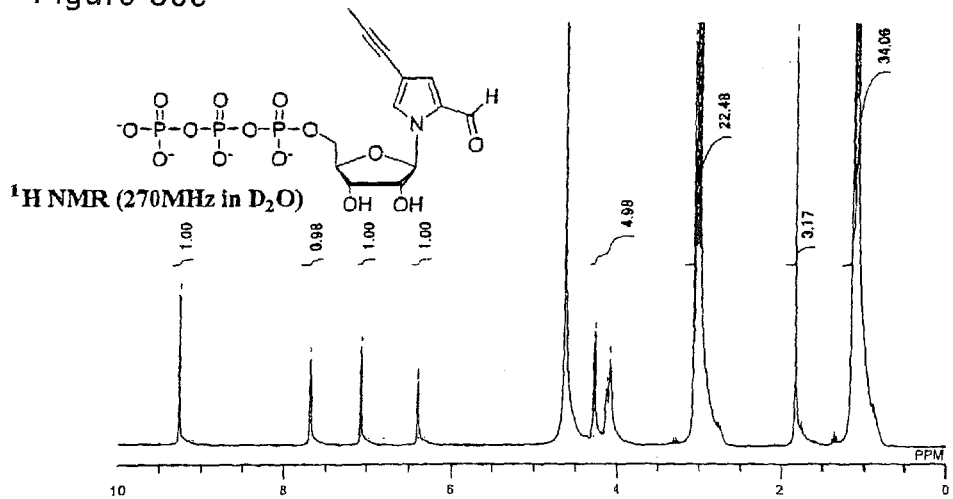

[FIG. 30c] FIG. 30c shows a $^1$H NMR (270 MHz, D$_2$O) spectrum of 4-propynyl-1-(β-D-ribofuranosyl)pyrrole-2-carbaldehyde 5'-triphosphate (Compound 20).

Figure 31A:
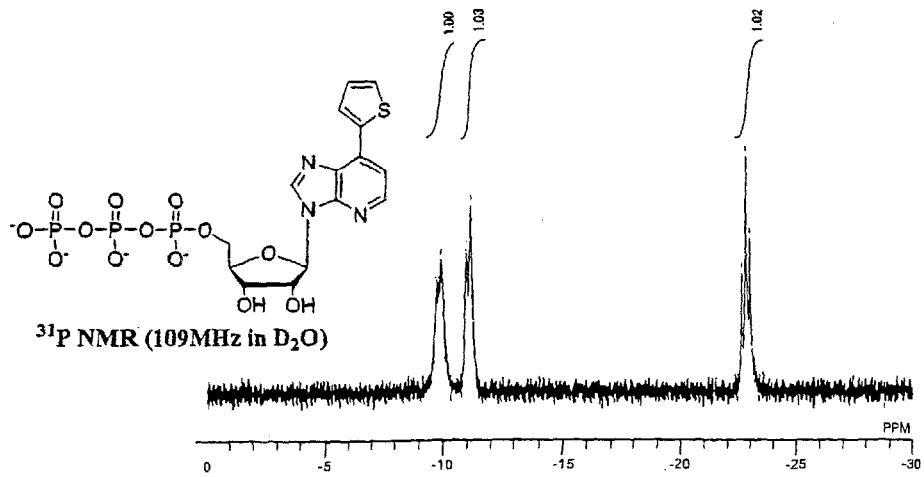

[FIG. 31a] FIG. 31a shows a $^{31}$P NMR (109 MHz, D$_2$O) spectrum of 7-(2-thienyl)-3-(β-D-ribofuranosyl)-3H-imidazo[4,5-b]pyridine 5'-triphosphate (Compound 14).

Figure 31B:
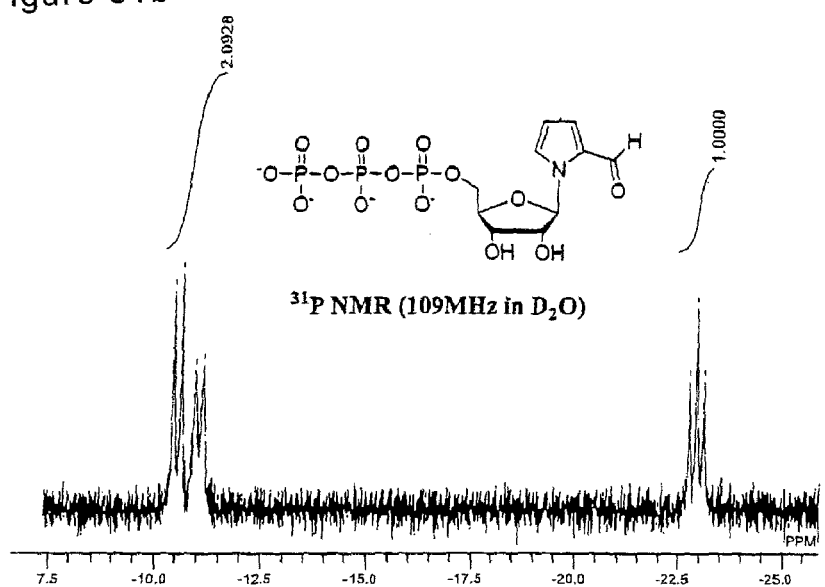

[FIG. 31b] FIG. 31b shows a $^{31}$P NMR (109 MHz, D$_2$O) spectrum of 1-(β-D-ribofuranosyl)pyrrole-2-carbaldehyde 5'-triphosphate (Compound 19).

Figure 31C:
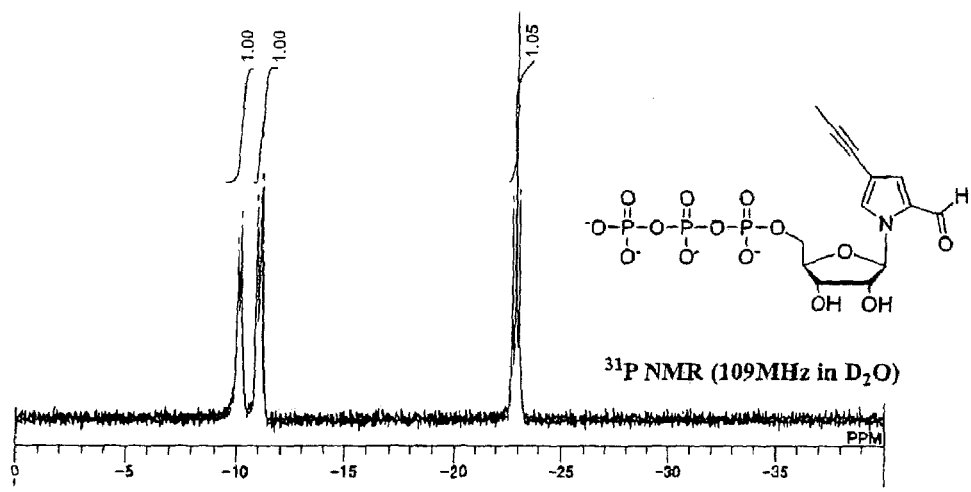

[FIG. 31c] FIG. 31c shows a $^{31}$P NMR (109 MHz, D$_2$O) spectrum of 4-propynyl-1-(β-D-ribofuranosyl)pyrrole-2-carbaldehyde 5'-triphosphate (Compound 20).

Figure 32:
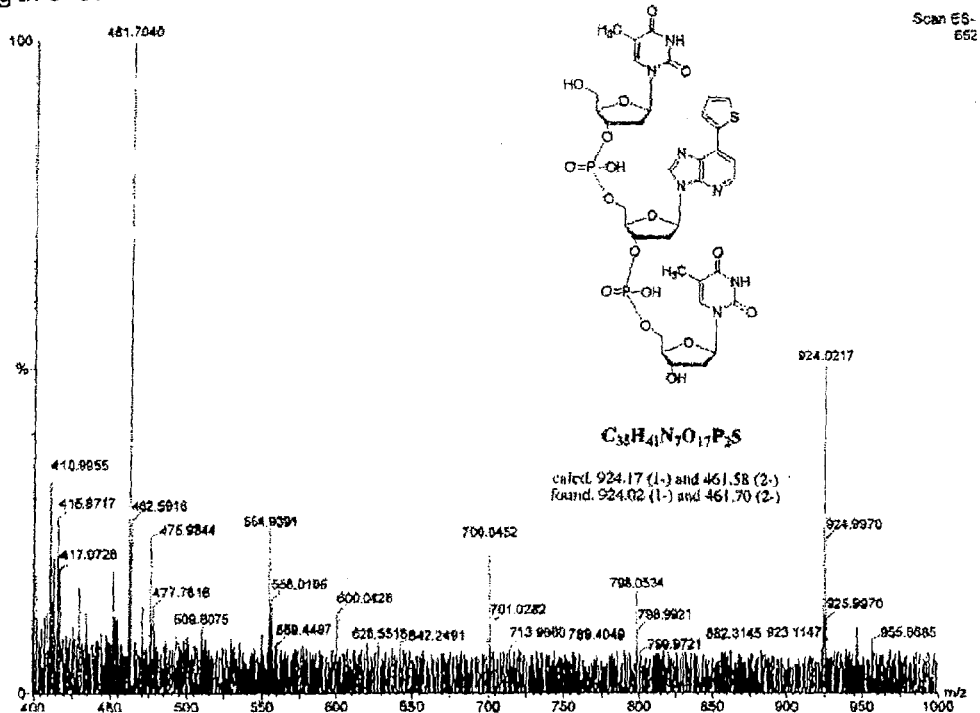

[FIG. 32] FIG. 32 shows the results of electrospray ionization mass spectrum (ESI-MS) for C$_{35}$H$_{40}$O$_{17}$P$_2$S. C$_{35}$H$_{40}$O$_{17}$P$_2$S: calcd: 924.17(1-); 461.58(2-), found: 924.02 (1-); 461.70(2-)

Figure 33:
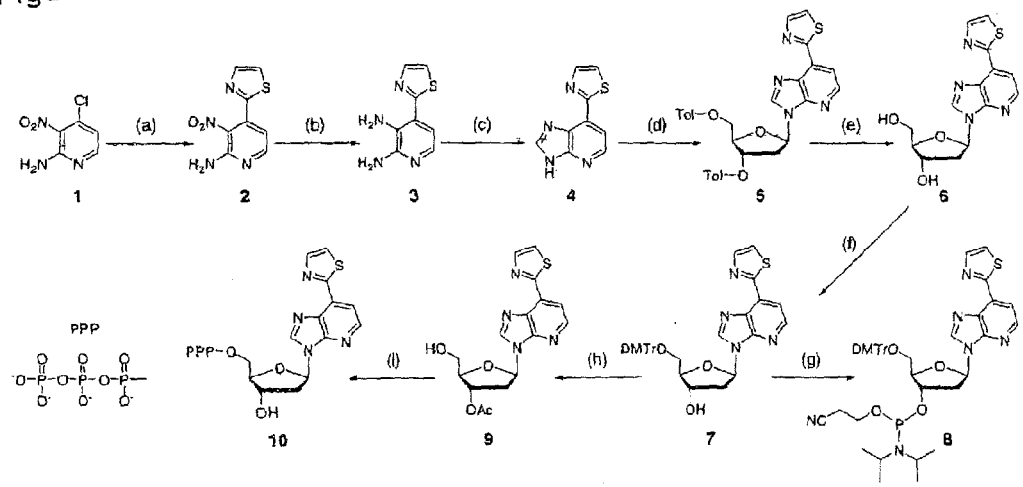

[FIG. 33] FIG. 33 shows a synthesis scheme for nucleoside derivatives of 7-(2-thiazolyl)-3H-imidazo[4,5-b]pyridine. Reagents and abbreviations: (a) dichlorobis(triphenylphosphine)palladium, 2-(tributylstanyl)thiazole, DMF; (b) palladium carbon, sodium borohydride, ethanol, ethyl acetate; (c) formic acid; (d) NaH, 2-deoxy-3,5-di-O-p-toluoyl-α-D-erythro-pentofuranosyl chloride, CH$_3$CN; (e) ammonia-saturated methanol; (f) 4,4'-dimethoxytrityl chloride, pyridine; (g) 2-cyanoethyl-N,N-diisopropylamino chloro phosphoroamidite, diisopropylethylamine, THF; (h) acetic anhydride, pyridine, then dichloroacetic acid, dichloromethane; (i) 2-chloro-4H-1,3,2,-benzodioxaphosphorin-4-one, dioxane, pyridine, tri-n-butylamine, bis(tributylammonium)pyrophosphate, I$_2$/pyridine, water, NH$_4$OH. Tol: toluoyl; DMT: 4,4'-dimethoxytrityl; Ac: acetyl.

Figure 34:
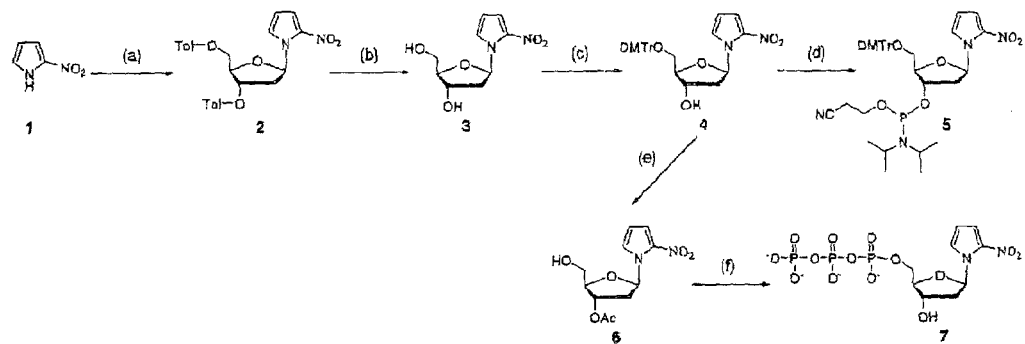

[FIG. 34] FIG. 34 shows a synthesis scheme for nucleoside derivatives of 2-nitropyrrole (Compound 1). Reagents and abbreviations: (a) NaH, 2-deoxy-3,5-di-O-p-toluoyl-α-D-erythro-pentofuranosyl chloride, CH$_3$CN; (b) ammonia-saturated methanol; (c) 4,4'-dimethoxytrityl chloride, pyridine; (d) 2-cyanoethyl-N,N'-diisopropylamino chloro phosphoramidite, diisopropylethylamine, THF; (e) acetic anhydride, pyridine, then dichloroacetic acid, dichloromethane; (f) 2-chloro-4H-1,3,2-benzodioxaphosphorin-4-one, dioxane, pyridine, tri-n-butylamine, bis(tributylammonium)pyrophosphate, I$_2$/pyridine, water, NH$_4$OH. Tol: toluoyl; DMT: 4,4'-dimethoxytrityl; Ac: acetyl.

Figure 35:
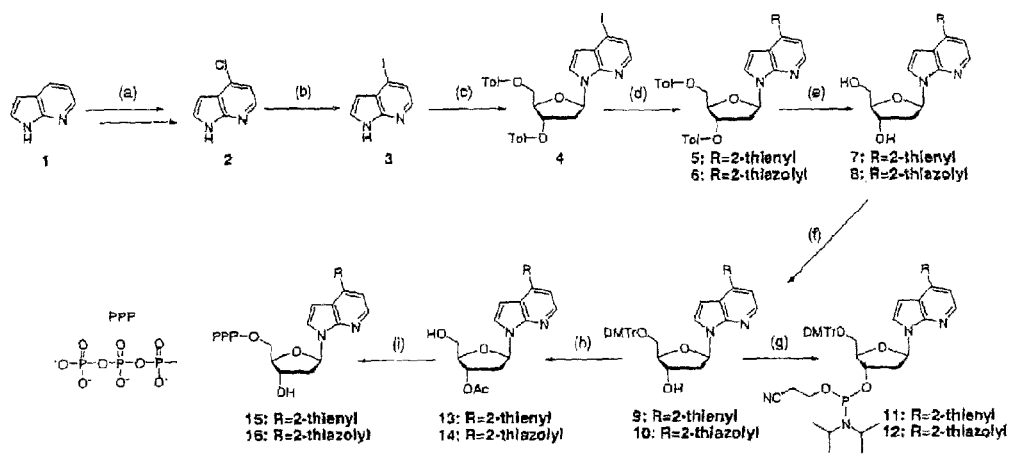

[FIG. 35] FIG. 35 shows a synthesis scheme for nucleoside derivatives of 4-(2-thienyl)-1H-pyrrolo[2,3-b]pyridine (DDs) and 4-(2-thienyl)-1H-pyrrolo[2,3-b]pyridine (DDv). Reagents and abbreviations: (a) mCPBA, EtOAc, then methanesulfonyl chloride, DMF; (b) NaI, CH$_3$COCl, CH$_3$CN; (c) NaH, 2-deoxy-3,5-di-O-p-toluoyl-α-D-erythro-pentofuranosyl chloride, CH$_3$CN; (d) dichlorobis(triphenylphosphine) palladium, 2-(tributylstanyl)thiophene or 2-(tributylstanyl)thiazole, DMF; (e) ammonia-saturated methanol; (f) 4,4'-dimethoxytrityl chloride, pyridine; (g) 2-cyanoethyl-N,N-diisopropylamino chloro phosphoroamidite, diisopropylethylamine, THF; (h) acetic anhydride, pyridine, then dichloroacetic acid, dichloromethane; (i) 2-chloro-4H-1,3,2,-benzodioxaphosphorin-4-one, dioxane, pyridine, tri-n-butylamine, bis(tributylammonium)pyrophosphate, I$_2$/pyridine, water, NH$_4$OH. Tol: toluoyl: DMT: 4,4'-dimethoxytrityl; Ac: acetyl.

Figure 36:
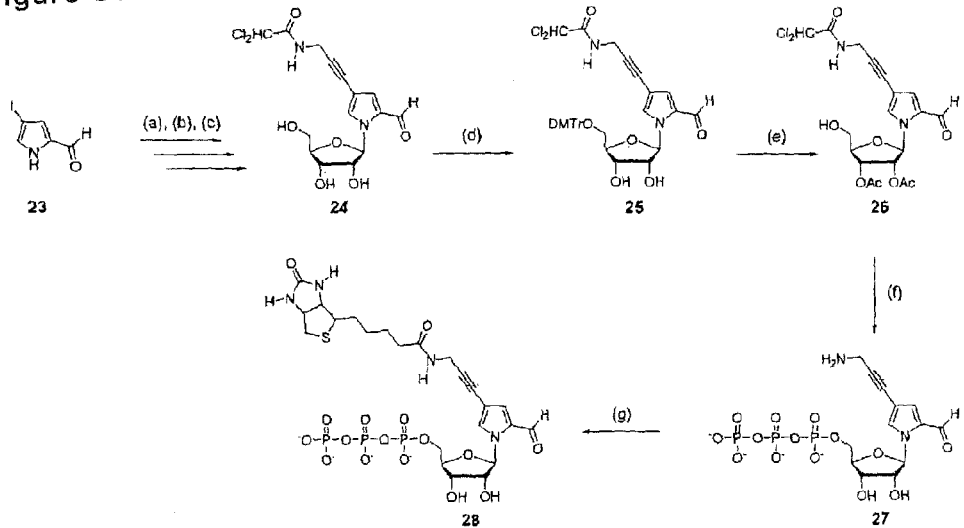

[FIG. 36] FIG. 36 shows a synthesis scheme for 1-(β-D-ribofuranosyl)-4-[(3-biotinamido-1-propynyl)]pyrrole-2-carbaldehyde 5'-triphosphate (Compound 28). Reagents and abbreviations: (a) NaH, CH$_3$CN, then 2,3,5-tri-O-benzyl-D-ribofuranosyl chloride; (b) BBr$_3$, dichloromethane; (c) 3-(dichloroacetamido)-1-propyne, tetrakis(triphenylphosphine)palladium, CuI, triethylamine, DMF; (d) 4,4'-dimethyltrityl chloride, pyridine; (e) acetic anhydride, pyridine, then dichloroacetic acid, dichloromethane; (f) 2-chloro-4H-1,3,2-benzodioxaphosphorin-4-one, dioxane, pyridine, tri-n-butylamine, bis(tributylammonium)pyrophosphate, DMF, then I$_2$/pyridine, water, NH$_4$OH; (g) biotin-N-hydroxysuccinimide, DMF, sodium carbonate buffer (pH 8.6), then NH$_4$OH. DMTr: 4,4'-dimethoxytrityl; Ac: acetyl.

Figure 37:
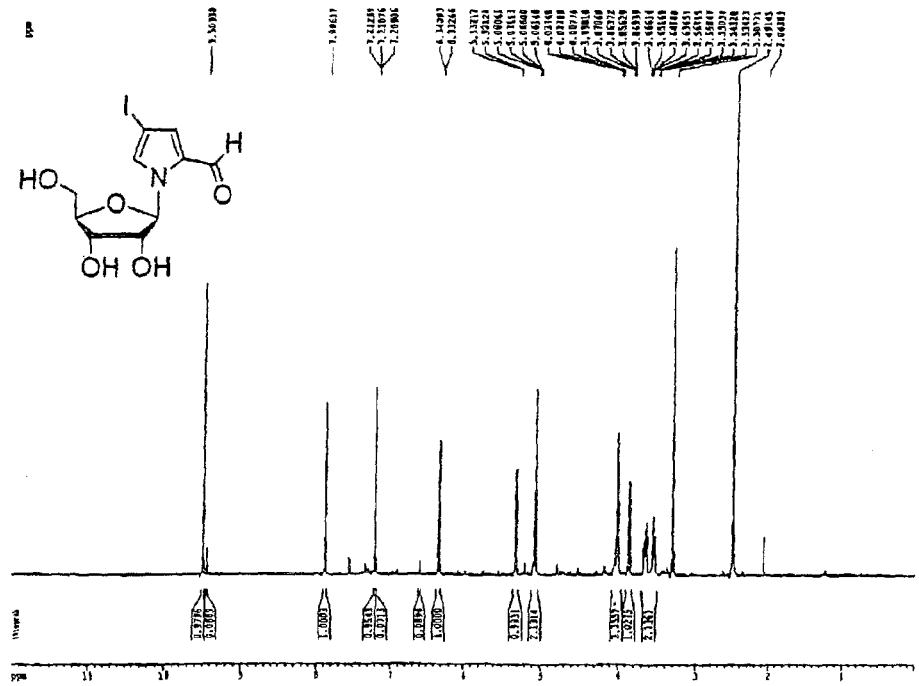

[FIG. 37] FIG. 37 shows a $^1$H NMR (500 MHz, DMSO-d6) spectrum for ribonucleoside of 4-iodopyrrole-2-carbaldehyde.

Figure 38A:
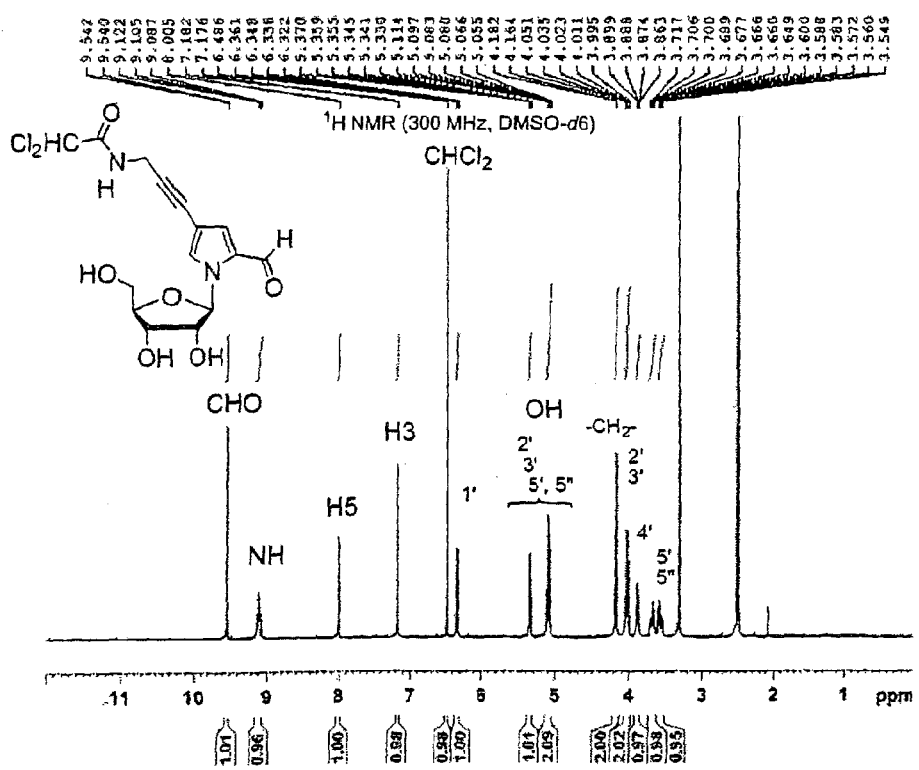

[FIG. 38a] FIG. 38 shows NMR spectra for 1-(β-D-ribofuranosyl)-4-[(3-dichloroacetamido)-1-propynyl]pyrrole-2-carbaldehyde (Compound 24). FIG. 38a shows a $^1$H NMR (300 MHz, DMSO-d6) spectrum of Compound 24.

Figure 38B:
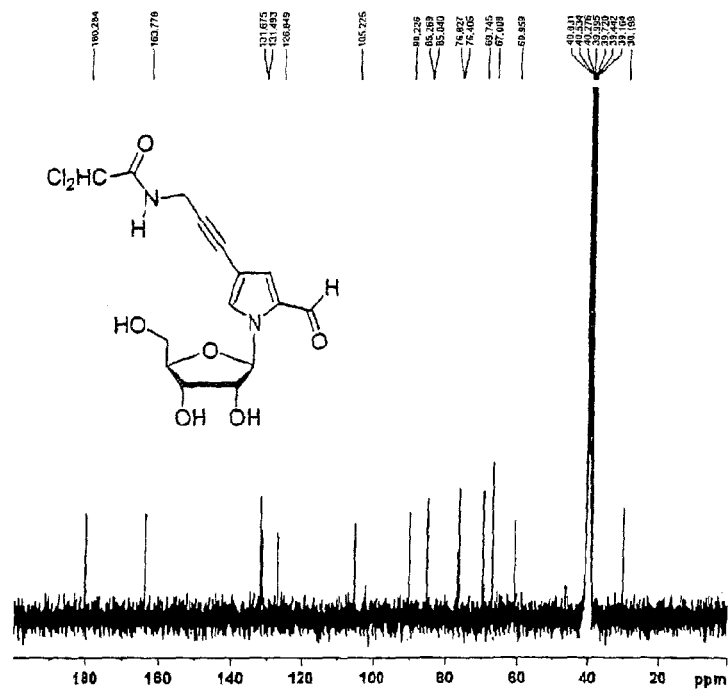

[FIG. 38b] FIG. 38 shows NMR spectra for 1-(β-D-ribofuranosyl)-4-[(3-dichloroacetamido)-1-propynyl]pyrrole-2-carbaldehyde (Compound 24). FIG. 38b shows a $^{13}$C NMR (75 MHz, DMSO-d6) spectrum of Compound 24.

Figure 38C:
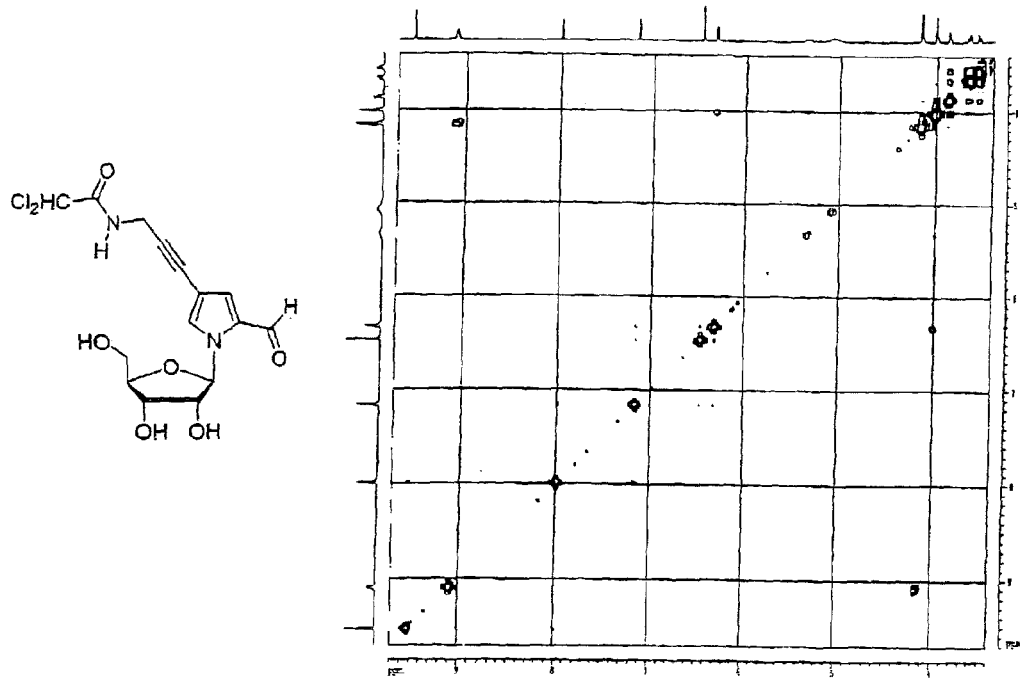

[FIG. 38c] FIG. 38 shows NMR spectra for 1-(β-D-ribofuranosyl)-4-[(3-dichloroacetamido)-1-propynyl]pyrrole-2-carbaldehyde (Compound 24). FIG. 38c shows a 2D COSY spectrum of Compound 24.

Figure 38D:
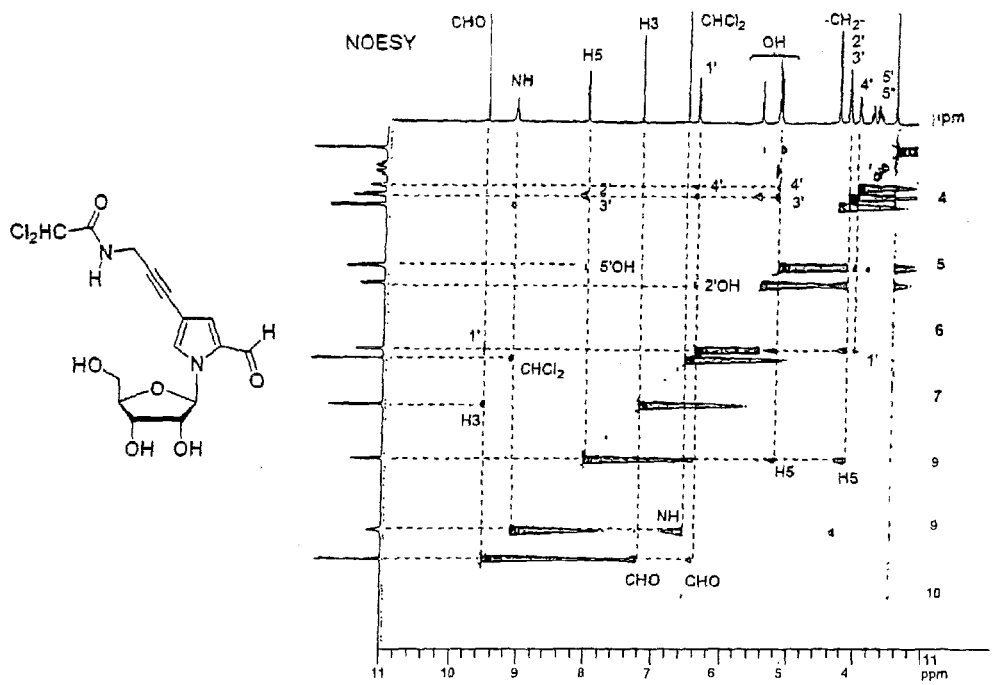

[FIG. 38d] FIG. 38 shows NMR spectra for 1-(β-D-ribofuranosyl)-4-[(3-dichloroacetamido)-1-propynyl]pyrrole-2-carbaldehyde (Compound 24). FIG. 38d shows a 2D NOESY spectrum of Compound 24.

Figure 38E:
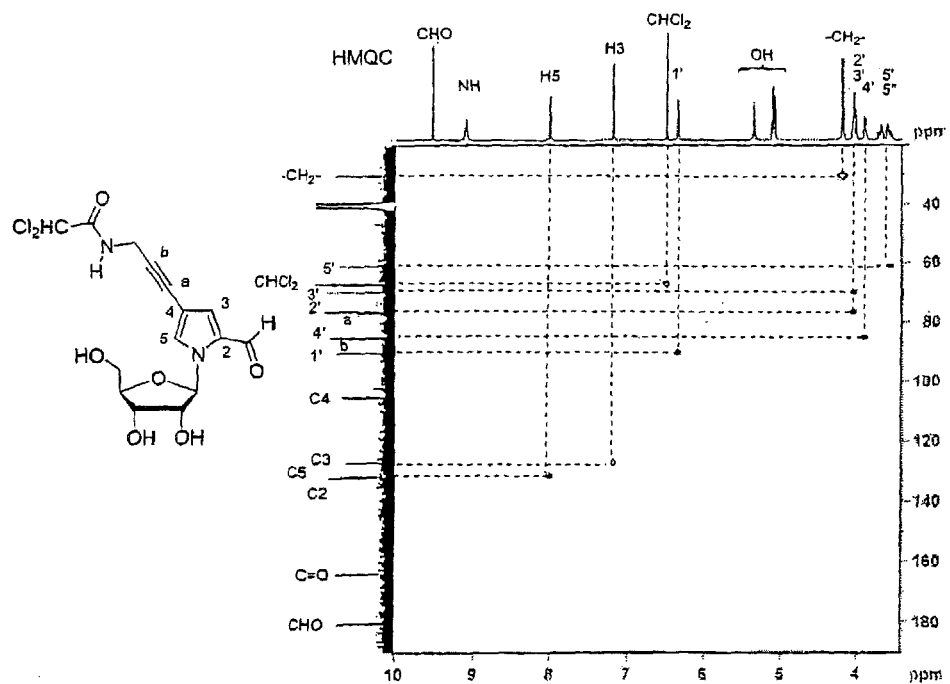

[FIG. 38e] FIG. 38 shows NMR spectra for 1-(β-D-ribofuranosyl)-4-[(3-dichloroacetamido)-1-propynyl]pyrrole-2-carbaldehyde (Compound 24). FIG. 38e shows a 2D HMQC spectrum of Compound 24.

Figure 38F:
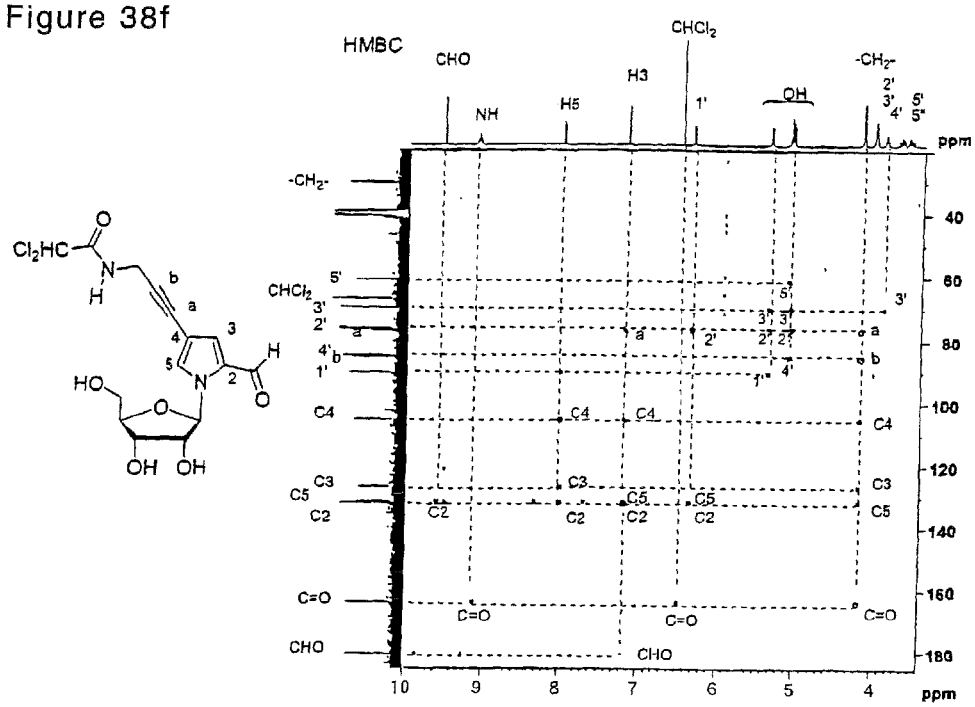

[FIG. 38f] FIG. 38 shows NMR spectra for 1-(β-D-ribofuranosyl)-4-[(3-dichloroacetamido)-1-propynyl]pyrrole-2-carbaldehyde (Compound 24). FIG. 38f shows a 2D HMBC spectrum of Compound 24.

Figure 38G:
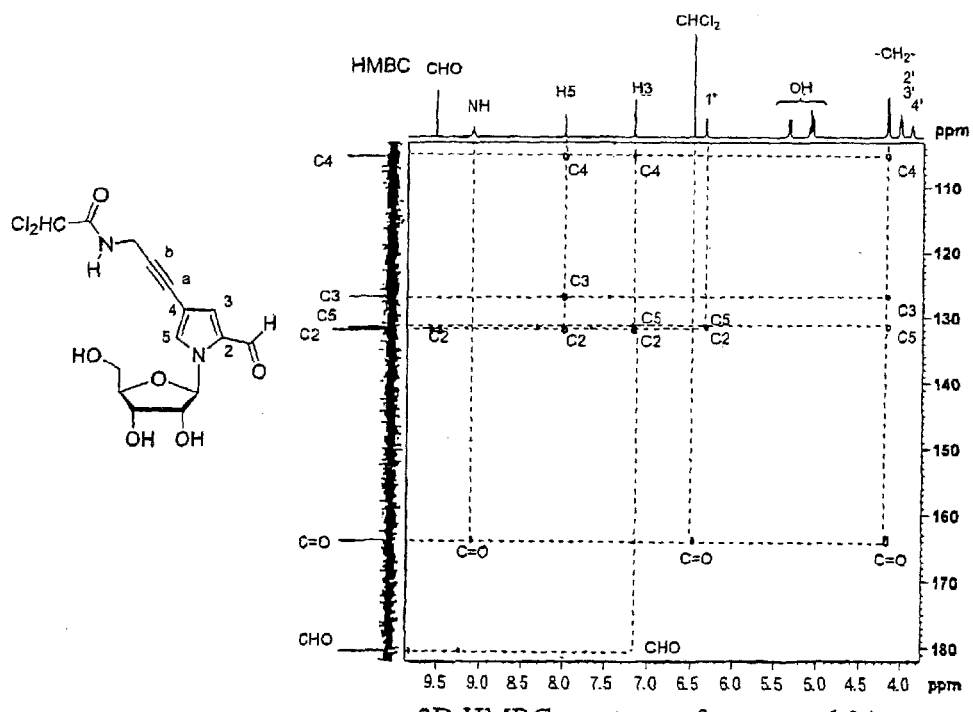

[FIG. 38g] FIG. 38 shows NMR spectra for 1-(β-D-ribofuranosyl)-4-[(3-dichloroacetamido)-1-propynyl]pyrrole-2-carbaldehyde (Compound 24). FIG. 38g shows a 2D HMBC spectrum of Compound 24 (enlarged).

Figure 39:
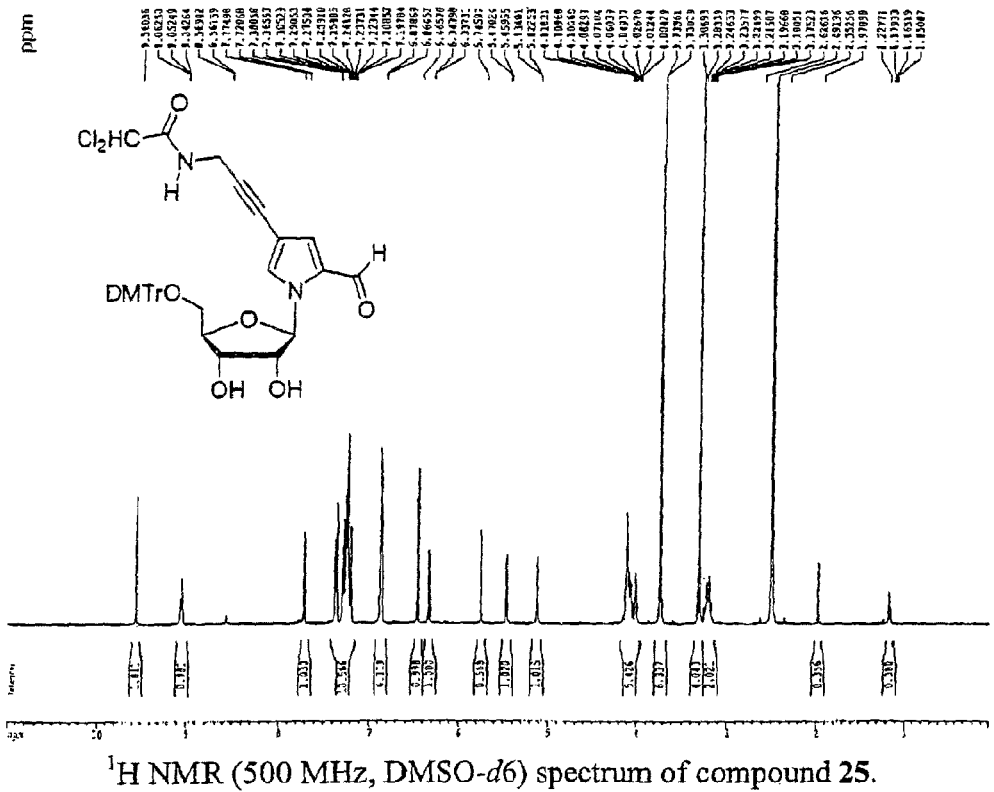

[FIG. 39] FIG. 39 shows a $^1$H NMR (500 MHz, DMSO-d6) spectrum of 1-[5-O-(4,4'-dimethoxytrityl)-≈-D-ribofuranosyl]-4-[(3-dichloroacetamido)-1-propynyl]pyrrole-2-carbaldehyde (Compound 25).

Figure 40:
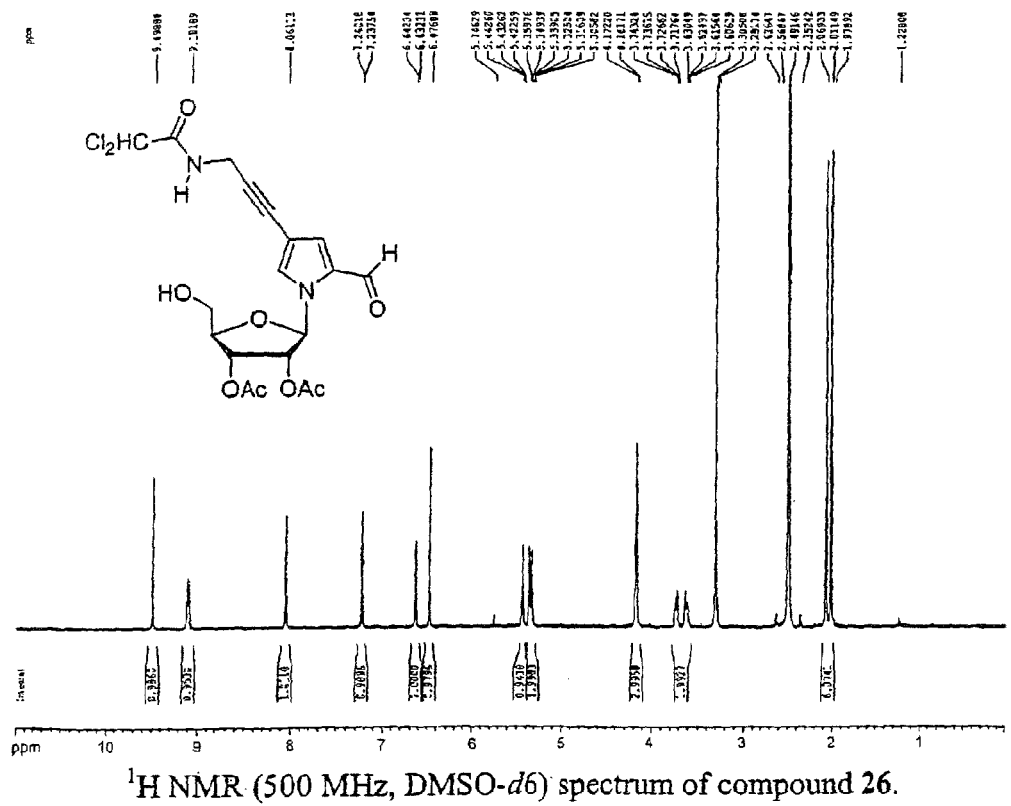

[FIG. 40] FIG. 40 shows a $^1$H NMR (500 MHz, DMSO-d6) spectrum of 1-(2,3-di-O-acetyl-β-D-ribofuranosyl)-4-[(3-dichloroacetamido)-1-propynyl]pyrrole-2-carbaldehyde (Compound 26).

Figure 41:
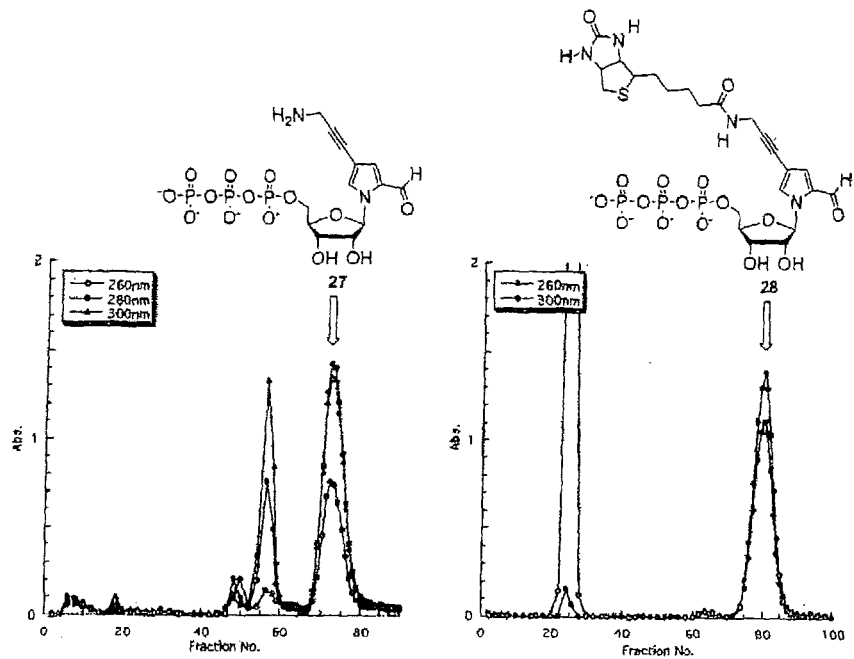

[FIG. 41] FIG. 41 shows DEAE Sephadex ion exchange column elution patterns of 1-(β-D-ribofuranosyl)-4-[(3-amino-1-propynyl)]pyrrole-2-carbaldehyde 5'-triphosphate (Compound 27) and 1-(β-D-ribofuranosyl)-4-[(3-biotinamido-1-propynyl)]pyrrole-2-carbaldehyde 5'-triphosphate (Compound 28).

Figure 42:
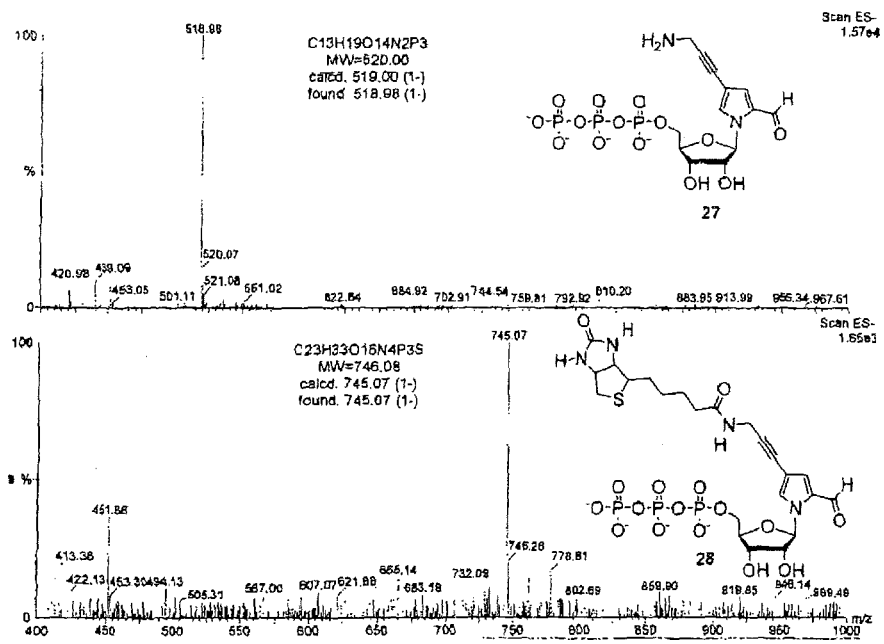

[FIG. 42] FIG. 42 shows ESI mass spectra of 1-(β-D-ribofuranosyl)-4-[(3-amino-1-propynyl)]pyrrole-2-carbaldehyde 5'-triphosphate (Compound 27; upper) and 1-(β-D-ribofuranosyl)-4-[(3-biotinamido-1-propynyl)]pyrrole-2-carbaldehyde 5'-triphosphate (Compound 28; lower).

Figure 43A:
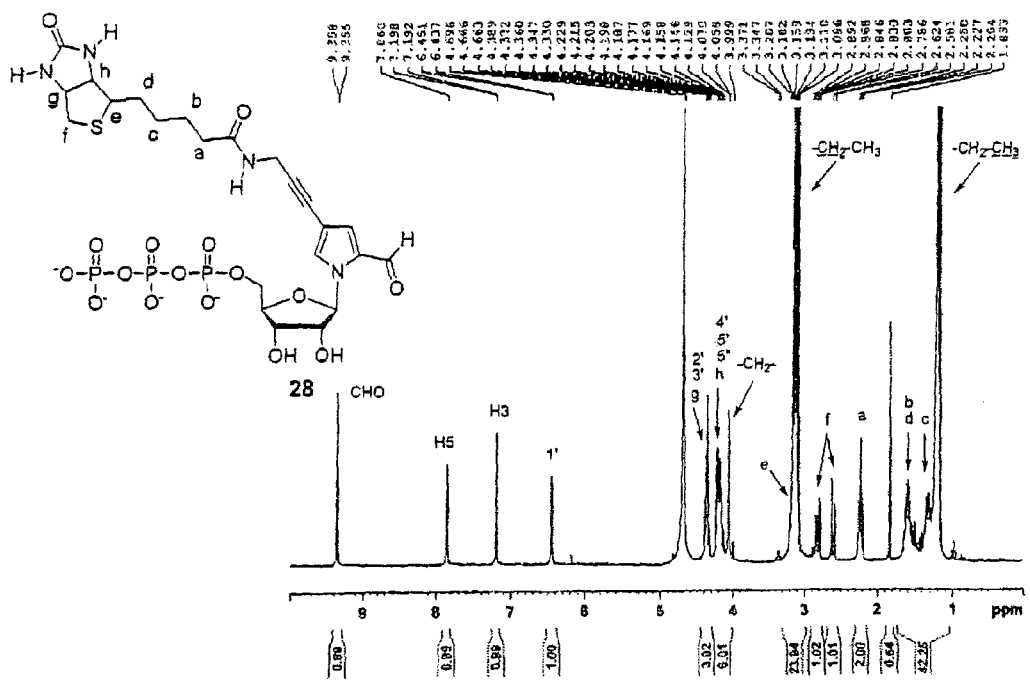

[FIG. 43a] FIG. 43 shows NMR spectra for 1-(β-D-ribofuranosyl)-4-[(3-biotinamido-1-propynyl)]pyrrole-2-carbaldehyde 5'-triphosphate (Compound 28). FIG. 43a shows a $^1$H NMR (300 MHz, D$_2$O) spectrum of Compound 28.

Figure 43B:
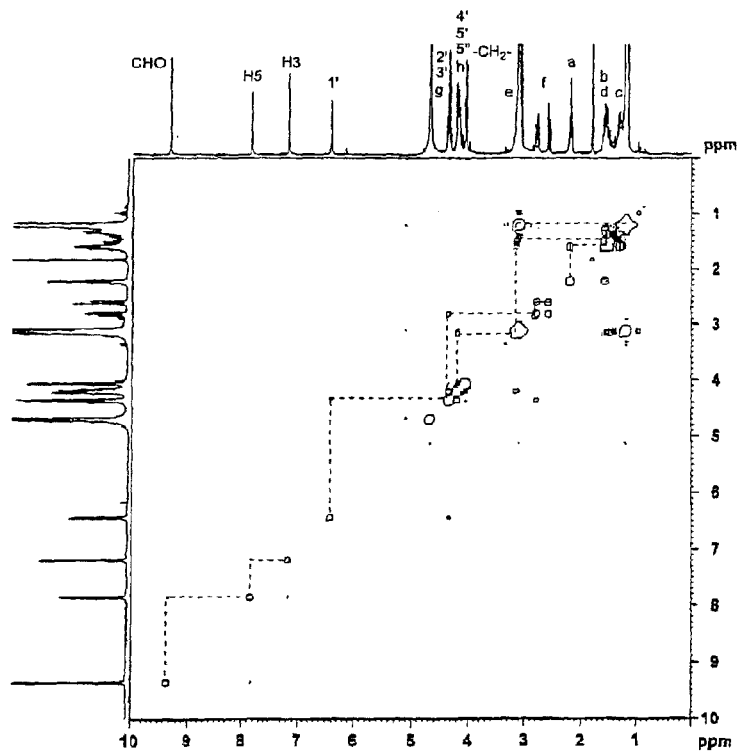

[FIG. 43b] FIG. 43 shows NMR spectra for 1-(β-D-ribofuranosyl)-4-[(3-biotinamido-1-propynyl)]pyrrole-2-carbaldehyde 5'-triphosphate (Compound 28). FIG. 43b shows a 2D COSY spectrum of Compound 28.

Figure 43C:
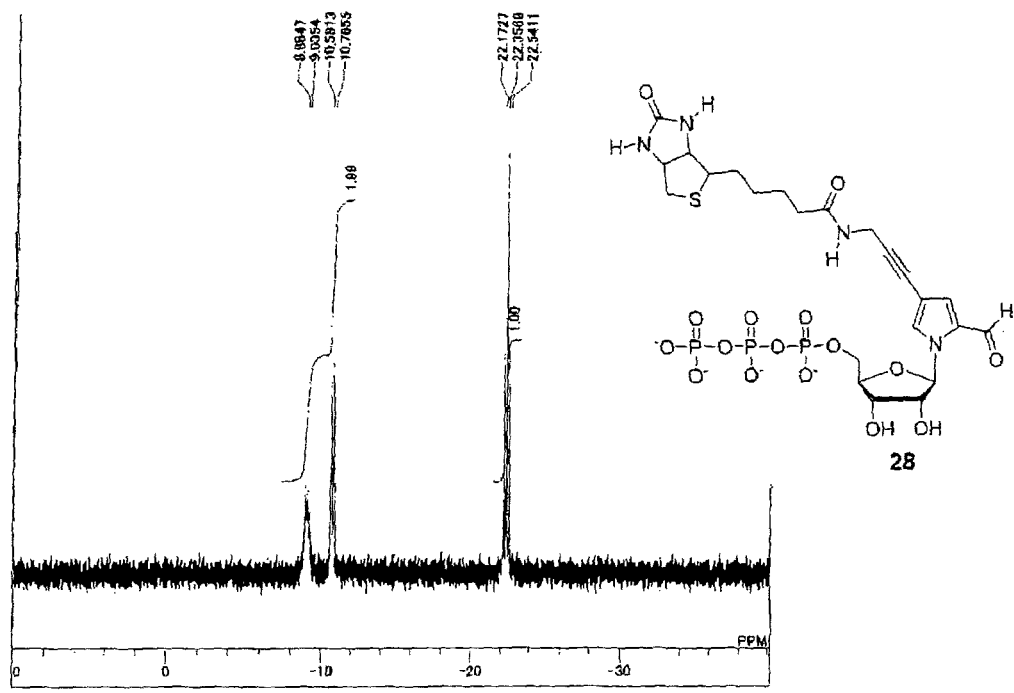

[FIG. 43c] FIG. 43 shows NMR spectra for 1-(β-D-ribofuranosyl)-4-[(3-biotinamido-1-propynyl)]pyrrole-2-carbaldehyde 5'-triphosphate (Compound 28). FIG. 43c shows a $^{31}$P NMR (109 MHz, D$_2$O) spectrum of Compound 28.

Figure 44A:
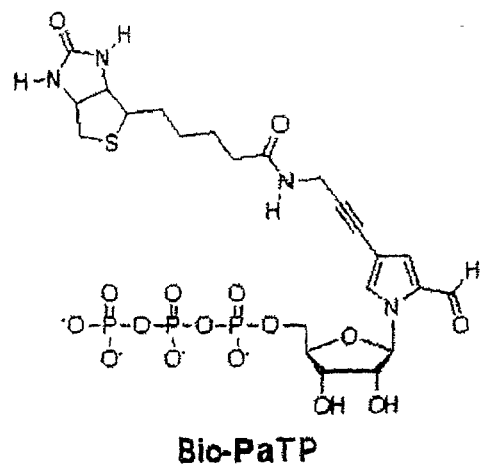

[FIG. 44a] FIG. 44a shows the chemical structure of biotinylated PaTP (Bio-PaTP; Compound 28).

Figure 44B:
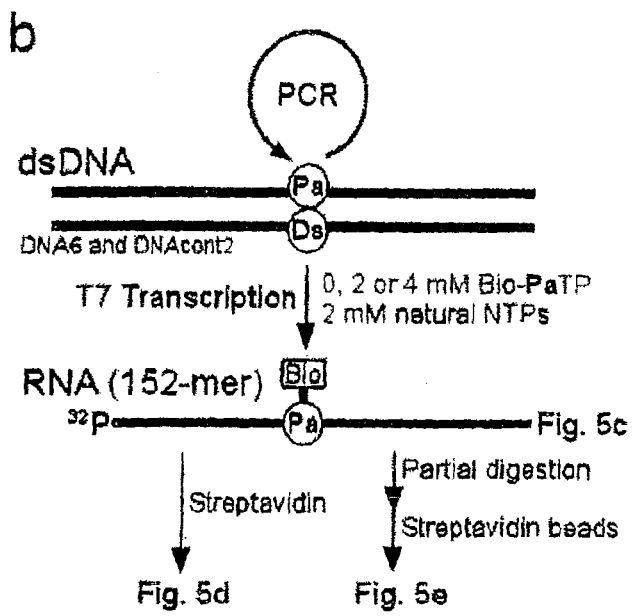

[FIG. 44b] FIG. 44b shows an experimental scheme for transcription and transcript analysis on site-specific biotinylation of RNA molecules by T7 transcription through Ds-Pa base pairing.

Figure 44C:
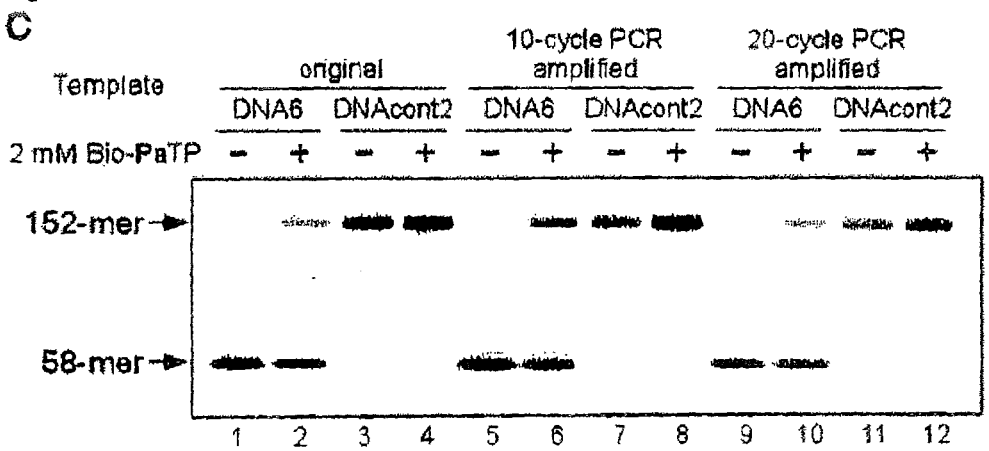

[FIG. 44c] FIG. 44c is a photograph showing gel electrophoresis of transcripts obtained in the site-specific biotinylation experiment on RNA molecules by T7 transcription through Ds-Pa base pairing. Lanes 1-4 indicate the results with the use of templates obtained by ligation, while Lanes 5-12 indicate the results with the use of templates obtained by PCR amplification. The templates used were DNA6 (Lanes 1, 2, 5, 6, 9 and 10) and DNAcont2 (as a control; Lanes 3, 4, 7, 8, 11 and 12). Transcription reaction was performed in the presence (2 mM) or absence of Bio-PaTP together with natural NTPs (2 mM). The transcripts were labeled with [γ-$^{32}$P] GTP.

Figure 44D:
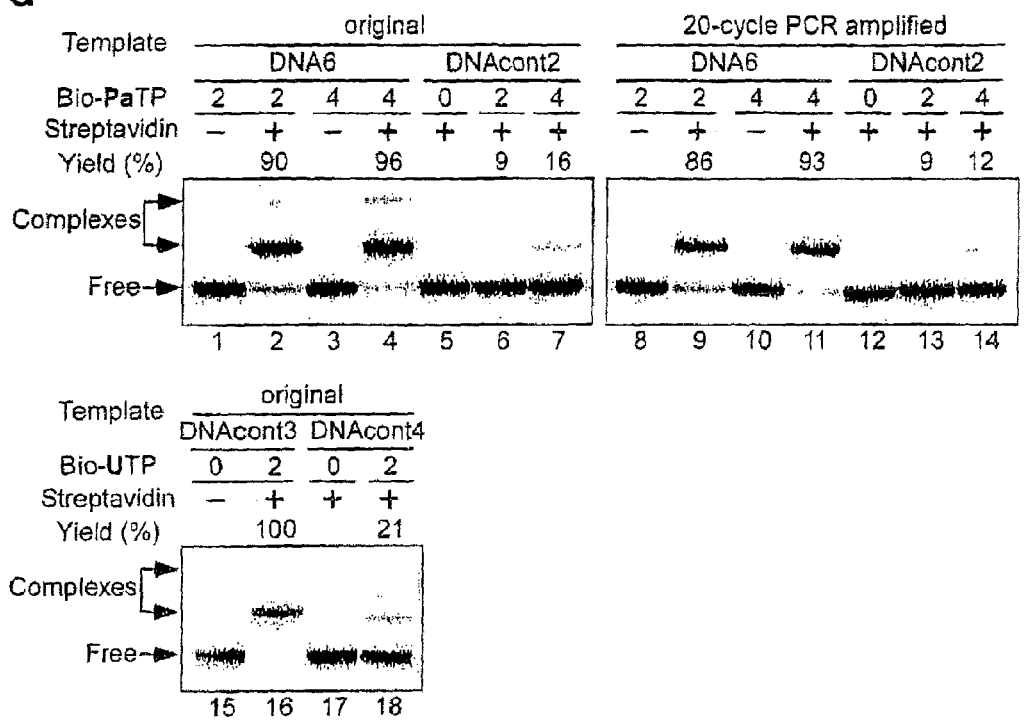

[FIG. 44d] FIG. 44d is photographs showing the results of gel shift assay for analysis of biotinylated transcripts. 152-mer RNAs transcribed with Bio-PaTP from DNA6 template obtained by ligation and DNAcont2 template obtained by PCR amplification (20 cycles), as well as 152-mer RNAs transcribed with biotinylated UTP (Bio-UTP) from DNAcont5 and DNAcont6 templates obtained by ligation were mixed with streptavidin. Biotinylated RNA-streptavidin complexes were separated from free RNAs on a 7% polyacrylamide-7 M urea gel, and the percentages (yields) of the complexes were determined from their band intensity.

Figure 44E:
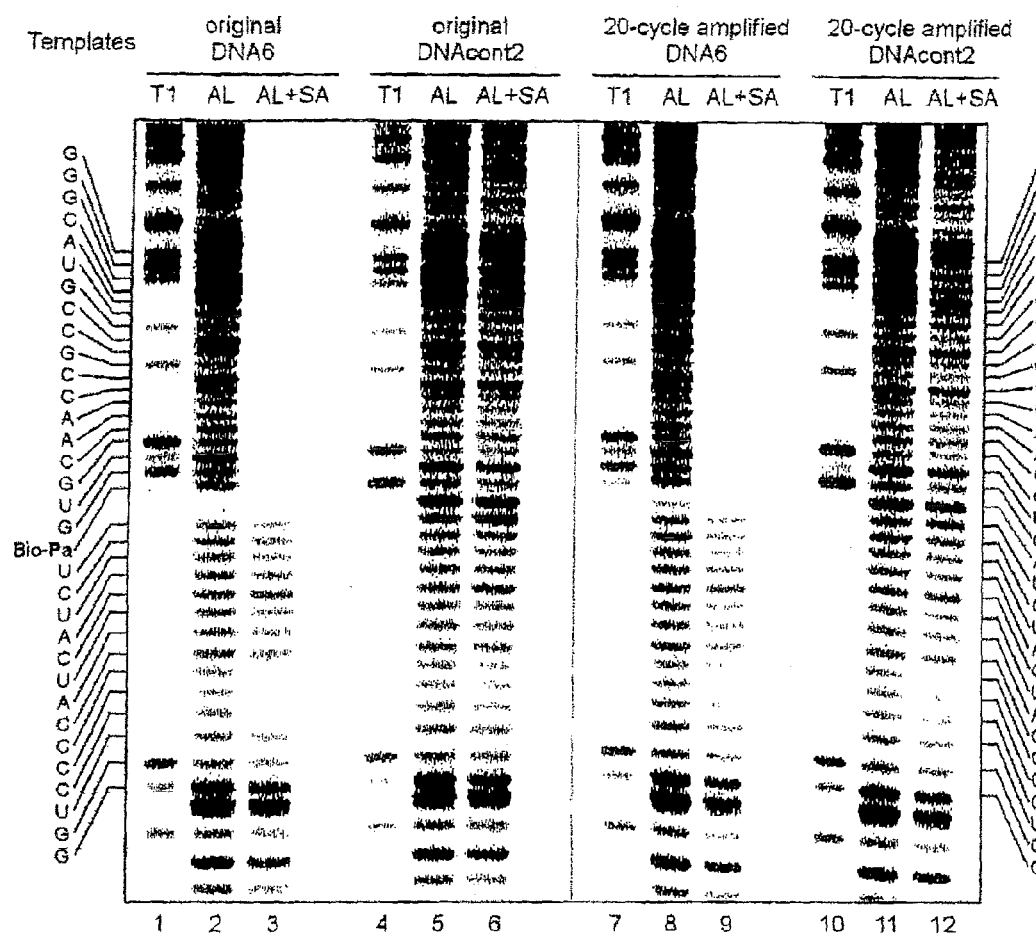

[FIG. 44e] FIG. 44e is a photograph showing the results of sequence analysis on 152-mer transcripts containing Bio-Pa or A at position 59. The 5'-terminally $^{32}$P-labeled transcripts were partially digested with RNase T1 (T1) or alkali (AL). A portion of each partially alkali-digested transcript was treated with streptavidin magnetic beads to capture RNA fragments containing Bio-Pa (AL+SA), and the rest was electrophoresed. The digested fragments were each analyzed on a 10% polyacrylamide-7 M urea gel.

Figure 45:
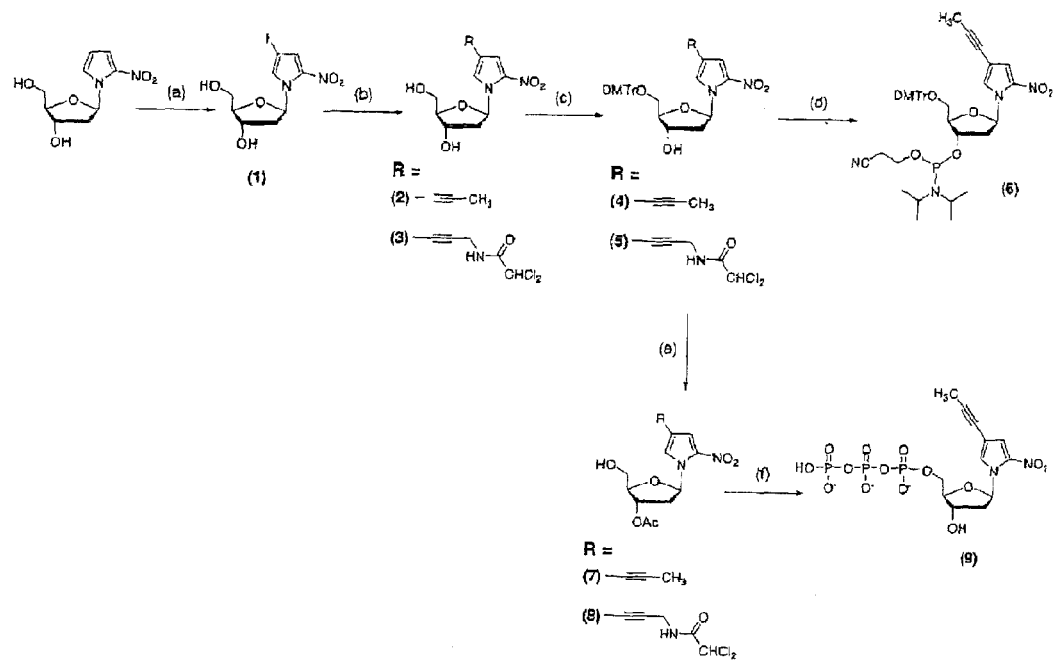

[FIG. 45] FIG. 45 shows a synthesis scheme for 4-position modified nucleoside derivatives of 2-nitropyrrole. Reagents and abbreviations: (a) N-iodosuccinimide, CH$_3$CN; (b) propynyl-1-tributyltin, Pd(PPh$_3$)$_2$Cl$_2$, DMF or N-(2-propynyl)-dichloroacetamide, Pd(PPh$_3$)$_4$, CuI, triethylamine, DMF; (c) 4,4'-dimethoxytrityl chloride, pyridine; (d) 2-cyanoethyl-N,N-diisopropylamino chloro phosphoramidite, diisopropylethylamine, THF; (e) acetic anhydride, pyridine, then dichloroacetic acid, dichloromethane; (f) 2-chloro-4H-1,3,2-benzodioxaphosphorin-4-one, dioxane, pyridine, tri-n-butylamine, bis(tributylammonium)pyrophosphate, I$_2$/pyridine, water, NH$_4$OH. DMTr: 4,4'-dimethoxytrityl; Ac: acetyl.

Figure 46:
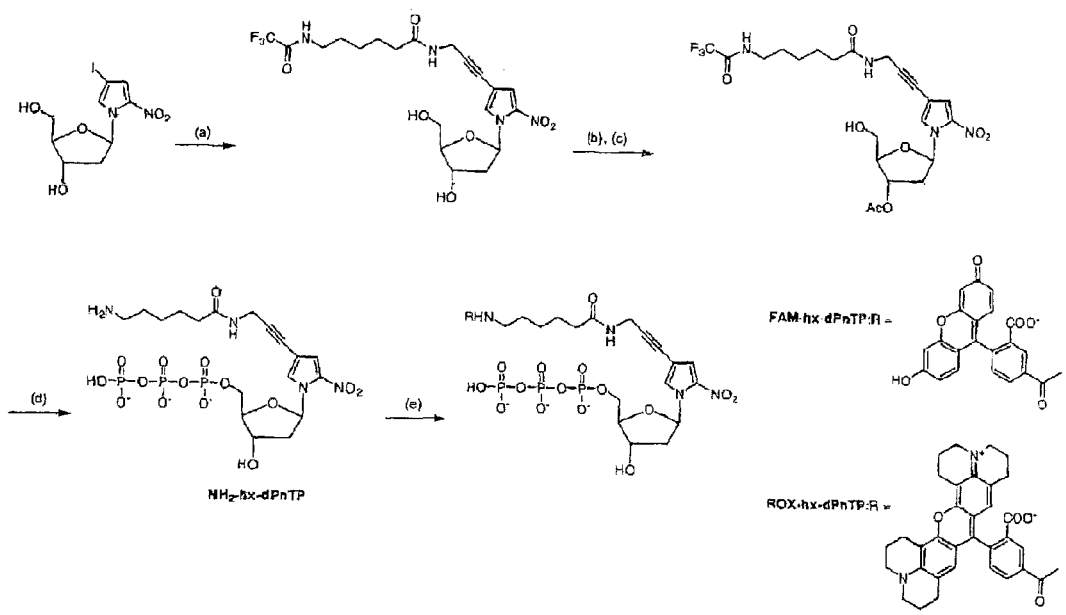

[FIG. 46] FIG. 46 shows a synthesis scheme for NH$_2$-hx-dPnTP, ROX-hx-dPnTP and FAM-hx-dPnTP. Reagents and abbreviations: (a) CuI, Pd[P(C$_6$H$_5$)$_3$]$_4$, DMF, triethylamine, room temperature, then N-(2-propynyl)-6-trifluoroacetamidohexanamide; (b) DMTr-Cl, pyridine, room temperature; (c) acetic anhydride, pyridine, room temperature, then dichloroacetic acid, dichloromethane, 0° C.; (d) 2-chloro-4H-1,3,2-benzodioxaphosphorin-4-one/dioxane, pyridine, tri-n-butylamine, bis(tri-n-butylammonium)pyrophosphate, DMF, then I$_2$/pyridine, water, NH$_4$OH, room temperature; (e) R—N-hydroxysuccinimidyl ester (R=FAM or ROX)/DMF, 0.1 M NaHCO$_3$—Na$_2$CO$_3$ buffer (pH 8.5), room temperature, 8 hours, then NH$_4$OH.

Figure 47:
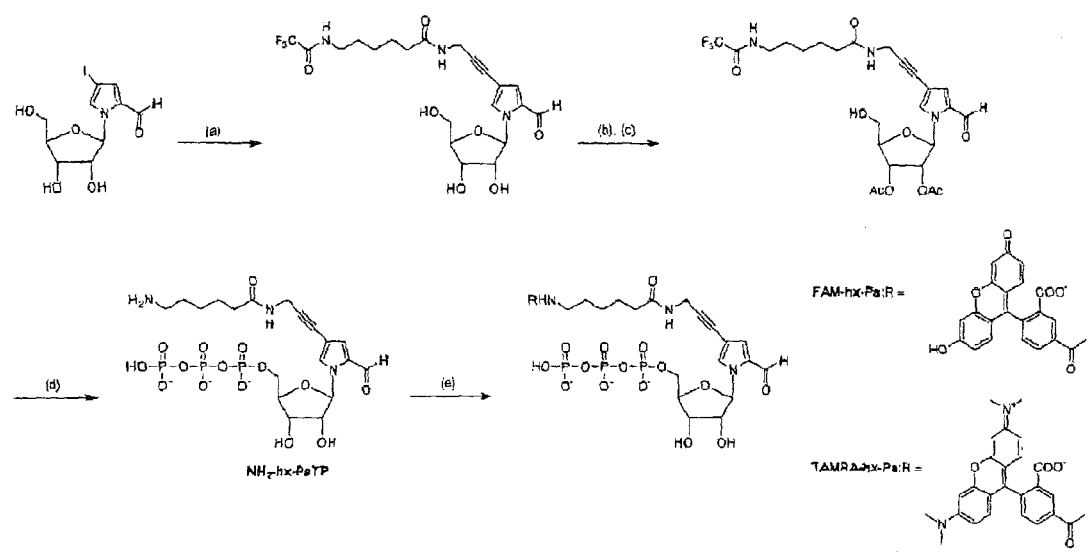

[FIG. 47] FIG. 47 shows a synthesis scheme for NH$_2$-hx-PaTP, FAM-hx-PaTP and TAMRA-hx-PaTP. Reagents and abbreviations: (a) CuI, Pd[P(C$_6$H5)$_3$]$_4$, DMF, triethylamine, room temperature, then N-(2-propynyl)-6-trifluoroacetamidohexanamide; (b) DMTr-Cl, pyridine, room temperature; (c) acetic anhydride, pyridine, room temperature, then dichloroacetic acid, dichloromethane, 0° C.; (d) 2-chloro-4H-1,3,2-benzodioxaphosphorin-4-one/dioxane, pyridine, tri-n-butylamine, bis(tri-n-butylammonium)pyrophosphate, DMF, then I$_2$/pyridine, water, NH$_4$OH, room temperature; (e) R—N-hydroxysuccinimidyl ester (R=FAM or TAMRA)/DMF, 0.1 M NaHCO$_3$—Na$_2$CO$_3$ buffer (pH 8.5), room temperature, 8 hours, then NH$_4$OH.

[FIG. 48] FIG. 48 shows a scheme for incorporation of substrate Pn having an amino group or a fluorescent dye into DNA (55-mer) through replication using Klenow fragment, along with the results obtained.

Figure 49:
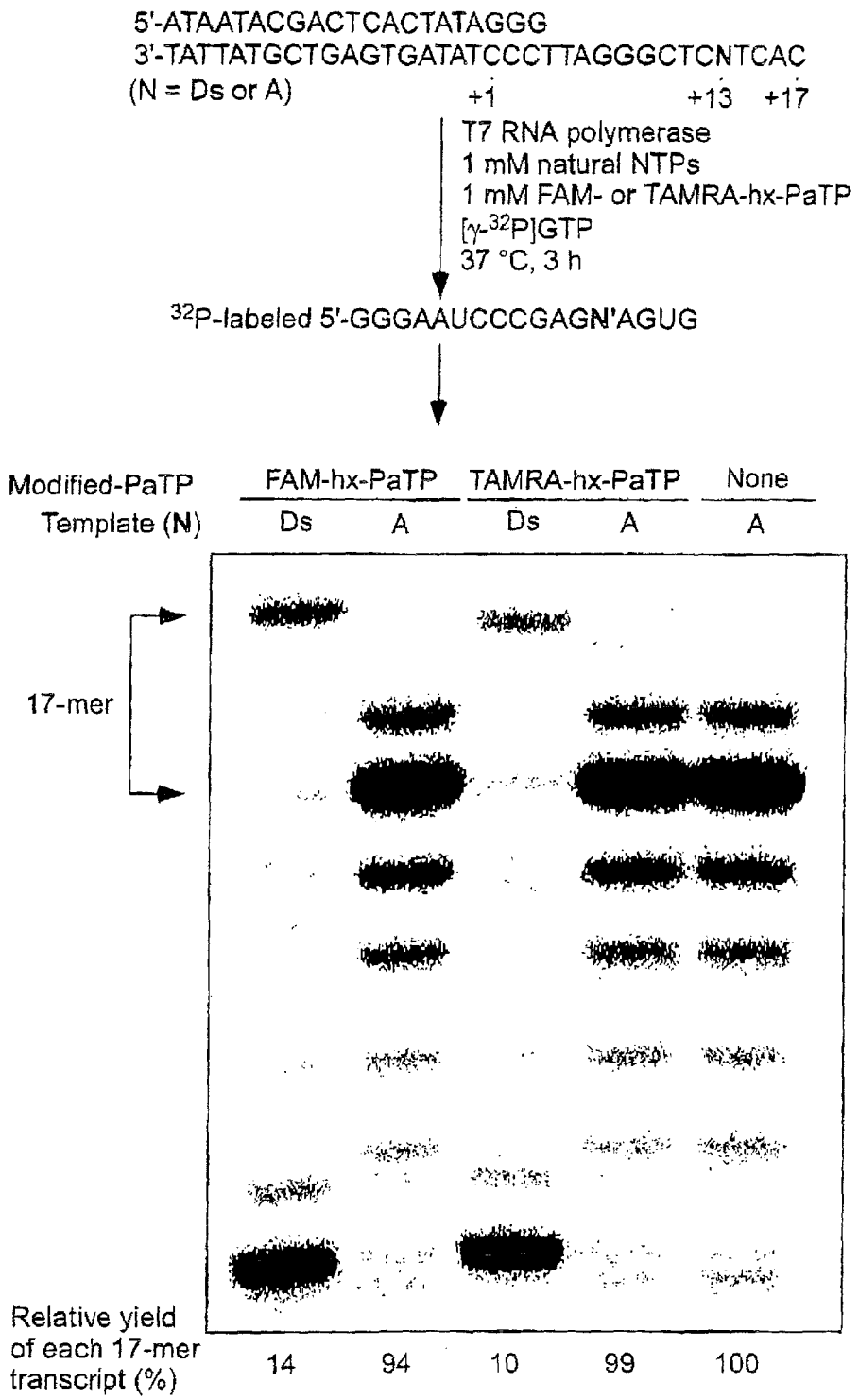

[FIG. 49] FIG. 49 shows a scheme for incorporation of substrate Pa having a fluorescent dye into RNA (17-mer) through transcription using T7 RNA polymerase, along with the results obtained.

EXAMPLES

The present invention will now be further described in the following examples, which are not intended to limit the technical scope of the invention. Based on the detailed description, various modifications and changes will be apparent to those skilled in the art, and such modifications and changes fall within the technical scope of the invention.

Example I Chemical Synthesis-1

1. General Methods and Materials

All reagents and solvents were purchased from standard suppliers and were used without further purification. Thin-layer chromatography (TLC) was performed using 0.25 mm silica gel 60 plates containing a 254 nm fluorescence indicator (Merck) to monitor transcription reaction. $^1$H NMR, $^{13}$C NMR and $^{31}$P NMR spectra were recorded on JEOL EX270 and BRUKER nuclear magnetic resonance spectrometers (300 MHz and 600 MHz). Nucleoside purification was performed on a Gilson HPLC system equipped with a preparative C18 column (Waters Microbond Sphere, 150×19 mm). Triphosphate derivatives were purified with a DEAE-Sephadex A-25 column (300×15 mm) and an analytical C18 column (Synchropak RPP, 250×4.6 mm, Eichrom Technologies).

High-resolution mass spectra (HRMS) and electrospray ionization mass spectra (ESI-MS) were recorded on a JEOL HX-110 or JM700 mass spectrometer and a Waters micro mass ZMD4000 equipped with a Waters 2690 LC system, respectively. Fluorescence measurement was accomplished by using a FP-6500 spectral fluorometer (JASCO).

Pyrrole-2-carbaldehyde (Non-patent Document 39) and 4-propynylpyrrole-2-carbaldehyde (Non-patent Document 40) were synthesized as described in these prior documents.

2. Explanation of Compound Synthesis

Synthesis of 7-(2-thienyl)-3H-imidazo[4,5-b]pyridine was accomplished through the reactions shown in FIG. 22. More specifically, 7-(2-thienyl)-3H-imidazo[4,5-b]pyridine (Compound 4) was synthesized from 2-amino-3-nitro-4-chloropyridine (Compound 1) (Non-patent Document 41) in 3 steps (72%). A deoxyribonucleoside of 7-(2-thienyl)-3H-imidazo[4,5-b]pyridine (shown as Compound 6) was obtained as a single product from Compound 4 in a yield of 61% by reaction of 1-chloro-2-deoxy-3,5-di-O-toluoyl-α-D-erythro-pentofuranose (Non-patent Document 42) with a sodium salt of Compound 4, followed by deprotection of the toluoyl groups from Compound 5 with methanolic ammonium.

A ribonucleoside of 7-(2-thienyl)-3H-imidazo[4,5-b]pyridine (shown as Compound 11) was synthesized by reaction between tetra-O-acetyl-β-D-ribofuranose and 4 at 200° C. with a catalytic amount of chloroacetic acid. Compound 11 was obtained in a yield of 29% after deprotection with ammonia-saturated methanol and purification by RP-HPLC.

The structures of Nucleosides 6 and 11 were confirmed by NMR and high-resolution mass spectroscopy (NMR spectra of Compounds 6 and 11 in the section "1. General methods and materials"). The aromatic proton peaks of Compounds 6 and 11 showed the same chemical shifts. The HMBC and HSQC spectra of Compounds 6 and 11 indicated that an N-glycosidic linkage was formed between sugar Cl' and N-3 position of the imidazo[4,5-b]pyridine base moiety. Further, the inventors of the present invention confirmed that the thienyl moiety of Compounds 6 and 11 was attached at the 7-position of the imidazo[4,5-b]pyridine ring, as is seen from their 2D NOESY and 2D HMBC spectra. The anomeric configurations of Compounds 6 and 11 were confirmed to be β by their 2D NOESY and 1D NOE spectra. The main results of the 1D NOE experiment are that H1' proton irradiation causes enhancements of 2% and 3% in the H4' signal and enhancements of 8% and 9% in the H2 signal in Compounds 6 and 11, respectively. In the differential NOE experiment, H2 proton irradiation caused enhancements of 9% and 10% in the H1' signal and an enhancement of 3% to 5% in the H2' and H3' signals. Thus, based on the NOE experiment, the anomeric configurations of Compounds 6 and 11 were determined to be β. Compound 6 was converted into its amidite form in a standard manner, and the formation of a Tp(6)pT trimer was confirmed by electrospray ionization mass spectrometry (ESI-MS) (see the trimer's mass spectrum in "nucleoside derivatives of pyrrole-2-carbaldehyde and 4-propynylpyrrole-2-carbaldehyde, as well as 6-amino-9-(2-deoxy-β-D-ribofuranosyl)purine 5'-γ-amidotriphosphate"). Nucleoside 5'-triphosphates shown as Compounds 10 and 14 were synthesized in a standard manner (Non-patent Document 43) for use as substrates in enzymatic reactions.

Synthesis of nucleoside derivatives of pyrrole-2-carbaldehyde (Compound 15) and 4-propynylpyrrole-2-carbaldehyde (Compound 16) was accomplished by the reactions shows in FIG. 23. Synthesis of deoxynucleoside derivatives of Compounds 15 and 16 has been reported (Non-patent Documents 39 and 40). Ribonucleosides of Compounds 15 and 16 were synthesized by reaction of 2,3,5-tri-O-benzyl-D-ribofuranosyl chloride (Non-patent Document 44) with a sodium salt of Compound 15 or 16, followed by BBr$_3$ treatment to deprotect the benzyl groups, thereby obtaining ribonucleosides shown as Compounds 17 (yield 15%) and 18 (yield 7%) in 2 steps.

The structures of Compounds 17 and 18 were confirmed by NMR (see NMR spectra of Compounds 17 and 18 shown in FIG. 25) and high-resolution mass spectroscopy. The HMBC and HSQC spectra of Compounds 17 and 18 indicated that an N-glycosidic linkage was formed between sugar and pyrrole base moiety at the Cl' carbon. The anomeric configurations of Compounds 17 and 18 were confirmed by the NOE experiment (differential NOE and NOESY spectra).

The main results of the differential NOESY spectrum experiment are as follows. H1' proton irradiation caused an enhancement of 3% to 4% in the H4' signal. H2' (and/or H3') proton irradiation caused an enhancement of 9% to 10% in the H5 signal. The NOESY spectra of Compounds 17 and 18 showed cross peaks between H1' and H4', between H1' and CHO proton, and between H5 and H2' (and/or H3'). Thus, based on NOE NMR, the anomeric configurations of Compounds 17 and 18 were determined to be β. The ribonucleosides shown as Compounds 17 and 18 were converted into their ribonucleoside 5'-triphosphate form in a standard manner (Non-patent Document 45).

Nucleoside 5'-triphosphates were synthesized as disclosed in prior art documents (Non-patent Documents 43 and 45). Synthesis of 5'-γ-amidotriphosphates was accomplished in a standard manner (Non-patent Document 43) with modifications. Protected nucleosides shown as Compounds 9 and 21 were phosphitylated with 2-chloro-4H-1,3,2-benzodioxaphosphorin-4-one. The protected nucleoside phosphite derivatives were converted into $P^2,P^3$-dioxo-$P^1$-5'-nucleosidylcyclotriphosphites by treatment with pyrophosphate. After treatment with iodine/water, the resulting 5'-trimetaphosphates were treated with concentrated aqueous ammonia to give nucleoside 5'-γ-amidotriphosphates.

Purification of these 5'-γ-amidotriphosphates was performed by anion exchange DEAE Sephadex column chromatography and RP-HPLC. The DEAE column elution patterns and electrospray ionization mass spectra of deoxyadenosine 5'-γ-amidotriphosphate are shown in FIGS. 26 and 27.

During 5'-γ-amidotriphosphate synthesis, 5'-triphosphate of deoxyadenosine was also formed, and the 5'-γ-amidotriphosphate and 5'-triphosphate were in the ratio of 4.8:1, as calculated from their fraction absorbance. Compound 22 was eluted relatively faster than deoxyadenosine 5'-phosphate (dATP) and separated by DEAE column purification. The 5'-γ-amidotriphosphate was confirmed for its molecular weight by ESI-MS spectrometry. The difference between Compound 22 and dATP was 1 m/z. After final purification by HPLC, the nucleoside 5'-γ-amidotriphosphates were obtained as triethylammonium salts and confirmed for their structure by NMR spectroscopy ($^1$H and $^{31}$P NMR). γ-Phosphate signals from deoxyadenosine 5'-γ-amidotriphosphate and Compound 6 were shifted to lower magnetic field (−0.50 and −0.52 p.p.m), as compared to those of 5'-phosphates of Compounds 6, 11, 17 and 18. This phenomenon was also observed in guanosine 5'-γ-amidotriphosphate.

3. Detailed Explanation of Synthesis (1) 2-Amino-3-nitro-4-(2-thienyl)pyridine (Compound 2)

To a solution of 2-amino-3-nitro-4-chloropyridine (Compound 1) (Non-patent Document 41) (1.74 g, 10 mmol) and dichlorobis(triphenylphosphine)palladium (II) (350 mg, 0.50 mmol) in DMF (50 ml), 2-(tributylstanyl)thiophene (3.82 ml, 12 mmol) was added under an argon atmosphere. The resulting mixture was stirred at 100° C. for 4 hours. The mixture was poured into water (250 ml) and then extracted with ethyl acetate (250 ml×3). After drying over Na$_2$SO$_4$, the solvent was distilled off under reduced pressure. The residue was applied to flash silica gel chromatography using methylene chloride:ethyl acetate (100:1 to 49:1) as an eluent to give 2.07 g of Compound 2 (Rf 0.30 on methylene chloride:ethyl acetate=19:1) in a yield of 93%.

$^1$H NMR (270 MHz, CDCl$_3$) δ 8.17 (d, 1H, J=5.1 Hz), 7.4 (dd, 1H, J=5.0 and 1.1 Hz), 7.12 (dd, 1H, J=3.6 and 1.1 Hz), 7.07 (dd, 1H, J=5.0 and 3.6 Hz), 6.77 (d, 1H, J=5.1 Hz), 5.66 (bs, 2H).

HRMS (FAB, 3-NBA, matrix) C$_9$H$_8$N$_3$O$_2$S (M+1): calcd, 222.0337; found, 222.0337.

(2) 2,3-Diamino-4-(2-thienyl)pyridine (Compound 3)

To a mixture of Compound 2 (2.06 g, 9.3 mmol) and 466 mg palladium carbon (10% by weight) in ethanol (130 ml)

and ethyl acetate (65 ml), 28 ml of 1 M aqueous sodium borohydride was added at 0° C. The resulting mixture was stirred at 0° C. for 1 hour. To the mixture, 43 ml of 5% aqueous ammonium chloride was added. The mixture was filtered through celite. The filtrate was diluted with 500 ml water. After evaporation of ethanol and ethyl acetate, the mixture was extracted with ethyl acetate (250 ml×3). After drying over $Na_2SO_4$, the solvent was distilled off. The residue was purified by flash silica gel chromatography using methylene chloride:ethyl acetate (19:1 to 93:7) as an elution solvent to give 1.46 g of Compound 3 (Rf 0.24 on methylene chloride: ethyl acetate=9:1) in a yield of 82%.

$^1$H NMR (270 MHz, $CDCl_3$) δ 7.64 (d, 1H, J=5.1 Hz), 7.40 (dd, 1H, J=5.1 and 1.1 Hz), 7.23 (dd, 1H, J=3.5 and 1.1 Hz), 7.14 (dd, 1H, J=5.1 and 3.5 Hz), 6.74 (d, 1H, J=5.1 Hz), 4.26 (bs, 2H), 3.72 (bs, 2H).

HRMS (FAB, 3-NBA matrix) $C_9H_{10}N_3S$ (M+1): calcd, 192.0595; found, 192.0588.

(3) 7-(2-Thienyl)-3H-imidazo[4,5-b]pyridine (Compound 4)

A solution of Compound 3 (956 mg, 5.0 mmol) in formic acid (15 ml) was refluxed for 12 hours. To the reaction mixture, 24 ml of 28% $NH_4OH$ was added on an ice-cold bath. The resulting precipitate was filtered, washed with $H_2O$ and ethyl ether, and then dried at 60° C. for 12 hours to give 7-(2-thienyl)-3H-imidazo[4,5-b]pyridine (970 mg, 96%).

$^1$H NMR (300 MHz, DMSO-$d_6$) δ 13.20 (s, 1H), 8.48 (s, 1H), 8.30 (m, 2H), 7.78 (dd, 1H, J=1.0 and 5.1 Hz), 7.54 (d, 1H, J=5.1 Hz), 7.25 (dd, 1H, J=3.8 and 4.9 Hz).

$^{13}$C NMR (75 MHz, DMSO-$d_6$) δ 113.12, 128.00, 128.71, 129.24, 130.00, 131.16, 137.60, 143.44, 144.09, 148.66.

HRMS (FAB, 3-NBA matrix) $C_{10}H_8N_3S$ (M+1): calcd, 202.0439; found, 202.0444.

(4) 7-(2-Thienyl)-3-[2-deoxy-3,5-di-O-(toluoyl)-β-D-ribofuranosyl]-3H-imidazo[4,5-b]pyridine (Compound 5)

To a solution of Compound 4 (403 mg, 2.0 mmol) in $CH_3CN$ (32 ml), NaH (96 mg, 2.4 mmol, 60% dispersion in mineral oil) was added. The resulting mixture was stirred at room temperature for 1 hour. To the mixture, 2-deoxy-3,5-di-O-p-toluoyl-α-D-erythro-pentofuranosyl chloride (933 mg, 2.4 mmol) (Non-patent Document 42) was added. After stirring at room temperature for 2.5 hours, the reaction mixture was partitioned between ethyl acetate and water. The organic layer was washed three times with saturated aqueous sodium chloride, dried over $Na_2SO_4$, and then evaporated under reduced pressure. The product was purified by silica gel column chromatography (0.5% methanol in $CH_2Cl_2$) to give Compound 5 (714 mg, 65%).

$^1$H NMR (270 MHz, $CDCl_3$) δ 8.32 (d, 1H, J=5.3 Hz), 8.26 (s, 1H), 8.16 (dd, 1H, J=3.8 and 1.2 Hz), 7.93 (m, 4H), 7.50 (dd, 1H, J=5.1 and 1.2 Hz), 7.47 (d, 1H, J=5.3 Hz), 7.22 (m, 5H), 6.68 (dd, 1H, J=8.6 and 5.8 Hz), 5.82 (m, 1H), 4.69 (m, 3H), 3.18 (ddd, 1H, J=14.2, 8.6 and 6.4 Hz), 2.86 (ddd, 1H, J=14.2, 5.8 and 2.0 Hz), 2.43 (s, 3H), 2.37 (s, 3H).

HRMS (FAB, 3-NBA matrix) $C_{31}H_{28}N_3O_5S$ (M+1): calcd, 554.1750; found, 554.1748.

(5) 7-(2-Thienyl)-3-(2-deoxy-β-D-ribofuranosyl)-3H-imidazo[4,5-b]pyridine (Compound 6)

To 1.33 g (2.40 mmol) of Compound 5, ammonia-saturated methanol (120 ml) was added at 0° C. The solution was stirred at room temperature for 2 hours. After the reaction, the solvent was distilled off and the residue was purified by flash silica gel chromatography using methylene chloride:ethanol (97:3 to 93:7) as an elution solvent to give 717 mg of Compound 6 in a yield of 94%.

$^1$H NMR (300 MHz, DMSO-$d_6$) δ 8.75 (s, 1H), 8.35 (d, 1H, J=5.1 Hz), 8.30 (d, 1H, J=3.7 Hz), 7.83 (d, 1H, J=5.1 Hz), 7.65 (d, 1H, J=5.1 Hz), 7.28 (t, 1H, J=4.2 Hz), 6.54 (t, 1H, J=6.9 Hz), 5.34 (d, 1H, J=4.1 Hz), 5.11 (t, 1H, J=5.7 Hz), 4.46 (m, 1H), 3.91 (m, 1H), 3.60 (m, 2H), 2.89 (m, 1H), 2.37 (m, 1H).

$^{13}$C NMR (75 MHz, DMSO-$d_6$) δ 147.10, 144.04, 143.62, 137.06, 132.00, 131.00, 129.78, 129.06, 128.07, 113.93, 87.88, 83.72, 70.80, 61.74, 39.40.

HRMS (FAB, 3-NBA matrix) $C_{15}H_{16}N_3O_3S$ (M+1): calcd, 318.0912; found, 318.0905.

UV: λmax, 311 nm; ε=2.04×10$^4$ in 25 mM sodium phosphate buffer (pH 6.8).

(6) 7-(2-Thienyl)-3-[2-deoxy-5-O-(4,4'-dimethoxytrityl)-β-D-ribofuranosyl]-3H-imidazo[4,5-b]pyridine (Compound 7)

A 317 mg (1.0 mmol) portion of Compound 6 was azeotroped three times with dry pyridine. To this, 5.0 ml anhydrous pyridine was added and dimethoxytrityl chloride (356 mg, 1.1 mmol) was further added. The mixture was stirred overnight at room temperature, poured into water (50 ml) and then extracted with methylene chloride (50 ml×3). After drying over $Na_2SO_4$, the solvent was distilled off under reduced pressure. The residue was purified by flash silica gel chromatography using methylene chloride:ethyl acetate (9:1 to 13:7) as an elution solvent to give 550 mg of Compound 7 in a yield of 89%.

$^1$H NMR (270 MHz, $CDCl_3$) δ 8.29 (d, 1H, J=5.1 Hz), 8.22 (s, 1H), 8.17 (dd, 1H, J=3.8 and 1.1 Hz), 7.49 (dd, 1H, J=5.1 and 1.1 Hz), 7.44 (d, 1H, J=5.1 Hz), 7.37 (m, 2H), 7.27 (m, 5H), 7.20 (m, 3H), 6.78 (m, 4H), 6.57 (dd, 1H, J=6.5 and 6.2 Hz), 4.66 (m, 1H), 4.12 (m, 1H), 3.75 (s, 3H), 3.75 (s, 3H), 3.42 (dd, 1H, J=10.1 and 4.6 Hz), 3.38 (dd, 1H, J=10.1 and 5.4 Hz), 2.86 (m, 1H), 2.56 (ddd, 1H, J=13.8, 6.5 and 4.6 Hz), 2.06 (d, 1H, J=3.5 Hz).

HRMS (FAB, 3-NBA matrix) $C_{36}H_{34}N_3O_5S$ (M+1): calcd, 620.2219; found, 620.2230.

(7) 7-(2-Thienyl)-3-[2-deoxy-5-O-(4,4'-dimethoxytrityl)-β-D-ribofuranosyl]-3H-imidazo[4,5-b]pyridine 2-cyanoethyl-N,N-diisopropylphosphoramidite (Compound 8)

Compound 7 (425 mg, 0.69 mmol) was azeotroped three times with anhydrous pyridine and then three times with anhydrous acetonitrile. This was dissolved in anhydrous acetonitrile (4.6 ml), followed by addition of 2-cyanoethyl tetraisopropylphosphorodiamidite (262 μl, 0.82 mmol)) and a 0.45 M acetonitrile solution of tetrazole (1.68 ml). This mixture was stirred for 1 hour at room temperature. After addition of anhydrous methanol (90 μl), the mixture was poured into water (50 ml) and extracted with 1% triethylamine (v/v)-containing methylene chloride (50 ml×3). After drying over $Na_2SO_4$, the solvent was distilled off under reduced pressure. The residue was purified by flash silica gel chromatography using 2% triethylamine (v/v)-containing hexane:ethyl acetate (4:1 to 3:2) as an elution solvent to give 490 mg of Compound 8 in a yield of 87%.

$^1$H NMR (270 MHz, DMSO-$d_6$) δ 8.65 (m, 1H), 8.27 (m, 1H), 8.23 (m, 1H), 7.81 (m, 1H), 7.62 (m, 1H), 7.26 (m, 3H), 7.18 (m, 7H), 6.75 (m, 4H), 6.54 (m, 1H), 4.81 (m, 1H), 4.13 (m, 1H), 3.84-3.45 (m, 1OH), 3.21 (m, 3H), 2.82-2.48 (m, 3H) 1.13 (m, 12H).
$^{31}$P NMR (109 MHz, DMSO-$d_6$) δ 148.76 ppm and 148.14 ppm.
HRMS (FAB, 3-NBA matrix) $C_{45}H_{51}N_5O_6SP$ (M+1): calcd, 820.3298; found, 820.3325.

(8) 7-(2-Thienyl)-3-(2-deoxy-3-O-acetyl-β-D-ribofuranosyl)-3H-imidazo[4,5-b]pyridine (Compound 9)

Compound 7 (124 mg, 0.20 mmol) was azeotroped three times with anhydrous pyridine. This was dissolved in anhydrous pyridine (2.0 ml), and 38 µl (0.40 mmol) of acetic anhydride was further added thereto. The resulting mixture was stirred at room temperature for 2 days. The mixture was poured into water (50 ml) and extracted with methylene chloride (50 ml×3). After drying over $Na_2SO_4$, the solvent was distilled off under reduced pressure. The residue was dissolved in 20 ml anhydrous methylene chloride, and 200 µl dichloroacetic acid was added thereto at 0° C. After stirring at 2° C. for 15 minutes, the mixture was poured into 8 ml saturated aqueous sodium bicarbonate, diluted with 42 ml water, and then extracted with methylene chloride (50 ml×3). After drying over $Na_2SO_4$, the solvent was distilled off under reduced pressure. The residue was purified by flash silica gel chromatography using methylene chloride:ethyl acetate (9:1 to 3:2) as an elution solvent to give 65 mg of Compound 9 in a yield of 88%.
$^1$H NMR (270 MHz, CDCl$_3$) δ 8.29 (d, 1H, J=5.4 Hz), 8.18 (dd, 1H, J=3.8 and 1.1 Hz), 8.13 (s, 1H), 7.53 (dd, 1H, J=5.0 and 1.1 Hz), 7.50 (d, 1H, J=5.4 Hz), 7.20 (dd, 1H, J=5.0 and 3.8 Hz), 6.69 (m, 1H), 6.37 (dd, 1H, J=10.1 and 5.4 Hz), 5.58 (m, 1H), 4.28 (m, 1H), 3.96 (m, 2H), 3.32 (ddd, 1H, J=15.9, 10.1 and 5.9 Hz), 2.41 (m, 1H), 2.12 (s, 3H).
HRMS (FAB, 3-NBA matrix) $C_{17}H_{18}N_3O_4S$ (M+1): calcd, 360.1018; found, 360.0993.

(9) 7-(2-Thienyl)-3-(β-D-ribofuranosyl)-3H-imidazo[4,5-b]pyridine (Compound 11)

A mixture of Compound 4 (80 mg, 0.4 mmol), tetra-O-acetyl-β-D-ribofuranose (130 mg, 0.4 mmol) and chloroacetic acid (2 mg) was heated at 200° C. for 5 minutes. The resulting dark syrup was treated with methanolic ammonia (40 ml) at room temperature for 18 hours. After the solvent was distilled off under reduced pressure, the residue was diluted with 30% aqueous $CH_3CN$, and the product was purified by reversed-phase HPLC to give Compound 11 (39 mg, 29%, 2 steps).
$^1$H NMR (300 MHz, DMSO-$d_6$) δ 8.78 (s, 1H), 8.36 (d, 1H, J=5.2 Hz), 8.31 (dd, 1H, J=1.0 and 3.7 Hz), 7.84 (dd, 1H, J=0.9 and 5.1 Hz), 7.66 (d, 1H, J=5.2 Hz), 7.28 (dd, 1H, J=3.7 and 5.0 Hz), 6.08 (d, 1H, J=5.8 Hz), 5.49 (d, 1H, J=6.0 Hz), 5.26 (t, 1H, J=6.5 Hz), 5.20 (d, 1H, J=4.9 Hz), 4.67 (q, 1H, J=5.8 Hz), 4.20 (q, 1H, J=4.9 Hz), 4.00 (m, 1H), 3.71 (m, 1H), 3.59 (m, 1H).
$^{13}$C NMR (75 MHz, DMSO-$d_6$) δ 147.29, 144.07, 143.91, 137.00, 132.13, 131.08, 129.86, 129.14, 128.10, 114.02, 87.76, 85.57, 73.48, 70.43, 61.43.
HRMS (FAB, 3-NBA matrix) $C_{15}H_{16}N_3O_4S$ (M+1): calcd, 334.0862; found, 334.0871.

(10) 7-(2-Thienyl)-3-[5-O-(4,4'-dimethoxytrityl)-β-D-ribofuranosyl]-3H-imidazo[4,5-b]pyridine (Compound 12)

Compound 11 (99 mg, 0.29 mmol) was azeotroped three times with anhydrous pyridine and then dissolved in pyridine (3.0 ml). To this solution, 4,4'-dimethoxytrityl chloride (106 mg, 0.31 mmol) was added, and the resulting mixture was stirred at room temperature for 2 hours. The reaction mixture was poured into 5% aqueous $NaHCO_3$ and then extracted with ethyl acetate. The organic layer was washed three times with saturated aqueous sodium chloride, dried over $Na_2SO_4$, and then evaporated under reduced pressure to remove the solvent. The product was purified by silica gel column chromatography (1% methanol-$CH_2Cl_2$) to give Compound 12 (131 mg, 71%).
$^1$H NMR (600 MHz, CDCl$_3$) δ 8.39 (s, 1H), 8.28 (d, 1H, J=5.2 Hz), 8.25 (d, 1H, J=3.4 Hz), 7.52 (t, 2H, H=5.7 Hz), 7.22 (m, 2H), 7.14 (m, 7H), 6.69 (m, 5H), 6.04 (d, 1H, J=6.2 Hz), 4.77 (m, 1H), 4.48 (m, 1H), 4.34 (d, 1H, J=4.6 Hz), 3.70 (s, 6H), 3.46 (dd, 1H, J=3.4 and 10.5 Hz), 3.23 (dd, 1H, J=2.9 and 10.5 Hz).
HRMS (FAB, 3-NBA matrix) $C_{36}H_{34}N_3O_6S$ (M+1): calcd, 636.2168; found, 636.2173.

(11) 7-(2-Thienyl)-3-(2,3-di-O-acetyl-β-D-ribofuranosyl)-3H-imidazo[4,5-b]pyridine (Compound 13)

Compound 12 (120 mg, 0.19 mmol) was azeotroped three times with anhydrous pyridine. This was dissolved in anhydrous pyridine (1.9 ml), and 72 µl (0.76 mmol) of acetic anhydride was further added thereto. This mixture was stirred at room temperature for 7 hours and poured into 5% $NaHCO_3$ (50 ml) and ethyl acetate (50 ml). The organic layer was washed once with saturated aqueous sodium chloride, dried over $Na_2SO_4$, and then evaporated under reduced pressure to remove the solvent. The residue was azeotroped twice with toluene and dissolved in $CH_2Cl_2$ (19 ml), followed by addition of 190 µl dichloroacetic acid at 0° C. This reaction mixture was stirred at 0° C. for 15 minutes. The mixture was poured into 5% $NaHCO_3$ and extracted with $CH_2Cl_2$. The organic layer was washed once with saturated aqueous sodium chloride, dried over $Na_2SO_4$, and then evaporated under reduced pressure to remove the solvent. The product was purified by flash silica gel chromatography using a 2% methanol-methylene chloride solution as a solvent to give 77 mg of Compound 13 in a yield of 93%.
$^1$H NMR (300 MHz, DMSO-$d_6$) δ 8.79 (s, 1H), 8.37 (d, 1H, J=5.2 Hz), 8.29 (dd, 1H, J=1.2 and 3.7 Hz), 7.84 (dd, 1H, J=1.1 and 5.1 Hz), 7.68 (d, 1H, J=5.2 Hz), 7.27 (dd, 1H, J=3.7 and 5.1 Hz), 6.38 (d, 1H, J=6.8 Hz), 6.02 (dd, 1H, J=5.6 and 6.6 Hz), 5.54 (m, 2H), 4.26 (m, 1H), 3.71 (m, 2H), 2.14 (s, 3H), 1.98 (s, 3H).
$^{13}$C NMR (75 MHz, DMSO-$d_6$) δ 169.55, 169.22, 146.98, 144.39, 143.85, 136.74, 132.50, 131.02, 130.11, 129.32, 128.14, 114.36, 85.20, 83.63, 72.34, 71.23, 61.05, 20.44, 20.13.
HRMS (FAB, 3-NBA matrix) $C_{19}H_{20}N_3O_6S$ (M+1): calcd, 418.1073; found, 418.1049.

(12) 1-(β-D-Ribofuranosyl)pyrrole-2-carbaldehyde (Compound 17)

To a solution of pyrrole-2-carbaldehyde (330 mg, 3.5 mmol) in $CH_3CN$ (18 ml), NaH (60% oil dispersion, 152 mg, 3.8 mmol) was added and stirred at room temperature for 45 minutes, followed by addition of a solution of 2,3,5-tri-O-benzyl-D-ribofuranosyl chloride (3.1 mmol) (Non-patent Document 44) in $CH_3CN$ (18 ml). The reaction mixture was stirred at room temperature for 4 hours. The product was partitioned between ethyl acetate and water, and the organic layer was washed three times with saturated aqueous sodium chloride, dried over $Na_2SO_4$, and then evaporated under reduced pressure to remove the solvent. The residue was purified by silica gel chromatography (eluted with 20% ethyl acetate in hexane) to give crude 1-(2,3,5-tri-O-benzyl-D-ribofuranosyl)pyrrole-2-carboxyaldehyde (506 mg). After the crude 1-(2,3,5-tri-O-benzyl-D-ribofuranosyl)pyrrole-2-carboxyaldehyde (506 mg, 1.0 mmol) was azeotroped with toluene, $CH_2Cl_2$ (17 ml) was added to the residue. To this solution, $BBr_3$ (1 M solution, 3.0 ml) was added at −78° C. and stirred for 2.5 hours, followed by addition of a 50% methanol-$CH_2Cl_2$ solution (25 ml). After the solution was stirred at −78° C. for 10 minutes, 28% $NH_4OH$ (0.5 ml) was added. The reaction mixture was further stirred until it reached room temperature. The product was partitioned between $CH_2Cl_2$ and $H_2O$, and the aqueous layer was washed three times with $CH_2Cl_2$ and evaporated under reduced pressure to remove the solvent. The product was purified by reversed-phase C18 HPLC to give 1-(β-D-ribofuranosyl)pyrrole-2-carbaldehyde (108 mg, 15%, 2 steps).

$^1H$ NMR (270 MHz, DMSO-$d_6$) δ 9.54 (s, 1H), 7.74 (s, 1H), 7.06 (dd, 1H, J=1.6 and 4.0 Hz), 6.39 (d, 1H, J=4.3 Hz), 6.30 (dd, 1H, J=3.0 and 4.0 Hz), 5.27 (d, 1H, J=5.6 Hz), 5.05 (d, 1H, J=4.9 Hz), 5.00 (t, 1H, J=5.3 Hz), 4.02 (m, 2H), 3.85 (m, 1H), 3.52 (m, 2H).

$^{13}C$ NMR (75 MHz, DMSO-$d_6$) δ 179.41, 131.68, 128.24, 124.94, 110.23, 89.34, 84.33, 75.64, 69.50, 60.82.

HRMS (FAB, 3-NBA matrix) $C_{10}H_{14}NO_5$ (M+1): calcd, 228.0872; found, 228.0863.

(13) 4-Propynyl-1-(β-D-ribofuranosyl)pyrrole-2-carbaldehyde (Compound 18)

4-Propynyl-1-(β-D-ribofuranosyl)pyrrole-2-carbaldehyde (Compound 18) was synthesized in the same manner as used for Compound 17, starting with 4-propynyl-2-pyrrolecarbaldehyde (Compound 16) (Non-patent Document 40) (266 mg, 2.0 mmol). After purification by RP-HPLC, Compound 18 was obtained (39 mg, 7%, 2 steps).

$^1H$ NMR (300 MHz, DMSO-$d_6$) δ 9.50 (s, 1H), 7.91 (s, 1H), 7.09 (d, 1H, J=1.8 Hz), 6.32 (d, 1H, J=3.6 Hz), 5.32 (d, 1H, J=5.5 Hz), 5.07 (t, 1H, J=5.2 Hz), 5.05 (d, 1H, J=4.2 Hz), 4.01 (m, 1H), 3.86 (m, 1H), 3.66 (ddd, 1H, J=3.4, 5.3 and 11.9 Hz), 3.55 (ddd, 1H, J=3.6, 4.9 and 12.1 Hz), 1.97 (s, 3H).

$^{13}C$ NMR (75 MHz, DMSO-$d_6$) δ 179.60, 131.15, 130.43, 126.13, 106.22, 89.62, 85.26, 84.49, 75.86, 73.17, 69.30, 60.53, 3.79.

HRMS (FAB, 3-NBA matrix) $C_{13}H_{16}NO_5$ (M+1): calcd, 266.1028; found, 266.1023.

(14) Synthesis of nucleoside 5'-triphosphates of 7-(2-thienyl)-3H-imidazo[4,5-b]pyridine A protected nucleoside (0.1 mmol, Compound 9 or 13) was azeotroped with pyridine to dryness. The residue was dissolved in a mixed solvent of pyridine (100 μl) and dioxane (300 μl). To this, a 1 M dioxane solution of 2-chloro-4H-1,3,2-benzodioxaphosphorin-4-one (110 μl, 0.11 mmol) was added. After 10 minutes, tributylamine (100 μl) and 0.5M bis(tributylammonium) pyrophosphate in DMF (300 μl, 0.15 mmol) were quickly added to the reaction mixture. This mixture was stirred at room temperature for 10 minutes, followed by addition of 1% iodine in pyridine/water (98/2, v/v) (2.0 ml). After 15 minutes, 150 μl of 5% aqueous $NaHSO_3$ was added, and 5.0 ml water was further added thereto. After the solution was stirred at room temperature for 30 minutes, 20 ml of concentrated aqueous ammonia was added to cause ammonolysis at room temperature for 2 hours. The solvent was distilled off under reduced pressure, and the product was purified by DEAE Sephadex (A-25) column chromatography (eluted with a linear gradient of 50 mM to 1 M TEAB) and then purified on a C18-HPLC column (eluted with a linear gradient of 0% to 30% $CH_3CN$ in 100 mM triethylammonium acetate) to give the desired nucleoside 5'-triphosphate.

7-(2-Thienyl)-3-(2-deoxy-β-ribofuranosyl)-3H-imidazo[4,5-b]pyridine 5'-triphosphate (Compound 10)

$^1H$ NMR (270 MHz, $D_2O$) δ 8.51 (s, 1H), 8.09 (d, 1H, J=5.3 Hz), 7.78 (d, 1H, J=3.6 Hz), 7.56 (d, 1H, J=4.9 Hz), 7.36 (d, 1H, J=5.3 Hz), 7.12 (t, 1H, J=4.9 Hz), 6.41 (t, 1H, J=7.3 Hz), 4.16 (m, 1H), 4.04 (m, 2H), 3.01 (q, 18H, J=7.3 Hz), 2.72 (m, 1H), 2.46 (m, 1H), 1.09 (t, 27H, J=7.3 Hz).

$^{31}P$ NMR (109 MHz, $D_2O$) δ −9.94 (d, 1P, J=20.1 Hz), −10.72 (d, 1P, J=20.1 Hz), −22.58 (t, 1P, J=20.1 Hz).

Electrospray ionization mass spectroscopy (ESI-MS) $C_{15}H_{18}N_3O_{12}P_3S$; calcd, 555.97 (M−H)−; found, 555.69 (M−H)−.

7-(2-Thienyl)-3-(β-D-ribofuranosyl)-3H-imidazo[4,5-b]pyridine 5'-triphosphate (Compound 14)

$^1H$ NMR (300 MHz, $D_2O$) δ 8.74 (s, 1H), 8.32 (d, 1H, J=5.4 Hz), 8.01 (d, 1H, J=3.5 Hz), 7.68 (dd, 1H, J=1.1 and 5.1 Hz), 7.64 (d, 1H, J=5.1 Hz), 7.25 (dd, 1H, J=3.5 and 5.1 Hz), 6.25 (d, 1H, J=6.0 Hz), 4.82 (m, 1H), 4.57 (m, 1H), 4.36 (m, 1H), 4.20 (m, 2H), 3.11 (q, 18H, J=7.3 Hz), 1.19 (t, 27H, J=7.3 Hz).

$^{31}P$ NMR (109 MHz, $D_2O$) δ −9.80 (d, 1P, J=20.1 Hz), −11.03 (d, 1P, J=18.9 Hz), −22.78 (t, 1P, J=20.1 and 18.9 Hz).

Electrospray ionization mass spectroscopy (ESI-MS) $C_{15}H_{18}N_3O_{13}P_3S$; calcd, 571.97 (M−H)−; found, 571.74 (M−H)−.

(15) Synthesis of nucleoside 5'-γ-amidotriphosphate of adenine or 7-(2-thienyl)-imidazo[4,5-b]pyridine (Non-patent Documents 43, 47 and 48)

A protected nucleoside (0.1 mmol, Compound 21 (Non-patent Document 46) or Compound 9) was azeotroped with pyridine to dryness. The residue was dissolved in a mixture of pyridine (100 μl) and dioxane (300 μl). To this, a 1 M dioxane solution of 2-chloro-4H-1,3,2-benzodioxaphosphorin-4-one (110 μl, 0.11 mmol) was added. After 10 minutes, tributylamine (100 μl) and 0.5 M bis(tributylammonium) pyrophosphate in DMF (300 μl, 0.15 mmol) were quickly added to the reaction mixture and stirred at room temperature for 10 minutes, followed by addition of 1% iodine in pyridine/water (98/2, v/v) (2.0 ml). After 15 minutes, 150 μl of 5% aqueous $NaHSO_3$ was added. After the solvent was distilled off under reduced pressure, 20 ml of 28% aqueous ammonia was added to the residue to cause ammonolysis at 60° C. for 5 hours (for deoxyadenosine 5'-γ-amidotriphosphate) or at room temperature for 2 hours (for 5'-γ-amidotriphosphate of Compound 6). After the solvent was distilled off under reduced pressure, the product was purified by DEAE Sephadex (A-25) column chromatography (eluted with a linear gradient of 50 mM to 1 M TEAB) and then purified on a C18-HPLC column (eluted with a linear gradient of 0% to 30% $CH_3CN$ in 100 mM triethylammonium acetate) to give the desired nucleoside 5'-γ-amidotriphosphate.

6-Amino-9-(2-deoxy-β-D-ribofuranosyl)purine 5'-γ-amidotriphosphate (Compound 22)

$^1H$ NMR (270 MHz, $D_2O$) δ 8.35 (s, 1H), 8.11 (s, 1H), 6.37 (t, 1H, J=6.9 Hz), 4.16 (m, 1H), 4.03 (m, 2H), 3.05 (q, 18H, J=7.3 Hz), 2.70 (m, 1H), 2.48 (m, 1H), 1.13 (t, 27H, J=7.3 Hz).

$^{31}$P NMR (109 MHz, D$_2$O) δ −0.50 (d, 1P, J=19.5 Hz), −10.77 (d, 1P, J=19.5 Hz), −22.14 (t, 1P, 20.1 Hz).

Electrospray ionization mass spectroscopy (ESI-MS) C$_{10}$H$_{17}$N$_6$O$_{11}$P$_3$; calcd, 489.01 (M−H)−; found, 488.98 (M−H)−.

7-(2-Thienyl)-3-(2-deoxy-β-D-ribofuranosyl)-3H-imidazo[4,5-b]pyridine 5'-γ-amidotriphosphate (Y-amidotriphosphate of Compound 10)

$^1$H NMR (270 MHz, D$_2$O) δ 8.57 (s, 1H), 8.16 (d, 1H, J=5.3 Hz), 7.85 (d, 1H, J=3.6 Hz), 7.58 (d, 1H, J=4.9 Hz), 7.45 (d, 1H, J=5.3 Hz), 7.15 (t, 1H, J=4.6 Hz), 6.48 (t, 1H, J=6.9 Hz), 4.18 (m, 1H), 4.05 (m, 2H), 3.03 (q, 18H, J=7.3 Hz), 2.75 (m, 1H), 2.50 (m, 1H), 1.11 (t, 27H, J=7.3 Hz).
$^{31}$P NMR (109 MHz, D$_2$O) δ −0.52 (d, 1P, J=20.1 Hz), −10.75 (d, 1P, J=19.5 Hz), −22.14 (t, 1P, J=20.8 Hz).

Electrospray ionization mass spectroscopy (ESI-MS) C$_{15}$H$_{19}$N$_4$O$_{11}$P$_3$S; calcd, 554.99 (M−H)−; found, 555.01 (M−H)−.

(16) Nucleoside 5'-triphosphates of pyrrole-2-carbaldehyde and 4-propynylpyrrole-2-carbaldehyde (Non-patent Document 45)

To a solution containing 1-(β-D-ribofuranosyl)pyrrole-2-carbaldehyde (0.1 mmol) (Compound 17) or 4-propynyl-1-(β-D-ribofuranosyl)pyrrole-2-carbaldehyde (0.1 mmol) (Compound 18) and a proton sponge (33 mg, 0.15 mmol) in trimethyl phosphate (500 µl), POCl$_3$ (12 µl, 0.13 mmol) was added at 0° C. and stirred at 0° C. for 2 hours. To the reaction mixture, tri-n-butylamine (120 µl, 0.5 mmol) was added and a 0.5 M DMF solution of bis(tributylammonium)pyrophosphate (1.0 ml, 0.5 mmol) was further added thereto. After 5 minutes, 0.5 M aqueous triethylammonium bicarbonate (TEAB, 500 µl) was added to stop the reaction. The resulting crude product was purified by DEAE Sephadex (A-25) column chromatography (1.5 cm×30 cm, eluted with a linear gradient of 50 mM to 1 M TEAB) and then purified on a C18-HPLC column (Synchropak RPP, Eichrom Technologies, eluted with a gradient of 0% to 30% CH$_3$CN in 100 mM triethylammonium acetate).

1-(β-D-Ribofuranosyl)pyrrole-2-carbaldehyde 5'-triphosphate (Compound 19)

$^1$H NMR (270 MHz, D$_2$O) δ 9.28 (s, 1H), 7.64 (s, 1H), 7.08 (d, 1H, J=3.9 Hz), 6.45 (d, 1H, J=4.1 Hz), 6.32 (m, 1H), 4.32 (m, 2H), 4.10 (m, 3H), 3.03 (q, 18H, J=7.3 Hz), 1.11 (t, 27H, J=7.3 Hz).
$^{31}$P NMR (109 MHz, D$_2$O) δ −10.51 (d, 1P, J=19.5 Hz), −11.3 (d, 1P, J=20.1 Hz), −22.91 (t, 1H, J=20.1 Hz).

Electrospray ionization mass spectroscopy (ESI-MS) C$_{10}$H$_{16}$NO$_{14}$P$_3$: calcd, 465.97 (M−H)−; found, 465.85 (M−H)−.

4-Propynyl-1-(β-D-ribofuranosyl)pyrrole-2-carbaldehyde 5'-triphosphate (Compound 20)

$^1$H NMR (270 MHz, D$_2$O) δ 9.28 (s, 1H), 7.70 (s, 1H), 7.08 (s, 1H), 6.40 (d, 1H, J=4.0 Hz), 4.30 (m, 2H), 4.13 (m, 3H), 3.06 (q, 18H, J=7.3 Hz), 1.86 (s, 3H), 1.14 (t, 27H, J=7.3 Hz).
$^{31}$P NMR (109 MHz, D$_2$O) δ −10.10 (d, 1P, J=19.5 Hz), −11.02 (d, 1P, J=19.5 Hz), −22.82 (t, 1P, J=20.1 Hz).

Electrospray ionization mass spectroscopy (ESI-MS) C$_{13}$H$_{18}$NO$_{14}$P$_3$: calcd, 503.99 (M−H)−; found, 503.94 (M−H)−.

Example II

Chemical Synthesis-2

1. Synthesis of nucleoside derivatives of 7-(2-thiazolyl)-3H-imidazo[4,5-b]pyridine (Compound 4) (Dv) (FIG. 33)

The same procedure as shown in FIG. 22 for synthesis of nucleoside derivatives of 7-(2-thienyl)-3H-imidazo[4,5-b]pyridine (Compound 4 in Example I) (Ds) was repeated, except that 2-(tributylstanyl)thiazole was used in Reaction (a) for introducing a thiazolyl group.

However, with respect to amidite synthesis (g), 2-cyanoethyl-N,N-diisopropylamino chloro phosphoroamidite, diisopropylethylamine and THF were used in this example, although 2-cyanoethyl tetraisopropylphosphorodiamidite and 0.45 M tetrazole in acetonitrile were used in Example I-3(7) for synthesis of 7-(2-thienyl)-3-[2-deoxy-5-O-(4,4'-dimethoxytrityl)-β-D-ribofuranosyl]-3H-imidazo[4,5-b]pyridine 2-cyanoethyl-N,N-diisopropylphosphoroamidite (Compound 8). Although different reagents are used, the same amidite is produced.

2. Synthesis of Nucleoside Derivatives of 2-nitropyrrole (Compound 1) (Pn) (FIG. 34)

(1) Synthesis of 1-(2-deoxy-β-D-ribofuranosyl)-2-nitropyrrole (Compound 3)

2-Nitropyrrole (Compound 1) (Non-patent Document 49) (224 mg, 2.0 mmol) was dissolved in acetonitrile (20 ml), followed by addition of NaH (80 mg, 60% oil dispersion, 2.0 mmol). After stirring at room temperature for 30 minutes, 2-deoxy-3,5-di-O-p-toluoyl-α-D-erythro-pentofuranosyl chloride (855 mg, 2.2 mmol) was added and stirred at room temperature for 2 hours. The reaction mixture was washed with ethyl acetate and water, and the organic layer was washed with water and saturated aqueous sodium chloride. The organic layer was dried over anhydrous sodium sulfate, concentrated and then purified on a silica gel column to give Compound 2 (722 mg, 78%). Compound 2 (722 mg) was treated with methanolic ammonia (50 ml) to deprotect the toluoyl groups at room temperature for 12 hours, and purified on a silica gel column, followed by final HPLC purification to give Compound 3 (291 mg, 82%).

Compound 3: $^1$H NMR (270 MHz, DMSO-d6) δ 7.76 (bs, 1H), 7.26 (dd, 1H, J=1.6 and 3.6 Hz), 6.59 (t, 1H, J=5.9 Hz), 6.30 (t, 1H, J=3.6 Hz), 5.27 (d, 1H, J=4.3 Hz), 5.03 (t, 1H, J=5.3 Hz) 4.23 (m, 1H), 3.85 (m, 1H), 3.59 (m, 2H), 2.42 (m, 1H), 2.19 (m, 1H).

Electrospray ionization mass spectroscopy (ESI-MS) C$_9$H$_{11}$O$_5$N$_2$; calcd, 227.07 (M−H)−; found, 227.03 (M−H)−, C$_9$H$_{13}$O$_5$N$_2$; calcd, 229.08 (M+H)+; found, 229.06 (M+H)+.

(2) Synthesis of 1-[2-deoxy-5-O-(4,4'-dimethoxytrityl)-β-D-ribofuranosyl]-2-nitropyrrole 2-cyanoethyl-N,N-diisopropylphosphoroamidite (Compound 5)

Compound 3 (228 mg, 1.0 mmol) was azeotroped with pyridine, followed by addition of pyridine (10 ml) and 4,4'-dimethoxytrityl chloride (373 mg, 1.1 mmol). After stirring at room temperature for 1 hour, the reaction mixture was washed with ethyl acetate and 5% aqueous NaHCO$_3$, and the organic layer was washed with saturated aqueous sodium chloride. After drying over anhydrous sodium sulfate, the organic layer was concentrated and purified on a silica gel column to give Compound 4 (493 mg, 93%).

Compound 4 (265 mg, 0.5 mmol) was azeotroped with pyridine, followed by addition of THF (2.5 ml) and diisopropylethylamine (131 µl, 0.75 mmol). To this solution, 2-cyanoethyl-N,N-diisopropylamino chloro phosphoramidite (123 µl, 0.55 mmol) was added and stirred at room temperature for 1 hour. After addition of methanol (50 µl), the reaction mixture was diluted with ethyl acetate:triethylamine (20:1, v/v) and washed with 5% aqueous $NaHCO_3$. The organic layer was washed with saturated aqueous sodium chloride, dried over anhydrous sodium sulfate, concentrated and then purified on a silica gel column to give Compound 5 (315 mg, 86%).

(3) Synthesis of 1-(2-deoxy-β-D-ribofuranosyl)-2-nitropyrrole 5'-triphosphate (Compound 7)

Compound 4 (159 mg, 0.3 mmol) was azeotroped with pyridine, followed by addition of pyridine (3 ml) and acetic anhydride (57 µl, 0.6 mmol). The reaction mixture was stirred at room temperature for 12 hours. The reaction mixture was washed with ethyl acetate and 5% $NaHCO_3$, and then with 5% aqueous $NaHCO_3$. After drying over anhydrous sodium sulfate, the organic layer was concentrated, azeotroped with toluene, and then dissolved in methylene chloride (30 ml). To this reaction mixture, dichloroacetic acid (300 µl) was added at 0° C. and stirred for 15 minutes at 0° C. The reaction mixture was washed with 5% aqueous $NaHCO_3$, and the organic layer was washed with 5% $NaHCO_3$. After drying over anhydrous sodium sulfate, the organic layer was concentrated and purified on a silica gel column to give Compound 6 (73 mg, 91%).

Compound 6 (41 mg, 0.15 mmol) was azeotroped with pyridine, followed by addition of pyridine (150 µl) and dioxane (450 µl). To this solution, 2-chloro-4H-1,3,2-benzodioxaphosphorin-4-one (180 µl, 1 M in dioxane) was added and stirred for 10 minutes at room temperature. Tri-n-butylamine (150 µl) and bis(tributylammonium) pyrophosphate (450 µl, 0.5 M in DMF) were added to the reaction mixture, followed by stirring for 10 minutes. After 1% iodine in pyridine/$H_2O$, (98/2, v/v, 3.0 ml) was added and stirred for 15 minutes, 5% aqueous $NaHSO_3$ (225 µl) was added and the reaction mixture was then concentrated. After $H_2O$ (7.5 ml) was added and stirred at room temperature for 30 minutes, 28% aqueous ammonia (30 ml) was added and stirred at room temperature for 2 hours. The reaction mixture was concentrated, lyophilized and then purified on DEAE Sephadex A-25 (with a linear gradient of 50 mM to 1.0 M TEAB), followed by final HPLC purification to give Compound 7 of interest.

Compound 7:
Electrospray ionization mass spectroscopy (ESI-MS) $C_9H_{14}O_{14}N_2P_3$; calcd, 466.97 (M–H)$^-$; found, 466.70 (M–H)$^-$.

3. Synthesis of nucleoside derivatives of 4-(thienyl)-1H-pyrrolo[2,3-b]pyridine (DDs) and 4-(thienyl)-1H-pyrrolo[2,3-b]pyridine (DDv) (FIG. 35)

(1) Synthesis of 4-iodo-1H-pyrrolo[2,3-b]pyridine (Compound 3)

1H-Pyrrolo[2,3-b]pyridine (Compound 1) (5.3 g, 45 mmol) was dissolved in ethyl acetate (45 ml). To this solution, a solution of meta-chloroperbenzoic acid (14 g, 54 mmol) in ethyl acetate (30 ml) was added dropwise over 1 hour while stirring at 0° C. After dropwise addition, the reaction mixture was stirred at room temperature for 3 hours and then allowed to stand at 0° C. The crystal was filtered, washed with ethyl acetate and then dried under reduced pressure. This was dissolved in water (30 ml), adjusted to pH 10 with 30% $K_2CO_3$, and allowed to stand at room temperature for 1 hour and then at 0° C. for 1 hour. The precipitate was then filtered and washed with ether to give N-oxide (3.5 g, 58%). N-oxide (3.0 g, 22 mmol) was dissolved in DMF (16 ml) and heated at 50° C. A solution of methanesulfonyl chloride (4.7 ml, 60 mmol) in DMF (6.4 ml) was added dropwise at 70° C, and this reaction mixture was stirred at 75° C. for 2 hours. The reaction mixture was added to ice and then neutralized at 0° C. with 10 N NaOH. After stirring at room temperature for 1 hour, the resulting precipitate was filtered, washed with water and then dried at 60° C. under reduced pressure to give Compound 2 (2.7 g, 80%).

Compound 2 (2.7 g, 18 mmol) and NaI (13 g, 88 mmol) were dissolved in acetonitrile (28 ml). To this solution, $CH_3COCl$ (3.5 ml, 50 mmol) was added while stirring at room temperature. The reaction mixture was heated at 85° C. for 12 hours. After the reaction mixture was cooled to room temperature, 10% aqueous $Na_2CO_3$ (28 ml) and 10% aqueous $NaHSO_3$ (28 ml) were added sequentially and stirred at room temperature for 15 minutes. The reaction mixture was washed with ethyl acetate, and the organic layer was further washed with saturated aqueous sodium chloride. After drying over anhydrous sodium sulfate, the organic layer was concentrated and purified on a silica gel column to give 4-iodo-1-N-acetyl-pyrrolo[2,3-b]pyridine (2.0 g) and 4-iodo-1H-pyrrolo[2,3-b] pyridine (Compound 3) (2.3 g). 4-Iodo-1-N-acetyl-pyrrolo[2,3-b]pyridine (2.0 g, 7.0 mmol) was dissolved in ethanol (70 ml) and, after addition of 28% sodium methoxide in methanol (1.4 ml, 7.0 mmol), was then heated under reflux for 1 hour. The reaction mixture was concentrated and then partitioned between ethyl acetate and saturated aqueous ammonium chloride, and the organic layer was washed with saturated aqueous ammonium chloride. After drying over anhydrous sodium sulfate, the organic layer was concentrated and combined with Compound 3 (2.3 g) which had been previously obtained, followed by recrystallization from ethanol to give Compound 3 (4.0 g, 92%).

(2) Synthesis of 1-[2-deoxy-3,5-di-O-(toluoyl)-β-D-ribofuranosyl]-4-iodo-pyrrolo[2,3-b]pyridine (Compound 4)

To a solution of Compound 3 (950 mg, 3.9 mmol) in acetonitrile (39 ml), NaH (156 mg, 60% oil dispersion, 3.9 mmol) was added. After stirring at room temperature for 1 hour, 2-deoxy-3,5-di-O-p-toluoyl-α-D-erythro-pentofuranosyl chloride (1.8 g, 1.2 equivalents) was added and stirred at room temperature for 1.5 hours. The reaction mixture was washed with ethyl acetate and saturated aqueous ammonium chloride, and the organic layer was partitioned with saturated aqueous ammonium chloride and saturated aqueous sodium chloride. The organic layer was dried over anhydrous sodium sulfate, concentrated and then purified on a silica gel column to give Compound 4 (1.8 g, 77%).

(3) Synthesis of 1-(2-deoxy-β-D-ribofuranosyl)-4-(2-thienyl)-pyrrolo[2,3-b]pyridine (Compound 7) and 1-(2-deoxy-β-D-ribofuranosyl)-4-(2-thiazolyl)-pyrrolo[2,3-b]pyridine (Compound 8)

To a solution of Compound 4 (715 mg, 1.2 mmol) and dichlorobis(triphenylphosphine)palladium (42 mg, 0.06 mmol) in DMF (12 ml), 2-(tributylstanyl)thiophene (601 µl, 1.8 mmol) was added and stirred at 100° C. for 1 hour. The reaction mixture was partitioned between ethyl acetate and water, and the organic layer was washed with water and then with saturated aqueous sodium chloride. The organic layer was dried over anhydrous sodium sulfate, concentrated and then purified on a silica gel column to give Compound 5 (586 mg, 88%).

Compound 5 (580 mg) was treated with ammonia-saturated methanol (50 ml) to deprotect the toluoyl groups at room temperature for 12 hours, and purified on a silica gel column, followed by final HPLC purification to give Compound 7 (304 mg, 91%).

Compounds 6 and 8 were synthesized in the same manner, except for using 2-(tributylstanyl)thiazole. Their synthesis started with Compound 4 (600 mg, 1.0 mmol) to give Compounds 6 (449 mg, 81%) and 8 (245 mg, 97%).

Compound 7: $^1$H NMR (300 MHz, DMSO-d6) δ 8.27 (d, 1H, J=5.1 Hz), 7.87 (d, 1H, J=3.8 Hz), 7.83 (d, 1H, J=3.6 Hz), 7.79 (d, 1H, J=5.1 Hz), 7.41 (d, 1H, J=5.0 Hz), 7.28 (dd, 1H, J=3.7 and 5.0 Hz), 6.93 (d, 1H, J=3.8 Hz), 6.76 (dd, 1H, J=6.0 and 8.2 Hz), 5.28 (d, 1H, J=4.1 Hz), 5.02 (t, 1H, J=5.6 Hz), 4.39 (m, 1H), 3.85 (m, 1H), 3.56 (m, 2H), 2.57 (m, 1H), 2.26 (m, 1H).

Compound 8: $^1$H NMR (300 MHz, DMSO-d6) δ 8.38 (d, 1H, J=5.1 Hz), 8.13 (d, 1H, J=3.2 Hz), 8.01 (d, 1H, J=3.2 Hz), 7.96 (d, 1H, J=3.7 Hz), 7.72 (d, 1H, J=5.1 Hz), 7.15 (d, 1H, J=3.7 Hz), 6.79 (dd, 1H, J=6.1 and 8.0 Hz), 5.29 (d, 1H, J=4.0 Hz), 4.50 (t, 1H, J=5.5 Hz), 4.40 (m, 1H), 3.86 (m, 1H), 3.57 (m, 2H), 2.58 (m, 1H), 2.26 (m, 1H).

(4) Synthesis of 1-[2-deoxy-5-O-(4,4'-dimethoxytrityl)-β-D-ribofuranosyl]-4-(2-thienyl)-pyrrolo[2,3-b]pyridine 2-cyanoethyl-N,N-diisopropylphosphoroamidite (Compound 11) and 1-[2-deoxy-5-O-(4,4'-dimethoxytrityl)-β-D-ribofuranosyl]-4-(2-thiazolyl)-pyrrolo[2,3-b]pyridine 2-cyanoethyl-N,N-diisopropylphosphoroamidite (Compound 12)

Compound 7 (300 mg, 0.9 mmol) was azeotroped with pyridine, followed by addition of pyridine (9 ml) and 4,4'-dimethoxytrityl chloride (386 mg, 1.1 mmol). After stirring at room temperature for 1 hour, the reaction mixture was partitioned between ethyl acetate and 5% aqueous NaHCO$_3$, and the organic layer was washed with saturated aqueous sodium chloride. After drying over anhydrous sodium sulfate, the organic layer was concentrated and purified on a silica gel column to give Compound 9 (570 mg, 97%).

Compound 9 (290 mg, 0.47 mmol) was azeotroped with pyridine, followed by addition of THF (2.4 ml) and diisopropylethylamine (123 µl, 0.7 mmol). To this solution, 2-cyanoethyl-N,N-diisopropylamino chloro phosphoroamidite (115 µl, 0.52 mmol) was added and stirred at room temperature for 1 hour. After addition of methanol (50 µl), the reaction mixture was diluted with ethyl acetate:triethylaime (20:1, v/v) and partitioned with 5% aqueous NaHCO$_3$. The organic layer was washed with saturated aqueous sodium chloride, dried over anhydrous sodium sulfate, concentrated and then purified on a silica gel column to give Compound 11 (345 mg, 90%).

Starting with Compound 8 (220 mg, 0.7 mmol), the same procedure was repeated to synthesize Compounds 10 (424 mg, 99%) and 12 (227 mg, 86%).

(5) Synthesis of 1-(2-deoxy-β-D-ribofuranosyl)-4-(2-thienyl)-pyrrolo[2,3-b]pyridine 5'-triphosphate (Compound 15) and 1-(2-deoxy-β-D-ribofuranosyl)-4-(2-thiazolyl)-pyrrolo[2,3-b]pyridine 5'-triphosphate (Compound 16)

Compound 9 (247 mg, 0.4 mmol) was azeotroped with pyridine, followed by addition of pyridine (4 ml) and acetic anhydride (75 µl, 0.8 mmol). After stirring at room temperature for 12 hours, the reaction mixture was partitioned between ethyl acetate and 5% aqueous NaHCO$_3$, and the organic layer was washed with 5% aqueous NaHCO$_3$. This organic layer was dried over anhydrous sodium sulfate, concentrated and azeotroped with toluene. The residue was then dissolved in methylene chloride (40 ml). To this reaction mixture, dichloroacetic acid (400 µl) was added at 0° C. and stirred for 15 minutes at 0° C. The reaction mixture was partitioned with 5% aqueous NaHCO$_3$, and the organic layer was washed with 5% aqueous NaHCO$_3$. After drying over anhydrous sodium sulfate, the organic layer was concentrated and purified on a silica gel column to give Compound 13 (125 mg, 87%).

Compound 13 (36 mg, 0.1 mmol) was azeotroped with pyridine, followed by addition of pyridine (100 µl) and dioxane (300 µl). To this solution, 2-chloro-4H-1,3,2-benzodioxaphosphin-4-one (110 µl, 1 M in dioxane) was added and stirred for 10 minutes at room temperature. Tri-n-butylamine (100 µl) and bis(tributylammonium) pyrophosphate (300 µl, 0.5 M in DMF) were added to the reaction mixture, followed by stirring for 10 minutes. After 1% iodine in pyridine/H$_2$O (98:2, v/v, 2.0 ml) was added and stirred for 15 minutes, 5% aqueous NaHSO$_3$ (150 µl) was added and the reaction mixture was then concentrated. After H$_2$O (5 ml) was added and stirred at room temperature for 30 minutes, 28% aqueous ammonia (20 ml) was added and stirred at room temperature for 2 hours. The reaction mixture was concentrated, lyophilized and then purified on DEAE Sephadex A-25 (with a linear gradient of 50 mM to 1.0 mM TEAB), followed by final HPLC purification to give Compound 15.

Starting with Compound 10 (210 mg, 0.34 mmol), the same procedure was repeated to synthesize Compounds 14 (108 mg, 89%) and 16 (0.1 mmol synthesis scale).

Compound 15:
Electrospray ionization mass spectroscopy (ESI-MS) $C_{16}H_{18}O_{12}N_2P_3S$; calcd, 554.98 (M–H)$^-$; found, 554.73 (M–H)$^-$.

Compound 16: Electrospray ionization mass spectroscopy (ESI-MS) $C_{15}H_{17}O_{12}N_3P_3S$; calcd, 555.97 (M–H)$^-$; found, 555.82 (M–H)$^-$.

Example III

Biological Experiments

1. Procedures
In this example, the following procedures were used unless otherwise specified.

Single Nucleotide Insertion Experiment using KF exo$^-$

The single nucleotide insertion experiment was performed as described in documents (Non-patent Documents 30-32). A primer (20-mer) labeled with 6-carboxylfluorescein at the 5'-end was annealed with template DNA (35-mer) by heating at 95° C. and slow cooling to 4° C. in 100 mM Tris-HCl (pH 7.5) buffer containing 20 mM MgCl$_2$, 2 mM DTT and 0.1 mg/ml bovine serum albumin. The primer-template duplex solution (10 µM, 5 µl) was mixed with 2 µl enzyme solution of the Klenow fragment lacking exonuclease activity (KF exo$^-$, Amersham USB). After the mixture was incubated for 2 minutes, each dNTP solution (3 µl) was added to this solution to start the reaction at 37° C. The amount of the enzyme used (5-50 nM), the reaction time (1-35 minutes) and the gradient concentration of each dNTP (0.3-1500 µM) were adjusted to ensure conditions giving 25% or less products. The reaction was stopped with 10 µl stop solution (95% formamide and 20 mM EDTA), and the mixture was immediately heated at 75°

C. for 3 minutes. The diluted products were analyzed in an automated ABI377 DNA sequencer equipped with GeneScan software (version 3.0) (Non-patent Document 32). The relative velocity ($v_0$) was calculated by dividing the extent of reaction by the reaction time, and then normalized to the enzyme concentration (20 nM) for the various enzyme concentrations used. Kinetic parameters ($K_M$ and $V_{max}$) were obtained from Hanes-Woolf plots of [dNTP]/$v_0$ against [dNTP].

Each parameter was averaged from 3 to 8 data sets.

Primer Extension Reaction using KF

A 5'-$^{32}$P-labeled primer (23-mer) and template DNA (35-mer) were annealed into duplex form in 20 mM Tris-HCl (pH 7.5) buffer containing 14 mM MgCl$_2$ and 0.2 mM DTT. The duplex solution (400 nM, 5 µl) was mixed with each 5× dNTP solution (2 µl) on ice, followed by addition of 3 µl enzyme solution containing KF exo$^-$ (1 unit) or KF exo$^+$ (1 unit) (TAKARA) to start the reaction. After the reaction solution was incubated at 37° C. for 3 or 5 minutes, a dye solution (10 µl) containing 89 mM Tris-borate, 2 mM EDTA, 10 M urea and 0.05% BPB was added to stop the reaction. This solution was immediately heated at 75° C. for 3 minutes and then electrophoresed on a 15% polyacrylamide-7 M urea gel. The products on the gel were analyzed with a bio-imaging analyzer (model BAS2500, Fuji).

DNA Sequencing

Dideoxy-cycle sequencing (20 µl) was performed on a PTC-100 Program Thermal Controller (MJ Research) with 8 µl Ready Reaction Mix (BigDye1.1, Applied Biosystems) containing 0.3 pmol template and 4 pmol primer 1 or 2 in the presence or absence of 1 nmol dPa'TP. After 25 cycles of PCR (96° C. for 10 seconds, 50° C. for 5 seconds, and 60° C. for 4 minutes), the remaining dye terminators were removed from the reaction solution using a Centri-Sep™ spin column (Applied Biosystems), and this solution was then dried at 55° C. under reduced pressure. The residue was resuspended in a formamide solution (4 µl) and analyzed with an ABI 377 DNA sequencer equipped with a 6% polyacrylamide-6 M urea gel. The sequence data were analyzed with Applied Biosystems PRISM sequencing analysis v3.2 software.

PCR Amplification

A PTC-100 Controller was used to perform the reaction in 20 mM Tris-HCl buffer (pH 8.8) containing 10 mM KCl, 10 mM (NH$_4$)$_2$SO$_4$, 2 mM MgSO$_4$, 0.1% Triton X-100, 0.3 mM each dNTP (N=Pa, G, C and T) and dNTP$_N$ (N=Ds and A), 1 µM each primer 1 or 2, 2.3 nM double-stranded DNA fragment, and 0.04 units/µl Vent DNA polymerase (New England BioLabs). The PCR cycle was set as follows: 94° C. for 0.5 minutes, 45° C. for 0.5 minutes, and 65° C. for 4 minutes. In control PCR, 0.2 mM each natural dNTP and 0.01 units/µl Vent DNA polymerase were used, and the step of extension reaction was performed at 72° C. for 1 minute. The PCR products were stained with ethidium bromide on a 4% agarose gel, and the stained bands were quantified for their intensity with a Molecular Imager FX Pro system and Quantity One software (Bio-Rad). For sequencing analysis, the PCR products had been purified by gel electrophoresis (7% polyacrylamide-7 M urea gel) or filtration (Microcon YM-30 and Micropure-EZ).

T7 Transcription

Transcription (20 µl) was accomplished in 40 mM Tris-HCl buffer (pH 8.0) containing 24 mM MgCl$_2$, 2 mM spermidine, 5 mM DTT, 0.01% Triton X-100, 1-3 mM each natural NTP, 0-3 mM Pa'TP, 0-3 mM DsTP, 10 mM GMP, 2 µM template DNA (for 17-mer transcript synthesis) or 0.5 µM template DNA (for tRNA transcript synthesis), and 2.5 units/µl T7 RNA polymerase (TAKARA). To study the transcription efficiency, the transcription was performed in the presence of 2 µCi [γ-$^{32}$P]GTP (PerkinElmer, in place of GMP) for 17-mer transcript synthesis or [α-$^{32}$P]GTP (Amersham) for tRNA transcript synthesis. After incubation at 37° C. for 3 hours (17-mer synthesis) or 6 hours (tRNA synthesis), a urea-containing dye solution was added to stop the reaction. This solution was heated at 75° C. for 3 minutes and then electrophoresed on a 15% or 20% (17-mer) or 10% (tRNA) polyacrylamide-7 M urea gel. The products were analyzed with a bio-imaging analyzer. For nucleotide composition analysis in transcripts (Non-patent Documents 17 and 33), the transcripts were internally labeled with 2 µCi [α-$^{32}$P]UTP or [α-$^{32}$P]ATP (Amersham). After the transcription, the products were digested with 0.75 units of RNase T$_2$ at 37° C. for 2 hours in 10 µl of 15 mM sodium acetate buffer (pH 4.5). For 17-mer analysis, 0.05 A$_{260}$ units of E. coli tRNA (Sigma) was added to the digestion reaction solution. The digestion products were analyzed by 2D-TLC (HPTLC plate, 100×100 mm, Merck). The developing solvents used for the first and second dimensions were isobutyric acid-ammonia-water (66:1:33 v/v/v) and isopropyl alcohol-HCl-water (70:15:15 v/v/v or 75:15:10 v/v/v for Pa' transcripts), respectively. Spots of the labeled nucleotides on the TLC plate were analyzed with a bio-imaging analyzer.

Dideoxy-cycle Sequencing on PCR-amplified Products of DNA2 to DNA9

PCR for each DNA was accomplished by using a PTC-100 controller in Tris-HCl buffer (pH 8.8) containing 10 mM KCl, 10 mM (NH$_4$)$_2$SO$_4$, 2 mM MgSO$_4$, 0.1% Triton X-100, 0.3 mM each dNTP (N=Pa, G, C and T) and dNTP$_N$ (N=Ds and A), 1 µeach primer 1 or 2, 2.3 M double-stranded DNA fragment (DNA2 to DNA9), and 0.04 units/µl Vent DNA polymerase (New England BioLabs). The PCR cycle was set as follows: 94° C. for 0.5 minutes, 45° C. for 0.5 minutes, and 65° C. for 4 minutes. For sequencing, the PCR products had been purified by gel electrophoresis (7% polyacrylamide-7 M urea gel) or filtration (Microcon YM-30 and Micropure-EZ). After sequencing with or without dPa'TP, the sequences were determined using an ABI377 DNA sequencer equipped with a 6% polyacrylamide-6 M urea gel.

The positions of unnatural bases in DNA fragments can be confirmed by comparing both peak patterns obtained from sequencing with and without dPa'TP.

Aminoacylation of Unnatural Anticodon-containing tRNAs in E. coli Cell-free Translation System Aminoacylation of tRNA transcripts was studied in a rapid translation system (RTS-100, Roche) according to the manufacturer's protocol with minor modifications. The tRNA transcripts (0.4 µM) internally labeled with [α-$^{32}$P] were incubated at 30° C. for 30 minutes in the system (25 µl). The tRNAs were extracted with phenol saturated with sodium acetate (pH 4.5) and then analyzed by electrophoresis at 4° C. on a 10% polyacrylamide gel containing 0.2 M Tris-acetate (pH 4.75) and 3 mM EDTA (FIG. 5d, FIG. 21).

2. Sequencing of DNA Fragments Containing Ds

The position of Ds-Pa base pairing in DNA fragments was confirmed by dideoxynucleotide chain termination sequencing (Non-patent Document 33) supplemented with a nucleoside triphosphate derivative of Pa' (dPa'TP) (Non-patent Document 34) (Pa' is 4-propynylpyrrole-2-carbaldehyde which is a modified form of Pa). The efficiency of KF exo$^-$-mediated incorporation of dPa'TP opposite Ds in the template ($V_{max}/K_M$=2.2×10$^5$) is 3.9-fold higher than that of dPaTP opposite Ds in the template ($V_{max}/K_M$=5.7×10$^4$) (Tables 1 and 2). Thus, sequencing of Ds-containing strands was performed using a Taq DNA polymerase sequencing kit BigDye1.1 (Applied Biosystems) supplemented with dPa'TP. For sequencing and the subsequent experiments, double-stranded DNA fragments containing a Ds-Pa base pair (150-mer and 174-mer, DNA1 to DNA14) were prepared by primer extension or ligation of chemically synthesized DNA fragments (FIG. 6).

In sequencing of DNA1 containing 5'-CDsA/3'-GPaT, addition of 0.05 mM dPa'TP prevented the dye terminators of natural bases from being incorporated opposite Ds in the template. Thus, peaks of A, G, C and T all disappeared only at a site corresponding to Ds in the template (FIG. 3c). Namely, the position at which no peak appeared and a gap was observed in this sequencing indicates the unnatural base position.

Unlike DNA1, some of the other DNAs containing different sequences around the unnatural base showed no clear gap pattern in their sequencing with dPa'TP, (FIGS. 13-20). However, since the subsequent peaks following the position of template Ds almost disappeared in sequencing without dPa'TP (FIG. 3g), the unnatural base position in DNA can be confirmed by comparing both peak patterns obtained from sequencing with and without dPa'TP (e.g., FIGS. 3c and 3g).

3. PCR Amplification of DNA Fragments Containing Ds-Pa Base Pair

PCR amplification of DNA1 to DNA14 containing a Ds-Pa base pair (FIG. 6) (150-mer or 174-mer, 2.3 nM) was performed using thermophilic DNA polymerase having 3'→5' exonuclease activity (0.04 units/µl, VENT DNA polymerase, New England BioLabs) and a substrate mixture containing dDsTP$_N$, dPaTP, dATP$_N$, dGTP, dCTP and dTTP (0.3 mM each). The PCR cycle was set as follows: 94° C. for 30 seconds, 45° C. for 30 seconds, and 65° C. for 4 minutes.

Figure 1A:
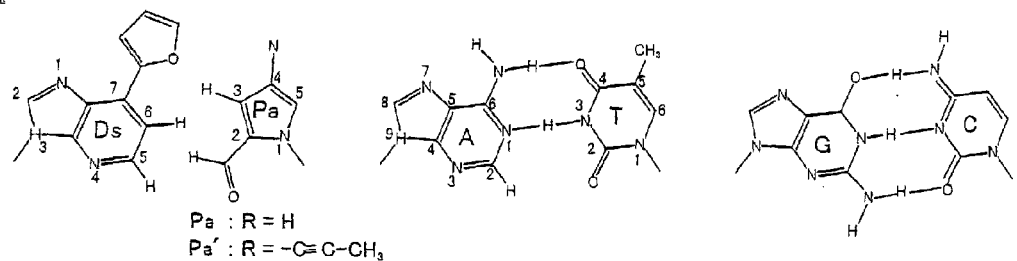
[FIG. 1a]
Figure 1B:
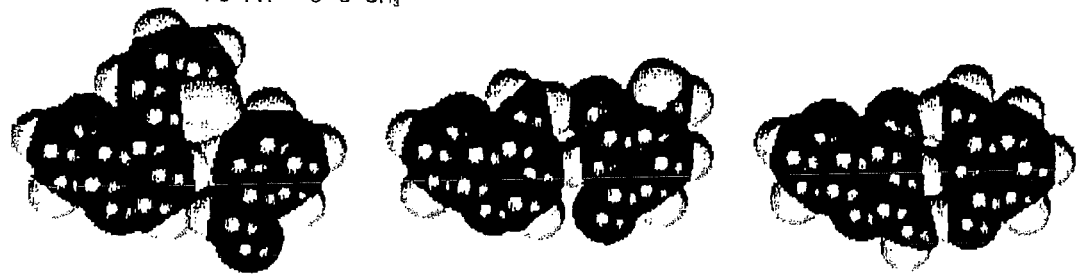
Figure 1C:
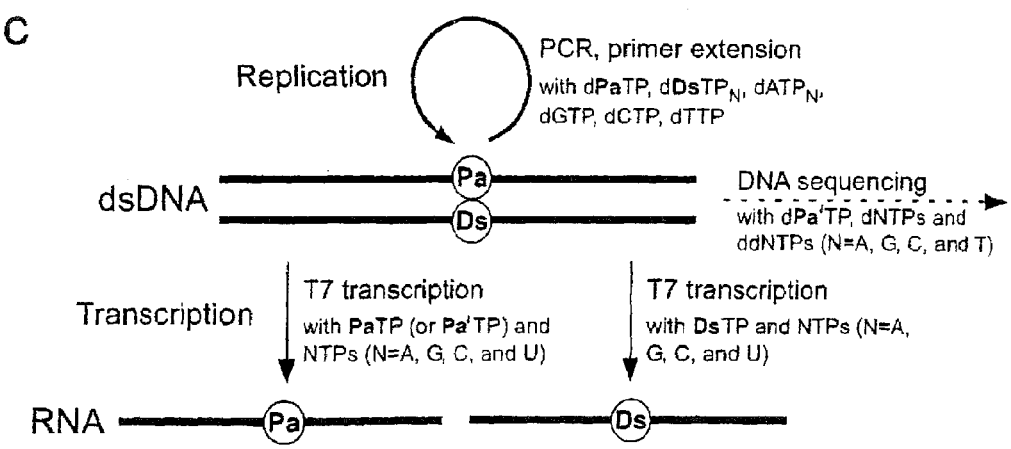
Figure 2A:
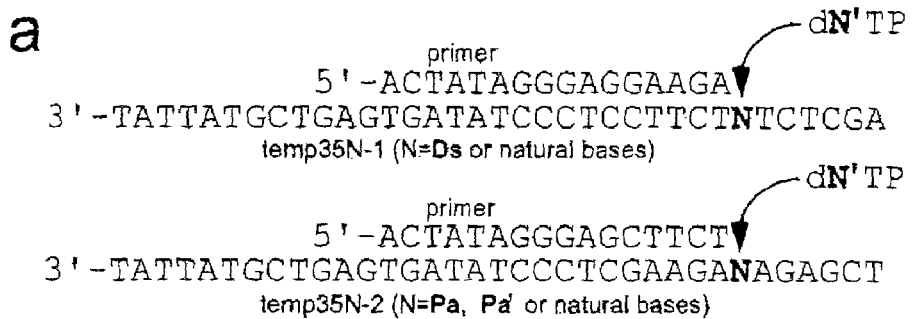
[FIG. 2a]
Figure 2B:
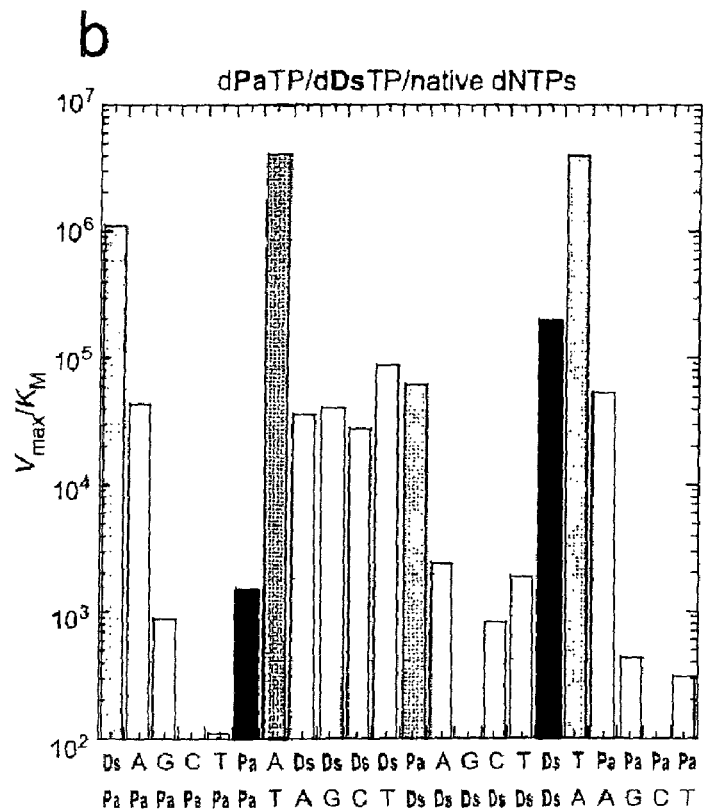
Figure 2C:
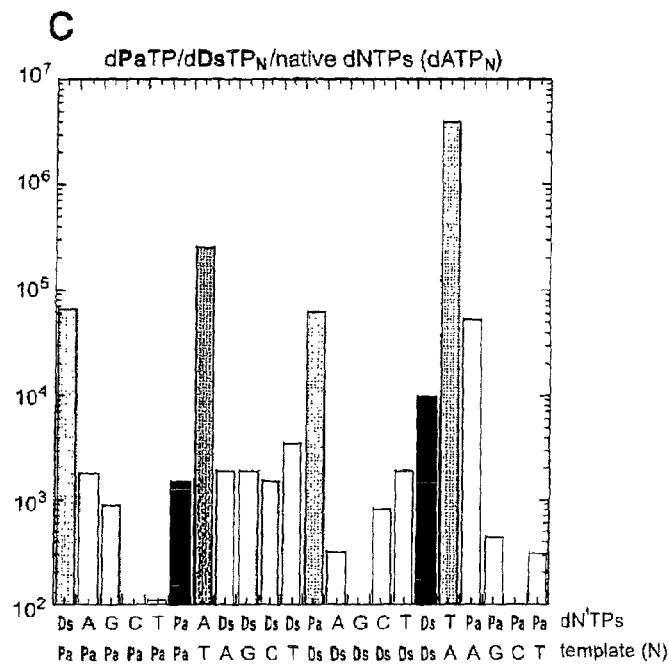
Figure 2D:
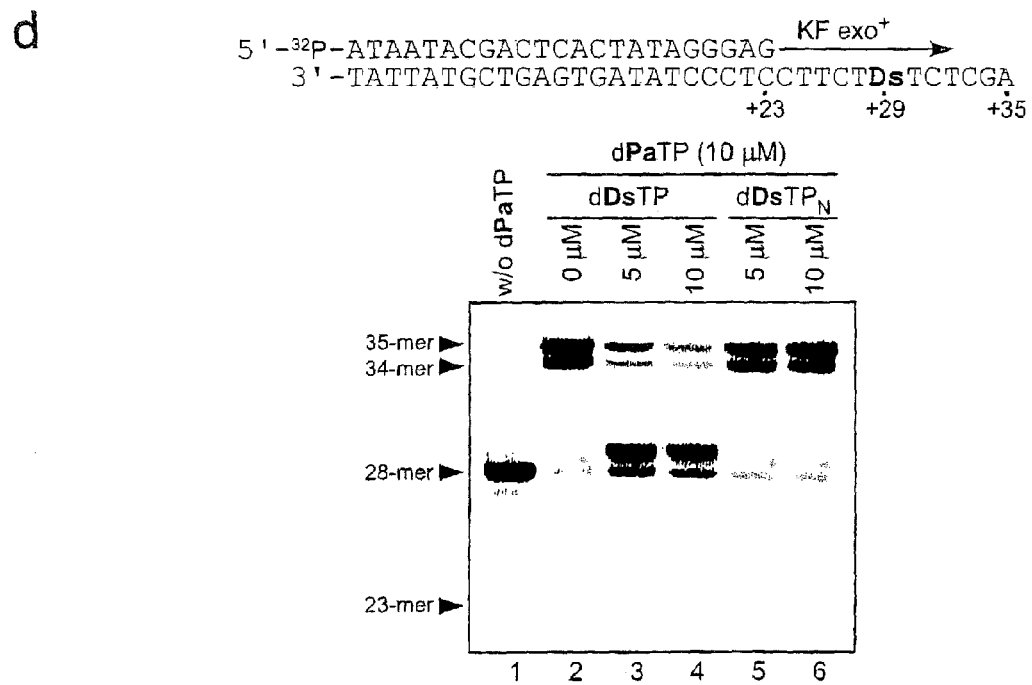
Figure 2E:
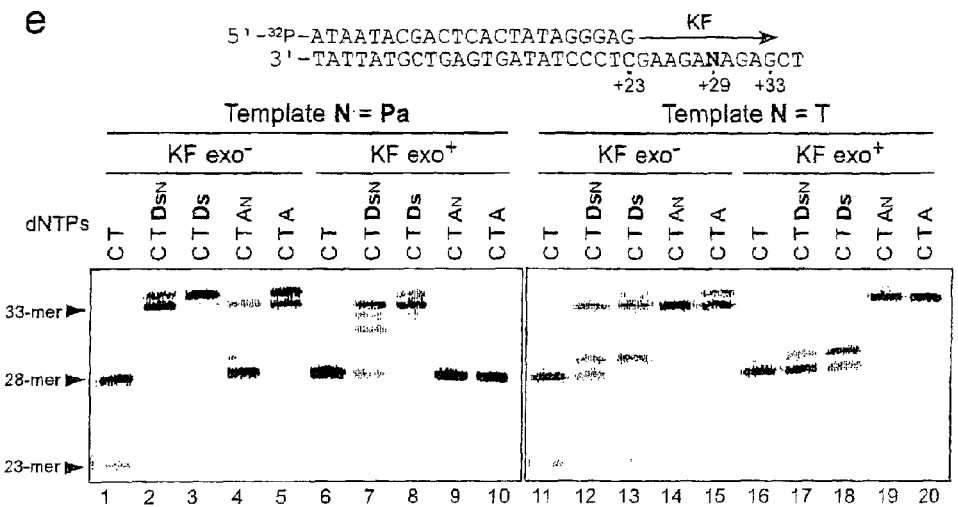
Figure 3A:
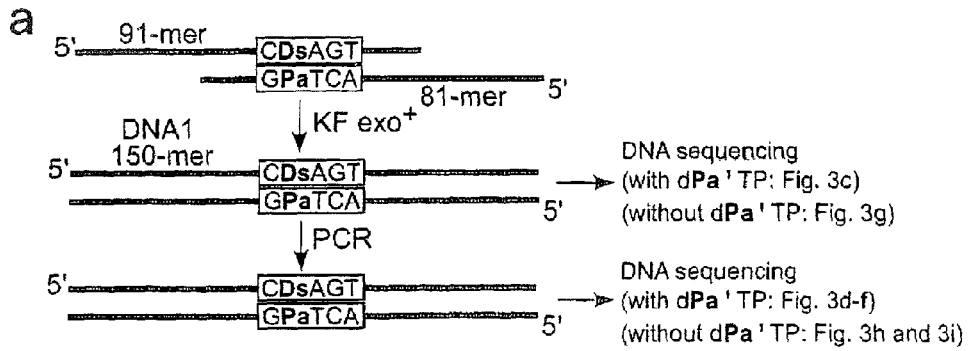
[FIG. 3a]
Figure 3B:
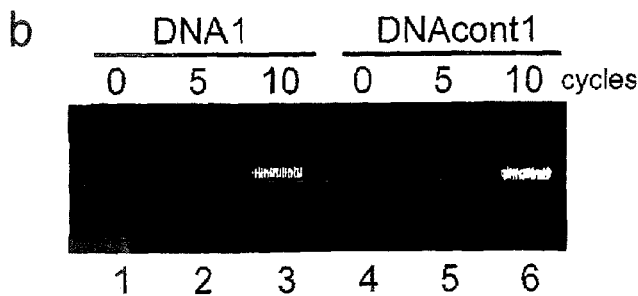
Figure 3C:
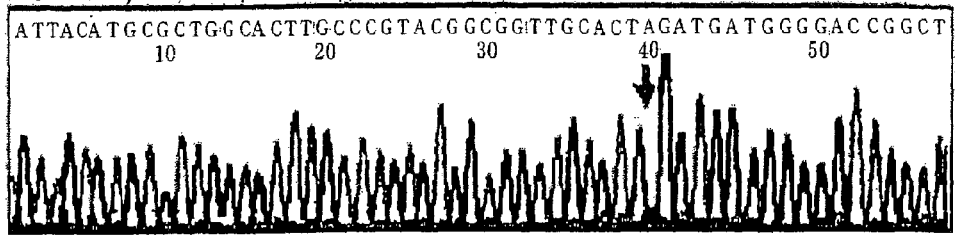
Figure 3D:
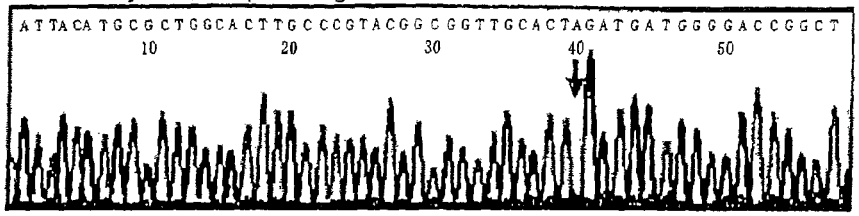
Figure 3E:
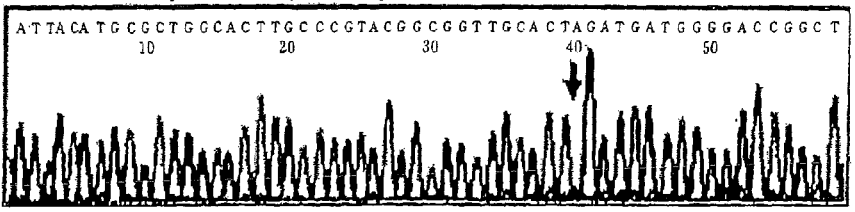
Figure 3F:
Figure 3G:
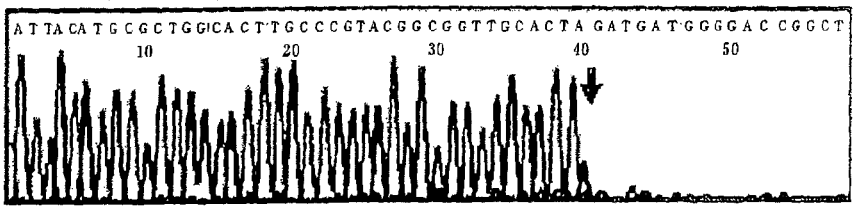
Figure 3H:
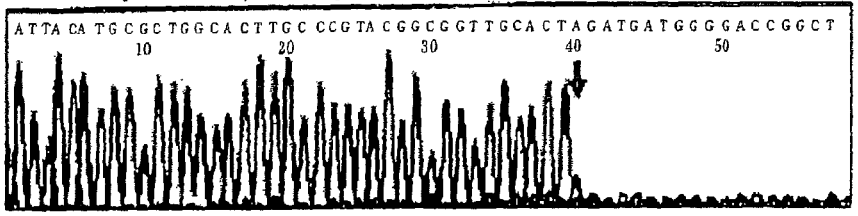
Figure 3I:
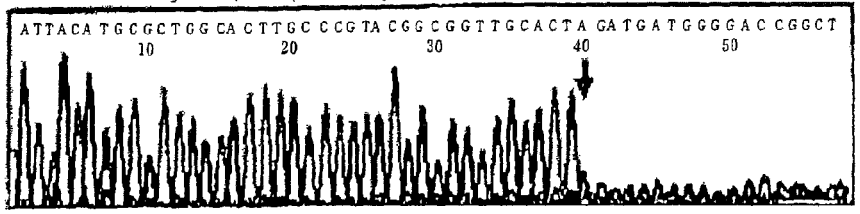
Figure 8:
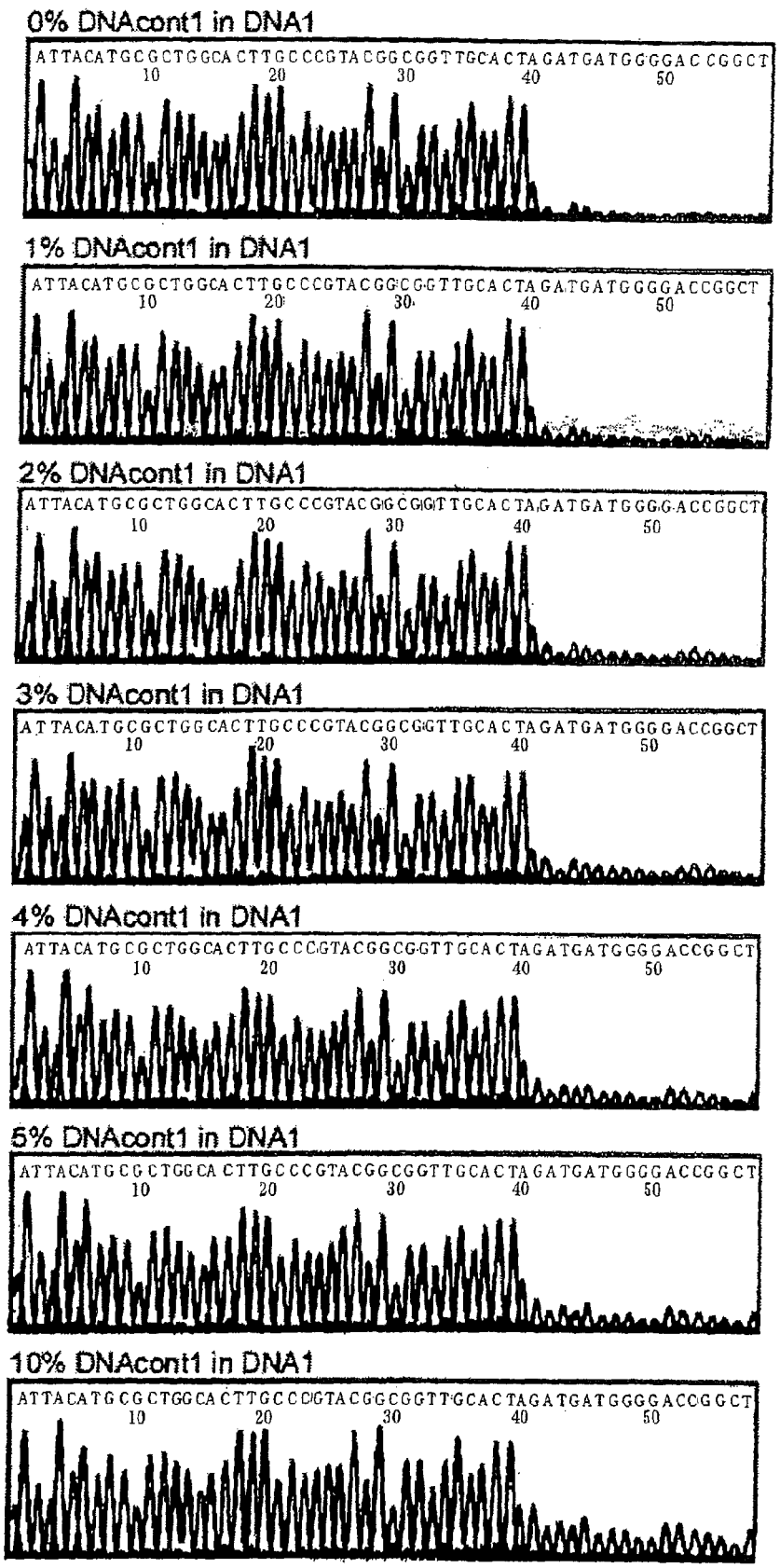
[FIG. 8]

The inventors of the present invention first tested DNA1 for its amplification selectivity and efficiency (FIG. 3a). After 10 cycles of PCR (FIG. 3b), the products were analyzed by sequencing with or without dPa'TP (FIGS. 3d and 3h). Further, additional 10 cycles of PCR (10+10 cycles in total) were performed on a part of the 10 cycle PCR product (FIGS. 3e and 3i). In sequencing with dPa'TP, the PCR products after 10 cycles and 10+10 cycles resulted in peak patterns similar to those of the original DNA1. In sequencing without dPa'TP (FIGS. 3g-3i), the read-through peaks following the unnatural base position in DNA1 were slightly increased with an increase in the number of PCR cycles. Thus, the height of read-through peaks can be used to determine the rate of PCR-induced mutation from the Ds-Pa base pair to a natural base pair. The mutation rate was determined from the height of read-through peaks in the PCR products (FIGS. 3g-3i), in comparison with the height of read-through peaks obtained by sequencing without dPa'TP for control DNA fragments containing 1-10% A-T base pair instead of Ds-Pa (FIG. 8). The mutation rate of the Ds-Pa base pair in DNA1 after 10 cycles and 10+10 cycles was ~1% and 3-4%, respectively. By using this procedure, it was also indicated that the use of γ-amidotriphosphate of A increased the selectivity of Ds-Pa base pairing during PCR. In PCR amplification of DNA1 performed using dDsTP$_N$, dPaTP and natural dNTPs, but not using dATP$_N$, the mutation rate was increased. After 10 cycles and 10+10 cycles, the mutation rate of the Ds-Pa base pair was ~5% and ~10%, respectively (FIG. 9). Moreover, in 10 cycle PCR in the absence of dDsTP$_N$ and dPaTP, the Ds-Pa base pair in DNA1 was completely replaced with an A-T base pair (FIG. 3f).

The amplification efficiency of DNA1 was evaluated from band intensity after dye staining of the PCR products on a gel or autoradiography of the products obtained with each labeled primer. The results (FIG. 3b) indicated that DNA1 was amplified 15-fold after 10 cycles of PCR, while a corresponding natural DNA fragment (DNAcont1) was amplified 37-fold after 10 cycles of PCR. The more accurate efficiency was obtained by autoradiography of PCR products with a 5'- or 3'-$^{32}$P-labeled primer (FIG. 10). The extension efficiency per cycle (Y) was determined using the equation: $N_f=N_0(1+Y)^n$ where $N_f$ is the final copy number of a product, $N_0$ is the initial copy number, and n is the number of PCR cycles (Non-patent Document 35). For DNA1, the efficiency (Y) of PCR with 1 to 10 cycles was 0.38 for extension from the 5'-primer and 0.29 for extension from the 3'-primer, and the Y value in PCR amplification of DNAcont1 under usual conditions was 0.43 and 0.35, respectively. Thus, the efficiency per cycle of PCR in the unnatural base pair system is 76-88% of that in the conventional natural base pair systems. Based on the thus obtained amplification efficiency of PCR products and the mutation rate of the Ds-Pa base pair determined by DNA sequencing, the fidelity of the Ds-Pa base pair in DNA1 during PCR (for 2-fold amplification of DNA1) is calculated to be 99.8% or more. However, this fidelity was found to depend on the purity of the chemically synthesized original DNA fragments, rather than the selectivity of Ds-Pa base pairing during PCR amplification (FIG. 11). Thus, the selectivity of the unnatural base pair system appears to be considerably higher than 99.8%.

The inventors of the present invention also studied amplification of the other DNA fragments (DNA2 to DNA14) containing different sequences around the Ds-Pa base pair. After 10 cycles of PCR, each DNA fragment was amplified 16- to 30-fold (FIG. 12), and the mutation rate of the Ds-Pa base pair was 1-3% for each DNA (FIGS. 13-20), except for amplification of DNA10 to DNA14 containing 5'-X(A)$_n$-3' sequences (where X=Ds or Pa, and n=2). The amplification efficiency of these DNA fragments after 10 cycles of PCR was less than 5-fold. This low efficiency is caused when substrates of Ds or Pa are consecutively incorporated subsequent to the incorporation of γ-amidotriphosphate of A. Thus, all the sequences containing unnatural bases, except for 5'-DsAA-3' and 5'-PaAA-3' sequences, can be used for DNA amplification.

4. T7 Transcription Mediated by Ds-Pa Base Pairing

Figure 4A:
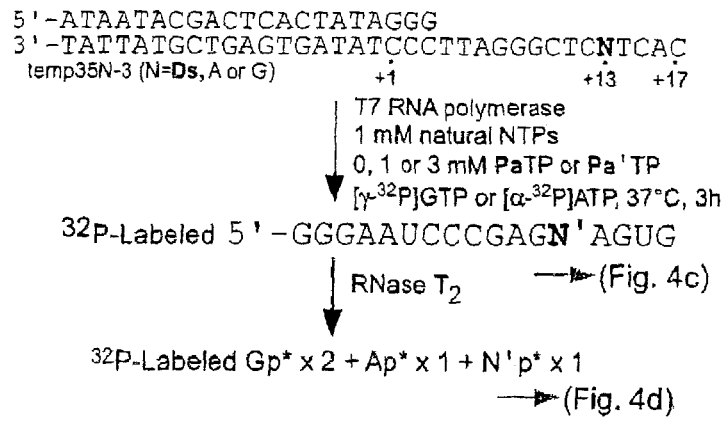
[FIG. 4a]
Figure 4B:
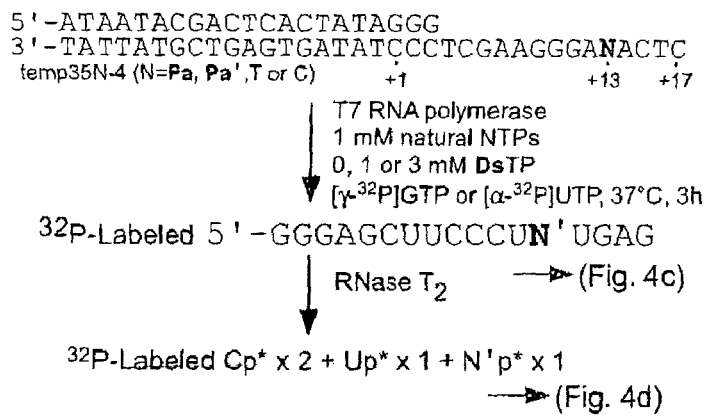
Figure 4C:
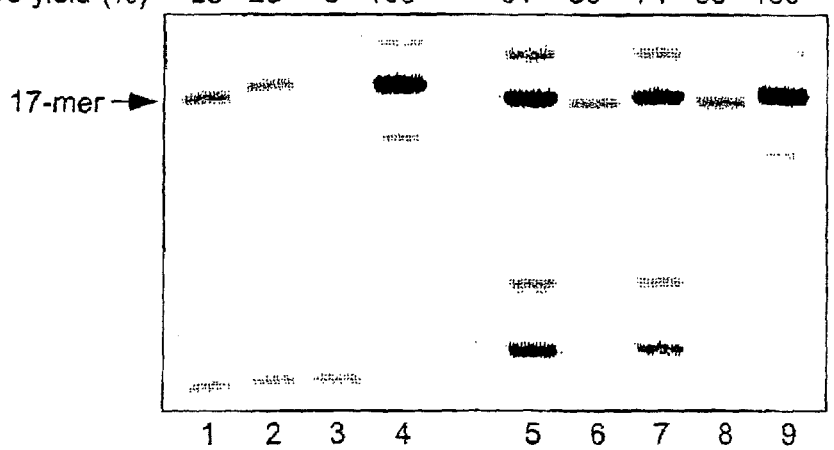
[FIG. 4c]

Ds-Pa and Ds-Pa' base pairings complementarily mediated site-specific incorporation of DsTP, PaTP and Pa'TP into RNA by T7 RNA polymerase. Transcription was studied with template DNA (35-mer) containing Ds, Pa or Pa' (FIGS. 4a and 4b). After 3 hour transcription with ribonucleoside triphosphates of the unnatural bases, the $^{32}$P-labeled transcripts were analyzed on a gel (FIG. 4c). The full-length transcripts (17-mer) containing Pa, Pa' and Ds had yields ranging from 28% to 91% (FIG. 4c, Lanes 1, 2, 5 and 7), relative to transcripts consisting only of natural bases obtained with template DNA composed of natural bases (FIG. 4c, Lane 9). In transcription of template DNAs containing the unnatural bases, the yields of transcripts obtained without adding substrates of the unnatural bases were significantly reduced (FIG. 4c, Lanes 3, 6 and 8).

Figure 4D:
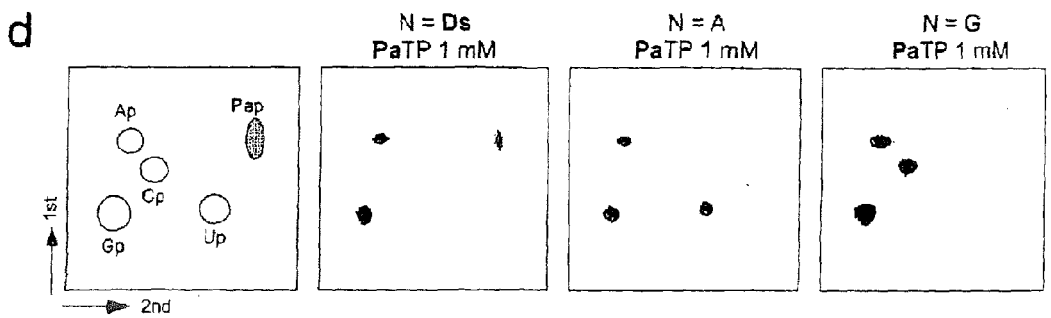
[FIG. 4d]
Figure 4E:
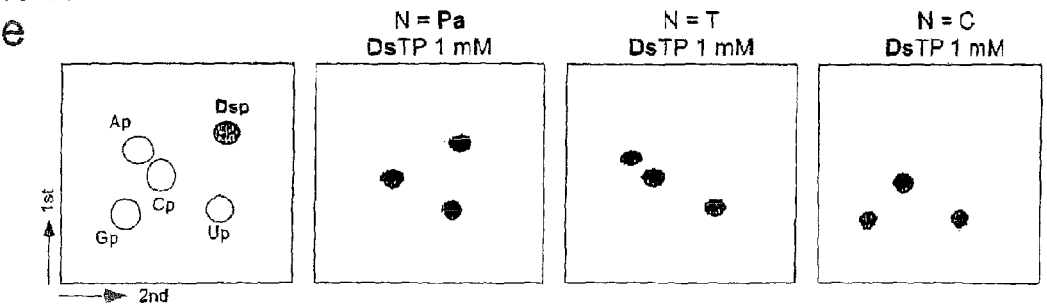

The high selectivity of Ds-Pa and Ds-Pa' base pairings in T7 transcription was confirmed by nucleotide composition analysis of internally $^{32}$P-labeled transcripts (Non-patent Documents 17 and 33) (FIGS. 4d and 4e, as well as Table 3).

TABLE 3

Nucleotide composition analysis of T7 transcripts

| | | [α-³²P] NTP | Natural NTP (mM) | Unnatural NTP (mM) | Composition of nucleotide incorporated as 5' neighbor of A or U[a] | | | | |
|---|---|---|---|---|---|---|---|---|---|
| Entry | Template | | | | Ap | Gp | Cp | Up | Np[b] |
| 1 | temp35Ds-3 | ATP | 1 | Pa (1) | 1.03[c] [1][d] (0.01)[e] | 1.97 [2] (0.04) | 0.01 [0] (<0.01) | 0.02 [0] (<0.01) | 0.97 [1] (0.04) |
| 2 | temp35Ds-3 | ATP | 1 | Pa (3) | 1.01 [1] (0.02) | 1.96 [2] (0.03) | 0.01 [0] (0.01) | 0.01 [0] (0.01) | 1.00 [1] (0.02) |
| 3 | temp35A-3 | ATP | 1 | Pa (1) | 0.99 [1] (0.01) | 1.96 [2] (0.02) | n.d.[f] [0] (—) | 1.04 [1] (0.02) | n.d. [0] (—) |
| 4 | temp35A-3 | ATP | 1 | Pa (3) | 0.99 [1] (0.01) | 1.97 [2] (0.02) | n.d. [0] (—) | 1.03 [1] (0.03) | n.d. [0] (—) |
| 5 | temp35G-3 | ATP | 1 | Pa (1) | 1.02 [1] (0.01) | 1.96 [2] (0.02) | 1.01 [1] (0.01) | 0.01 [0] (<0.01) | n.d. [0] (—) |
| 6 | temp35G-3 | ATP | 1 | Pa (3) | 1.01 [1] (0.03) | 1.98 [2] (0.04) | 1.00 [1] (0.02) | 0.01 [0] (<0.01) | n.d. [0] (—) |
| 7 | temp35Ds-3 | ATP | 1 | Pa' (1) | 1.03 [1] (0.02) | 2.00 [2] (0.04) | 0.01 [0] (0.01) | 0.02 [0] (0.01) | 0.95 [1] (0.03) |
| 8 | temp35Ds-3 | ATP | 1 | Pa' (3) | 1.01 [1] (0.02) | 1.99 [2] (0.03) | 0.01 [0] (0.01) | 0.02 [0] (0.01) | 0.97 [1] (0.04) |
| 9 | temp35A-3 | ATP | 1 | Pa' (1) | 0.99 [1] (0.03) | 1.98 [2] (0.03) | n.d. [0] (—) | 1.03 [1] (0.05) | n.d. [0] (—) |
| 10 | temp35A-3 | ATP | 1 | Pa' (3) | 0.99 [1] (0.01) | 1.99 [2] (0.01) | 0.01 [0] (0.01) | 1.00 [1] (0.01) | n.d. [0] (—) |
| 11 | temp35G-3 | ATP | 1 | Pa' (1) | 1.01 [1] (0.01) | 1.98 [2] (0.02) | 1.00 [1] (0.01) | 0.01 [0] (<0.01) | n.d. [0] (—) |
| 12 | temp35G-3 | ATP | 1 | Pa' (3) | 1.00 [1] (<0.01) | 1.98 [2] (0.01) | 1.01 [1] (0.01) | 0.01 [0] (<0.01) | n.d. [0] (—) |
| 13 | temp35Ds-3 | ATP | 1 | none | 1.31 [1] (0.02) | 2.18 [2] (0.02) | 0.15 [0] (<0.01) | 0.36 [0] (0.03) | n.d. [—] (—) |
| 14 | temp35Pa-4 | UTP | 1 | Ds (1) | 0.02 [0] (<0.01) | n.d. [0] (—) | 1.99 [2] (0.01) | 1.00 [1] (0.01) | 0.98 [1] (0.01) |
| 15 | temp35Pa-4 | UTP | 1 | Ds (3) | 0.01 [0] (<0.01) | n.d. [0] (—) | 1.99 [2] (0.03) | 1.01 [1] (0.01) | 0.99 [1] (0.02) |
| 16 | temp35Pa'-4 | UTP | 1 | Ds (1) | 0.05 [0] (<0.01) | n.d. [0] (—) | 1.98 [2] (0.01) | 1.02 [1] (0.01) | 0.94 [1] (0.01) |
| 17 | temp35Pa'-4 | UTP | 1 | Ds (3) | 0.02 [0] (<0.01) | n.d. [0] (—) | 1.99 [2] (0.01) | 1.02 [1] (0.01) | 0.96 [1] (0.01) |
| 18 | temp35C-4 | UTP | 1 | Ds (1) | 0.01 [0] (<0.01) | 0.98 [1] (<0.01) | 2.01 [2] (0.01) | 1.00 [1] (0.01) | n.d. [0] (—) |
| 19 | temp35C-4 | UTP | 1 | Ds (3) | 0.01 [0] (<0.01) | 0.97 [1] (0.02) | 2.03 [2] (0.04) | 1.00 [1] (0.02) | n.d. [0] (—) |
| 20 | temp35T-4 | UTP | 1 | Ds (1) | 0.99 [1] (0.01) | n.d. [0] (—) | 1.99 [2] (0.01) | 1.02 [1] (0.02) | n.d. [0] (—) |
| 21 | temp35T-4 | UTP | 1 | Ds (3) | 0.99 [1] (0.01) | n.d. [0] (—) | 2.00 [2] (0.01) | 1.01 [1] (0.02) | n.d. [0] (—) |
| 22 | temp35Pa-4 | UTP | 1 | none | 0.91 [1] (0.01) | 0.08 [0] (0.01) | 1.99 [2] (<0.01) | 1.02 [1] (0.01) | n.d. [—] (—) |
| 23 | temp35Pa'-4 | UTP | 1 | none | 0.97 [1] (0.01) | 0.02 [0] (<0.01) | 1.99 [2] (0.01) | 1.02 [1] (0.01) | n.d. [—] (—) |
| 24 | DNA11 | ATP | 3 | Pa' (3) | 5.08 [5] (0.02) | 5.98 [6] (0.04) | 6.88 [7] (0.03) | 0.09 [0] (<0.01) | 0.97 [1] (0.02) |
| 25 | DNA12 | ATP | 3 | Pa' (3) | 6.05 [6] (0.06) | 5.94 [6] (0.03) | 6.96 [7] (0.05) | 0.07 [0] (0.01) | 0.98 [1] (0.03) |
| 26 | DNAcont4 | ATP | 3 | none | 6.05 [6] (0.07) | 5.99 [6] (0.05) | 6.89 [7] (0.02) | 1.07 [1] (0.03) | n.d. [—] (—) |
| 27 | DNAcont4 | ATP | 3 | Pa' (3) | 6.04 [6] (0.10) | 6.00 [6] (0.10) | 6.90 [7] (0.05) | 1.06 [1] (0.03) | n.d. [0] (—) |
| 28 | DNA13 | ATP | 2 | Ds (2) | 5.04 [5] (0.05) | 6.02 [6] (0.08) | 6.93 [7] (0.05) | 0.05 [0] (0.01) | 0.96 [1] (0.03) |
| 29 | DNA14 | ATP | 2 | Ds (2) | 6.13 [6] (0.04) | 5.96 [6] (0.05) | 6.93 [7] (0.06) | 0.03 [0] (0.01) | 0.96 [1] (0.02) |
| 30 | DNAcont4 | ATP | 2 | none | 6.10 [6] (0.04) | 5.98 [6] (0.03) | 6.88 [7] (0.03) | 1.04 [1] (0.02) | n.d. [—] (—) |
| 31 | DNAcont4 | ATP | 2 | Ds (2) | 6.10 [6] (0.05) | 5.98 [6] (0.04) | 6.83 [7] (0.02) | 1.09 [1] (0.01) | 0.02 [0] (0.01) |
| 32 | DNA11 | UTP | 3 | Pa' (3) | 2.01 [2] (0.03) | 3.98 [4] (0.04) | 5.01 [5] (0.04) | 4.00 [4] (0.05) | 0.01 [0] (<0.01) |
| 33 | DNA12 | UTP | 3 | Pa' (3) | 2.00 [2] (0.02) | 3.94 [4] (0.04) | 4.05 [4] (0.02) | 4.01 [4] (0.06) | 0.01 [0] (<0.01) |
| 34 | DNAcont4 | UTP | 3 | none | 2.01 [2] (0.03) | 3.97 [4] (0.04) | 5.03 [5] (0.04) | 4.00 [4] (0.06) | n.d. [—] (—) |
| 35 | DNAcont4 | UTP | 3 | Pa' (3) | 2.02 [2] (0.02) | 4.00 [4] (0.09) | 5.01 [5] (0.07) | 3.97 [4] (0.05) | n.d. [0] (—) |
| 36 | DNA13 | UTP | 2 | Ds (2) | 2.00 [2] (0.03) | 3.97 [4] (0.10) | 4.99 [5] (0.07) | 4.03 [4] (0.06) | n.d. [0] (—) |

TABLE 3-continued

Nucleotide composition analysis of T7 transcripts

| Entry | Template | [α-$^{32}$P] NTP | Natural NTP (mM) | Unnatural NTP (mM) | Composition of nucleotide incorporated as 5' neighbor of A or U$^a$ | | | | |
|---|---|---|---|---|---|---|---|---|---|
| | | | | | Ap | Gp | Cp | Up | Np$^b$ |
| 37 | DNA14 | UTP | 2 | Ds (2) | 1.99 [2] (0.02) | 3.91 [4] (0.03) | 4.02 [4] (0.01) | 4.08 [4] (0.04) | 0.01 [0] (0.01) |
| 38 | DNAcont4 | UTP | 2 | none | 2.01 [2] (0.03) | 3.98 [4] (0.04) | 5.01 [5] (0.02) | 4.01 [4] (0.06) | n.d. [—] (—) |
| 39 | DNAcont4 | UTP | 2 | Ds (2) | 1.99 [2] (0.03) | 3.95 [4] (0.04) | 5.01 [5] (0.06) | 4.05 [4] (0.04) | 0.01 [0] (<0.01) |

$^a$Composition of nucleotides incorporated at the 5'-side of A (Entry Nos. 1-13 and 24-31) or U (Entry Nos. 14-23 and 32-39), as shown in FIGS. 4 and 5
$^b$Np = Pap, Pa'p or Dsp
$^c$The values were determined by using the following equation.
[Formula 27] (Radioactivity of each nucleotide)/[Total radioactivity of all nucleotides (3'-monophosphates)] × (Total number of nucleotides at 5' neighbor of [α-$^{32}$P]NTP)
$^d$The theoretical number of each nucleotide is shown in square brackets.
$^e$Standard deviations are shown in parentheses.
$^f$Not detected.

The internally $^{32}$P-labeled transcripts were digested with Rnase T$_2$, and the resulting labeled nucleoside 3'-monophosphates were analyzed by 2D thin-layer chromatography (2D-TLC). In the case of transcripts obtained with templates containing unnatural bases, each spot corresponding to Ds or Pa appeared on 2D-TLC, and there was no spot corresponding to misincorporation of natural substrates having shapes similar to those of the unnatural bases (e.g., CTP and UTP to PaTP, as well as ATP and GTP to DsTP) (FIG. 4d, N=Ds and FIG. 4e, N=Pa). In the case of transcripts obtained with templates composed entirely of natural bases, there was no spot corresponding to Pa or Ds (FIG. 4d, N=A and G, as well as FIG. 4e, N=T and C). The quantified amount of each nucleotide spot on 2D-TLC was extremely close to its theoretical value expected from the product sequence (Table 3, Entry Nos. 1-23), resulting in an estimated selectivity of 95% or more for Ds-Pa or Ds-Pa' base pairing during transcription.

As an application example, the inventors of the present invention prepared tRNA molecules (85-mer) containing unnatural anticodons CUPa', CPa'A, CUDs and CDsA through T7 transcription. For this purpose, the sequence of E. coli suppressor tRNA$^{Tyr}$ was used.

Figure 5A:
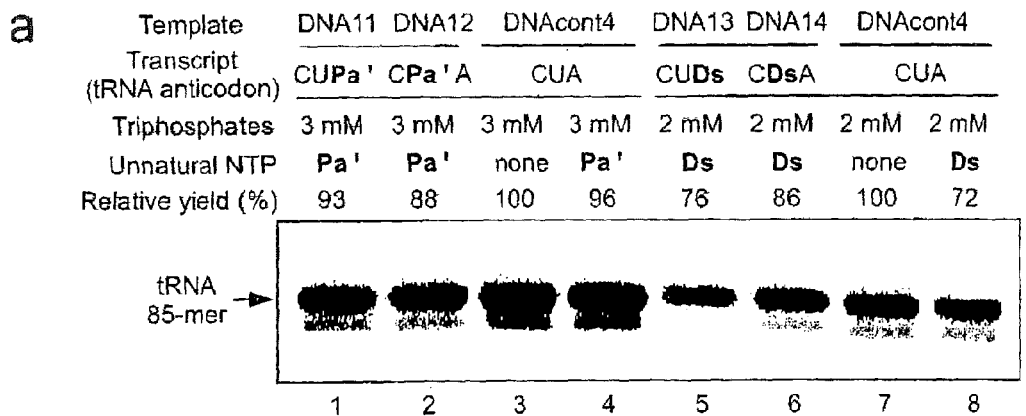
[FIG. 5a]
Figure 5B:
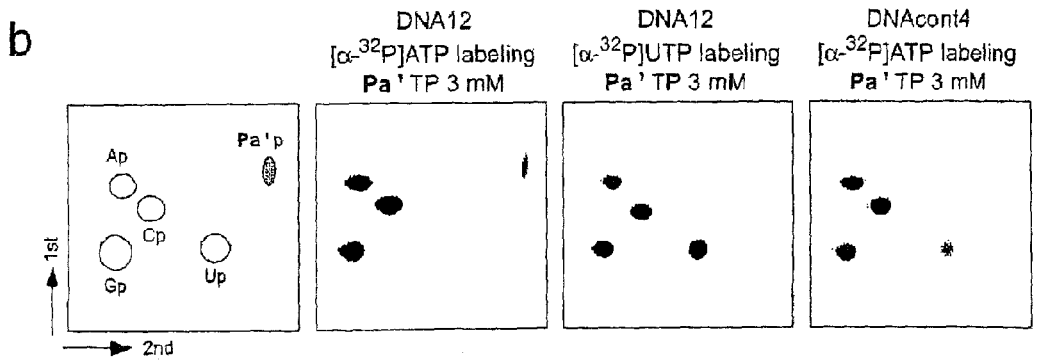
[FIG. 5b]
Figure 5C:
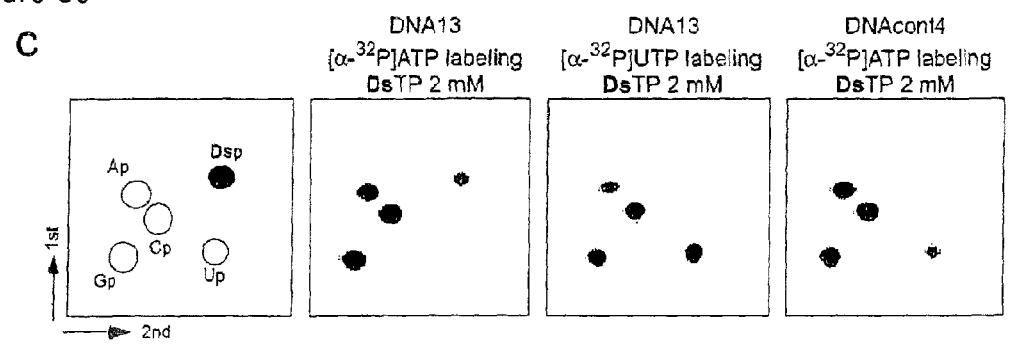
Figure 5D:
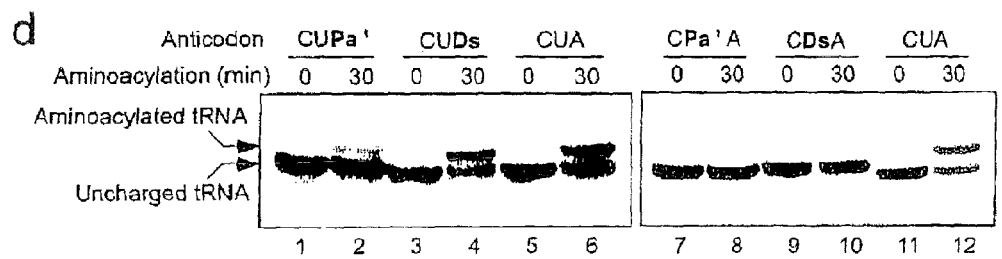
[FIG. 5d]

The transcription efficiency of PaTP or Pa'TP into 17-mer transcripts was relatively low, but transcription of Pa'-containing longer tRNAs (85-mer) showed high efficiency; the 85-mers had yields ranging from 88% to 93%, relative to tRNA transcripts having a CUA anticodon (FIG. 5a). For nucleotide composition analysis, the transcripts were internally labeled with [α-$^{32}$P]ATP or [α-$^{32}$P]UTP. Since the unnatural nucleotides are each located at the 5'-side of A, 3'-monophosphate of each unnatural nucleotide is labeled only with [α-$^{32}$P]ATP. Thus, spots corresponding to the unnatural nucleotides are detected by 2D-TLC only when the transcripts are labeled with [α-$^{32}$P]ATP (FIGS. 5b and 5c). The selectivity of both Pa' incorporation opposite template Ds and Ds incorporation opposite template Pa was 96s or more (Table 3, Entry Nos. 24-39).

Using the resulting tRNA transcripts, the inventors of the present invention studied aminoacylation in an E. coli extract (RTS 100 E. coli HY kit, Roche Diagnostics). tRNAs having CPa'A and CDsA anticodons were not aminoacylated, indicating that they avoided recognition by E. coli-derived aminoacyl tRNA synthetase (FIG. 5d, Lanes 7-10). In contrast, tRNAs having CUPa' and CUDs anticodons were aminoacylated (FIG. 5d, Lanes 1-4). The selectivity of aminoacylation of tRNAs having these unnatural anticodons is in good agreement with the selectivity of recognition between E. coli tRNA$^{Tyr}$ and tyrosyl tRNA synthetase (Non-patent Documents 36 and 37). These results confirm site-specific incorporation of unnatural bases into tRNA.

Example IV

Synthesis of Biotinylated PaTP

Biotinylated PaTP (i.e., 1-(β-D-ribofuranosyl)-4-[(3-biotinamido-1-propynyl)]pyrrole-2-carbaldehyde 5'-triphosphate; Compound 28, Bio-PaTP) was synthesized according to the scheme shown in FIG. 36.

(1) Synthesis of 1-(β-D-ribofuranosyl)-4-[(3-dichloroacetamido)-1-propynyl]pyrrole-2-carbaldehyde (Compound 24) (Reactions (a)-(c) in the scheme shown in FIG. 36):

To a solution containing 2,3,5-tri-O-benzyl-D-ribofuranose (1.0 g, 2.3 mmol) and CCl$_4$ (344 μl, 3.6 mmol) in THF (4.6 ml), hexamethylphosphorous triamide (562 μl, 3.0 mmol) was added at −78° C. This solution was stirred at −78° C. for 2 hours and then at room temperature for 30 minutes (Solution A). To 4-iodo-pyrrole-2-carboxyaldehyde (Compound 23) (830 mg, 3.7 mmol) in CH$_3$CN (25 mL), NaH (60% oil dispersion, 150 mg, 3.7 mmol) was added. The reaction mixture was stirred at room temperature for 30 minutes, followed by addition of 2,3,5-tri-O-benzyl-D-ribofuranosyl chloride in THF (Solution A). The reaction mixture was stirred at room temperature for 12 hours. The product was partitioned between ethyl acetate and water. The organic layer was washed three times with saturated NH$_4$Cl, dried over Na$_2$SO$_4$ and then concentrated under reduced pressure. The product was purified by silica gel column chromatography (eluted with 1% methanol in dichloromethane) to give 1-(2,3,5-tri-O-benzyl-D-ribofuranosyl)-4-iodopyrrole-2-carbaldehyde.

To 1-(2,3,5-tri-O-benzyl-D-ribofuranosyl)-4-iodopyrrole-2-carbaldehyde in dichloromethane (15 ml), BBr$_3$ (1 M, 8.5 ml) was added at −78° C. The reaction mixture was stirred for 2 hours, followed by addition of 50% methanol in CH$_2$Cl$_2$ (30 ml). After this solution was stirred at −78° C. for 10 minutes, 28% NH$_4$OH (4 ml) was added and the reaction mixture was stirred until it reached room temperature. The solution was added to CH$_2$Cl$_2$ and H$_2$O. The aqueous layer was partitioned and washed three times with $CH_2Cl_2$, and the residue was concentrated under reduced pressure. The product was purified by reversed-phase C18 HPLC to give 1-(β-D-ribofuranosyl)-4-iodopyrrole-2-carbaldehyde (330 mg).

1-(β-D-Ribofuranosyl)-4-iodopyrrole-2-carbaldehyde (176 mg, 0.5 mmol, containing α-anomer) was azeotroped with pyridine and toluene. 1-(β-D-Ribofuranosyl)-4-iodopyrrole-2-carbaldehyde (176 mg), tetrakis(triphenylphosphine) palladium (29 mg, 0.025 mmol), CuI (15 mg, 0.08 mmol) and triethylamine (105 μl, 0.75 mmol) were dissolved in DMF (1.8 ml), and a 1 M solution of 3-(dichloroacetamido)-1-propyne (0.75 mmol) in DMF (750 μl) was added thereto. The reaction mixture was stirred at room temperature for 12 hours. The product was partitioned between EtOAc and $H_2O$, and the organic layer was dried over $Na_2SO_4$ and concentrated under reduced pressure. The product was purified by silica gel column chromatography (10% methanol in dichloromethane) and RP-HPLC to give Compound 24 as a β-isomer (123 mg, 26%, total yield for 3 steps). The structure of Compound 24 was confirmed by NMR (FIG. 38) and high-resolution mass spectrometry. The HMQC (FIG. 38e) and HMBC (FIGS. 38f and 38g) spectra of Compound 24 indicated that an N-glycosidic linkage was formed between sugar and pyrrole base site at the Cl' carbon. Moreover, the cross peaks in the NOESY spectrum of Compound 24 (FIG. 38d) were similar to those of Compound 18 (FIG. 25j), and Compound 24 showed a cross peak between H1' and H4' protons. Thus, the anomeric configuration of Compound 24 was identified to be β.

Compound 24:
$^1$H NMR (300 MHz, DMSO-d6) δ 9.54 (d, 1H, J=0.8 Hz), 9.10 (t, 1H, J=5.2 Hz), 8.01 (s, 1H), 7.18 (d, 1H, J=1.8 Hz), 6.49 (s, 1H), 6.34 (d, 1H, J=3.5 Hz), 5.35 (d, 1H, J=5.6 Hz), 5.10 (m, 2H), 4.17 (d, 2H, J=5.4 Hz), 4.02 (m, 2H), 3.88 (m, 1H), 3.68 (ddd, 1H, J=3.4, 5.3, 12.1 Hz), 3.57 (ddd, 1H, J=3.5, 5.0, 12.1 Hz).
$^{13}$C NMR (75 MHz, DMSO-d6) δ 180.28, 163.78, 131.88, 131.49, 126.85, 105.23, 90.23, 85.26, 85.04, 76.83, 76.41, 69.75, 67.01, 60.96, 30.20.
HRMS (FAB, 3-NBA matrix) $C_{15}H_{17}N_2O_6Cl_2$ (M+1): calcd, 391.0464; found, 391.0462.

(2) Synthesis of 1-(2,3-di-O-acetyl-β-D-ribofuranosyl)-4-[(3-dichloroacetamido)-1-propynyl]pyrrole-2-carbaldehyde (Compound 26) (Reactions (d)-(e) in the scheme shown in FIG. 36):

Compound 24 (118 mg, 0.3 mmol) was azeotroped three times with pyridine. To the residue in pyridine (3.0 ml), 4,4'-dimethoxytrityl chloride (113 mg, 0.33 mmol) was added. The mixture was stirred at room temperature for 1 hour and then added to EtOAc and 5% $NaHCO_3$. The organic layer was washed with saturated NaCl, dried over $Na_2SO_4$ and then concentrated under reduced pressure. The product was purified by silica gel chromatography (1% methanol in dichloromethane) to give 197 mg of Compound 25 in a yield of 95%.

Compound 25 (188 mg, 0.27 mmol) was azeotroped three times with pyridine. To the residue in pyridine (2.7 ml), acetic anhydride (103 μl, 1.1 mmol) was added. The mixture was stirred at room temperature for 12 hours and then added to EtOAc and 5% $NaHCO_3$. The organic layer was washed with saturated NaCl, dried over $Na_2SO_4$ and then concentrated under reduced pressure. To the residue in dichloromethane (27 ml), dichloroacetic acid (270 μl) was added at 0° C. The mixture was stirred at 0° C. for 15 minutes, poured into 5% aqueous sodium bicarbonate, and then extracted with dichloromethane. After drying over $Na_2SO_4$, the solution was concentrated under reduced pressure. The product was purified by silica gel chromatography (1% methanol in dichloromethane) to give 118 mg of Compound 26 in a yield of 92%.

Compound 25:
$^1$H NMR (500 MHz, DMSO-d6) δ 9.56 (s, 1H), 9.05 (t, 1H, J=5.0 Hz), 7.72 (s, 1H), 7.38-7.20 (m, 10H), 6.87 (d, 4H, J=7.1 Hz), 6.47 (s, 1H), 6.34 (d, 1H, J=3.3 Hz), 5.47 (d, 1H, J=5.3 Hz), 5.13 (d, 1H, J=5.7 Hz), 4.12-4.00 (m, 5H), 3.73 (s, 6H), 3.22 (m, 2H).
HRMS (FAB, 3-NBA matrix) $C_{36}H_{35}N_2O_8Cl_2$ (M+1): calcd, 693.1770; found, 693.1721.

Compound 26: $^1$H NMR (500 MHz, DMSO-d6) δ 9.50 (s, 1H), 9.10 (bs, 1H), 8.06 (s, 1H), 7.24 (d, 1H, J=1.3 Hz), 6.64 (d, 1H, J=5.0 Hz), 6.48 (s, 1H), 5.43 (t, 1H, J=5.0 Hz), 5.35 (t, 1H, J=5.2 Hz), 5.32 (t, 1H, J=4.8 Hz), 4.17 (m, 3H), 3.73 (m, 1H), 3.62 (m, 1H), 2.07 (s, 3H), 2.01 (s, 3H).
HRMS (FAB, 3-NBA matrix) $C_{19}H_{21}N_2O_8Cl_2$ (M+1): calcd, 475.0675; found, 475.0687.

(3) Synthesis of 1-(β-D-ribofuranosyl)-4-[(3-biotinamido-1-propynyl)]pyrrole-2-carbaldehyde 5'-triphosphate (Compound 28) (Reactions (f)-(g) in the scheme shown in FIG. 36)

Protected nucleoside 26 (47 mg, 0.1 mmol) was dissolved in pyridine and concentrated under reduced pressure. The residue was dissolved in pyridine (100 μl) and dioxane (300 μl), followed by addition of a 1 M dioxane solution of 2-chloro-4H-1,3,2-benzodioxaphosphorin-4-one (110 μl, 0.11 mmol). After 10 minutes, tri-n-butylamine (100 μl) and 0.5 M bis(tributylammonium)pyrophosphate in DMF (300 μl, 0.15 mmol) were quickly added to the reaction mixture. The mixture was stirred at room temperature for 10 minutes, followed by addition of a 1% iodine solution in pyridine/water (98/2, v/v) (2.0 ml). After 15 minutes, a 5% aqueous solution of $NaHSO_3$ (150 μl) was added. The volatile components were removed by evaporation, and water (5.0 ml) was then added to the residue. The mixture was stirred at room temperature for 30 minutes and then treated with concentrated ammonia (20 ml) at room temperature for 12 hours. The solution was concentrated under reduced pressure, and the product was purified by DEAE Sephadex (A-25) column chromatography (eluted with a linear gradient of 50 mM to 1 M TEAB) and then by C18-HPLC (eluted with a gradient of 0% to 30% $CH_3CN$ in 100 mM triethylammonium acetate) to give Nucleoside 5'-triphosphate 27.

After lyophilization, Compound 27 in 0.1 M $NaHCO_3$-$Na_2CO_3$ buffer (5 ml, pH 8.6) was reacted with biotin-N-hydroxysuccinimide (900 μl, 0.14 M in DMF) at room temperature for 3 hours. The mixture was treated with 28% $NH_4OH$ (2 ml) for 1 hour. The product was purified by DEAE Sephadex (A-25) column chromatography (eluted with a linear gradient of 50 mM to 1 M TEAB) and then by C18-HPLC (eluted with a gradient of 0% to 30% $CH_3CN$ in 100 mM triethylammonium acetate) to give Nucleoside 5'-triphosphate 28 in a yield of 14% from Compound 26. The structure of Compound 28 was confirmed by $^1$H NMR (FIGS. 43a and 43b), $^{31}$P NMR (FIG. 43c) and mass spectrometry (FIG. 42). Proton signals from the biotin moiety in Compound 28 were identical with those of biotinylated yTP previously synthesized, and the $^{31}$P NMR spectrum in $D_2O$ showed typical phosphorus signals corresponding to nucleotide 5'-triphosphate.

Compound 27:
Electrospray ionization-mass spectroscopy (ESI-MS) $C_{13}H_{19}O_{14}N_2P_3$: calcd, 519.00 (M–H)$^-$; found, 518.98 (M–H)$^-$.

Compound 28: $^1$H NMR (300 MHz, D$_2$O) δ 9.36 (d, 1H, J=0.9 Hz), 7.86 (s, 1H), 7.20 (d, 1H, J=1.7 Hz), 6.44 (d, 1H, J=4.1 Hz), 4.39-4.33 (m, 3H), 4.23-4.15 (m, 4H), 4.06 (d, 2H, J=3.7 Hz), 3.18 (m, 1H), 3.12 (q, 24H, J=7.3 Hz), 2.82 (dd, 1H, J=4.9 and 13.1 Hz), 2.60 (d, 1H, J=13.0 Hz), 2.23 (t, 2H, J=7.0 Hz), 1.60 (m, 4H), 1.32 (m, 2H), 1.20 (t, 36H, J=7.3 Hz).

$^{31}$P NMR (107 MHz, D$_2$O) δ –8.96 (d, 1P, J=16.5 Hz), –10.67 (d, 1H, J=20.1 Hz), –22.36 (t, 1P, J=20.1 Hz).

Electrospray ionization-mass spectroscopy (ESI-MS) $C_{23}H_{33}O_{16}N_4P_3S$: calcd, 745.07 (M–H)$^-$; found, 745.07 (M–H)$^-$.

UV-visible spectrum (in 10 mM sodium phosphate buffer, pH 7.0),
λmax=258 nm (ε=1.1×10$^4$), 308 nm (ε=9.5×10$^3$).

Example V

Site-specific Biotinylation of RNA through T7 Transcription Mediated by Ds-Pa Artificial Base Pairing To study in more detail the selectivity and potential of Ds-Pa artificial base pairing in both transcription and PCR amplification, site-specific biotinylation was performed on 152-mer RNA molecules.

Site-specific Biotinylation of RNA (152-mer)

Transcription (20 μl) was performed for 6 hours at 37° C. using 3 μCi [γ-$^{32}$P]GTP, 2 mM each natural NTP, 0-4 mM Bio-PaTP (biotinylated Pa substrate: chemically synthesized as shown in Example IV), and 30 nM template (DNA6 and DNAcont2 (see FIG. 6), obtained by both ligation and PCR amplification).

For control reactions using DNAcont5 and DNAcont6 obtained by ligation (see FIG. 6), transcription was performed only with 2 mM ATP, GTP and CTP in the presence or absence of 2 mM Bio-UTP (biotin-16-uridine-5'-triphosphate, Roche Applied Science). The products were analyzed and purified on a 7-10% polyacrylamide-7 M urea gel.

The biotinylated RNA transcripts were detected by gel shift assay using streptavidin. A mixture (10 μl) of 2 pmol $^{32}$P-labeled transcript and 100 pmol streptavidin (Promega) was incubated at 20° C. for 1 hour in 10 mM Tris-HCl buffer (pH 7.6) containing 50 mM NaCl and 10 mM EDTA. The biotinylated RNA-streptavidin complexes were analyzed by electrophoresis on a 7% polyacrylamide-7 M urea gel. To determine the position where Bio-Pa was introduced, each RNA (152-mer) was labeled with [γ-$^{32}$P]ATP (Perkin Elmer) after 5'-dephosphorylation with calf intestinal alkaline phosphatase (Takara). The labeled RNA was partially digested with RNase T1 at 55° C. for 12 minutes in 13.3 mM sodium citrate buffer (pH 5.0) containing 4.7 M urea, 0.7 mM EDTA and 0.17 mg/ml E. coli tRNA, or with alkali at 90° C. for 15 minutes in 32 mM sodium carbonate buffer (pH 9.1) containing 0.6 mM EDTA. The alkali-digested RNA solution (9 μl) was mixed with 11 μl of 20 mM Tris-HCl buffer (pH 7.6) containing 150 mM NaCl, and the mixture (10 μl) was then incubated with streptavidin magnetic beads (0.4 mg) (New England BioLabs) for 5 minutes at room temperature to capture the biotinylated RNA. An aliquot (5 μl) of the supernatant was analyzed together with other digested samples on a 10% polyacrylamide-7 M urea gel.

Results

Biotin-linked Pa (Bio-Pa) was introduced into RNA through T7 transcription mediated by Ds-Pa base pairing when using a template obtained by either ligation or PCR amplification. To analyze incorporation of Bio-Pa into RNA molecules (152-mer), DNA6 and DNAcont2 templates (see FIG. 6) were used to perform T7 transcription in the presence of natural substrate NTPs (2 mM) and Bio-PaTP (2 or 4 mM). The transcription efficiency through Ds-Pa base pairing was 47% to 85% (FIG. 44c, Lanes 2, 6 and 10), relative to the case of using DNAcont2, a DNA fragment containing natural bases alone (FIG. 44c, Lanes 3, 7 and 11). In transcription using DNA6 template obtained by either ligation or PCR amplification, the amount of the full-length product was significantly reduced in the absence of Bio-PaTP (FIG. 44c, Lanes 1, 5 and 9). These results indicate that very little replacement of the Ds-Pa base pair with a natural base pair occurred during PCR amplification of DNA6.

The selectivity of Bio-Pa incorporation into RNA was evaluated by gel shift assay on the biotinylated transcripts using streptavidin. Since binding between streptavidin and biotin is very strong and specific, the percentages of the gel-shifted transcripts would be almost identical with the rate of biotin incorporation through transcription (i.e., yields of the biotinylated transcripts). In transcription using 2 mM Bio-PaTP (equivalent to natural substrates) and DNA6 template obtained by ligation, 90% of the transcripts were biotinylated (FIG. 44d, Lane 2), and the incorporation rate was improved to 96% when the Bio-PaTP concentration was increased (4 mM) (FIG. 44d, Lane 4). With respect to Bio-PaTP misincorporation opposite natural bases, the yields of the biotinylated transcripts were 9% and 16%, as evaluated in transcription experiments using DNAcont2 as a template in the presence of 2 and 4 mM Bio-PaTP, respectively (FIG. 44d, Lanes 6 and 7). These misincorporations were estimated to be only 0.06% (9% for total) and 0.12% (16% for total) per base position in the 152-mer transcripts. In transcription using the template obtained by PCR amplification (20 cycles), the incorporation rate of Bio-Pa was reduced by about 3-4% (FIG. 44d, Lanes 9 and 11). This value was in agreement with the mutation rate at the Ds-Pa base pair site (3-4%) estimated by sequence analysis (FIG. 3i). Interestingly, Bio-Pa misincorporation opposite natural bases was not increased when transcription was performed in the presence of natural and artificial base substrates using DNAcont2 template obtained by PCR amplification (20 cycles) (FIG. 44d, Lanes 13 and 14). Thus, misincorporation of Ds and Pa opposite natural bases would be very low during PCR amplification.

Moreover, the selectivity of Ds-Pa base pairing during T7 transcription was compared to that of natural A-T(U) base pairing. To evaluate misincorporation of Bio-UTP opposite bases G, C and T in the template strand, control DNA containing only one A (DNAcont5) or no A (DNAcont6) in the coding region of the template strand was synthesized (see FIG. 6). Transcription using DNAcont5 or DNAcont6 as a template was performed under the same conditions as used in the Ds-Pa base pair system, except for using 0 or 2 mM Bio-UTP and other natural substrates (2 mM ATP, GTP and CTP). In transcription of DNAcont5, the transcripts were completely biotinylated by incorporation of Bio-U opposite A (FIG. 44d, Lane 16). However, in transcription of DNAcont6, 21% of the transcripts were biotinylated by misincorporation of Bio-U opposite bases G, C and T in the template strand (FIG. 44d, Lane 18). Thus, the misincorporation rate of Bio-PaTP opposite natural bases (9% and 16% in FIG. 44d, Lanes 6 and 7, respectively) was found to be lower than that of biotin-linked UTP (Bio-UTP) opposite natural bases (21%). It should be noted that this Bio-U misincorporation rate (21%) was higher than the misincorporation rate of Bio-Pa opposite natural bases (16%) even under conditions where Bio-PaTP was present in an amount of 2 molar equivalents relative to natural substrates. Thus, during T7 transcription, selective elimination of Bio-Pa misincorporation at the natural base sites in the template strand is higher than that of Bio-U misincorporation opposite bases G, T and C in the template strand, although Bio-Pa incorporation opposite Ds is slightly less efficient than Bio-U incorporation opposite A.

To determine the incorporation site of Bio-Pa in the transcripts, the biotinylated transcripts were analyzed for their sequences. If Bio-Pa is precisely introduced into the transcripts opposite Ds in the template, the transcripts will be biotinylated at position 59. The 5'-terminally $^{32}$P-labeled transcripts were partially digested with alkali or RNase T1, and the resulting products were analyzed by electrophoresis. In sequence ladders of the transcripts containing Bio-Pa, bands corresponding to fragments larger than 59-mer were shifted (FIG. 44e, Lanes 2 and 8). The alkali-digested fragments were further treated with streptavidin to capture the biotinylated fragments, and the rest was electrophoresed, indicating that the fragments larger than 59-mer almost disappeared (FIG. 44e, Lanes 2 and 9). These results prove site-specific incorporation of Bio-Pa at position 59 in the transcripts. Further, transcripts from the templates obtained by PCR amplification (20 cycles) (FIG. 44e, Lanes 7-12) produced the same patterns as those from the templates obtained by ligation (FIG. 44e, Lanes 1-6).

Thus, site-specific biotinylation of RNA based on this approach is useful for immobilizing RNA molecules without loss of RNA activity. Since the artificial base Pa even modified with a bulky residue such as biotin was efficiently incorporated into RNA, a series of functional 4-modified Pa bases (e.g., fluorophore-linked Pa) can also be incorporated into RNA.

Example VI

Synthesis of 4-Position Modified Nucleoside Derivatives of 2-nitropyrrole

4-Position modified nucleoside derivatives of 2-nitropyrrole were synthesized according to the scheme shown in FIG. 45.

(1) Synthesis of 1-(2-deoxy-β-D-ribofuranosyl)-4-iodo-2-nitropyrrole (Compound 1 in FIG. 45)

1-(2-Deoxy-β-D-ribofuranosyl)-2-nitropyrrole (700 mg, 3.1 mmol) was dissolved in CH$_3$CN (12 ml), followed by addition of N-iodosuccinimide (1.38 g, 6.1 mmol). After stirring at room temperature for 12 hours, the reaction mixture was partitioned between ethyl acetate and water, and the organic layer was washed twice with water. After drying over anhydrous sodium sulfate, the organic layer was concentrated and purified on a silica gel column (CH$_2$Cl$_2$:MeOH=50:1, v/v) and by HPLC (25%-40% CH$_3$CN, 10 minutes, 40%-50% CH$_3$CN, 5 minutes) to give Compound 1 (607 mg, 56%). Recovered unreacted starting materials: 219 mg (31%).

Compound 1

$^1$H NMR (500 MHz, DMSO-d6): δ 7.90 (d, 1H, J=2.1 Hz), 7.40 (d, 1H, J=2.1 Hz), 6.54 (t, 1H, J=5.6 Hz), 5.27 (d, 1H, J=4.5 Hz), 5.10 (t, 1H, J=5.2 Hz), 4.23 (m, 1H), 3.83 (m, 1H), 3.65 (m, 1H), 3.56 (m, 1H), 2.40 (m, 1H), 2.23 (m, 1H).

HRMS (FAB, 3-NBA matrix) C$_9$H$_{12}$IN$_2$O$_5$ (M+1): calcd, 354.9791; found, 354.9784.

(2) Synthesis of 1-(2-deoxy-β-D-ribofuranosyl)-4-propynyl-2-nitropyrrole (Compound 2)

1-(2-Deoxy-β-D-ribofuranosyl)-4-iodo-2-nitropyrrole (Compound 1) (280 mg, 0.79 mmol) and Pd(PPh$_3$)$_2$Cl$_2$ (56 mg, 0.08 mmol) were dissolved in DMF (7.9 ml), followed by addition of tributyl(1-propynyl)tin (481 μl, 1.6 mmol). The reaction mixture was heated at 100° C. for 1.5 hours, concentrated and then purified on a silica gel column (CH$_2$Cl$_2$: MeOH, 50:1, v/v) and by HPLC (34%-35% CH$_3$CN, 13 minutes) to give Compound 2 (125 mg, 60%).

Compound 2:

$^1$H NMR (300 MHz, DMSO-d6): δ 7.92 (d, 1H, J=2.2 Hz), 7.27 (d, 1H, J=2.2 Hz), 6.55 (t, 1H, J=5.7 Hz), 5.28 (d, 1H, J=4.5 Hz), 5.11 (t, 1H, J=5.2 Hz), 4.24 (m, 1H), 3.85 (m, 1H), 3.67 (ddd, 1H, J=3.6, 5.3, 12.1 Hz), 3.57 (m, 1H), 2.43 (m, 1H), 2.23 (m, 1H), 1.99 (s, 3H).

$^{13}$C NMR (75 MHz, DMSO-d6): δ 136.21, 129.17, 117.08, 105.29, 88.74, 88.30, 86.75, 72.91, 69.21, 60.83, 42.58, 4.29.

HRMS (FAB, 3-NBA matrix) C$_{12}$H$_{15}$N$_2$O$_5$ (M+1): calcd, 267.0981; found, 267.0991.

(3) Synthesis of 1-(2-deoxy-β-D-ribofuranosyl)-4-(dichloroacetamido-1-propynyl)-2-nitropyrrole (Compound 3)

1-(2-Deoxy-β-D-ribofuranosyl)-4-iodo-2-nitropyrrole (Compound 1) (354 mg, 1.0 mmol), Pd(PPh$_3$)$_4$ (58 mg, 0.05 mmol), CuI (30 mg, 0.16 mmol) and triethylamine (209 μl, 1.5 mmol) were dissolved in DMF (3.5 ml), followed by addition of a 1 M DMF solution of N-(2-propynyl)-dichloroacetamide (1.5 ml, 1.5 mmol). After stirring at room temperature for 12 hours, the reaction mixture was partitioned between ethyl acetate and water, and the organic layer was washed three times with water. After drying over anhydrous sodium sulfate, the organic layer was concentrated and purified on a silica gel column (CH$_2$Cl$_2$:MeOH, 20:1, v/v) and by HPLC (34%-35% CH$_3$CN, 12 minutes) to give Compound 3 (317 mg, 81%).

Compound 2 (200 mg, 0.75 mmol) was azeotroped with pyridine, followed by addition of pyridine (7.5 ml) and 4,4'-dimethoxytrityl chloride (280 mg, 0.83 mmol). After stirring at room temperature for 1 hour, the reaction mixture was partitioned between ethyl acetate and 5% NaHCO$_3$, and the organic layer was washed with saturated aqueous sodium chloride. After drying over anhydrous sodium sulfate, the organic layer was concentrated and purified on a silica gel column (CH$_2$Cl$_2$:MeOH, 200:1, v/v) to give Compound 4 (365 mg, 86%). Compound 4 (190 mg, 0.33 mmol) was azeotroped with pyridine, followed by addition of THF (1.7 ml) and diisopropylethylamine (87 μl, 1.5 equivalents). To this solution, 2-cyanoethyl-N,N-diisopropylamino chloro phosphoramidite (82 l, 0.37 mmol) was added and stirred at room temperature for 1 hour. After addition of methanol (50 μl), the reaction mixture was diluted with ethyl acetate:triethylamine (20:1, v/v) and partitioned with 5% NaHCO$_3$. The organic layer was washed with saturated aqueous sodium chloride, dried over anhydrous sodium sulfate, concentrated and then purified on a silica gel column (CH$_2$Cl$_2$:hexane, 1:4, v/v, 2% triethylamine) to give Compound 6 (223 mg, 87%).

Compound 4 (160 mg, 0.28 mmol) was azeotroped with pyridine, followed by addition of pyridine (2.8 ml) and acetic anhydride (53 μl, 0.56 mmol). After stirring at room temperature for 12 hours, the reaction mixture was partitioned between ethyl acetate and 5% NaHCO$_3$, and then washed with 5% NaHCO$_3$. The organic layer was dried over anhydrous sodium sulfate, concentrated, azeotroped with toluene, and then dissolved in methylene chloride (28 ml). To this reaction mixture, dichloroacetic acid (280 lµ) was added at 0° C. and stirred for 15 minutes at 0° C. The reaction mixture was partitioned with 5% NaHCO$_3$, and the organic layer was washed with 5% NaHCO$_3$. After drying over anhydrous sodium sulfate, the organic layer was concentrated and purified on a silica gel column to give Compound 7 (78 mg, 90%, 2 steps). Compound 7 (31 mg, 0.1 mmol) was azeotroped with pyridine, followed by addition of pyridine (100 µl) and dioxane (300 µl). To this solution, 2-chloro-4H-1,3,2-benzodioxaphosphorin-4-one (110 µl, 1 M in dioxane) was added and stirred for 10 minutes at room temperature. Tri-n-butylamine (100 µl) and bis(tributylammonium) pyrophosphate (300 µl, 0.5 M in DMF) were added to the reaction mixture, followed by stirring for 10 minutes. After a 1% iodine solution in pyridine/water (98/2, v/v, 2.0 ml) was added and stirred for 15 minutes, 5% NaHSO$_3$ (150 µl) was added and the reaction mixture was then concentrated. After H$_2$O (5.0 ml) was added and stirred at room temperature for 30 minutes, 28% aqueous ammonia (20 ml) was added and stirred at room temperature for 2 hours. The reaction mixture was concentrated, lyophilized and then purified on DEAE Sephadex A-25 (with a linear gradient of 50 mM to 1.0 M TEAB) to give Compound 9.

Compound 7:
$^1$H NMR (300 MHz, DMSO-d6): δ 7.90 (d, 1H, J=2.1 Hz), 7.30 (d, 1H, J=2.1 Hz), 6.60 (t, 1H, J=6.4 Hz), 5.22 (m, 2H), 4.13 (m, 1H), 3.65 (m, 2H), 2.62 (ddd, 1H, J=3.0, 6.0, 14.3 Hz), 2.43 (m, 1H), 2.08 (s, 3H), 2.00 (s, 3H).
HRMS (FAB, 3-NBA matrix) C$_{14}$H$_{17}$N$_2$O$_6$ (M+1): calcd, 309.1087; found, 309.1066.

Compound 9:
Electrospray ionization mass spectroscopy (ESI-MS) C$_{12}$H$_{17}$O$_{14}$N$_2$P$_3$; calcd, 504.98 (M–H)$^-$; found, 505.95 (M–H)$^-$.

(6) Synthesis of 1-(2-deoxy-3-O-acetyl-β-D-ribofuranosyl)-4-(dichloroacetamido-1-propynyl)-2-nitropyrrole (Compound 8)

Compound 3 (305 mg, 0.78 mmol) was azeotroped with pyridine, followed by addition of pyridine (7.8 ml) and 4,4'-dimethoxytrityl chloride (291 mg, 0.86 mmol). After stirring at room temperature for 1 hour, the reaction mixture was partitioned between ethyl acetate and 5% NaHCO$_3$, and the organic layer was washed with saturated aqueous sodium chloride. After drying over anhydrous sodium sulfate, the organic layer was concentrated and purified on a silica gel column (CH$_2$Cl$_2$:EtOAc, 9:1, v/v) to give Compound 5 (526 mg, 97%). Compound 5 (515 mg, 0.74 mmol) was azeotroped with pyridine, followed by addition of pyridine (7.4 ml) and acetic anhydride (280 µl, 3.0 mmol). After stirring at room temperature for 12 hours, the reaction mixture was partitioned between ethyl acetate and 5% NaHCO$_3$, and then washed with 5% NaHCO$_3$. The organic layer was dried over anhydrous sodium sulfate, concentrated, azeotroped with toluene, and then dissolved in methylene chloride (74 ml). To this reaction mixture, dichloroacetic acid (740 µl) was added at 0° C. and stirred for 15 minutes at 0° C. The reaction mixture was partitioned with 5% NaHCO$_3$, and the organic layer was washed with 5% NaHCO$_3$. After drying over anhydrous sodium sulfate, the organic layer was concentrated and purified on a silica gel column (CH$_2$Cl$_2$:MeOH, 50:1, v/v) to give Compound 8 (289 mg, 90%, 2 steps).

Compound 5: $^1$H NMR (300 MHz, DMSO-d6): δ 9.07 (t, 1H, J=5.3 Hz), 7.67 (d, 1H, J=2.2 Hz), 7.41-7.21 (m, 10H), 6.89 (dd, 4H, J=1.7, 8.9 Hz), 6.59 (t, 1H, J=5.4 Hz), 6.48 (s, 1H), 5.38 (d, 1H, J=4.9 Hz), 4.29 (m, 1H), 4.12 (d, 2H, J=4.4 Hz), 3.99 (m, 1H), 3.74 (s, 6H), 3.17 (m, 2H), 2.46-2.33 (m, 2H).
HRMS (FAB, 3-NBA matrix) C$_{35}$H$_{34}$N$_3$O$_8$Cl$_2$ (M+1): calcd, 694.1723; found, 694.1729.

Compound 8: $^1$H NMR (300 MHz, DMSO-d6): δ 9.12 (t, 1H, J=5.3 Hz), 7.96 (d, 1H, J=2.2 Hz), 7.36 (d, 1H, J=2.2 Hz), 6.61 (t, 1H, J=6.3 Hz), 6.49 (s, 1H), 5.23 (m, 2H), 4.18 (d, 2H, J=5.4 Hz), 4.13 (m, 1H), 3.68 (m, 2H), 2.63 (ddd, 1H, J=3.0, 6.0, 14.3 Hz), 2.44 (m, 1H), 2.07 (s, 3H).
HRMS (FAB, 3-NBA matrix) C$_{16}$H$_{18}$N$_3$O$_7$Cl$_2$ (M+1): calcd, 434.0522; found, 434.0549.

Example VII

Synthesis of NH$_2$-hx-dPnTP, ROX-hx-dPnTP and FAM-hx-dPnTP

In this example, NH$_2$-hx-dPnTP, ROX-hx-dPnTP and FAM-hx-dPnTP were synthesized as dPnTP derivatives according to the synthesis scheme shown in FIG. 46. These derivatives can be introduced into DNA, for example, through replication (PCR or primer extension). The derivative having an amino group can be used for DNA modification after incorporation, while the other derivatives having fluorescent groups can each be adapted for fluorescent labeling of DNA, FRET, etc.

(1) 1-(2-Deoxy-β-D-ribofuranosyl)-4-[3-(6-trifluoroacetamidohexanamido)-1-propynyl]-2-nitropyrrole (Step (a) in FIG. 46)

1-(2-Deoxy-β-D-ribofuranosyl)-4-iodo-2-nitropyrrole (354 mg, 1 mmol, containing α-anomer) was azeotroped twice with anhydrous acetonitrile in a 50 mL flask, followed by addition of copper iodide (31 mg, 160 µmol) and tetrakistriphenylphosphine palladium (0) (58 mg, 50 µmol). After these materials were dissolved in anhydrous DMF (5 mL), triethylamine (210 µL, 1.5 mmol) was added while stirring at room temperature and further stirred at room temperature under light-shielding conditions. To this mixture, a solution of N-(2-propynyl)-6-trifluoroacetamidohexanamide (396 mg, 1.5 mmol) in DMF (4 mL) was added dropwise and stirred overnight at room temperature. The reaction mixture was concentrated under reduced pressure, and the resulting crude product was purified by silica gel column chromatography (5-10% CH$_3$OH in CH$_2$Cl$_2$) and C18-HPLC (39-41% CH$_3$CN in H$_2$O, 15 minutes) to give the desired product as an amorphous substance (408 mg, yield 83%).

$^1$H NMR (270 MHz, DMSO-d6) δ 9.38 (brs, 1H), 8.28 (t, 1H, J=5.3 Hz), 7.95 (d, 1H, J=2.0 Hz), 7.30 (d, 1H, J=2.0 Hz), 6.54 (t, 1H, J=5.6 Hz), 5.29 (d, 1H, J=4.0 Hz), 5.20-5.05 (m, 1H), 4.30-4.20 (m, 1H), 4.05 (d, 2H, J=5.3 Hz), 3.83 (q, 1H, J=4.0 Hz), 3.70-3.50 (m, 2H), 3.14 (t, 2H, J=7.3 Hz), 2.50-2.36 (m, 1H), 2.30-2.17 (m, 1H), 2.08 (t, 2H, J=7.3 Hz), 1.58-1.40 (m, 4H), 1.28-1.16 (m, 2H).
HRMS (FAB, 3-NBA matrix) C$_{20}$H$_{26}$F$_3$N$_4$O$_7$ (M+1): calcd, 491.1754; found, 491.1761.

(2) 1-(2-Deoxy-3-O-acetyl-β-D-ribofuranosyl)-4-[3-(6-trifluoroacetamidohexanamido)-1-propynyl]-2-nitropyrrole (Steps (b) and (c))

1-(2-Deoxy-β-D-ribofuranosyl)-4-[3-(6-trifluoroacetamidohexanamido)-1-propynyl]-2-nitropyrrole (394 mg, 803

μmol) was azeotroped three times with anhydrous pyridine in a 50 mL flask and dissolved in anhydrous pyridine (4 mL). To this solution, dimethoxytrityl chloride (286 mg, 844 μmol) was added and stirred at room temperature for 1.5 hours. The reaction mixture was added to ethyl acetate/water, and the aqueous layer was removed. The organic layer was washed with saturated aqueous sodium bicarbonate, dried over magnesium sulfate and then evaporated to remove the solvent. The resulting crude product was purified by silica gel column chromatography (0-0.5% $CH_3OH$ in $CH_2Cl_2$) to give a tritylated product as an amorphous substance (543 mg). 1-(2-Deoxy-5-O-dimethoxytrityl-β-D-ribofuranosyl)-4-[3-(6-trifluoroacetamidohexanamido)-1-propynyl]-2-nitropyrrole (542 mg, 684 μmol) was azeotroped three times with anhydrous pyridine in a 30 mL flask and dissolved in anhydrous pyridine (7 mL). To this solution, acetic anhydride (169 μL, 1.79 mmol) was added and stirred overnight at room temperature. The reaction mixture was diluted with ethyl acetate, and the organic layer was washed with saturated aqueous sodium bicarbonate and saturated aqueous sodium chloride, dried over magnesium sulfate, and then evaporated to remove the solvent. The resulting crude product was dissolved in anhydrous dichloromethane (68 mL). To this solution, dichloroacetic acid (680 μL) was added while stirring at 0° C. and further stirred for 15 minutes. The reaction mixture was added to saturated aqueous sodium bicarbonate, and the aqueous layer was extracted with dichloromethane. The combined organic layers were dried over magnesium sulfate and then evaporated to remove the solvent. The resulting oil was purified by silica gel column chromatography (2% $CH_3OH$ in $CH_2Cl_2$) to give the desired product as an amorphous substance (328 mg, 77%, yield for 2 steps).

1-(2-Deoxy-3-O-acetyl-β-D-ribofuranosyl)-4-[3-(6-trifluoroacetamidohexanamido)-1-propynyl]-2-nitropyrrole (53 mg, 100 μmol) was azeotroped three times with anhydrous pyridine in a 10 mL flask, and the reaction vessel was then filled with argon gas. To this, anhydrous pyridine (100 μL) and anhydrous dioxane (300 μL) were added for dissolution purposes, followed by addition of a 1 M dioxane solution of 2-chloro-4H-1,2,3-dioxaphosphorin-4-one (110 μL, 110 μmol). After stirring at room temperature for 10 minutes, tri-n-butylamine (100 μL) and a 0.5 M DMF solution of bis(tri-n-butylammonium) pyrophosphate (300 μL) were added and stirred for 10 minutes. A 1% iodine/water/pyridine solution (2 mL) was added and stirred at room temperature for 15 minutes. After addition of 5% aqueous sodium bisulfite (150 μL), the reaction mixture was concentrated under reduced pressure. The resulting oil was mixed with water (5 mL) and stirred at room temperature for 30 minutes, followed by addition of concentrated aqueous ammonia (20 mL). After stirring for 8 hours, this mixture was purified by DEAE Sephadex A-25 column chromatography (1.5×30 cm, linear concentration gradient; 50 mM to 1 M TEAB solution) and C18-HPLC acetonitrile in 0.1 M triethylammonium acetate buffer, pH 7.0) to give the desired product.

$^1$H NMR (300 MHz, $D_2O$) δ 7.79 (s, 1H), 7.31 (s, 1H), 6.68 (t, 1H, J=5.6 Hz), 4.60-4.50 (m, 1H), 4.30-4.00 (m, 5H), 3.13 (q, 18H, J=7.3 Hz), 2.90 (t, 2H, J=7.5 Hz), 2.62-2.52 (m, 1H), 2.46-2.30 (m, 1H), 2.24 (t, 2H, J=7.0 Hz), 1.63-1.55 (m, 4H), 1.38-1.16 (m, 29H).

$^{31}$P NMR (121 MHz, $D_2O$) δ −8.26, −10.51, −22.05.

MS (ESI) $C_{18}H_{28}N_4O_{15}P_3$, [M−H]$^-$: calcd, 633.08; found, 633.00.

(4) 1-(2-Deoxy-β-D-ribofuranosyl)-4-[3-[6-(fluorescein-5-carboxamido)hexanamido]-1-propynyl]-2-nitropyrrole 5'-triphosphate (FAM-hx-dPnTP) (Step (e))

$NH_2$-hx-dPnTP (6 μmol) was dissolved in 0.1 M aqueous sodium bicarbonate (pH 8.5, 0.72 mL), followed by addition of a solution of 5-carboxyfluorescein N-hydroxysuccinimidyl ester (FAM-SE) (3.7 mg, 7.8 μmol) in DMF (500 μL). The mixture was reacted at room temperature for 8 hours with occasional shaking under light-shielding conditions. To this mixture, concentrated aqueous ammonia (0.5 mL) was added and reacted for 5 minutes with occasional shaking. This mixture was lyophilized and then purified by DEAE Sephadex A-25 column chromatography (1.5×30 cm, linear concentration gradient; 50 mM to 1 M TEAB solution) and C18-HPLC (concentration gradient; 0%-50% acetonitrile in 0.1 M triethylammonium acetate buffer, pH 7.0) to give the desired product.

$^1$H NMR (300 MHz, $D_2O$) δ 8.29 (s, 1H), 8.04 (d, 1H, J=7.5 Hz), 7.58 (brs, 1H), 7.26 (d, 1H, 7.5 Hz), 7.00-6.60 (m, 7H), 6.39 (brs, 1H), 4.50-4.35 (m, 1H), 4.40-3.90 (m, 5H), 3.50-3.30 (m, 2H), 3.12 (q, 18H, J=7.3 Hz), 2.41-2.10 (m, 4H), 1.75-1.50 (m, 4H), 1.45-1.10 (m, 29H).

$^{31}$P NMR (121 MHz, $D_2O$) δ −10.86, −10.86, −23.13.

MS (ESI) $C_{39}H_{38}N_4O_{21}P_3$ [M−H]$^-$: calcd, 991.12; found, 990.56

(5) 1-(2-Deoxy-β-D-ribofuranosyl)-4-[3-[6-(rhodamine-X-5-carboxamido)hexanamido]-1-propynyl]-2-nitropyrrole 5'-triphosphate (ROX-hx-dPnTP) (Step (e))

$NH_2$-hx-dPnTP (6 μmol) was dissolved in 0.1 M aqueous sodium bicarbonate (pH 8.5, 0.85 mL), followed by addition of a solution of 5-carboxy-X-rhodamine N-hydroxysuccinimidyl ester (ROX-SE) (5 mg, 7.92 μmol) in DMF (1 mL). This mixture was reacted at room temperature for 18 hours with occasional shaking under light-shielding conditions. To this mixture, concentrated aqueous ammonia (0.5 mL) was added and reacted for 5 minutes with occasional shaking. This mixture was lyophilized and then purified by DEAE Sephadex A-25 column chromatography (1.5×30 cm, linear concentration gradient; 50 mM to 1 M TEAB solution) and C18-HPLC (concentration gradient; 12.5%-50% acetonitrile in 0.1 M triethylammonium acetate buffer, pH 7.0) to give the desired product.

$^1$H NMR (300 MHz, $D_2O$) δ 8.28 (s, 1H), 8.03 (d, 1H, J=8.9 Hz), 7.47 (s, 1H), 7.19 (d, 1H, J=7.7 Hz), 6.68 (brs, 1H), 6.55 (brs, 1H), 6.43 (brs, 1H), 6.09 (brs, 1H), 4.40-4.25 (m, 1H), 4.15-3.70 (m, 5H), 3.60-3.27 (m, 10H), 3.12 (q, 18H, J=7.3 Hz), 2.95-2.70 (m, 4H), 2.65-2.40 (m, 4H), 2.40-2.15 (m, 3H), 2.05-1.70 (m, 9H), 1.60-1.50 (m, 4H), 1.50-1.15 (m, 29H).

$^{31}$P NMR (121 MHz, $D_2O$) δ −10.90, −11.59, −23.27.

MS(ESI) $C_{51}H_{56}N_6O_{19}P_3$ [M−H]$^-$: calcd, 1149.28; found, 1148.77

Example VIII

Synthesis of $NH_2$-hx-PaTP, FAM-hx-PaTP and TAMRA-hx-PaTP

In this example, $NH_2$-hx-PaTP, FAM-hx-PaTP and TAMRA-hx-PaTP were synthesized as rPaTP derivatives according to the synthesis scheme shown in FIG. 47. These derivatives can be introduced into RNA, for example, through transcription. The derivative having an amino group can be used for RNA modification after incorporation, while the other derivatives having fluorescent groups can each be adapted for fluorescent labeling of RNA, FRET, etc.

(1) 1-(β-D-Ribofuranosyl)-4-[(3-(6-trifluoroacetamidohexanamido)-1-propynyl)pyrrole-2-carbaldehyde (Step (a) in FIG. 47)

1-(β-D-Ribofuranosyl)-4-iodopyrrole-2-carbaldehyde (177 mg, 500 µmol, containing α-anomer) was azeotroped twice with anhydrous acetonitrile in a 10 mL flask, followed by addition of copper iodide (15 mg, 80 µmol) and tetrakistriphenylphosphine palladium (0) (29 mg, 25 µmol). After these materials were dissolved in anhydrous DMF (2.5 mL), triethylamine (105 µL, 750 µmol) was added while stirring at room temperature and further stirred at room temperature under light-shielding conditions. To this mixture, a solution of N-(2-propynyl)-6-trifluoroacetamidohexanamide (198 mg, 750 µmol) in DMF (2 mL) was added dropwise and stirred overnight at room temperature. The reaction mixture was concentrated under reduced pressure, and the resulting crude product was purified by silica gel column chromatography (10% $CH_3OH$ in $CH_2Cl_2$) and C18-HPLC (22-24% $CH_3CN$ in $H_2O$, 15 minutes) to give the desired product as an amorphous substance (126 mg, yield 51%).

$^1$H NMR (270 MHz, DMSO-d6) δ 9.52 (d, 1H, J=0.66 Hz), 9.38 (brs, 1H), 8.27 (t, 1H, J=5.3 Hz), 7.96 (s, 1H), 7.13 (d, 1H, J=1.6 Hz), 6.32 (d, 1H, J=3.6 Hz), 5.42-5.32 (brs, 1H), 5.18-5.05 (m, 2H), 4.08-3.95 (m, 4H), 3.90-3.84 (m, 1H), 3.70-3.50 (m, 2H), 3.20-3.10 (m, 2H), 2.08 (t, 2H, J=7.3 Hz), 1.55-1.40 (m, 4H), 1.30-1.15 (m, 2H).

HRMS (FAB, 3-NBA matrix) $C_{21}H_{27}F_3N_3O_7$ (M+1): calcd, 490.1801; found, 490.1815.

(2) 1-(2,3-Di-O-acetyl-β-D-ribofuranosyl)-4-[(3-(6-trifluoroacetamidohexanamido)-1-propynyl)pyrrole-2-carbaldehyde (Steps (b) and (c))

1-(β-D-Ribofuranosyl)-4-[(3-(6-trifluoroacetamidohexanamido)-1-propynyl)pyrrole-2-carbaldehyde (122 mg, 250 µmol) was azeotroped three times with anhydrous pyridine in a 10 mL flask and dissolved in anhydrous pyridine (4 mL). To this solution, dimethoxytrityl chloride (89 mg, 263 µmol) was added and stirred at room temperature for 2.5 hours. The reaction mixture was added to ethyl acetate/water, and the aqueous layer was removed. The organic layer was washed with saturated aqueous sodium bicarbonate, dried over magnesium sulfate and then evaporated to remove the solvent. The resulting crude product was purified by silica gel column chromatography (0-0.5% $CH_3OH$ in $CH_2Cl_2$) to give a tritylated product as an amorphous substance (150 mg). 1-(5-O-Dimethoxytrityl-β-D-ribofuranosyl)-4-[(3-(6-trifluoroacetamidohexanamido)-1-propynyl)pyrrole-2-carbaldehyde (149 mg, 188 µmol) was azeotroped three times with anhydrous pyridine in a 10 mL flask and dissolved in anhydrous pyridine (2 mL). To this solution, acetic anhydride (53 µL, 565 µmol) was added and stirred overnight at room temperature. The reaction mixture was diluted with ethyl acetate, and the organic layer was washed with saturated aqueous sodium bicarbonate and saturated aqueous sodium chloride, dried over magnesium sulfate, and then evaporated to remove the solvent. The resulting crude product was dissolved in anhydrous dichloromethane (19 mL). To this solution, dichloroacetic acid (280 µL) was added while stirring at 0° C. and further stirred for 15 minutes. The reaction mixture was added to saturated aqueous sodium bicarbonate, and the aqueous layer was extracted with dichloromethane. The combined organic layers were dried over magnesium sulfate and then evaporated to remove the solvent. The resulting oil was purified by silica gel column chromatography (1-2.5% $CH_3OH$ in $CH_2Cl_2$) to give the desired product as an amorphous substance (90 mg, 63%, yield for 2 steps).

$^1$H NMR (270 MHz, DMSO-d6) δ 9.49 (s, 1H), 9.39 (brs, 1H), 8.28 (t, 1H, J=5.3 Hz), 8.03 (s, 1H), 7.21 (d, 1H, J=1.6 Hz), 6.63 (d, 1H, J=5.3 Hz), 5.44 (brs, 1H), 5.40-5.28 (m, 3H), 4.20-4.15 (m, 1H), 4.05 (d, 2H, J=5.3 Hz), 3.80-3.56 (m, 2H), 3.20-3.10 (m, 2H), 2.14-1.98 (m, 8H), 1.55-1.40 (m, 4H), 1.30-1.15 (m, 2H).

HRMS (FAB, 3-NBA matrix) $C_{25}H_{31}F_3N_3O_9$ (M+1): calcd, 574.2012; found, 574.2061.

(3) 1-(β-D-Ribofuranosyl)-4-[3-(6-aminohexanamido)-1-propynyl]pyrrole-2-carbaldehyde 5'-triphosphate ($NH_2$-hx-PaTP) (Step (d))

1-(2,3-Di-O-acetyl-β-D-ribofuranosyl)-4-[(3-(6-trifluoroacetamidohexanamido)-1-propynyl)pyrrole-2-carbaldehyde (57 mg, 100 µmol) was azeotroped three times with anhydrous pyridine in a 10 mL flask, and the reaction vessel was then filled with argon gas. To this, anhydrous pyridine (100 µL) and anhydrous dioxane (300 µL) were added for dissolution purposes, followed by addition of a 1 M dioxane solution of 2-chloro-4H-1,2,3-dioxaphosphorin-4-one (110 µL, 110 µmol). After stirring at room temperature for 10 minutes, tri-n-butylamine (100 µL) and a 0.5 M DMF solution of bis(tri-n-butylammonium)pyrophosphate (300 µL) were added and stirred for 10 minutes. A 1% iodine/water/pyridine solution (2 mL) was added and stirred at room temperature for 15 minutes.

After addition of 5% aqueous sodium bisulfite (150 µL), the reaction mixture was concentrated under reduced pressure. The resulting oil was mixed with water (5 mL) and stirred at room temperature for 30 minutes, followed by addition of concentrated aqueous ammonia (20 mL). After stirring for 8 hours, this mixture was purified by DEAE Sephadex A-25 column chromatography (1.5×30 cm, linear concentration gradient; 50 mM to 1 M TEAB solution) and C18-HPLC (concentration gradient; 0%-50% acetonitrile in 0.1 M triethylammonium acetate buffer, pH 7.0) to give the desired product.

MS (ESI) $C_{19}H_{29}N_3O_{15}P_3$ [M−H]$^-$: calcd, 632.08; found, 632.00

(4) 1-(β-D-Ribofuranosyl)-4-[3-(6-(fluorescein-5-carboxamido)hexanamido)-1-propynyl]pyrrole-2-carbaldehyde 5'-triphosphate (FAM-hx-PaTP) (Step (e))

One-third of $NH_2$-hx-PaTP synthesized above was dissolved in 0.1 M aqueous sodium bicarbonate (pH 8.5, 2.5 mL), followed by addition of a solution of 5-carboxyfluorescein N-hydroxysuccinimidyl ester (9 mg, 19 µmol) in DMF (200 µL). The mixture was reacted at room temperature for 9 hours with occasional shaking under light-shielding conditions. To this mixture, concentrated aqueous ammonia (1 mL) was added and reacted for 1 hour with occasional shaking. This mixture was lyophilized and then purified by DEAE Sephadex A-25 column chromatography (1.5×30 cm, linear concentration gradient; 50 mM to 1 M TEAB solution) and C18-HPLC (concentration gradient; 0%-50% acetonitrile in 0.1 M triethylammonium acetate buffer, pH 7.0) to give the desired product.

$^1$H NMR (300 MHz, $D_2O$) δ 9.07 (s, 1H), 8.20 (s, 1H), 7.93 (d, 1H, J=7.9 Hz), 7.62 (brs, 1H), 7.13 (d, 1H, J=7.9 Hz), 7.00-6.60 (m, 7H), 6.10 (d, 1H, J=3.2 Hz), 4.25-3.80 (m, 7H), 3.40-3.20 (m, 2H), 3.04 (q, 18H, J=7.3 Hz), 2.16 (t, 2H, J=6.4 Hz), 1.65-1.45 (m, 4H), 1.40-1.00 (m, 29H).

$^{31}$P NMR (121 MHz, $D_2O$) δ −10.90, −11.38, −23.25.

MS (ESI) $C_{40}H_{39}N_3O_{21}P_3$ [M−H]$^-$: calcd, 990.13; found, 989.78.

(5) 1-(β-D-Ribofuranosyl)-4-[3-(6-(tetramethyl-rhodamine-5-carboxamido)hexanamido)-1-propynyl]pyrrole-2-carbaldehyde 5'-triphosphate (TAMRA-hx-PaTP) (Step (e))

One-third of $NH_2$-hx-PaTP synthesized above was dissolved in 0.1 M aqueous sodium bicarbonate (pH 8.5, 2.5 mL), followed by addition of a solution of 5-carboxytetramethylrhodamine N-hydroxysuccinimidyl ester (TAMRA-SE) (10 mg, 19 μmol) in DMF (1 mL). This mixture was reacted at room temperature for 9 hours with occasional shaking under light-shielding conditions. To this mixture, concentrated aqueous ammonia (1 mL) was added and reacted for 8 hours with occasional shaking. This mixture was lyophilized and then purified by DEAE Sephadex A-25 column chromatography (1.5×30 cm, linear concentration gradient; 50 mM to 1 M TEAB solution) and C18-HPLC (concentration gradient; 12.5%-50% acetonitrile in 0.1 M triethylammonium acetate buffer, pH 7.0) to give the desired product.

$^1$H NMR (300 MHz, $D_2O$) δ 9.07 (s, 1H), 8.26 (s, 1H), 8.02 (d, 1H, J=7.9 Hz), 7.69 (s, 1H), 7.35 (d, 1H, J=7.9 Hz), 7.10 (d, 1H, J=9.4 Hz), 7.01 (d, 1H, J=9.4 Hz), 6.88-6.70 (m, 3H), 6.39 (d, 2H, J=9.2 Hz), 6.06 (d, 1H, J=3.5 Hz), 4.20 (t, 1H, J=4.9 Hz), 4.10-3.80 (m, 6H), 3.55-3.30 (m, 2H), 3.25-3.00 (m, 30H), 2.25 (t, 2H, J=6.3 Hz), 1.75-1.55 (m, 4H), 1.40-1.10 (m, 29H).

$^{31}$P NMR (121 MHz, $D_2O$) δ −10.84, −11.56, −23.22.

MS (ESI) $C_{44}H_{49}N_5O_{19}P_3$ $[M-H]^-$: calcd, 1044.22; found, 1044.09.

Example IX

Incorporation of Amino Group- or Fluorescent Dye-Linked Substrate Pn into DNA (55-mer) through Replication using Klenow Fragment In this example, substrates of Pn having an amino group or a fluorescent dye (FAM) attached through a linker ($NH_2$-hx-dPnTP and FAM-hx-dPnTP, prepared in Example VII) were used to study the incorporation of these substrates into DNA through replication.

More specifically, experimental procedures as shown below were used. A solution (10 μl) containing a duplex between template DNA containing Ds at different positions (Template, 55-mer; 1Ds, 2Ds, 3Ds, 4Ds, 5Ds (SEQ ID NOs: 33-37) or a control (SEQ ID NO: 38)) and a primer fluorescently labeled with fluorescein (Primer, 20-mer) was mixed with a deoxynucleoside triphosphate solution diluted with sterilized water (5 μl) and Klenow fragment lacking 3'-5' exonuclease activity (2 U, 5 μl) to cause primer extension reaction (20 μl scale). The reaction was performed using 200 nM Template-Primer, 100 μM or 200 μM dNTPs (N=A, G, C, T), 10 μM $NH_2$-hx-dPnTP or FAM-hx-dPnTP, and 0.1 U/μl Klenow fragment (GE Health Care) in 50 mM Tris-HCl (pH 7.5), 10 mM $MgCl_2$, 1 mM DTT, 0.05 mg/ml BSA. After reaction at 37° C. for 5 minutes, 10 M urea (20 μl) was added to this solution to stop the reaction. The solution was heated at 75° C. for 3 minutes, and the reaction products were then analyzed by electrophoresis on a 10% polyacrylamide-7 M urea gel. Bands of the reaction products were detected with a fluorescence image analyzer (Molecular Imager, Bio-Rad, FAM detection mode).

The results obtained are shown in FIGS. 48B and 48C. The amount of the full-length product was higher in the presence of $NH_2$-hx-dPnTP (FIGS. 48B and 48C) or FAM-hx-dPnTP of Pn, indicating that these modified dPnTP substrates were incorporated into DNA opposite Ds in the template DNA.

Example X

Incorporation of Fluorescent Dye-linked Substrate Pa into RNA (17-mer) through Transcription Using T7 RNA Polymerase In this example, substrates of Pa having a fluorescent dye (FAM or TAMRA) attached through a linker (FAM-hx-PaTP and TAMRA-hx-PaTP, prepared in Example VIII) were used to study the incorporation of these substrates into RNA through transcription.

More specifically, experimental procedures as shown below were used. In 10 mM Tris-HCl buffer (pH 7.6) containing 10 mM NaCl, template strand DNA (35-mer, 10 μM) was annealed with its complementary strand DNA of the promoter region (21-mer, 10 μM). Transcription reaction was performed using 2 μCi [γ-$^{32}$P]GTP, 1 mM NTPs, 1 mM FAM- or TAMRA-hx-PaTP, 2 μM template DNA, and 50 units of T7 RNA polymerase (Takara) in 40 mM Tris-HCl buffer (pH 8.0), 24 mM $MgCl_2$, 2 mM spermidine, 5 mM DTT, 0.01% Triton X-100. After reaction at 37° C. for 3 hours, 10 M urea (20 μL) was added to this solution to stop the reaction. The solution was heated at 75° C. for 3 minutes, and the transcripts were then analyzed by electrophoresis on a 20% polyacrylamide-7 M urea gel.

The results obtained are shown in FIG. 49. The band mobility of the transcript (17-mer) on electrophoresis was slow only when template DNA containing Ds was used, indicating that these modified PaTP substrates were introduced into RNA opposite Ds in the template. The transcription efficiency was 14% for FAM-hx-PaTP and 10% for TAMRA-hx-PaTP, when compared to the control experiment with natural substrates alone (FIG. 49, rightmost lane indicated as "None").

INDUSTRIAL APPLICABILITY

The inventors of the present invention have developed an unnatural base pair system ensuring highly practical selectivity during replication and transcription, which enables the creation of new biotechnologies with expanded genetic alphabet. Hydrophobic Ds-Pa base pairing allows PCR amplification of DNA fragments containing the same. Moreover, Ds-Pa base pairing also allows site-specific incorporation of Ds and Pa into RNA through normal T7 transcription. Thus, this system provides a novel technique for creation of new functional artificial DNAs and RNAs. In addition, modified substrates and hydrophobic base pairs are scientifically important in further elucidation of mechanisms for replication and transcription.

To avoid undesired base pairings (e.g., Ds-Ds and natural-unnatural base pairings) during replication, the inventors of the present invention have achieved high selectivity of unnatural base pairing by combination of 5'-γ-amidotriphosphates with usual 5'-triphosphates. 5'-γ-Amidotriphosphates are useful as DNA polymerase substrates for recognizing proper complementarity between pairing bases. Recently, 5'-γ-P-aminonaphthalene-5-sulfonate triphosphate, which is another member of 5'-γ-modified triphosphates, has been reported to improve the fidelity of reverse transcription (Non-patent Document 38). These findings suggest that recognition of γ-modified triphosphates by DNA polymerases requires more accurate geometric fitting between pairing bases than that between usual triphosphate substrates. The combination of 5'-γ-amidotriphosphates and polymerases having 3'-5' exonuclease activity can also be applied to other unnatural base pairs.

The Ds-Pa base pair provides the first case where hydrophobic base pairs are functional during transcription. This suggests that shape complementarity between pairing bases is also important in hydrophobic base pairing during transcription, as already shown for replication.

The Ds-Pa base pair system is very useful for the purpose of creating novel functional RNA molecules. Since 4-propynylpyrrole-2-carbaldehyde (Pa') is also introduced in a site-specific manner into RNA opposite Ds in the template, a series of 4-position modified Pa base derivatives can also be introduced into RNA. In this case, template DNA can be amplified by PCR of a DNA fragment containing a Ds-Pa base pair. Thus, the Ds-Pa base pair system provides a powerful tool for creating nucleic acids having functional artificial components at desired sites.

The invention claimed is:

1. A method for replicating a nucleic acid, wherein a deoxyribonucleoside 5'-triphosphate, in which the hydroxyl group of phosphoric acid at the γ-position is substituted with a group selected from the group consisting of an amino group, a methylamino group, a dimethylamino group, a mercapto group and a fluoro group, is used as a substrate during replication reaction.

2. The method according to claim 1, wherein the substituent is an amino group.

3. The method according to claim 1 or 2, wherein a DNA polymerase having exonuclease activity is used during the replication reaction.

4. The method according to claim 1, wherein the polymerase having exonuclease activity is selected from the group consisting of the Klenow fragment, T4 DNA polymerase and thermophilic DNA polymerases, each having 3'→5' exonuclease activity.

5. The method according to claim 1, wherein the deoxyribonucleoside 5'-triphosphate used as a substrate has an unnatural base.

6. The method according to claim 1, wherein the deoxyribonucleoside 5'-triphosphate used as a substrate has a natural base.

7. The method according to claim 1, wherein the deoxyribonucleoside 5'-triphosphate used as a substrate has a base represented by the following formula 1:

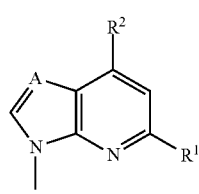

(1)

wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH.

8. The method according to claim 1, wherein the deoxyribonucleoside 5'-triphosphate used as a substrate has a base represented by the following formula 2:

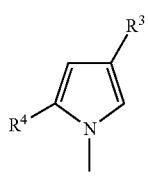

(2)

wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group.

9. A deoxyribonucleoside 5'-triphosphate, in which the hydroxyl group of phosphoric acid at the γ-position is substituted with a group selected from the group consisting of an amino group, a dimethylamino group, a mercapto group and a fluoro group.

10. A deoxyribonucleoside 5'-triphosphate having an unnatural base, in which the hydroxyl group of phosphoric acid at the γ-position is substituted with a group selected from the group consisting of an amino group, a methylamino group, a dimethylamino group, a mercapto group and a fluoro group.

11. A deoxyribonucleoside 5'-triphosphate having a natural base, in which the hydroxyl group of phosphoric acid at the γ-position is substituted with a group selected from the group consisting of an amino group, a dimethylamino group, a mercapto group and a fluoro group.

12. A method for replicating a nucleic acid comprising incorporating into a nucleic acid a deoxyribonucleoside 5'-triphosphate according to claim 1, in which the hydroxyl group of phosphoric acid at the γ-position is substituted with a group selected from the group consisting of an amino group, a methylamino group, a dimethylamino group, a mercapto group and a fluoro group.

13. A nucleic acid, in which a nucleotide having a base represented by the following formula 1:

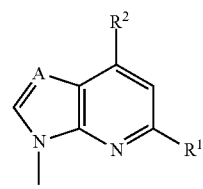

(3)

wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH forms a base pair with a nucleotide having a base represented by the following formula 2:

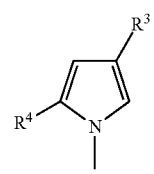

(2)

wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group.

14. The nucleic acid according to claim 13, wherein the base of formula 1 is selected from the group consisting of:
A1) a 7-(2-thienyl)-3H-imidazo[4,5-b]pyridin-3-yl group;
A2) a 7-(2-thiazolyl)-3H-imidazo[4,5-b]pyridin-3-yl group;
A3) a 7-(1H-2-imidazolyl)-3H-imidazo[4,5-b]pyridin-3-yl group;
A4) a 5-amino-7-(2-thienyl)-3H-imidazo[4,5-b]pyridin-3-yl group;

A5) a 5-amino-7-(2-thiazolyl)-3H-imidazo[4,5-b]pyridin-3-yl group;

A6) a 5-amino-7-(1H-2-imidazolyl)-3H-imidazo[4,5-b]pyridin-3-yl group;

A7) a 4-(2-thienyl)-1H-pyrrolo[2,3-b]pyridin-1-yl group;

A8) a 4-(2-thiazolyl)-1H-pyrrolo[2,3-b]pyridin-1-yl group;

A-9) a 4-(1H-2-imidazolyl)-1H-pyrrolo[2,3-b]pyridin-1-yl group;

A-10) a 6-amino-4-(2-thienyl)-1H-pyrrolo[2,3-b]pyridin-1-yl group;

A-11) a 6-amino-4-(2-thiazolyl)-1H-pyrrolo[2,3-b]pyridin-1-yl group; and

A-12) a 6-amino-4-(H-2-imidazolyl)-1H-pyrrolo [2,3-b]pyridin-1-yl group.

15. The nucleic acid according to claim 13, wherein the base of formula 2 is selected from the group consisting of:

B1) a 2-formyl-1H-pyrrol-1-yl group;

B2) a 2-formyl-4-iodo-1H-pyrrol-1-yl group;

B3) a 2-formyl-4-methyl-1H-pyrrol-1-yl group;

B4) a 2-formyl-4-(1-propyn-1-yl)-1H-pyrrol-1-yl group;

B5) a 2-formyl-4-(2-substituted aminovinyl)-1H-pyrrol-1-yl group;

B6) a 2-formyl-4-(3-substituted amino-1-propyn-1-yl)-1H-pyrrol-1-yl group;

B7) a 2-nitro-1H-pyrrol-1-yl group;

B8) a 2-nitro-4-iodo-1H-pyrrol-1-yl group;

B9) a 2-nitro-4-methyl-1H-pyrrol-1-yl group;

B10) a 2-nitro-4-(1-propyn-1-yl)-1H-pyrrol-1-yl group;

B11) a 2-nitro-4-(2-substituted aminovinyl)-1H-pyrrol-1-yl group; and

B12) a 2-nitro-4-(3-substituted amino-1-propyn-1-yl)-1H-pyrrol-1-yl group.

16. The nucleic acid according to any one of claims 13 to 15, which forms a base pair(s) in the step of transcription, reverse transcription, replication or translation.

17. A method for preparing a nucleic acid containing a nucleotide having a base represented by the following formula 1:

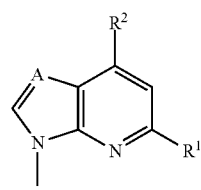

(1)

wherein $R^1$ is hydrogen or an amino group, $R^2$ is a substituted or unsubstituted 2-thienyl group, a substituted or unsubstituted 2-thiazolyl group, or a substituted or unsubstituted 1H-2-imidazolyl group, and A is N or CH, wherein the method comprises effecting transcription, reverse transcription or replication by using, as a template, a nucleic acid containing a nucleotide having a base represented by the following formula 2:

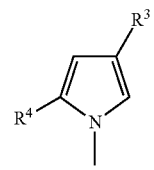

(2)

wherein $R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and $R^4$ is a formyl group or a nitro group, whereby the nucleotide having a base of formula 1 is incorporated at a site complementary to the nucleotide having a base of formula 2.

18. A method for preparing a nucleic acid containing a nucleotide having a base represented by the following formula 2:

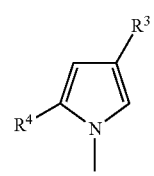

(2)

wherein $R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and $R^4$ is a formyl group or a nitro group, wherein the method comprises effecting transcription, reverse transcription or replication by using, as a template, a nucleic acid containing a nucleotide having a base represented by the following formula 1:

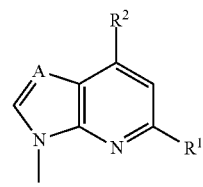

(1)

wherein $R^1$ is hydrogen or an amino group, $R^2$ is a substituted or unsubstituted 2-thienyl group, a substituted or unsubstituted 2-thiazolyl group, or a substituted or unsubstituted 1H-2-imidazolyl group, and A is N or CH, whereby the nucleotide having a base of formula 2 is incorporated at a site complementary to the nucleotide having a base of formula 1.

19. A nucleic acid containing a nucleotide having a base of formula 1 and/or formula 2, which is prepared by the method according to claim 17 or 18.

20. The nucleic acid according to claim 19, which is tRNA, mRNA, antisense DNA or RNA, a ribozyme, an aptamer or siRNA.

21. A ribonucleoside 5'-triphosphate having a base represented by the following formula 1:

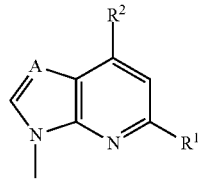
(1)

wherein
$R^1$ is hydrogen or an amino group,
$R^2$ is a substituted or unsubstituted 2-thienyl group, a substituted or unsubstituted 2-thiazolyl group, or a substituted or unsubstituted 1H-2-imidazolyl group, and
A is N or CH.

22. A ribonucleoside 5'-triphosphate having a base represented by the following formula 2:

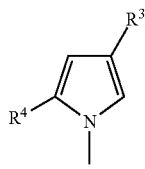
(2)

wherein
$R^3$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^4$ is a formyl group or a nitro group.

23. A 5'-O-(4,4'-dimethoxytrityl)-3'-O-(2-cyanoethyl N,N-diisopropylphosphoroamidite) deoxyribonucleoside having a base represented by the following formula 3:

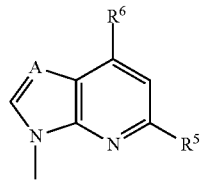
(3)

wherein
$R^5$ is hydrogen or a substituted amino group,
$R^6$ is a substituted or unsubstituted 2-thienyl group, a substituted or unsubstituted 2-thiazolyl group, or a substituted or unsubstituted 1H-2-imidazolyl group, and
A is N or CH.

24. A 5'-O-(4,4'-dimethoxytrityl)-3'-O-(2-cyanoethyl N,N-diisopropylphosphoroamidite) deoxyribonucleoside having a base represented by the following formula 4:

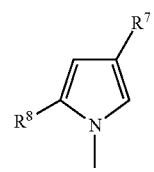
(4)

wherein
$R^7$ is a group selected from hydrogen, an iodo group, a substituted or unsubstituted $C_1$-$C_3$ alkyl group, a substituted or unsubstituted $C_2$-$C_3$ alkenyl group, or a substituted or unsubstituted $C_2$-$C_3$ alkynyl group, and
$R^8$ is a formyl group or a nitro group,
excluding the case where $R^7$ is hydrogen or a 1-propynyl group and $R^8$ is a formyl group.

25. A nucleic acid containing a nucleotide having a base represented by formula 2, which is prepared by the method according to claim 18, wherein the substituent $R^3$ in formula 2 is a $C_1$-$C_3$ alkyl group, a $C_2$-$C_3$ alkenyl group or a $C_2$-$C_3$ alkynyl group, each being substituted with biotin or a fluorescent molecule.

26. The ribonucleoside 5'-triphosphate according to claim 22, wherein $R^3$ is a $C_1$-$C_3$ alkyl group, a $C_2$-$C_3$ alkenyl group or a $C_2$-$C_3$ alkynyl group, each being substituted with biotin or a fluorescent molecule.

27. The 5'-O-(4,4'-dimethoxytrityl)-3'-O-(2-cyanoethyl N,N-diisopropylphosphoroamidite) deoxyribonucleoside according to claim 24, wherein $R^7$ is a $C_1$-$C_3$ alkyl group, a $C_2$-$C_3$ alkenyl group or a $C_2$-$C_3$ alkynyl group, each being substituted with biotin or a fluorescent molecule.

* * * * *